US012503474B2

(12) United States Patent
Koolman et al.

(10) Patent No.: US 12,503,474 B2
(45) Date of Patent: Dec. 23, 2025

(54) SUBSTITUTED PYRROLO[1,2-B]PYRIDAZINES AS ANTHELMINTICS

(71) Applicant: BOEHRINGER INGELHEIM VETMEDICA GMBH, Ingelheim am Rhein (DE)

(72) Inventors: Hannes Fiepko Koolman, Biberach an der Riss (DE); Bart Herlé, Biberach an der Riss (DE)

( * ) Notice: Subject to any disclaimer, the term of this patent is extended or adjusted under 35 U.S.C. 154(b) by 0 days.

(21) Appl. No.: 18/622,428

(22) Filed: Mar. 29, 2024

(65) Prior Publication Data

US 2024/0254133 A1 Aug. 1, 2024

Related U.S. Application Data

(62) Division of application No. 18/050,567, filed on Oct. 28, 2022, now Pat. No. 11,999,742.

(60) Provisional application No. 63/263,367, filed on Nov. 1, 2021.

(51) Int. Cl.
*C07D 237/26* (2006.01)
*C07D 487/04* (2006.01)
*C07D 491/052* (2006.01)
*C07D 513/04* (2006.01)

(52) U.S. Cl.
CPC ....... *C07D 487/04* (2013.01); *C07D 491/052* (2013.01); *C07D 513/04* (2013.01)

(58) Field of Classification Search
CPC .................................................... C07D 237/26
USPC ........................................................ 544/235
See application file for complete search history.

(56) References Cited

U.S. PATENT DOCUMENTS 4,464,372 A 8/1984 Bristol et al.
5,434,150 A 7/1995 Austel et al.
6,900,208 B2 5/2005 Salvati et al.
6,911,543 B2 6/2005 Walker et al.
7,030,112 B2 4/2006 Salvati et al.
7,153,854 B2 12/2006 Abe et al.
7,300,932 B2 11/2007 Fox et al.
7,306,631 B2 12/2007 Glenn, Jr. et al.
7,420,056 B2 9/2008 Kuehnert et al.
7,456,192 B2 11/2008 Imbert et al.
7,476,685 B2 1/2009 Araki et al.
7,723,336 B2 5/2010 Vaccaro et al.
7,893,085 B2 2/2011 Savy et al.
7,919,628 B2 4/2011 Hachtel et al.
7,956,068 B2 6/2011 Carson et al.
7,964,204 B2 6/2011 Lahm et al.
8,030,327 B2 10/2011 Sato et al.
8,252,795 B2 8/2012 Fink et al.
8,431,593 B2 4/2013 Hutchison et al.
8,450,354 B2 5/2013 Mjalli et al.
8,772,301 B2 7/2014 Hardy et al.
9,023,850 B2 5/2015 Lahm et al.
9,556,169 B2 1/2017 Chatterjee et al.
9,718,816 B2 8/2017 Chesworth et al.
9,802,961 B2 10/2017 Clark et al.
9,868,749 B2 1/2018 Alexander et al.
9,873,703 B2 1/2018 Ali et al.
10,138,248 B2 11/2018 Buesking et al.
2004/0242587 A1 12/2004 Fu
2006/0074102 A1 4/2006 Cusack et al.
2007/0027093 A1 2/2007 Ogawa et al.
2007/0275962 A1 11/2007 Koul et al.
2011/0105457 A1 5/2011 Taniyama et al.
2011/0195933 A1 8/2011 Katz et al.
2011/0206607 A1 8/2011 Olsson et al.
2011/0245274 A1 10/2011 Nanchen et al.
2012/0065200 A1 3/2012 Barbosa et al.
2012/0083476 A1 4/2012 Breitenbucher et al.
2012/0219500 A1 8/2012 Sakurai et al.
2013/0071415 A1 3/2013 Babu et al.
2013/0203692 A1 8/2013 Soll et al.
(Continued)

FOREIGN PATENT DOCUMENTS

CA 3117343 A1 4/2020
CL 202100033 7/2021
(Continued)

OTHER PUBLICATIONS

Database Registry [Online], May 1, 2020 (May 1, 2020), Life Chemicals Inc.: "Imidazo[1,2-b]pyridazine-6-carboxamide, N-(1,2,3,4-tetrahydro-1-naphthalenyl)-", XP055837558, Database accession No. 2415490-08-1 compound with the Registry No. 2415490-08-1.
(Continued)

*Primary Examiner* — Douglas M Willis

(57) ABSTRACT

This invention provides for compounds of the formula:

(I)

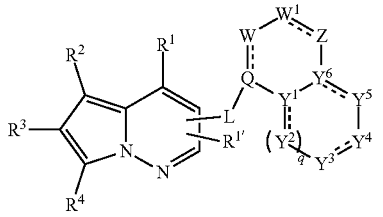

wherein the variables are defined herein, or salt thereof, compositions comprising these compounds, and methods for the treatment, control and/or prevention of a parasitic infestation and/or infection in an animal in need thereof by administering an effective amount of these compounds to said animal.

27 Claims, No Drawings

(56) References Cited

U.S. PATENT DOCUMENTS

| | | | |
|---|---|---|---|
| 2014/0045826 | A1 | 2/2014 | Shakespeare et al. |
| 2014/0066434 | A1 | 3/2014 | Shakespeare |
| 2015/0126523 | A1 | 5/2015 | Meng |
| 2016/0106102 | A1 | 4/2016 | Kuebbeler et al. |
| 2016/0333012 | A1 | 11/2016 | Chatterjee et al. |
| 2017/0369486 | A1 | 12/2017 | Acharya et al. |
| 2018/0230157 | A1 | 8/2018 | Bacon et al. |
| 2019/0071447 | A1 | 3/2019 | Kohler et al. |
| 2019/0233425 | A1 | 8/2019 | Bayly et al. |
| 2019/0352275 | A1 | 11/2019 | Meldrum et al. |
| 2020/0024264 | A1 | 1/2020 | Hubsch et al. |
| 2020/0237771 | A1 | 7/2020 | Hallur et al. |
| 2022/0047569 | A1 | 2/2022 | Kazmi et al. |

FOREIGN PATENT DOCUMENTS

| | | | |
|---|---|---|---|
| CL | 202202346 | A | 9/2021 |
| CL | 202201662 | A | 2/2023 |
| CL | 202201739 | A1 | 3/2023 |
| EC | SP21001265 | A | 2/2021 |
| EC | SP21070788 | A | 12/2021 |
| EP | 1277754 | B1 | 7/2005 |
| EP | 3078664 | A1 | 10/2016 |
| EP | 3643711 | A1 | 4/2020 |
| JP | 2009203214 | A | 9/2009 |
| JP | 2011140452 | A | 7/2011 |
| JP | 2012012299 | A | 1/2012 |
| JP | 2016505529 | A | 2/2016 |
| RU | 2004136978 | A | 6/2005 |
| WO | 2000053602 | A1 | 9/2000 |
| WO | 2005066177 | A1 | 7/2005 |
| WO | 2006004191 | A1 | 1/2006 |
| WO | 2007123855 | A2 | 11/2007 |
| WO | 2008019309 | A1 | 2/2008 |
| WO | 2010017046 | A1 | 2/2010 |
| WO | 2011058109 | A1 | 5/2011 |
| WO | 2011137587 | A1 | 11/2011 |
| WO | 2011146401 | A1 | 11/2011 |
| WO | 2012100342 | A1 | 8/2012 |
| WO | 2012107533 | A1 | 8/2012 |
| WO | 2014078802 | A1 | 5/2014 |
| WO | 2015066277 | A1 | 5/2015 |
| WO | 2017093180 | A1 | 6/2017 |
| WO | 2017125898 | A1 | 7/2017 |
| WO | 2017178416 | A1 | 10/2017 |
| WO | 2018087036 | A1 | 5/2018 |
| WO | 2018197401 | A1 | 11/2018 |
| WO | 2019002132 | A1 | 1/2019 |
| WO | 2019025341 | A1 | 2/2019 |
| WO | 2019115768 | A1 | 6/2019 |
| WO | 2019215182 | A1 | 11/2019 |
| WO | 2020002124 | A1 | 1/2020 |
| WO | 2020012336 | A1 | 1/2020 |
| WO | 2020014068 | A1 | 1/2020 |
| WO | 2020083971 | A2 | 4/2020 |
| WO | 2020131629 | A1 | 6/2020 |
| WO | 2020131631 | A1 | 6/2020 |
| WO | 2020191091 | A1 | 9/2020 |
| WO | 2020219871 | A1 | 10/2020 |
| WO | 2020247747 | A1 | 12/2020 |
| WO | 2021018839 | A1 | 2/2021 |
| WO | 2021030379 | A1 | 2/2021 |
| WO | 2021032934 | A1 | 2/2021 |
| WO | 2021122906 | A1 | 6/2021 |
| WO | 2021122911 | A1 | 6/2021 |
| WO | 2021127443 | A1 | 6/2021 |
| WO | 2021130731 | A1 | 7/2021 |
| WO | 2021173713 | A1 | 9/2021 |
| WO | 2021204930 | A1 | 10/2021 |
| WO | 2021231571 | A1 | 11/2021 |
| WO | 2021242581 | A1 | 12/2021 |
| WO | 2022106469 | A2 | 5/2022 |
| WO | 2022117783 | A1 | 6/2022 |
| WO | 2022122987 | A1 | 6/2022 |
| WO | 2022122988 | A1 | 6/2022 |
| WO | 2022152918 | A1 | 7/2022 |

OTHER PUBLICATIONS

Database Registry (Online) Chemical Abstracts Service, Columbus, Ohio, US; Jul. 17, 2016, XP002799055, Database accession No. 1953874-77-5, 2-Benzofurancarboxamide,3,4,7-trimethyl-N-(octahydro-4-benzofuranyl).

Database Registry (Online) Chemical Abstracts Service, Columbus, Ohio, US; Oct. 15, 2017, XP002799056, Database accession No. 2134947-60-5, 2-Benzofurancarboxamide,3,4,7-trimethyl-N-(4,5,6,7-tetrahydro-1-methyl-1H-indazol-4-yl).

Database Registry (Online) Chemical Abstracts Service, Columbus, Ohio, US; Aug. 15, 2011, XP002799057, Database accession No. 1318005-39-8, 2-Benzofurancarboxamide, N-(6-bromo-3,4-dihydro-2H-1-benzopyran-4-yl)-3,7-dimethyl.

Database Registry (Online) Chemical Abstracts Service, Columbus, Ohio, US; Dec. 23, 2015, XP002799058, Database accession No. 1835595-46-4, 2-Benzofurancarboxamide, N-(6-amino-1,2,3,4-tetrahydro-1-naphthalenyl)-3,4,7-trimethyl-, hydrochloride (1:1).

Database Registry (Online) Chemical Abstracts Service, Columbus, Ohio, US; Nov. 18, 2018, XP002799059, Database accession No. 2249355-47-1, 2-Benzofurancarboxamide, N-(6,7-dihydro-5H-pyrrolo[1,2-a]imidazol-7-yl)-3,7-dimethyl.

Database Registry (Online) Chemical Abstracts Service, Columbus, Ohio, US; Jul. 4, 2016, XP002799060, Database accession No. 1944784-28-4, 2-Benzofurancarboxamide, 5-bromo-7-methyl-N-(4,5,6,7-tetrahydro-2-methyl-2H-indazol-4-yl).

Preston, "Low cost whole-organism screening of compounds for anthelmintic activity", International Journal for Parasitology, vol. 45, pp. 333-343.

Database Registry (Online) Chemical Abstracts Service, Columbus, Ohio, US; Nov. 15, 2018, Database accession No. 2248503-07-1, 2-Benzofurancarboxamide, 7-methyl-N-[(8R)-5,6,7,8-tetrahydro-8-quinolinyl]—(CA Index Name).

Database Registry (Online) Chemical Abstracts Service, Columbus, Ohio, US; Dec. 23, 2015, Database accession No. 1835595-45-3, 2-Benzofurancarboxamide, N-(6-amino-1,2,3,4-tetrahydro-1-naphthalenyl)-3,4,7-trimethyl—(CA Index Name).

Database Registry (Online) Chemical Abstracts Service, Columbus, Ohio, US; Dec. 23, 2015, Database accession No. 1835526-11-8, 2-Benzofurancarboxamide, N-(6-amino-1,2,3,4-tetrahydro-1-naphthalenyl)-3,7-dimethyl-, hydrochloride (1:1) (CA Index Name).

Database Registry (Online) Chemical Abstracts Service, Columbus, Ohio, US; Dec. 23, 2015, Database accession No. 1835526-10-7, 2-Benzofurancarboxamide, N-(6-amino-1,2,3,4-tetrahydro-1-naphthalenyl)-3,7-dimethyl—(CA Index Name).

Database Registry (Online) Chemical Abstracts Service, Columbus, Ohio, US; Feb. 7, 2012, Database accession No. 1355505-50-8, 2-Benzofurancarboxamide, N-(1,2,5,6,7,8-hexahydro-2-oxo-5-quinolinyl)-3,7-dimethyl—(CA Index Name).

Database Registry (Online) Chemical Abstracts Service, Columbus, Ohio, US; May 24, 2011, Database accession No. 1299845-91-2, 2-Benzofurancarboxamide, N-[1-(1,1-dimethylethyl)-4,5,6,7-tetrahydro-1H-indazol-4-yl]-3,7-dimethyl—(CA Index Name).

Database Registry (Online) Chemical Abstracts Service, Columbus, Ohio, US; May 24, 2011, Database accession No. 1299836-12-7, 2-Benzofurancarboxamide, N-(6-fluoro-3,4-dihydro-2H-1-benzothiopyran-4-yl)-3,7-dimethyl—(CA Index Name).

Koyanagi, T. & Haga, T. Bioisosterism in Agrochemicals. 15-24 (1995).

Meanwell, N. A Synopsis of Some Recent Tactical Application of Bioisosteres in Drug Design. Journal of Medicinal Chemistry, 54(8), 2529-2591. https://doi.org/10.1021/jm1013693 (Year: 2011).

SUBSTITUTED PYRROLO[1,2-B]PYRIDAZINES AS ANTHELMINTICS

FIELD OF THE INVENTION

This patent application relates to new antiparasitic compounds, compositions comprising the compounds, and methods of using the compounds to prevent, treat and/or control parasites that harm animals and humans.

CROSS REFERENCE TO RELATED APPLICATIONS

This application claims the benefit of priority to U.S. Provisional Application No. 63/263,367 filed on Nov. 1, 2021, which is incorporated herein by reference in its entirety.

INCORPORATION BY REFERENCE

All references cited herein, are incorporated by reference herein, in their entirety.

BACKGROUND OF THE INVENTION

Animals, such as mammals and birds, are often susceptible to parasite infestations. These parasites may be ectoparasites, such as fleas and ticks. Animals and humans also suffer from endoparasitic infections including, for example, helminthiasis which is most frequently caused by a group of parasitic worms described as nematodes or roundworms. These parasites cause severe economic losses in pigs, sheep, horses, and cattle as well as affecting companion animals (e.g. cats and dogs) and poultry. Endoparasites include those which occur in the gastrointestinal tract of animals and humans such as from the genuses *Ancylostoma, Necator, Ascaris, Strongyloides, Trichinella, Capillaria, Toxocara, Toxascaris, Trichuris* and *Enterobius*. Other parasites which are found in the blood or other tissues and organs include filarial worms and the extra intestinal stages of *Strongyloides* and *Trichinella.*

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period." L3 larvae migrate during blood feeding of the mosquito to the tip of the mosquito's mouth parts (labium), leave the mosquito, and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet. Parasitol.* 2005 Oct. 24 133 (2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al., (*Vet. Parasitol.* 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (see also Blagburn et al., "Evidence of genetic selection following treatment of heartworm-infected, microfilaremic dog with increasing dosages of ivermectin," 58th annual meeting of American Association of Veterinary Parasitologists, p. 64, 20-23 Jul. 2013 American Heartworm Society, 2010. Heartworm Preventive Resistance. Is it Possible, vol. 37. Bulletin of the American Heartworm Society, pp. 5.). Bowman also reviews various studies in which LOE to macrocyclic lactone treatment have been observed from peer-reviewed journals, reports to the Center for Veterinary Medicine (CVM) of the Food and Drug Administration in the U.S. (Bowman, *Parasites & Vectors* 2012, 5:138). Pulaski et al. described the establishment of macrocyclic lactone resistant *Dirofilaria immitis* isolates in experimentally infected dogs (Pulaski et al., Parasites & Vectors 2014, 7:494). Similarly, Snyder et al. report a controlled laboratory study with a recent isolate of *Dirofilaria immitis*, in which treatment with ivermectin and milbemycin oxime did not prevent maturation of inoculated L3 stage larvae. Blagburn et al. describe the comparison of four commercial heartworm preventative therapies against the MP3 laboratory strain of *Dirofilaria immitis* in which three of four products failed to prevent infections with adult heartworms (Blagburn et al., *Veterinary* Parasitology, 2011, 176, 189-194. Further reports of evidence of macrocyclic lactone resistant isolates of *Dirofilaria immits* are reported in Bourguinat et al., *Veterinary* Parasitology, 2011, 181, 388-392; Geary et al., *Topics in Com-*

*panion Animal Medicine,* 2011, vol. 26, no. 4, p. 187; Trends in Parasitology, October 2004, vol. 20, no. 10, p. 477; Bourguinat et al., *Veterinary Parasitology,* 2011, 176, p. 374-381. In addition, WO 2016/161369 describes in the examples a study in which treatment of dogs infected with L3 stage *Dirofilaria immitis* of the JYD-34 isolate were treated with an ivermectin oral solution, Profender® Tablets (emodepside+praziquantel) or a combination of an ivermectin oral solution and Profender® Tablets at two dosages. The ivermectin and Profender® Tablet groups resulted in less than 50% efficacy and the lower dosage of the ivermectin+Profender® Tablet group resulted in only 81% efficacy. Thus, there is an ongoing need to develop new anthelmintic agents with improved activity against *Dirofilaria immitis* and other endoparasites.

WO 2017/178416 A1 provides pyrazolopyrimidine derivatives for the control, treatment and/or prevention of helminths. This publication describes anthelmintic compounds having a different 5-6 fused nitrogen-containing heteroaryl core.

WO 2018/197401 A1 provides bicyclic pyrazole derivatives for the control, treatment and/or prevention of helminths.

WO 2018/087036 A1 provides quinolone-3-carboxamide derivatives for the control, treatment and/or prevention of helminths.

WO 2019/025341 provides quinoline compounds for the treatment, control and/or prevention of helminth infections and WO 2019/002132 A1 describes azaquinone derivatives for the control, treatment and/or prevention of helminths. WO 2019/215182 A1 also describes quinoline derivates for the treatment and control of helminth infections.

WO 2020/083971 A2 describes additional carboxamide compounds substituted with bicyclic ring systems for the treatment and control of parasitic infections.

WO 2021/204930 describes substituted condensed azines containing a bicyclic nitrogen-containing bicyclic ring system that have anthelmintic properties.

WO 2021/018839 A1 describes isoquinoline derivatives for use in the treatment of parasite infections; and WO 2019/115768 A1 describes a process for preparing anthelmintic 4-amino-quinoline-3-carboxyamide derivatives.

WO 2020/131629 A1, WO 2020/131631 A1 and WO 2020/247747 A1 describes bicyclic derivatives which are useful in the control of endoparasites, including heartworm, in warm-blooded animals.

WO 2021/122906 A1 describes anthelmintic compounds comprising azaindole compounds and WO 2021/122911 A1 describes quinoline compounds that are useful for the treatment of disease caused by helminths such as *Dirofilaria immitis.*

WO 2020/014068 A1 describes anthelmintic heterocyclic compounds having a core having a core bicyclic pyrazolo [1,5-a]pyridine ring system that were found to be active against *Dirofilaria immitis*. The pyrazolo[1,5-a]pyridine ring system of the compounds described in this publication is a 5-6-fused ring system having two nitrogen atoms, one at the 5-6 ring junction and the other in the 5-membered ring.

WO 2020/191091 A1 describes aza-benzothiophene and aza-benzofuran compounds that are useful for the control or prevention of parasitic infections, including against infections by *Dirofilaria immitis.*

WO 2022/106469 A2 describes N-(2,3-Dihydro-1,4-benzoxazin-4-yl)-3-isopropyl-7-(2,3,5-trifluorophenyl)benzothiophene-2-carboxamide derivatives and similar compounds for the treatment of heartworm infections.

WO 2022/117783 A1 describes bicyclic compounds of formula (I) and (I') disclosed for the treatment and/or control of endoparasite infections in warm-blooded animals.

WO 2022/122987 A1 describes anthelmintic compounds comprising a pyridine structure for the treatment of heartworm disease caused by *Dirofilaria immitis.*

WO 2022/122988 A1 describes anthelmintic compounds comprising a thienopyridine structure for the treatment of heartworm disease caused by *Dirofilaria immitis.*

WO 2022/152918 A1 describes azaquinazoline derivatives for use in treating or preventing *Dirofilaria immitis* infections in a mammal.

SUMMARY OF THE INVENTION

The present application provides for novel anthelmintic and antiparasitic pyrrolopyridazine heterocyclic compounds with improved activity against endoparasites. The application is also directed to compositions comprising the compounds, methods and uses of the compounds for eradicating, controlling, and/or preventing a parasitic infection and/or infestation in animals including humans. The compounds may be administered to animals, particularly mammals, fish and birds, to treat, control and/or prevent parasitic infections.

An aspect of the present invention includes a compound of Formula (I):

(I)

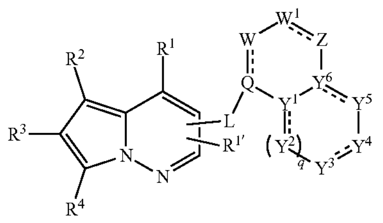

or salt thereof, wherein variables $R^1$, $R^{1'}$, $R^2$, $R^3$, $R^4$, $Y^1$, $Y^2$, $Y^3$, $Y^4$, $Y^5$, $Y^6$, L, Q, W, $W^1$, Z and q are defined herein, and the dashed bonds (⚋) signifies a single or double bond.

The invention also includes a composition comprising a compound of Formula (I), or a salt thereof, and a pharmaceutically acceptable carrier. The compounds and compositions of the invention may be administered to animals, particularly mammals, fish and birds, to prevent, control and/or treat parasitic infections in animals. In particular, the compounds and compositions of the invention may be administered to cats, dogs, horses, chickens, pigs, sheep and cattle, with the aim of substantially ridding these hosts of endoparasites.

In an embodiment, compounds of Formula (I) and compositions comprising said compounds are effective against endoparasites, such as filariae (e.g. *Dirofilaria immitis*), and nematodes including, but not limited to, hookworms, whipworms and roundworms of the digestive tract of animals and humans. In certain embodiments, compounds of Formula (I) and compositions comprising said compounds are effective against *Dirofilaria immitis* (heartworm) isolates that are less sensitive to treatment with macrocyclic lactones. In another embodiment, the compounds and compositions of the invention are effective for treating, controlling and/or preventing infections of animals with nematodes that are less sensitive to treatment with commercially available or known active agents.

In an embodiment, the invention includes a combination of a compound of Formula (I) with at least a second active agent, which may broaden the scope of protection afforded to animals against endoparasites and/or ectoparasites.

Another embodiment includes a method for the treatment, control and/or prevention of a parasitic infection in an animal comprising administering a compound of Formula (I) to the animal. Another embodiment includes a use of a compound of Formula (I) for the treatment, control and/or prevention of a parasitic infection in an animal and the use of the compound of Formula (I) in the preparation of a medicament for the treatment, control and/or prevention of a parasitic infection in an animal.

Thus, the invention includes the following non-limiting embodiments:

(a) a compound of Formula (I), or a salt thereof, which is an active endoparasiticide;

(b) a veterinary composition comprising a parasiticidally effective amount of a compound of Formula (I), or a salt thereof, in combination with a pharmaceutically acceptable carrier or diluent;

(c) a veterinary composition comprising a parasiticidally effective amount of a compound of Formula (I), or a salt thereof, in combination with one or more additional active agents (i.e., active ingredient not encompassed by Formula (I)) and a pharmaceutically acceptable carrier or diluent;

(d) a method for treating a parasitic infection and/or infestation in or on an animal comprising administering a parasiticidally effective amount a compound of Formula (I), or a salt thereof, optionally with one or more additional active agents (i.e., active ingredient not encompassed by Formula (I)), to the animal in need thereof;

(e) a method for the prevention of a parasitic infection and/or infestation of an animal, which comprises administering a parasiticidally effective amount of a compound of Formula (I), or a salt thereof, optionally with one or more additional active agents (i.e., active ingredient not encompassed by Formula (I)), to the animal in need thereof;

(f) a compound of Formula (I), or a salt thereof, optionally with one or more additional active agents (i.e., active ingredient not encompassed by Formula (I)), for use in the treatment, control and/or prevention of a parasitic infection and possibly also a parasitic infestation in an animal;

(g) a use of a compound of Formula (I), or a salt thereof, optionally with one or more additional active agents (i.e., active ingredient not encompassed by Formula (I)), for the manufacture of a veterinary medicament for the treatment, control and/or prevention of a parasitic infection and/or infestation in an animal; and (h) a method of preparation of the compounds of Formula (I).

Definitions

It is noted that in this disclosure and particularly in the claims and/or paragraphs, terms such as "comprises", "comprised", "comprising" and the like can be interpreted as "includes", "included", "including", and the like; and that terms such as "consisting essentially of" and "consists essentially of" are interpreted as allowing for elements not explicitly recited, but excluding elements that are found in the prior art or that affect a basic or novel characteristic of the invention.

Unless defined otherwise, all technical and scientific terms used herein have the same meaning as is commonly understood by one of skill in the art to which this invention belongs at the time of filing. Terms not specifically defined herein should be given the meanings that would be given to them by one of skill in the art in light of the disclosure and the context. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. As used in the specification, however, unless specified to the contrary, the following terms have the meaning indicated and the following conventions are adhered to.

In the groups, radicals, or moieties defined herein, the number of carbon atoms is often specified preceding the group, for example, $C_{1-6}$-alkyl means an alkyl group or radical having 1 to 6 carbon atoms. In general, in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last-named subgroup is the radical attachment point, for example, the substituent "aryl-$C_{1-3}$-alkylene" means an aryl group which is bound to a $C_{1-3}$-alkyl-group, the latter of which is bound to the core or to the group to which the substituent is attached.

In case a compound of the present invention is depicted in the form of a chemical name and as a formula, in case of any discrepancy the formula shall prevail. An asterisk may be used in sub-formulas to indicate the bond which is connected to the core molecule as defined.

The numeration of the atoms of a substituent starts with the atom which is closest to the core or to the group to which the substituent is attached. For example, the term "3-carboxypropyl-group" represents the following substituent:

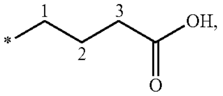 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

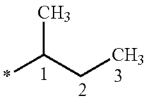 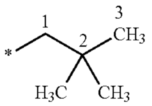 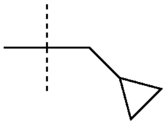

The asterisk or " " may be used in sub-formulas to indicate the bond which is connected to core

molecule as defined.

The term "substituted" as used herein, means that one or more hydrogens on the designated atom are replaced by a group selected from a defined group of substituents, provided that the designated atom's normal valence is not exceeded, and that the substitution results in a stable compound. Likewise, the term "substituted" may be used in connection with a chemical moiety instead of a single atom, e.g. "substituted alkyl", "substituted aryl" or the like.

Unless indicated otherwise for a specific embodiment of the invention, the term "optionally substituted" as used herein is meant to indicate that a given radical is optionally substituted by one or more of the following moieties: halogen, hydroxyl, oxo (C═O), alkyl, haloalkyl, cycloalkyl, cycloalkenyl, carboxyl, acyl, acyloxy, acetyl, alkylcarbonyl, haloalkylcarbonyl, alkoxycarbonyl, haloalkoxycarbonyl, aminocarbonyl, alkylaminocarbonyl, dialkylaminocarbonyl, haloalkylaminocarbonyl, dihaloalkylaminocarbonyl, amino, alkyl- or dialkylamino, amido, arylamino, alkoxy, haloalkoxy, aryloxy, alkylthio, haloalkylthio, nitro, cyano, azido, thiol, thioamido, imino, amidino, guanidino, carbonate, $R_3Si$— or $R_3SiO$— where R is $C_1$-$C_6$-alkyl, $C_1$-$C_6$-haloalkyl or aryl, $SF_5$, sulfate, alkylsulfonyl, haloalkylsulfonyl, alkoxysulfonyl, haloalkoxysulfonyl, arylsulfonyl, alkylsulfinyl, haloalkylsulfinyl, arylsulfinyl, sulfamoyl, sulfoximine, sulfinimine, sulfonimidamide, sulfonediimine, phosphonyl, phosphinyl, phosphoryl, phosphine, phosphonamidate, phosphinamidate, phosphinate, phosphine oxide, thioester, anhydride, oxime, hydrazine, carbamate, phosphate, phosphonate, aryl, heteroaryl and heterocyclyl.

In some embodiments, unless indicated otherwise for a specific embodiment of the invention, the term "optionally substituted" includes substitution of a core group with halogen (chloro, fluoro, bromo, iodo), hydroxyl, oxo, $C_1$-$C_6$-alkyl, $C_1$-$C_6$-haloalkyl, 3- to 8-membered cycloalkyl, 5- to 8-membered cycloalkenyl, carboxyl, amino, amido, thioamide, imino, amidino, guanidino, carbonate, tri-$C_1$-$C_6$-alkylsilyl, tri-$C_1$-$C_6$-alkylsiloxy, sulfate, $C_1$-$C_6$-alkylamino, $C_1$-$C_6$-dialkylamino, phenylamino, $C_1$-$C_6$-alkoxy, $C_1$-$C_6$-haloalkoxy, phenoxy, cyano, azido, thiol, nitro, $SF_5$, acetyl, $C_1$-$C_6$-alkoxycarbonyl, $C_1$-$C_6$-alkoxycarbonyloxy, $C_1$-$C_6$-haloalkoxycarbonyl, $C_1$-$C_6$-alkylcarbonyl, $C_1$-$C_6$-alkylcarbonyloxy, $C_1$-$C_6$-haloalkylcarbonyl, aminocarbonyl, $C_1$-$C_6$-alkylaminocarbonyl, $C_1$-$C_6$-dialkylaminocarbonyl, aminocarbonyloxy, $C_1$-$C_6$-alkylaminocarbonyloxy, $C_1$-$C_6$-dialkylaminocarbonyloxy, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, phenylsulfinyl, $C_1$-$C_6$-alkylsulfonyl, phenylsulfonyl, $C_1$-$C_6$-alkoxysulfonyl, $C_1$-$C_6$-haloalkylthio, $C_1$-$C_6$-haloalkylsulfinyl, $C_1$-$C_6$-haloalkylsulfonyl, $C_1$-$C_6$-haloalkoxysulfonyl, phenyl, 5- or 6-membered heteroaryl, 5- or 6-membered heterocyclyl, sulfamoyl, sulfoximine, sulfinimine, sulfonimidamide, sulfonediimine, phosphonyl, phosphinyl, phosphoryl, phosphine, phosphonamidate, phosphinamidate, phosphinate, phosphine oxide, thioester, anhydride, oxime, hydrazine, carbamate, phosphate or phosphonate.

In other embodiments, unless indicated otherwise for a specific embodiment of the invention, the term "optionally substituted" includes substitution of a core group with halogen (chloro, fluoro, bromo, iodo), hydroxyl, $C_1$-$C_3$-alkyl, $C_1$-$C_3$-haloalkyl, 3- to 8-membered cycloalkyl, 5-8-membered cycloalkenyl, amino, $C_1$-$C_3$-alkylamino, $C_1$-$C_3$-dialkylamino, $C_1$-$C_3$-alkoxy, $C_1$-$C_3$-haloalkoxy, cyano, nitro, $SF_5$, acetyl, $C_1$-$C_3$-alkoxycarbonyl, $C_1$-$C_3$-haloalkoxycarbonyl, $C_1$-$C_3$-alkylcarbonyl, $C_1$-$C_3$-haloalkylcarbonyl, aminocarbonyl, $C_1$-$C_3$-alkylaminocarbonyl, $C_1$-$C_3$-dialkylaminocarbonyl, $C_1$-$C_3$-haloalkylaminocarbonyl, $C_1$-$C_3$-dihaloalkylaminocarbonyl, $C_1$-$C_3$-alkylthio, $C_1$-$C_3$-alkylsulfinyl, $C_1$-$C_3$-alkylsulfonyl, $C_1$-$C_3$-haloalkylthio, $C_1$-$C_3$-haloalkylsulfinyl, $C_1$-$C_3$-haloalkylsulfonyl, phenyl, 5- or 6-membered heteroaryl, 5- or 6-membered heterocyclyl.

In certain embodiments, unless indicated otherwise for a specific embodiment of the invention, the term "optionally substituted" includes substitution by halogen (chloro, fluoro, bromo and iodo), methyl, ethyl, n-propyl, iso-propyl, n-butyl, iso-butyl, sec-butyl, tert-butyl, cyclopropyl, cyclobutyl, cyclopentyl, cyclohexyl, hydroxyl, thiol, amino, methylamino, ethylamino, propylamino, butylamino, dimethylamino, diethylamino, methoxy, ethoxy, propoxy, $CF_3$, $CF_2CF_3$, —$OCF_3$, —$OCF_2CF_3$, —$SCH_3$, —$SCF_3$, —$S(O)CH_3$, —$S(O)CF_3$, —$S(O)_2CH_3$, —$S(O)_2CF_3$, aziridinyl, azetidinyl, morpholino, piperidinyl, pyridyl and phenyl.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as solvates thereof such as for instance hydrates.

Unless specifically indicated, also "pharmaceutically acceptable salts" as defined in more detail below shall encompass solvates thereof such as for instance hydrates.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of animals without excessive toxicity, irritation, allergic response, or other problem or complication, and commensurate with a reasonable benefit/risk ratio.

As used herein, “pharmaceutically acceptable salt” refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid. Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent such as ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term “halogen” denotes fluorine, chlorine, bromine and iodine.

The term “$C_{1-n}$-alkyl”, wherein n is an integer selected from 2, 3, 4, 5 or 6, preferably 4, 5, or 6, either alone or in combination with another radical, denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term “$C_{1-n}$-alkylene”, wherein n is an integer selected from 2, 3, 4, 5 or 6, preferably 4, 5 or 6, either alone or in combination with another radical, denotes an acyclic, saturated, branched or linear chain divalent alkyl radical containing from 1 to n carbon atoms. For example, the term $C_{1-4}$-alkylene includes-$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$ —$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —CH 2-$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$—and—$C(CH_3)$ $(CH_2CH_3)$—.

The term “$C_{2-m}$-alkenyl” is used for a group “$C_{2-m}$-alkyl”, wherein m is an integer selected from 3, 4, 5 or 6, preferably 4, 5 or 6, if at least two carbon atoms of said group are bonded to each other by a double bond.

The term “$C_{2-m}$-alkenylene” is used for a group “$C_{2-m}$-alkylene”, wherein m is an integer selected from 3, 4, 5 or 6, preferably 4, 5 or 6, if at least two carbon atoms of said group are bonded to each other by a double bond.

The term “$C_{2-m}$-alkynyl” is used for a group “$C_{2-m}$-alkyl”, wherein m is an integer selected from 3, 4, 5 or 6, preferably 4, 5 or 6, if at least two carbon atoms of said group are bonded to each other by a triple bond.

The term “$C_{2-m}$-alkynylene” is used for a group “$C_{2-m}$-alkylene”, wherein m is an integer selected from 3, 4, 5 or 6, preferably 4, 5 or 6, if at least two of those carbon atoms of said group are bonded to each other by a triple bond.

The term “$C_{3-k}$-cycloalkyl”, wherein k is an integer selected from 4, 5, 6, 7 or 8, preferably 4, 5 or 6, either alone or in combination with another radical, denotes a cyclic, saturated, unbranched hydrocarbon radical with 3 to k C atoms. For example the term $C_{3-7}$-cycloalkyl includes cyclopropyl, cyclobutyl, cyclopentyl, cyclohexyl and cycloheptyl.

The term “$C_{3-k}$-cycloalkenyl”, wherein k is an integer selected from 4, 5, 6, 7 or 8, preferably 4, 5 or 6, either alone or in combination with another radical, denotes a cyclic, unsaturated, but non-aromatic, unbranched hydrocarbon radical with 3 to k C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term “halo” added to an “alkyl”, “alkylene”, “alkenyl”, “alkenylene”, “alkynyl”, “alkynylene”, “cycloalkyl”, “cycloalkenyl” or “alkoxy” group defines an alkyl, alkylene, alkenyl, alkenylene, alkynyl, alkynylene, cycloalkyl, cycloalkenyl or alkoxy group, wherein one or more hydrogen atoms are replaced by a halogen atom selected from among fluorine, chlorine, bromine or iodine, preferably fluorine and chlorine, particularly preferred is fluorine. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term “fluoroalkyl” as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term “alkoxy” refers to an alkyl-O—, wherein alkyl is as defined above. Similarly, the terms “alkenyloxy”, “alkynyloxy”, “haloalkoxy”, “haloalkenyloxy”, “haloalkynyloxy”, “cycloalkoxy”, “cycloalkenyloxy”, “halocycloalkoxy”, and “halocycloalkenyloxy” refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined herein. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethyl-butoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term “carbocyclyl” or “carbocycle”, either alone or in combination with another radical, means a mono-, bi- or tricyclic ring structure consisting of 3 to 14 carbon atoms. The term “carbocyclyl” or “carbocycle” refers to fully saturated, partially saturated and aromatic ring systems. The term “carbocyclyl” or “carbocycle” encompasses fused, bridged and spirocyclic systems. Examples include:

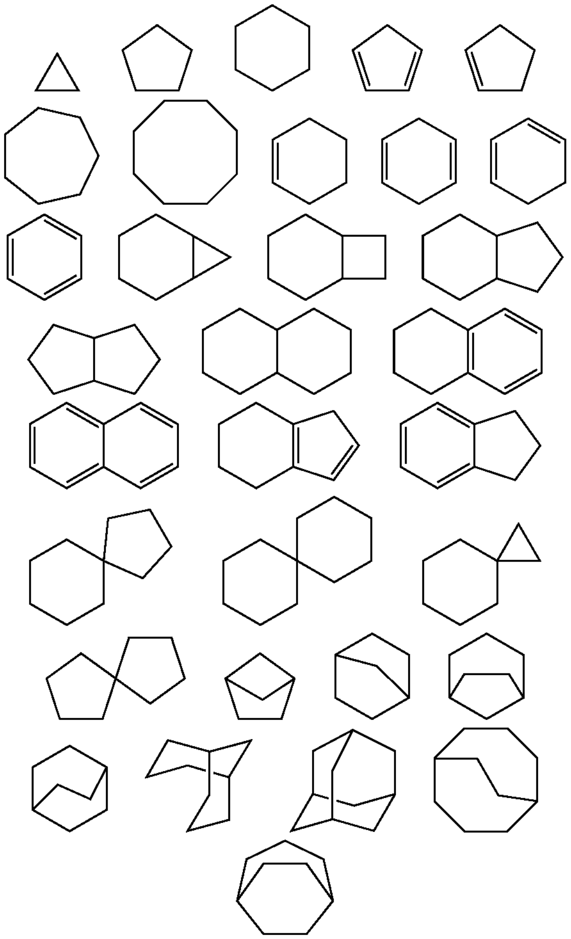

The term “aryl”, either alone or in combination with another radical, denotes a carbocyclic aromatic monocyclic group containing 6 carbon atoms, which is optionally further fused to a second five- or six-membered, carbocyclic group which is aromatic, fully saturated or partially saturated. The term “aryl” includes, but is not limited to, phenyl, indanyl, indenyl, naphthyl, anthracenyl, phenanthrenyl, tetrahydronaphthyl and dihydronaphthyl.

The term “aralkyl” refers to an aryl group that is bonded to the parent compound through a diradical alkylene bridge, $(-CH_2-)$ n, where n is 1-6 and where “aryl” is as defined herein.

The term “heterocyclyl” or “heterocycle” means a saturated or unsaturated mono- or polycyclic ring system optionally comprising aromatic rings, containing one or more heteroatoms selected from N, O, S, S(O) or $S(O)_2$ consisting of 3 to 14 ring atoms, wherein none of the heteroatoms is part of the aromatic ring. The term “heterocyclyl” or “heterocycle” is intended to include all possible isomeric forms. Thus, the term “heterocyclyl” or “heterocycle” includes the following exemplary structures (not depicted as radicals as each form is optionally attached through a covalent bond to any atom so long as appropriate valences are maintained):

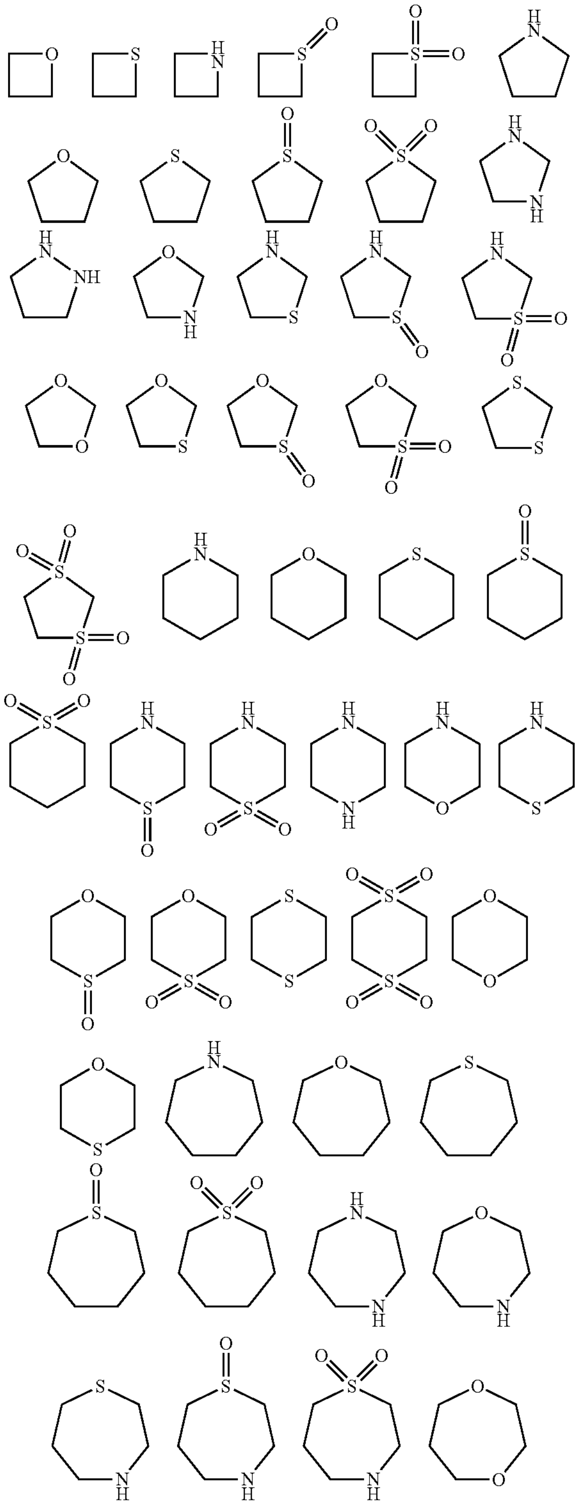

-continued
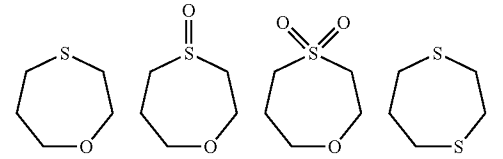
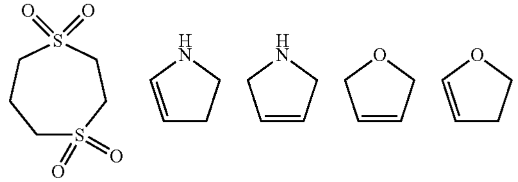
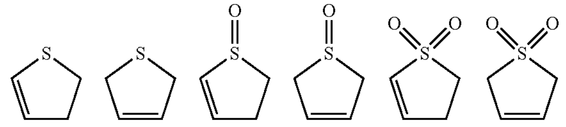
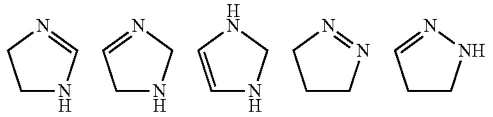
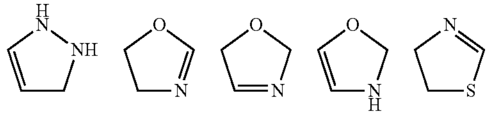
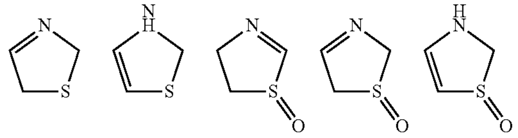
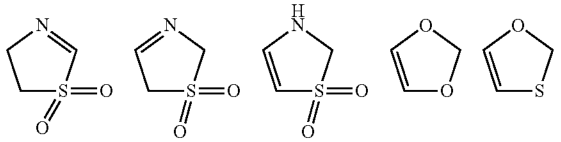
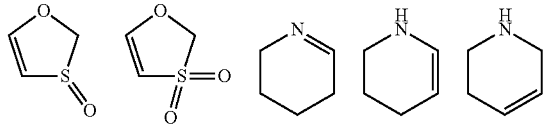
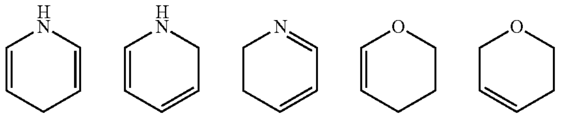
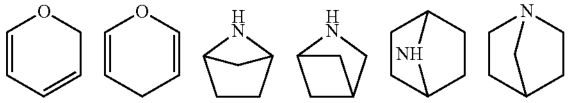
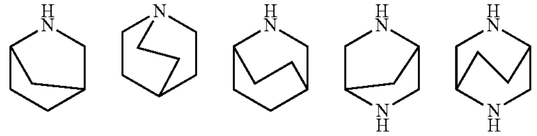
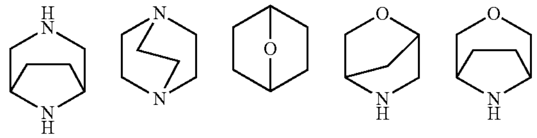
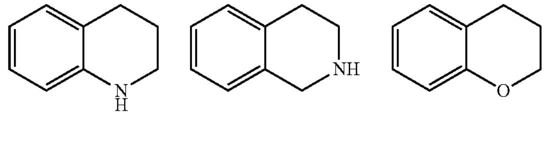
-continued
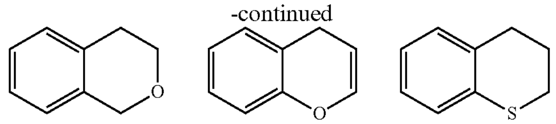
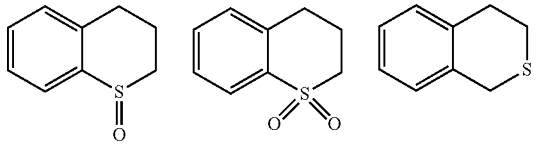
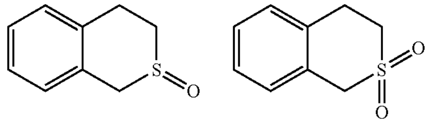
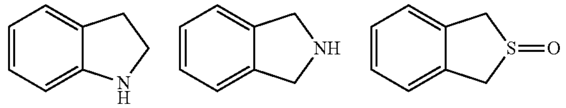
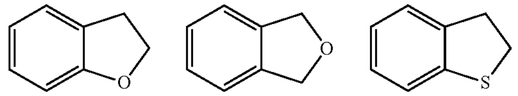
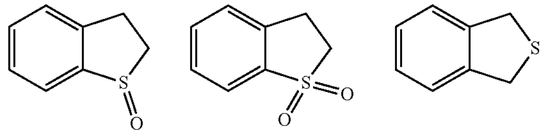
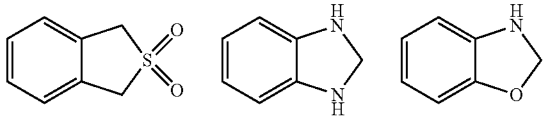
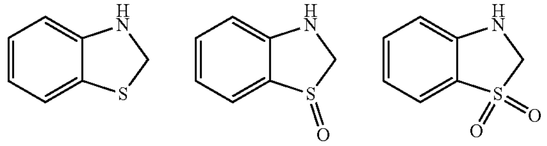
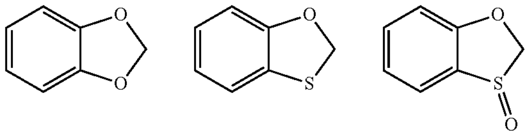
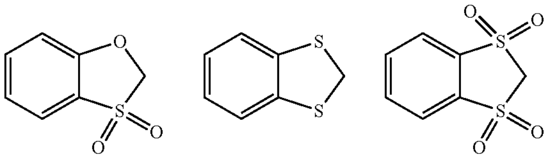
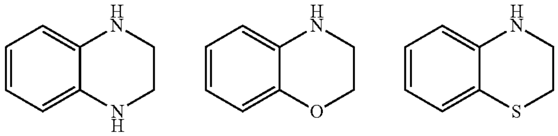
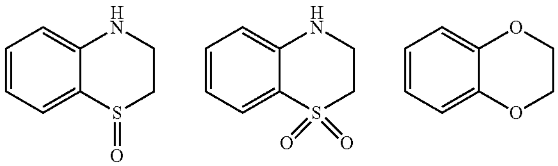
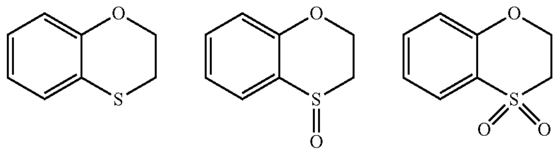

-continued

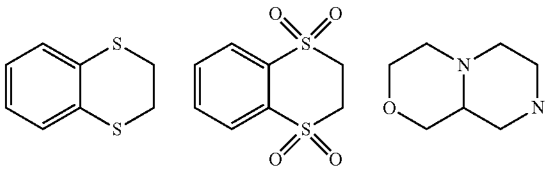

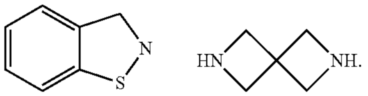

The term “heteroaryl” means a mono- or polycyclic ring system, comprising at least one aromatic ring, containing one or more heteroatoms selected from N, O, S, S(O) or $S(O)_2$, consisting of 5 to 14 ring atoms, wherein at least one of the heteroatoms is part of an aromatic ring. The term “heteroaryl” is intended to include all the possible isomeric forms. Thus, the term “heteroaryl” includes the following exemplary structures (not depicted as radicals as each form is optionally attached through a covalent bond to any atom so long as appropriate valences are maintained):

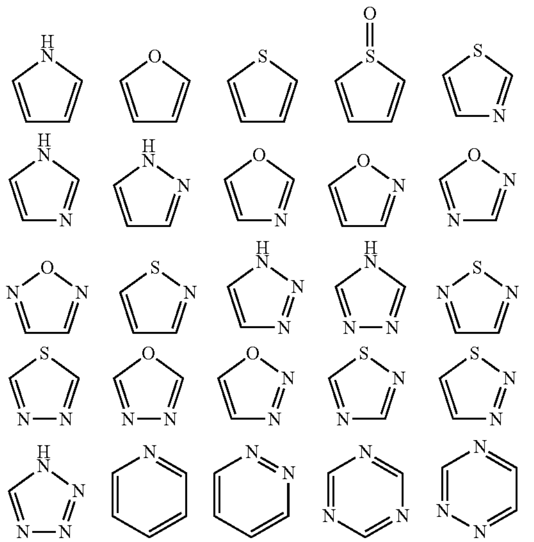

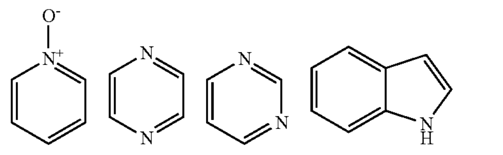

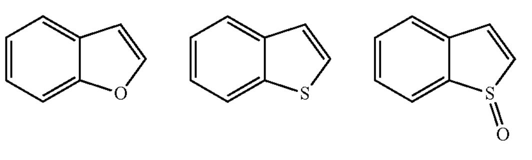

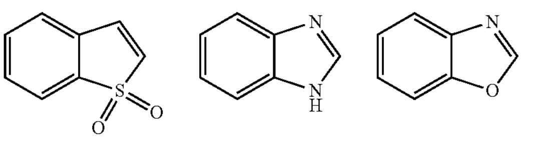

-continued

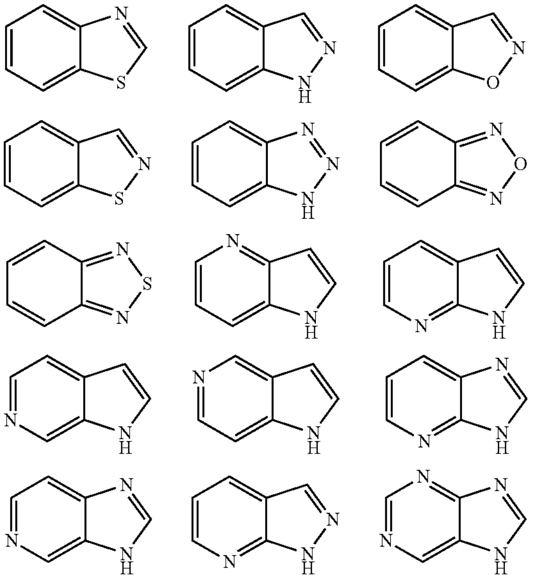

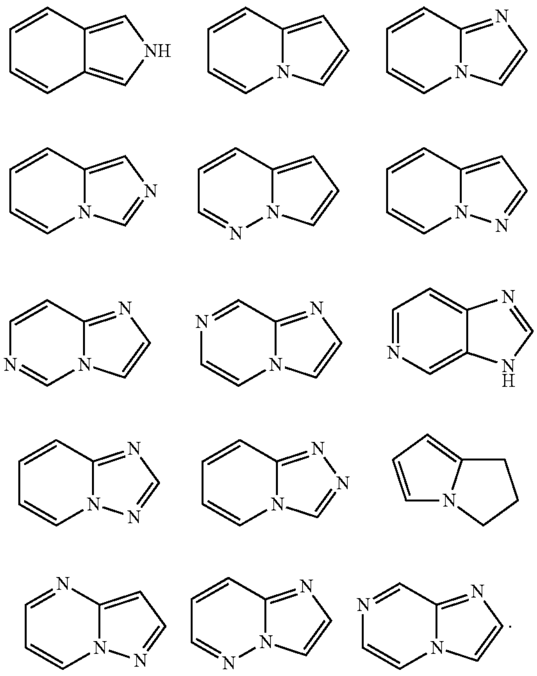

Many of the terms given herein may be used repeatedly in the definition of a formula or group and in each case have one of the meanings given herein, independently of one another.

The term “bicyclic ring systems” means groups consisting of 2 joined cyclic substructures including spirocyclic, fused, and bridged ring systems.

The term “tricyclic ring systems” means groups consisting of 3 joined cyclic substructures including spirocyclic, fused, and bridged ring systems.

As used herein, the term “control” in connection with “parasitic infections and/or infestations in animals” means that the parasitic infection and/or infestation is ameliorated or improved, sustainedly reduced in incidence and/or prevented from worsening as regards the animal.

DETAILED DESCRIPTION

An embodiment of the present invention includes a compound of Formula (I):

(I)

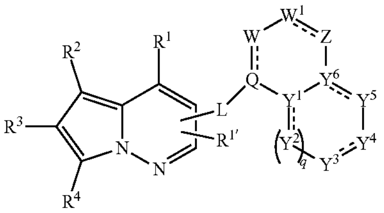

or a salt thereof, wherein:

L is L1, L2, L3, L4, L5, L6, L7, L8, L9, L10, L11, L12, L13, L14, L15, L16 or L17:

(L1)

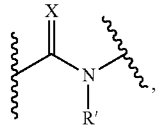

(L2)

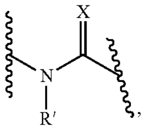

(L3)

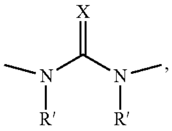

(L4)

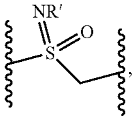

(L5)

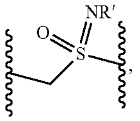

(L6)

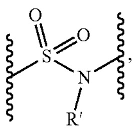

(L7)

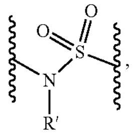

(L8)

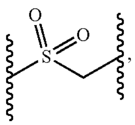

-continued (L9)

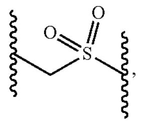

(L10)

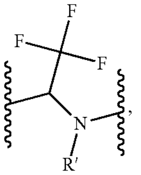

(L11)

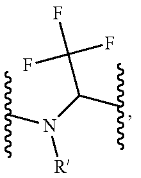

(L12)

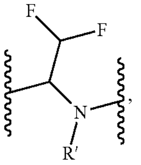

(L13)

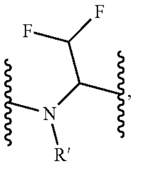

(L14)

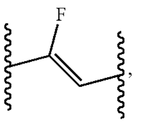

(L15)

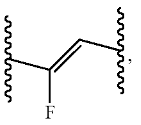

(L16)

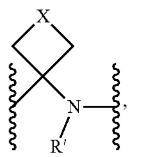

(L17)

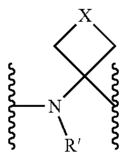

R' is hydrogen, optionally substituted alkyl, optionally substituted haloalkyl, optionally substituted cycloalkyl, optionally substituted aralkyl, optionally substituted aryl, or two R' on the same L group together may form a 2- to 4-membered carbon chain to make a heterocycle;

$R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^1$ is hydrogen, halogen, alkyl or haloalkyl;

$R^2$ is hydrogen, cyano, halogen, hydroxyl, optionally substituted alkyl, optionally substituted alkoxy, optionally substituted alkoxyalkyl, optionally substituted aminoalkyl, optionally substituted alkylaminoalkyl, optionally substituted dialkylaminoalkyl, optionally substituted alkenyl, optionally substituted alkynyl, optionally substituted aryl; optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted;

$R^3$ is hydrogen, cyano, halogen, hydroxyl, optionally substituted alkyl, optionally substituted alkoxy, optionally substituted alkoxyalkyl, optionally substituted aminoalkyl, optionally substituted alkylaminoalkyl, optionally substituted dialkylaminoalkyl, optionally substituted alkenyl, optionally substituted alkynyl, optionally substituted aryl; optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ is hydrogen, optionally substituted alkyl, optionally substituted alkenyl, optionally substituted alkynyl, optionally substituted cycloalkyl, optionally substituted cycloalkenyl, optionally substituted optionally alkylcarbonyl, substituted alkoxycarbonyl, aminocarbonyl, optionally substituted alkylaminocarbonyl, optionally substituted dialkylaminocarbonyl, —$S(O)_p$(optionally substituted alkyl), —$SF_5$, optionally substituted heterocyclyl, optionally substituted aryl, optionally substituted 5- to 10-membered heteroaryl, a spirocyclic heterocyclyl-carbocyclyl group, a spirocyclic heterocyclyl-heterocyclyl group, a spirocyclic carbocyclyl-carbocyclyl group, a spirocyclic carbocyclyl-heterocyclyl group or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, nitro, hydroxyl, optionally substituted alkyl, optionally substituted alkenyl, optionally substituted alkynyl, optionally substituted alkoxy, optionally substituted alkoxyalkyl, optionally substituted aminoalkyl, optionally alkylaminoalkyl, substituted optionally substituted dialkylaminoalkyl, optionally substituted cycloalkyl, optionally substituted cycloalkoxy, optionally substituted alkylcarbonyl, optionally substituted alkoxycarbonyl, optionally substituted aminocarbonyl, optionally substituted alkylaminocarbonyl, optionally substituted di(alkyl)aminocarbonyl, optionally substituted alkylcarbonyloxy, optionally substituted alkylcarbonylamino, optionally substituted aryl, optionally substituted heteroaryl, —$SF_5$, —$SO_p$(optionally substituted alkyl or haloalkyl); or $R^5$ together with $R^{5'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H or optionally substituted alkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^6$ and $R^7$ are independently hydrogen, halogen, optionally substituted alkyl, optionally substituted alkenyl, optionally substituted alkynyl, optionally substituted cycloalkyl, optionally substituted alkoxy, or optionally substituted cycloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^8$ is hydrogen or $C_1$-$C_4$-alkyl;

$R^9$ is hydrogen, halogen, alkyl, haloalkyl, cycloalkyl, alkenyl or alkynyl; Q is C—$R^9$ or N;

X is O, S or N—R';

$Y^1$ and $Y^6$ are each independently N, C, or —$CR^5$—;

$Y^2$, $Y^3$, $Y^4$ and $Y^5$ are each independently N, NR', S, O, —$CR^5$—or $CR^5R^{5'}$;

W is $CR^6$, $CROR^7$, O, $SO_p$, N or N—$R^8$, or W is absent;

$W^1$ is $CR^6$, $CR^6R^7$, O, $SO_p$, N or N—$R^8$;

Z is $CR^7$, $CR^6R^7$, O, $SO_p$, N or N—$R^8$, and wherein at most three of $Y^1$, $Y^2$, $Y^3$, $Y^4$, $Y^5$ and $Y^6$ are heteroatoms;

q is 0 or 1;

p is independently in each occurrence is 0, 1, or 2; and the dashed bonds (----) signifies a single or double bond;

or salt thereof;

wherein "optionally substituted" indicates that the group recited may be optionally substituted with halogen, hydroxyl, oxo, alkyl, haloalkyl, cycloalkyl, cycloalkenyl, carboxyl, acyl, acyloxy, acetyl, alkylcarbonyl, haloalkylcarbonyl, alkoxycarbonyl, haloalkoxycarbonyl, aminocarbonyl, alkylaminocarbonyl, dialkylaminocarbonyl, haloalkylaminocarbonyl, dihaloalkylaminocarbonyl, amino, alkyl- or dialkylamino, amido, arylamino, alkoxy, haloalkoxy, alkylthio, haloalkylthio, aryloxy, nitro, cyano, azido, thiol, thioamido, imino, amidino, guanidino, carbonate, $R^3Si$—or $R^3SiO$— where R is alkyl, haloalkyl or aryl, $SF_5$, sulfate, alkylsulfonyl, haloalkylsulfonyl, alkoxysulfonyl, alkylsulfinyl, haloalkylsulfinyl, sulfamoyl, sulfoximine, sulfinimine, sulfonimidamide, sulfonediimine, phosphonyl, phosphinyl, phosphoryl, phosphine, phosphonamidate, phosphinamidate, phosphinate, phosphine oxide, thioester, anhydride, oxime, hydrazine, carbamate, phosphate, phosphonate, aryl, heteroaryl and heterocyclyl.

In another embodiment, the present invention includes a compound of Formula (I) as described above, or a salt thereof, wherein variables $R^{1\prime}$, $R^2$, $R^3$, $R^4$, L, Q, W, $W^1$, Z, $Y^1$, $Y^2$, $Y^3$, $Y^4$, $Y^5$, $Y^6$ and q have the same definitions as described above for Formula (I); the dashed bonds (----) signify a single or double bond; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4- or 5-membered-heterocyclyl group, which may include one to three additional heteroatoms selected from the group consisting of N, O, Si and S and may be optionally substituted;

wherein "optionally substituted" indicates that the group recited may be optionally substituted with the same groups defined for "optionally substituted" for the broadest embodiment of Formula (I) above.

In another embodiment, the present invention includes a compound of Formula (I) as described above, or a salt thereof, wherein variables $R^{1\prime}$, $R^2$, $R^3$, $R^4$, L, Q, W, $W^1$, Z, $Y^1$, $Y^2$, $Y^3$, $Y^4$, $Y^5$, $Y^6$ and q have the same definitions as described above for Formula (I); the dashed bonds (----) signify a single or double bond; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 6-, 7- or 8-membered-heterocyclyl group, which may include one to three additional heteroatoms selected from the group consisting of N, O, Si and S and may be optionally substituted;

wherein "optionally substituted" indicates that the group recited may be optionally substituted with the same groups defined for "optionally substituted" for the broadest embodiment of Formula (I) above.

In another embodiment, the invention provides a compound of Formula (I), or a salt thereof, wherein:

R' is hydrogen, optionally substituted $C_1$-$C_6$-alkyl, $C_1$-$C_6$-haloalkyl, optionally substituted $C_3$-$C_8$-cycloalkyl, or optionally substituted phenyl;

$R^1$ is hydrogen, cyano, halogen, hydroxyl, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, optionally substituted aryl, optionally substituted aryloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl, —$SF_5$, tri-$C_1$-$C_6$-alkylsilyl, tri-$C_1$-$C_6$-alkylsilyloxy, —$SO_p$(optionally substituted $C_1$-$C_6$-alkyl or $C_1$-$C_6$-haloalkyl), or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^1$ is hydrogen, halogen, $C_1$-$C_3$-alkyl or $C_1$-$C_3$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkenyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SF_5$, —$S(O)_p$($C_1$-$C_6$-alkyl or $C_1$-$C_6$-haloalkyl), optionally substituted 3- to 7-membered heterocyclyl containing from one to three heteroatoms selected from the group consisting of N, O and S; optionally substituted phenyl, optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, nitro, hydroxyl, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted $C_1$-$C_6$-alkylcarbonyl, optionally substituted $C_1$-$C_6$-alkoxycarbonyl, aminocarbonyl, optionally substituted $C_1$-$C_6$-alkylaminocarbonyl, di($C_1$-$C_6$-alkyl)aminocarbonyl, optionally substituted $C_1$-$C_6$-alkylcarbonyloxy, optionally substituted $C_1$-$C_6$-alkylcarbonylamino, optionally substituted phenyl, optionally substituted 5- or 6-membered heteroaryl, —$SF_5$, —$SO_p$(optionally substituted $C_1$-$C_6$-alkyl or $C_1$-$C_6$-haloalkyl); or $R^5$ together with $R^{5'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^9$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl; and L, Q, X, $Y^1$, $Y^2$, $Y^3$, $Y^4$, $Y^5$, $Y^6$, W, $W^1$, Z, $R^6$, $R^7$, $R^8$, q, p and the dashed bonds (- - - -) are as defined above for the compound of Formula (I);

wherein the term "optionally substituted" indicates that the group recited is optionally substituted by one or more halogen (chloro, fluoro, bromo, iodo), $C_1$-$C_6$-alkyl, $C_1$-$C_6$-haloalkyl, 3- to 8-membered cycloalkyl, amino, $C_1$-$C_6$-alkylamino, $C_1$-$C_6$-haloalkylamino, $C_1$-$C_6$-dialkylamino, $C_1$-$C_6$-dihaloalkylamino, $C_1$-$C_6$-alkoxy, $C_1$-$C_6$-haloalkoxy, cyano, nitro, $SF_5$, $C_1$-$C_6$-trialkylsilyl, $C_1$-$C_6$-trialkylsiloxy, acyl, acyloxy, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, phenyl, 5- or 6-membered heteroaryl or 5- or 6-membered heterocyclyl.

In another embodiment, the invention provides a compound of Formula (I), or a salt thereof, wherein:

R' is hydrogen, optionally substituted $C_1$-$C_6$-alkyl, $C_1$-$C_6$-haloalkyl, optionally substituted $C_3$-$C_8$-cycloalkyl, or optionally substituted phenyl;

$R^1$ is hydrogen, cyano, halogen, hydroxyl, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, optionally substituted aryl, optionally substituted aryloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl, —$SF_5$, tri-$C_1$-$C_6$-alkylsilyl, tri-$C_1$-$C_6$-alkylsilyloxy, —$SO_p$(optionally substituted $C_1$-$C_6$-alkyl or $C_1$-$C_6$-haloalkyl), or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4- or 5-membered-heterocyclyl group, which may include one to three additional heteroatoms selected from the group consisting of N, O, Si and S and may be optionally substituted;

$R^{1'}$ is hydrogen, halogen, $C_1$-$C_3$-alkyl or $C_1$-$C_3$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$ (optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkenyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SF_5$, —$S(O)_p$($C_1$-$C_6$-alkyl or $C_1$-$C_6$-haloalkyl), optionally substituted 3- to 7-membered heterocyclyl containing from one to three heteroatoms selected from the group consisting of N, O and S; optionally substituted phenyl, optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, nitro, hydroxyl, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted $C_1$-$C_6$-alkylcarbonyl, optionally substituted $C_1$-$C_6$-alkoxycarbonyl, aminocarbonyl, optionally substituted $C_1$-$C_6$-alkylaminocarbonyl, di($C_1$-$C_6$-alkyl)aminocarbonyl, optionally substituted $C_1$-$C_6$-alkylcarbonyloxy, optionally substituted $C_1$-$C_6$-alkylcarbonylamino, optionally substituted phenyl, optionally substituted 5- or 6-membered heteroaryl, —$SF_5$, —$SO_p$(optionally substituted $C_1$-$C_6$-alkyl or $C_1$-$C_6$-haloalkyl); or $R^5$ together with $R^{5'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^9$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl; and L, Q, X, $Y^1$, $Y^2$, $Y^3$, $Y^4$, $Y^5$, $Y^6$, W, $W^1$, Z, $R^6$, $R^7$, $R^8$, q, p and the dashed bonds (- - - -) are as defined above for the compound of Formula (I);

wherein the term "optionally substituted" indicates that the group recited is optionally substituted by one or more halogen (chloro, fluoro, bromo, iodo), $C_1$-$C_6$-alkyl, $C_1$-$C_6$-haloalkyl, 3- to 8-membered cycloalkyl, amino, $C_1$-$C_6$-alkylamino, $C_1$-$C_6$-haloalkylamino, $C_1$-$C_6$-dialkylamino, $C_1$-$C_6$-dihaloalkylamino, $C_1$-$C_6$-alkoxy, $C_1$-$C_6$-haloalkoxy, cyano, nitro, $C_1$-$C_6$-trialkylsilyl, $C_1$-$C_6$-trialkylsiloxy, $SF_5$, acyl, acyloxy, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, phenyl, 5- or 6-membered heteroaryl or 5- or 6-membered heterocyclyl.

In yet another embodiment, the invention provides a compound of Formula (I), or a salt thereof, wherein:

R' is hydrogen, optionally substituted $C_1$-$C_6$-alkyl, $C_1$-$C_6$-haloalkyl, optionally substituted $C_3$-$C_8$-cycloalkyl, or optionally substituted phenyl;

$R^1$ is hydrogen, cyano, halogen, hydroxyl, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, optionally substituted aryl, optionally substituted aryloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl, —$SF_5$, tri-$C_1$-$C_6$-alkylsilyl, tri-$C_1$-$C_6$-alkylsilyloxy, —$SO_p$(optionally substituted $C_1$-$C_6$-alkyl or $C_1$-$C_6$-haloalkyl), or —$NR^aR^b$, wherein $R^a$ and $R^b$ are independently H or optionally substituted $C_1$-$C_6$-alkyl; or $R^a$ and $R^b$ may form, with the nitrogen to which they are attached, a 6-, 7-, or 8-membered-heterocyclyl group, which may include one to three additional heteroatoms selected from the group consisting of N, O, Si and S and may be optionally substituted;

$R^1$ is hydrogen, halogen, $C_1$-$C_3$-alkyl or $C_1$-$C_3$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$ (optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkenyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SF_5$, —$S(O)_p$($C_1$-$C_6$-alkyl or $C_1$-$C_6$-haloalkyl), optionally substituted 3- to 7-membered heterocyclyl containing from one to three heteroatoms selected from the group consisting of N, O and S; optionally substituted phenyl, optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$- haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, nitro, hydroxyl, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted $C_1$-$C_6$-alkylcarbonyl, optionally substituted $C_1$-$C_6$-alkoxycarbonyl, aminocarbonyl, optionally substituted $C_1$-$C_6$-alkylaminocarbonyl, di($C_1$-$C_6$-alkyl)aminocarbonyl, optionally substituted $C_1$-$C_6$-alkylcarbonyloxy, optionally substituted $C_1$-$C_6$-alkylcarbonylamino, optionally substituted phenyl, optionally substituted 5- or 6-membered heteroaryl, —$SF_5$, —$SO_p$(optionally substituted $C_1$-$C_6$-alkyl or $C_1$-$C_6$-haloalkyl); or $R^5$ together with $R^{5'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^9$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl; and L, Q, X, $Y^1$, $Y^2$, $Y^3$, $Y^4$, $Y^5$, $Y^6$, W, $W^1$, Z, $R^6$, $R^7$, $R^8$, q, p and the dashed bonds (----) are as defined above for the compound of Formula (I);

wherein the term "optionally substituted" indicates that the group recited is optionally substituted by one or more halogen (chloro, fluoro, bromo, iodo), $C_1$-$C_6$-alkyl, $C_1$-$C_6$-haloalkyl, 3- to 8-membered cycloalkyl, amino, $C_1$-$C_6$-alkylamino, $C_1$-$C_6$-haloalkylamino, $C_1$-$C_6$-dialkylamino, $C_1$-$C_6$-dihaloalkylamino, $C_1$-$C_6$-alkoxy, $C_1$-$C_6$-haloalkoxy, cyano, nitro, $C_1$-$C_6$-trialkylsilyl, $C_1$-$C_6$-trialkylsiloxy, $SF_5$, acyl, acyloxy, acetyl, $C_1$-$C_6$-alkoxycarbonyl, $C_1$-$C_6$-haloalkoxycarbonyl, $C_1$—$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, phenyl, 5- or 6-membered heteroaryl or 5- or 6-membered heterocyclyl.

In another embodiment, the present invention includes a compound of Formula (I) as described above, or a salt thereof, wherein variables $R^{1'}$, $R^2$, $R^3$, $R^4$, L, Q, W, $W^1$, Z, $Y^1$, $Y^2$, $Y^3$, $Y^4$, $Y^5$, $Y^6$ and q have the same definitions as described above for Formula (I); the dashed bonds (----) signify a single or double bond; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 6-, 7- or 8-membered-heterocyclyl group, which may include one to three additional heteroatoms selected from the group consisting of N, O, Si and S and may be optionally substituted;

wherein "optionally substituted" indicates that the group recited may be optionally substituted with the same groups defined for "optionally substituted" for the broadest embodiment of Formula (I) above; and with the proviso that the compound below is excluded:

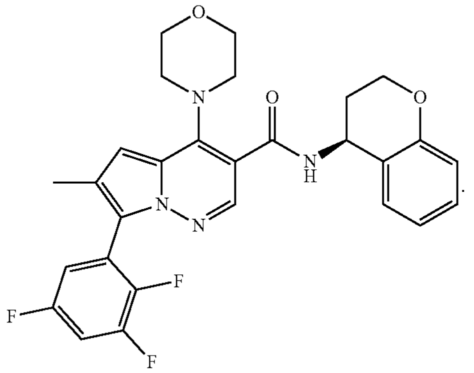 [SMILES: Cc1cc2c(N3CCOCC3)c(C(=O)N[C@H]3CCOc4ccccc43)cnn2c1-c1cc(F)cc(F)c1F]

An embodiment of the present invention includes a compound of Formula (IA):

(IA)

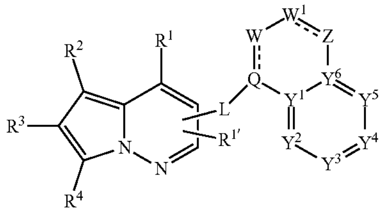

or a salt thereof, wherein:

L is L1, L2, L6, L7, L16 or L17:

(L1)

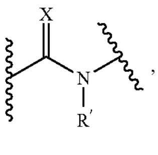
,

-continued (L2)

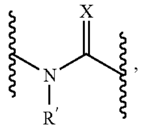

(L6)

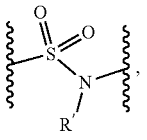

(L7)

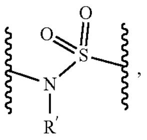

(L16)

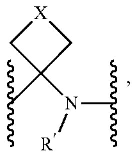

(L17)

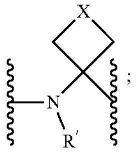

R' is hydrogen, optionally substituted alkyl, optionally substituted haloalkyl or optionally substituted aralkyl;

$R^1$ is hydrogen, halogen, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted cycloalkyl, optionally substituted cycloalkenyl, optionally substituted heterocyclyl or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^1$ is hydrogen, halogen, optionally substituted alkyl or haloalkyl;

$R^2$ is hydrogen, cyano, halogen, hydroxyl, optionally substituted alkyl, optionally substituted alkoxy, optionally substituted alkoxyalkyl, optionally substituted aminoalkyl, optionally substituted alkylaminoalkyl, optionally substituted dialkylaminoalkyl, optionally substituted alkenyl or optionally substituted alkynyl;

$R^3$ is hydrogen, cyano, halogen, hydroxyl, optionally substituted alkyl, optionally substituted alkoxy, optionally substituted alkoxyalkyl, optionally substituted aminoalkyl, optionally substituted alkylaminoalkyl, optionally substituted dialkylaminoalkyl, optionally substituted alkenyl or optionally substituted alkynyl;

$R^4$ is optionally substituted cycloalkyl, optionally substituted cycloalkenyl, optionally substituted heterocyclyl, optionally substituted spirocyclic heterocyclyl-carbocyclyl group, optionally substituted spirocyclic heterocyclyl-heterocyclyl group, optionally substituted spirocyclic carbocyclyl-carbocyclyl group, optionally substituted spirocyclic carbocyclyl-heterocyclyl group, optionally substituted phenyl, optionally substituted 5- or 6-membered heteroaryl, or —$NR^aR^b$, wherein $R^a$ and $R^b$ are independently H, alkyl or haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, optionally substituted alkyl, optionally substituted alkenyl, optionally substituted alkynyl, optionally substituted alkoxy;

$R^9$ is hydrogen, halogen, alkyl or haloalkyl;

$R^6$ and $R^7$ are independently hydrogen, halogen, optionally substituted alkyl, optionally substituted alkenyl, optionally substituted alkynyl, optionally substituted alkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

Q is C—$R^9$ or N;

X is O, S or N—R';

$Y^1$ and $Y^6$ are independently C or N;

$Y^2$, $Y^3$, $Y^4$ and $Y^5$ are each independently N or —$CR^5$;

W is $CR^6$, $CR^6R^7$ or W is absent;

$W^1$ is $CR^6$ or $CR^6R^7$;

Z is $CR^6$, $CR^6R^7$ or O;

wherein at most three of $Y^1$, $Y^2$, $Y^3$, $Y^4$, $Y^5$ and $Y^6$ are N; and the dashed bonds (----) signifies a single or double bond;

a stereoisomer, tautomer, N-oxide, hydrate, solvate, or salt thereof;

wherein "optionally substituted" indicates that the group recited may be optionally substituted with halogen, hydroxyl, alkyl, haloalkyl, cycloalkyl, carboxyl, acyl, acyloxy, acetyl, alkylcarbonyl, haloalkylcarbonyl, alkoxycarbonyl, haloalkoxycarbonyl, aminocarbonyl, alkylaminocarbonyl, dialkylaminocarbonyl, haloalkylaminocarbonyl, dihaloalkylaminocarbonyl, amino, alkyl- or dialkylamino, amido, alkoxy, haloalkoxy, alkylthio, haloalkylthio, cyano, thiol, thioamido, aryl, heteroaryl, aryloxy, arylamino, heterocyclyl, $SF_5$, trialkylsilyl, trialkylsiloxy, alkylsulfonyl, alkoxysulfonyl or alkylsulfinyl.

In another embodiment, the present invention includes a compound of Formula (IA), or a salt thereof, as described above, wherein variables $R^{1'}$, $R^2$, $R^3$, $R^4$, L, Q, W, $W^1$, Z, $Y^1$, $Y^2$, $Y^3$, $Y^4$, $Y^5$ and $Y^6$ have the same definitions as for Formula (IA); the dashed bonds (----) signify a single or double bond; and $R^1$ is hydrogen, halogen, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted cycloalkyl, optionally substituted cycloalkenyl, optionally substituted heterocyclyl or —$NR^aR^b$, wherein $R^a$ and $R^b$ are independently H or optionally substituted alkyl; or $R^a$ and $R^b$ may form, with the nitrogen to which they are attached, a 3-, 4-, 5-membered-heterocyclyl group, which may include one to three additional heteroatoms selected from the group consisting of N, O, Si and S and may be optionally substituted;

wherein "optionally substituted" indicates that the group recited may be optionally substituted with same substituents defined for "optionally substituted" for the broadest embodiment of the compound of Formula (IA) described above.

In still another embodiment, the present invention includes a compound of Formula (IA) as described above, or a salt thereof, wherein variables $R^{1'}$, $R^2$, $R^3$, $R^4$, L, Q, W, $W^1$, Z, $Y^1$, $Y^2$, $Y^3$, $Y^4$, $Y^5$ and $Y^6$ have the same definitions as for Formula (IA); the dashed bonds (----) signify a single or double bond; and $R^1$ is hydrogen, halogen, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted cycloalkyl, optionally substituted cycloalkenyl, optionally substituted heterocyclyl or —$NR^aR^b$, wherein $R^a$ and $R^b$ are independently H or optionally substituted alkyl; or $R^a$ and $R^b$ may form, with the nitrogen to which they are attached, a 6-, 7-, 8-membered-heterocyclyl group, which may include one to three additional heteroatoms selected from the group consisting of N, O, Si and S and may be optionally substituted;

wherein "optionally substituted" indicates that the group recited may be optionally substituted with the same groups as defined "optionally substituted" for the broadest embodiment of Formula (IA) described above.

In another embodiment, the invention provides a compound of Formula (IA), or a salt thereof, wherein:

R' is hydrogen, optionally substituted $C_1$-$C_6$-alkyl, $C_1$-$C_6$-haloalkyl, or optionally substituted benzyl;

$R^1$ is hydrogen, halogen, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$—$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, optionally substituted $C_3$-$C_8$-cycloalkyl, optionally substituted $C_3$-$C_8$-cycloalkenyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^{1'}$ hydrogen, halogen, optionally substituted $C_1$-$C_6$-alkyl or $C_1$-$C_6$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^4$ is optionally substituted $C_3$-$C_8$-cycloalkyl, optionally substituted $C_3$-$C_8$-cycloalkenyl, optionally substituted 3- to 7-membered heterocyclyl containing from one to three heteroatoms selected from the group consisting of N, O and S; optionally substituted phenyl or optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5-to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy;

$R^6$ and $R^7$ are independently hydrogen, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^9$ is hydrogen, halogen, $C_1$-$C_6$-alkyl or $C_1$-$C_6$-haloalkyl; and

L, Q, X, $Y^1$, $Y^2$, $Y^3$, $Y^4$, $Y^5$, $Y^6$, W, $W^1$, Z and the dashed bonds (----) are as defined above for the compound of Formula (IA);

wherein the term "optionally substituted" indicates that the group recited is optionally substituted by one or more halogen (chloro, fluoro, bromo, iodo), hydroxyl, $C_1$-$C_6$-alkyl, $C_1$-$C_6$-haloalkyl, 3-to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, $SF_5$, $C_1$-$C_6$-trialkylsilyl, $C_1$-$C_6$-trialkylsiloxy, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl or $C_1$-$C_6$-haloalkylsulfonyl.

In another embodiment, the invention provides a compound of Formula (IA), or a salt thereof, wherein:

R' is hydrogen, optionally substituted $C_1$-$C_6$-alkyl, $C_1$-$C_6$-haloalkyl, or optionally substituted benzyl;

$R^1$ is hydrogen, halogen, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$- haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$—$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, optionally substituted $C_3$-$C_8$-cycloalkyl, optionally substituted $C_3$-$C_8$-cycloalkenyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5-membered-heterocyclyl group, which may include one to three additional heteroatoms selected from the group consisting of N, O, Si and S and may be optionally substituted;

$R^{1'}$ hydrogen, halogen, optionally substituted $C_1$-$C_6$-alkyl or $C_1$-$C_6$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^4$ is optionally substituted $C_3$-$C_8$-cycloalkyl, optionally substituted $C_3$-$C_8$-cycloalkenyl, optionally substituted 3- to 7-membered heterocyclyl containing from one to three heteroatoms selected from the group consisting of N, O and S; optionally substituted phenyl or optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5-to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy;

$R^6$ and $R^7$ are independently hydrogen, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^9$ is hydrogen, halogen, $C_1$-$C_6$-alkyl or $C_1$-$C_6$-haloalkyl; and

L, Q, X, $Y^1$, $Y^2$, $Y^3$, $Y^4$, $Y^5$, $Y^6$, W, $W^1$, Z and the dashed bonds (- - - -) are as defined above for the compound of Formula (IA);

wherein the term "optionally substituted" indicates that the group recited is optionally substituted by one or more halogen (chloro, fluoro, bromo, iodo), hydroxyl, $C_1$-$C_6$-alkyl, $C_1$-$C_6$-haloalkyl, 3-to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, $SF_5$, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl or $C_1$-$C_6$-haloalkylsulfonyl.

In another embodiment, the invention provides a compound of Formula (IA), or a salt thereof, wherein:

R' is hydrogen, optionally substituted $C_1$-$C_6$-alkyl, $C_1$-$C_6$-haloalkyl, or optionally substituted benzyl;

$R^1$ is hydrogen, halogen, optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$—$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, optionally substituted $C_3$-$C_8$-cycloalkyl, optionally substituted $C_3$-$C_8$-cycloalkenyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 6-, 7-, or 8-membered-heterocyclyl group, which may include one to three additional heteroatoms selected from the group consisting of N, O, Si and S and may be optionally substituted;

$R^{1'}$ hydrogen, halogen, optionally substituted $C_1$-$C_6$-alkyl or $C_1$-$C_6$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^4$ is optionally substituted $C_3$-$C_8$-cycloalkyl, optionally substituted $C_3$-$C_8$-cycloalkenyl, optionally substituted 3- to 7-membered heterocyclyl containing from one to three heteroatoms selected from the group consisting of N, O and S; optionally substituted phenyl or optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5-to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^5$ and $R^{5'}$ are independently in each occurrence, hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy;

$R^6$ and $R^7$ are independently hydrogen, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^9$ is hydrogen, halogen, $C_1$-$C_6$-alkyl or $C_1$-$C_6$-haloalkyl; and

L, Q, X, $Y^1$, $Y^2$, $Y^3$, $Y^4$, $Y^5$, $Y^6$, W, $W^1$, Z and the dashed bonds (----) are as defined above for the compound of Formula (IA);

wherein the term “optionally substituted” indicates that the group recited is optionally substituted by one or more halogen (chloro, fluoro, bromo, iodo), hydroxyl, $C_1$-$C_6$-alkyl, $C_1$-$C_6$-haloalkyl, 3-to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, $SF_5$, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl or $C_1$-$C_6$-haloalkylsulfonyl.

In some embodiments of Formula (IA):

$R^1$ is optionally substituted $C_1$-$C_4$-alkyl, optionally substituted $C_1$-$C_4$-alkoxy, optionally substituted $C_2$-$C_4$-alkenyl, optionally substituted $C_2$-$C_4$-alkynyl, optionally substituted, saturated or partially unsaturated 5-, 6-, or 7-membered heterocycle group, optionally substituted heteroaryl, or —$NR^aR^b$, wherein $R^a$ and $R^b$ are independently optionally substituted alkyl; or $R^a$ and $R^b$ may form, with the nitrogen to which they are attached, a 3-, 4-5-, 6-, 7-, or 8-membered-heterocyclyl group, which may include one to three additional heteroatoms selected from the group consisting of N, O and S and may be optionally substituted;

$R^{1'}$ is hydrogen;

R' is hydrogen or $C_1$-$C_4$-alkyl;

$R^2$ is hydrogen, halogen, optionally substituted $C_1$-$C_4$-alkyl or optionally substituted $C_1$-$C_4$-alkoxy;

$R^3$ is hydrogen, halogen, optionally substituted $C_1$-$C_4$-alkyl or optionally substituted $C_1$-$C_4$-alkoxy;

$R^4$ is phenyl which may be optionally substituted with 1, 2, or 3 substituents; and $R^5$ and $R^{5'}$ are independently hydrogen, halogen, cyano, $C_1$-$C_4$-alkyl or $C_1$-$C_4$haloalkyl, wherein “optionally substituted” indicates that the group recited may be optionally substituted with the same groups as defined “optionally substituted” for the broadest embodiment of Formula (IA) described above.

In some embodiments of Formula (IA):

$R^1$ is optionally substituted $C_1$-$C_4$-alkyl, optionally substituted $C_1$-$C_4$-alkoxy, optionally substituted $C_2$-$C_4$-alkenyl, optionally substituted $C_2$-$C_4$-alkynyl, optionally substituted, saturated or partially unsaturated 5-, 6-, or 7-membered heterocycle group, optionally substituted heteroaryl, or —$NR^aR^b$, wherein $R^a$ and $R^b$ are independently optionally substituted alkyl; or $R^a$ and $R^b$ may form, with the nitrogen to which they are attached, a 3-, 4-5-membered-heterocyclyl group, which may include one to three additional heteroatoms selected from the group consisting of N, O and S and may be optionally substituted;

$R^{1'}$ is hydrogen;

R' is hydrogen or $C_1$-$C_4$-alkyl;

$R^2$ is hydrogen, halogen, optionally substituted $C_1$-$C_4$-alkyl or optionally substituted $C_1$-$C_4$-alkoxy;

$R^3$ is hydrogen, halogen, optionally substituted $C_1$-$C_4$-alkyl or optionally substituted $C_1$-$C_4$-alkoxy;

$R^4$ is phenyl which may be optionally substituted with 1, 2, or 3 substituents; and $R^5$ and $R^{5'}$ are independently hydrogen, halogen, cyano, $C_1$-$C_4$-alkyl or $C_1$-$C_4$haloalkyl, wherein “optionally substituted” indicates that the group recited may be optionally substituted with the same groups as defined “optionally substituted” for the broadest embodiment of Formula (IA) described above.

In another embodiment of Formula (IA):

$R^1$ is optionally substituted $C_1$-$C_4$-alkyl, optionally substituted $C_1$-$C_4$-alkoxy, optionally substituted $C_2$-$C_4$-alkenyl, optionally substituted $C_2$-$C_4$-alkynyl, optionally substituted, saturated or partially unsaturated 5-, 6-, or 7-membered heterocycle group, optionally substituted heteroaryl, or —$NR^aR^b$, wherein $R^a$ and $R^b$ are independently optionally substituted alkyl; or $R^a$ and $R^b$ may form, with the nitrogen to which they are attached, a 6-, 7-, or 8-membered-heterocyclyl group, which may include one to three additional heteroatoms selected from the group consisting of N, O and S and may be optionally substituted;

$R^{1'}$ is hydrogen;

R' is hydrogen or $C_1$-$C_4$-alkyl;

$R^2$ is hydrogen, halogen, optionally substituted $C_1$-$C_4$-alkyl or optionally substituted $C_1$-$C_4$-alkoxy;

$R^3$ is hydrogen, halogen, optionally substituted $C_1$-$C_4$-alkyl or optionally substituted $C_1$-$C_4$-alkoxy;

$R^4$ is phenyl which may be optionally substituted with 1, 2, or 3 substituents; and $R^5$ and $R^{5'}$ are independently hydrogen, halogen, cyano, $C_1$-$C_4$-alkyl or $C_1$-$C_4$haloalkyl, wherein “optionally substituted” indicates that the group recited may be optionally substituted with the same groups as defined “optionally substituted” for the broadest embodiment of Formula (IA) described above.

In still another embodiment, the present invention includes a compound of Formula (IA) as described above, or a salt thereof, wherein variables $R^{1'}$, $R^2$, $R^3$, $R^4$, L, Q, W, $W^1$, Z, $Y^1$, $Y^2$, $Y^3$, $Y^4$, $Y^5$ and $Y^6$ have the same definitions as for Formula (IA); the dashed bonds (----) signify a single or double bond; and $R^1$ is hydrogen, halogen, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted cycloalkyl, optionally substituted cycloalkenyl, optionally substituted heterocyclyl or —$NR^aR^b$, wherein $R^a$ and $R^b$ are independently H or optionally substituted alkyl; or $R^a$ and $R^b$ may form, with the nitrogen to which they are attached, a 6-, 7-, 8-membered-heterocyclyl group, which may include one to three additional heteroatoms selected from the group consisting of N, O, Si and S and may be optionally substituted;

wherein "optionally substituted" indicates that the group recited may be optionally substituted with the same groups as defined "optionally substituted" for the broadest embodiment of Formula (IA) described above; and with the proviso that the compound below is excluded:

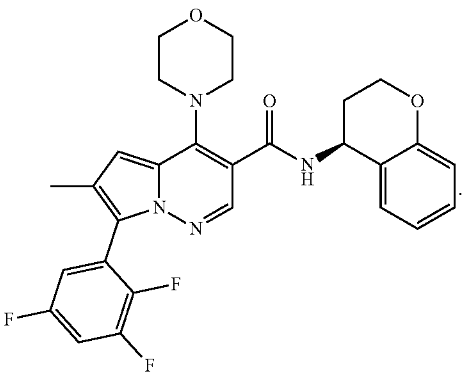 [SMILES: Cc1cc2c(N3CCOCC3)c(C(=O)N[C@H]3CCOc4ccccc43)cnn2c1-c1cc(F)cc(F)c1F]

In one embodiment, L is L1. In another embodiment, L is L2. In another embodiment, L is L3. In another embodiment, L is L4. In another embodiment, L is L5. In another embodiment, L is L6. In another embodiment, L is L7. In another embodiment, L is L8. In another embodiment, L is L9. In another embodiment, L is L10. In another embodiment, L is L11. In another embodiment, L is L12. In another embodiment, L is L13. In another embodiment, L is L14. In another embodiment, Lis L15. In another embodiment, L is L16. In another embodiment, L is L17.

In some embodiments of Formula (I) or Formula (IA), $R^1$ is hydrogen.

In some embodiments, $R^1$ is $C_1$-$C_4$-alkyl, $C_1$-$C_4$-haloalkyl, $C_1$-$C_4$-haloalkyl, amino, $C_1$-$C_4$-alkylamino, or di-($C_1$-$C_4$-alkyl) amino.

In some embodiments, $R^1$ is dimethylamino.

In some embodiments, $R^1$ is $C_1$-$C_4$-alkyl or $C_1$-$C_4$-haloalkyl.

In another embodiment, $R^1$ is halogen.

In another embodiment, $R^1$ is chloro or fluoro.

In another embodiment, $R^1$ is $C_1$-$C_4$-alkyl-$SO_p$—, $C_1$-$C_4$-haloalkyl-$SO_p$—or —$SF_5$.

In other embodiments, $R^1$ is hydroxy-$C_1$-$C_4$-alkyl, $C_1$-$C_4$-alkoxy-$C_1$-$C_4$-alkyl, $C_1$-$C_4$-haloalkoxy-$C_1$-$C_4$-alkyl or $C_1$-$C_4$-haloalkoxy-$C_1$-$C_4$-haloalkyl.

In another embodiment, $R^1$ is hydroxy-$C_1$-$C_3$-alkyl.

In another embodiment, $R^1$ is —$C(CH_3)_2OH$.

In another embodiment, $R^1$ is methyl, ethyl, propyl, butyl, pentyl, isopropyl (i-Pr), tert-butyl (t-butyl), prop-1-en-2-yl, 2-fluoroprop-2-yl, 1,1-difluoroethyl or 2-hydroxyprop-2-yl.

In some embodiments, $R^1$ is methyl, ethyl, n-propyl, isopropyl, n-butyl, sec-butyl, isobutyl or tert-butyl.

In other embodiments, $R^1$ is isopropyl or tert-butyl.

In one embodiment, $R^1$ is tert-butyl.

In another embodiment, $R^1$ is $C_1$-$C_3$-alkoxy or $C_1$-$C_3$-haloalkoxy.

In another embodiment, $R^1$ is $OCH_3$ or $OCH_2CH_3$.

In another embodiment, $R^1$ is $OCF_3$ or $SCF_3$.

In another embodiment, $R^1$ is $CF_3$, —$CH_2CF_3$, —$CHFCF_3$ or —$CF_2CF_3$.

In some embodiments, $R^1$ is $C_2$-$C_4$-alkenyl or $C_2$-$C_4$-haloalkenyl.

In some embodiments, $R^1$ is optionally substituted cyclopentyl or optionally substituted cyclohexyl.

In other embodiments, $R^1$ is optionally substituted cyclopropyl or optionally substituted cyclobutyl.

In another embodiment, $R^1$ is optionally substituted cyclopropyl.

In one embodiment, $R^1$ is cyclopropyl substituted by one or more $C_1$-$C_6$-alkyl or $C_1$-$C_6$-haloalkyl groups.

In another embodiment, $R^1$ is cyclopropyl substituted by one or more methyl or $CF_3$ groups.

In some embodiments, $R^1$ is an optionally substituted, saturated or unsaturated 6-membered heterocyclyl group.

In one embodiment, $R^1$ is —$NR^aR^b$, wherein $R^a$ and $R^b$ are independently hydrogen or $C_1$-$C_6$ alkyl. In another embodiment $R^1$ is —$NR^aR^b$, wherein $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O and S and may be optionally substituted.

In another embodiment $R^1$ is —$NR^aR^b$, wherein $R^a$ and $R^b$ may form, with the nitrogen to which they are attached, a 3- or 4-membered heterocyclyl group, which may be optionally substituted by one or more $C_1$-$C_4$-alkyl, $C_1$-$C_4$-haloalkyl or halogen.

In another embodiment, $R^1$ is —$NR^aR^b$, wherein $R^a$ and $R^b$ may form, with the nitrogen to which they are attached, a 4-membered azetidinyl group, which may be optionally substituted by one or more halogen.

In another embodiment $R^1$ is —$NR^aR^b$, wherein $R^a$ and $R^b$ may form, with the nitrogen to which they are attached, a 4-membered heterocyclyl group, which is substituted by one or two halogen atoms. In another embodiment, $R^1$ is —$NR^aR^b$, wherein $R^a$ and $R^b$ may form, with the nitrogen to which they are attached, a 4-membered heterocyclyl group, which is substituted by one or two fluoro atoms.

In another embodiment, $R^1$ is $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl.

In some embodiments, $R^1$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^1$ is optionally substituted phenyl.

In some embodiments, $R^1$ is aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, pyranyl, dihydropyranyl, tetrahydropyranyl, thiopyranyl, dihydrothiopyranyl, tetrahydrothiopyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^1$ is aziridinyl, azetidinyl, oxetanyl, pyrrolidinyl or pyrrolyl, all of which are optionally substituted by one or more $C_1$-$C_4$-alkyl, $C_1$-$C_4$-haloalkyl or halogen.

In some embodiments, $R^1$ is morpholinyl, piperidinyl or piperazinyl, each of which are optionally substituted by one or more $C_1$-$C_4$-alkyl, $C_1$-$C_4$-haloalkyl or halogen.

In some embodiments, $R^1$ is aziridinyl or azetidinyl, optionally substituted by one or more $C_1$-$C_4$-alkyl, $C_1$-$C_4$-haloalkyl or halogen.

In other embodiments, $R^1$ is aziridinyl or azetidinyl, optionally substituted by one or more $C_1$-$C_3$-alkyl, $C_1$-$C_3$-haloalkyl, chloro or fluoro.

In other embodiments, $R^1$ is aziridinyl or azetidinyl, optionally substituted by one or more methyl, ethyl, trifluoromethyl, $-CH_2CF_3$, $-CF_2CF_3$, chloro or fluoro.

In other embodiments, $R^1$ is aziridinyl or azetidinyl, optionally substituted by one or more methyl or fluoro.

In another embodiment, $R^1$ is azetidinyl substituted by one or more fluoro.

In yet another embodiment, $R^1$ is azetidinyl substituted by two fluoro.

In another embodiment, $R^1$ is azetidinyl substituted by one or more methyl groups.

In another embodiment, $R^1$ is azetidinyl substituted by one or more fluoro and one or more methyl groups.

In yet another embodiment, $R^1$ is an azetidinyl selected from the following groups:

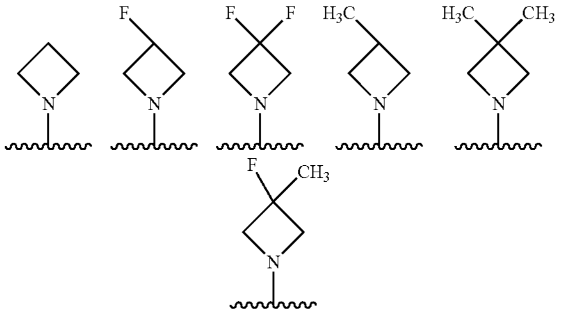

In some embodiments, $R^1$ is pyrrolidinyl, pyrrolyl, imidazolyl, pyrazolyl, triazolyl, tetrazolyl, oxazolyl, thiazolyl, isoxazolyl, isothiazolyl each optionally substituted by one or more $C_1$-$C_4$-alkyl, $C_1$-$C_4$-haloalkyl or halogen.

In other embodiments, $R^1$ is morpholinyl, piperidinyl or piperazinyl, optionally substituted with one or more $C_1$-$C_4$-alkyl, $C_1$-$C_4$-haloalkyl or halogen.

In other embodiments, $R^1$ is morpholinyl, piperidinyl or piperazinyl, optionally substituted with one or more $C_1$-$C_3$-alkyl, $C_1$-$C_3$-haloalkyl, chloro or fluoro.

In other embodiments, $R^1$ is morpholinyl, piperidinyl or piperazinyl, optionally substituted with one or more methyl, ethyl, trifluoromethyl, $-CH_2CF_3$, $-CF_2CF_3$, chloro or fluoro.

In another embodiment, $R^1$ is morpholinyl.

In one embodiment, $R^{1'}$ is hydrogen.

In another embodiment, $R^{1'}$ is $C_1$-$C_3$-alkyl.

In another embodiment, $R^{1'}$ is methyl.

In another embodiment, $R^{1'}$ is $C_1$-$C_3$-haloalkyl.

In another embodiment, $R^{1'}$ is $CF_3$.

In another embodiment, $R^{1'}$ is halogen.

In some embodiments, $R^2$ is hydrogen, $C_1$-$C_4$-alkyl, $C_1$-$C_4$-haloalkyl, amino, $C_1$-$C_4$-alkylamino, or di-($C_1$-$C_4$alkyl) amino.

In some embodiments, $R^2$ is methyl.

In another embodiment, $R^2$ is hydrogen, methyl, ethyl, n-propyl, iso-propyl, n-butyl, sec-butyl, iso-butyl or tert-butyl.

In another embodiment, $R^2$ is hydrogen, $CF_3$, $-CH_2CF_3$, $-CHFCF_3$ or $-CF_2CF_3$.

In one embodiment, $R^2$ is $CF_3$.

In some embodiments, $R^2$ is hydrogen.

In some embodiments, $R^2$ is halogen.

In another embodiment, $R^2$ is fluoro, bromo or chloro.

In another embodiment, $R^2$ is hydrogen, halogen, $C_1$-$C_4$alkyl or $C_1$-$C_4$haloalkyl;

In another embodiment, $R^2$ is hydrogen, chloro, fluoro, bromo, methyl or $CF_3$.

In another embodiment, $R^2$ is hydrogen, $C_1$-$C_4$-alkoxy, $C_1$-$C_4$-haloalkoxy or $S(O)_p$($C_1$-$C_4$-alkyl or $C_1$-$C_4$-haloalkyl) where p is 0, 1 or 2.

In another embodiment, $R^2$ is methoxy, ethoxy, propoxy or butoxy.

In another embodiment, $R^2$ is methylthio, ethylthio, propylthio or butylthio.

In another embodiment, $R^2$ is $-OCF_3$ or $-SCF_3$.

In some embodiments, $R^2$ is $C_2$-$C_4$-alkenyl or $C_2$-$C_4$-haloalkenyl.

In some embodiments, $R^2$ is optionally substituted cyclopentyl or optionally substituted cyclohexyl.

In some embodiments, $R^2$ is an optionally substituted, saturated or unsaturated 6-membered heterocyclyl group.

In some embodiments, $R^2$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^2$ is optionally substituted phenyl.

In other embodiments, $R^2$ is phenyl substituted with 1, 2, or 3 substituents, which are independently halo, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^2$ is a 5- or 6-membered heteroaryl with 1 or 2 substituents, which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In one embodiment, $R^2$ is pyridinyl optionally substituted with halogen, cyano, nitro, $C_1$-$C_3$-alkyl, $C_1$-$C_3$-haloalkyl, $C_1$-$C_3$-alkoxy, $C_1$-$C_3$-haloalkoxy or ($C_1$-$C_3$-alkyl or $C_1$-$C_3$-haloalkyl)$S(O)_p$.

In some embodiments, $R^2$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^2$ is aziridinyl, azetidinyl, oxetanyl, pyrrolidinyl, pyrrolyl, or morpholinyl, all of which are optionally substituted by one or more halogen.

In some embodiments, $R^3$ is hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, $R^3$ is hydrogen, methyl, ethyl, n-propyl, iso-propyl, n-butyl, sec-butyl, iso-butyl or tert-butyl.

In a particular embodiment, $R^3$ is methyl

In another embodiment, $R^3$ is hydrogen, $CF_3$, $—CH_2CF_3$, $—CHFCF_3$ or $—CF_2CF_3$.

In some embodiments, $R^3$ is hydrogen.

In some embodiments, $R^3$ is halogen.

In another embodiment, $R^3$ is fluoro, bromo or chloro.

In a particular embodiment, $R^3$ is chloro.

In another embodiment, $R^3$ is hydrogen, halogen, $C_1$-$C_4$alkyl or $C_1$-$C_4$haloalkyl;

In another embodiment, $R^3$ is hydrogen, chloro, fluoro, bromo, methyl or $CF_3$.

In another embodiment, $R^3$ is hydrogen, $C_1$-$C_4$-alkoxy, $C_1$-$C_4$-haloalkoxy or $S(O)_p$($C_1$-$C_4$-alkyl or $C_1$-$C_4$-haloalkyl) where p is 0, 1 or 2.

In another embodiment, $R^3$ is methoxy, ethoxy, propoxy or butoxy.

In another embodiment, $R^3$ is methylthio, ethylthio, propylthio or butylthio.

In another embodiment, $R^3$ is $—OCF_3$ or $—SCF_3$.

In some embodiments, $R^3$ is $C_1$-$C_4$-alkenyl or $C_1$-$C_4$-haloalkenyl.

In some embodiments, $R^3$ is optionally substituted cyclopentyl or optionally substituted cyclohexyl.

In some embodiments, $R^3$ is an optionally substituted, saturated or unsaturated 6-membered heterocyclyl group.

In some embodiments, $R^3$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^3$ is optionally substituted phenyl.

In other embodiments, $R^3$ is phenyl substituted with 1, 2, or 3 substituents, which are independently halogen, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^3$ is a 5- or 6-membered heteroaryl with 1 or 2 substituents, which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In one embodiment, $R^3$ is pyridinyl optionally substituted with halo, cyano, nitro, $C_1$-$C_3$-alkyl, $C_1$-$C_3$-haloalkyl, $C_1$-$C_3$-alkoxy, $C_1$-$C_3$-haloalkoxy or ($C_1$-$C_3$-alkyl or $C_1$-$C_3$-haloalkyl)$S(O)_p$.

In some embodiments, $R^3$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^3$ is aziridinyl, azetidinyl, oxetanyl, pyrrolidinyl, pyrrolyl, or morpholinyl, all of which are optionally substituted by one or more halogen.

In some embodiments, $R^4$ is 6- to 10-membered aryl optionally substituted with 1, 2, 3, 4 or 5 substituents.

In some embodiments, $R^4$ is $C_1$-$C_4$-alkyl or $C_1$-$C_4$-haloalkyl.

In some embodiments, $R^4$ is methyl, ethyl, n-propyl, n-butyl, iso-propyl, tert-butyl, sec-butyl or iso-butyl.

In other embodiments, $R^4$ is $CF_3$, $—CH_2CF_3$, $—CHFCF_3$ or $—CF_2CF_3$.

In some embodiments, $R^4$ is optionally substituted $C_3$-$C_8$-cycloalkyl. In yet other embodiments, $R^4$ is optionally substituted $C_3$-$C_6$-cycloalkyl. In yet other embodiments, $R^4$ is optionally substituted $C_3$-$C_8$-cycloalkenyl or $C_3$-$C_6$-cycloalkenyl. In some embodiments, $R^4$ is optionally substituted cyclopentyl or cyclohexyl. In other embodiments, $R^4$ is optionally substituted cyclopropyl or cyclobutyl.

In one embodiment, $R^4$ is cyclohexyl optionally substituted by one or more halo, $C_1$-$C_3$-alkyl or $C_1$-$C_3$-haloalkyl. In another embodiment, $R^4$ is cyclohexyl substituted by 1 or 2 fluoro, chloro or $CF_3$.

In some embodiments, $R^4$ is optionally substituted piperidinyl, morpholinyl, tetrahydrofuranyl or dihydrofuranyl. In some embodiments, $R^4$ is piperidinyl, morpholinyl, tetrahydrofuranyl or dihydrofuranyl substituted with one or more halogen, $C_1$-$C_6$-alkyl or $C_1$-$C_6$-haloalkyl. In another embodiment, $R^4$ is piperidinyl, morpholinyl, tetrahydrofuranyl or dihydrofuranyl substituted with one or more methyl, chloro or fluoro.

In some embodiments, $R^4$ is 5- to 10-membered heteroaryl optionally substituted with 1, 2, 3, 4 or 5 substituents. In one embodiment, the 5- to 10-membered heteroaryl is pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl or pyrrolopyrimidyl.

In other embodiments, $R^4$ is an optionally substituted spirocyclic heterocyclyl-carbocyclyl group, an optionally substituted spirocyclic heterocyclyl-heterocyclyl group, an optionally substituted spirocyclic carbocyclyl-carbocyclyl group or an optionally substituted spirocyclic carbocyclyl-heterocyclyl group. In other embodiments, $R^4$ is a 5- to 11-membered optionally substituted spirocyclic heterocyclyl-carbocyclyl group, a 5- to 11-membered optionally substituted spirocyclic heterocyclyl-heterocyclyl group, a 5- to 11-membered optionally substituted spirocyclic carbocyclyl-carbocyclyl group or a 5- to 11-membered optionally substituted spirocyclic carbocyclyl-heterocyclyl group. Non-limiting examples of spirocyclic carbocyclyl-carbocyclyl, spirocyclic carbocyclyl-heterocyclyl and spirocyclic heterocyclyl-heterocyclyl groups are shown below for illustration.

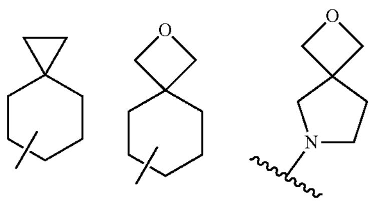

However, it will be apparent to persons skilled in the art that the second ring of the spirocyclic group may be joined at any available carbon of the first ring. It will also be understood that the first ring of the spirocyclic group may be bonded to the molecule at any available atom. Thus, the present invention includes 3-, 4-, 5-, 6- and 7-membered carbocyclic or heterocyclic rings as defined herein joined to a second 3-, 4-, 5-, 6- and 7-membered carbocyclic or heterocyclic ring at any available carbon atom of the first ring.

In some embodiments, $R^4$ is phenyl substituted with 1 to 4 substituents. In another embodiment, $R^4$ is phenyl substituted by 1 to 3 substituents. In yet another embodiment, $R^4$ is phenyl substituted by 1 or 2 substituents. In some embodiments, $R^4$ is phenyl substituted by 1, 2, 3 or 4 substituents which are independently halogen, cyano, nitro, alkylsulfonyl, haloalkylsulfonyl, alkyl, alkenyl, alkynyl, cycloalkyl, cycloalkenyl, phenyl, substituted phenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is para-substituted phenyl.

In some embodiments, $R^4$ is meta-substituted phenyl.

In some embodiments, $R^4$ is ortho-substituted phenyl.

In some embodiments, $R^4$ is halophenyl.

In some embodiments, $R^4$ is haloalkylphenyl.

In some embodiments, $R^4$ is haloalkoxyphenyl.

In some embodiments, $R^4$ is phenyl substituted with 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is 2,3-disubstituted phenyl.

In some embodiments, $R^4$ is 2,4-disubstituted phenyl.

In some embodiments, $R^4$ is 2,5-disubstituted phenyl.

In some embodiments, $R^4$ is a 2,6-disubstituted phenyl.

In some embodiments, $R^4$ is a 3,5-disubstituted phenyl.

In other embodiments, $R^4$ is a 3,4-disubstitued phenyl.

In other embodiments, $R^4$ is a 3,6-disubstituted phenyl.

In some embodiments, $R^4$ is dihalophenyl, e.g., dichlorophenyl; difluorophenyl; or chlorophenyl, fluorophenyl.

In some embodiments, $R^4$ is 2,3-dihalophenyl.

In other embodiments, $R^4$ is 2,3-dichlorophenyl or 2,3-difluorophenyl.

In another embodiment, $R^4$ is 3,5-dichlorophenyl or 2,3-difluorophenyl.

In some embodiments, $R^4$ is chlorophenyl. In another embodiment, $R^4$ is fluorophenyl. In another embodiment, $R^4$ dichlorophenyl. In another embodiment, $R^4$ is difluorophenyl. In yet another embodiment, $R^4$ is 3,5-dichlorophenyl. In another embodiment, $R^4$ is 3,5-difluorophenyl. In another embodiment, $R^4$ is 2,6-dichlorophenyl. In another embodiment, $R^4$ is 2,6-difluorophenyl.

In some embodiments, $R^4$ is phenyl substituted with 3 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is trihalophenyl, e.g., trichlorophenyl; trifluorophenyl; or chloro-, chloro-, fluorophenyl, or fluoro-, fluoro-, chlorophenyl.

In another embodiment, $R^4$ is 2,3,5-trihalophenyl. In another embodiment, $R^4$ is 2,4,6-trihalophenyl. In one embodiment, $R^4$ is 2,5-dichloro-4-fluorophenyl. In one embodiment, $R^4$ is 2,4,6-trifluorophenyl. In another embodiment, $R^4$ is 2,4,6-trichlorophenyl. In one embodiment, $R^4$ is 2,6-dichloro-4-fluorophenyl. In another embodiment, $R^4$ is 2,3,5-trifluorophenyl. In another embodiment, $R^4$ is 2,3,5-trichlorophenyl. In another embodiment, $R^4$ is 2,3-difluoro-5-chlorophenyl. In another embodiment, $R^4$ is 2,3-dichloro-5-fluorophenyl.

In some embodiments, $R^4$ is phenyl substituted with halogen and haloalkyl.

In some embodiments, $R^4$ is phenyl substituted with halogen and haloalkoxy.

In some embodiments, $R^4$ is phenyl substituted with haloalkyl and haloalkoxy.

In some embodiments, $R^4$ is phenyl substituted with 2 halogen and haloalkyl.

In some embodiments, $R^4$ is phenyl substituted with 2 halogen and haloalkoxy.

In some embodiments, $R^4$ is phenyl substituted with 1 haloalkyl, 1 halogen, and 1 haloalkoxy.

In some embodiments, $R^4$ is phenyl substituted with 1 halogen and 2 haloalkyl.

In some embodiments, $R^4$ is 5-membered heteroaryl optionally substituted with 1 or 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is 6-membered heteroaryl optionally substituted with 1 or 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is 2-pyridyl optionally substituted with 1 or 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is 3-pyridyl optionally substituted with 1 or 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is 4-pyridyl optionally substituted with 1 or 2 substituents which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^4$ is 4-pyridyl which is unsubstituted or substituted with 1 or 2 chloro or fluoro. In yet another embodiment $R^4$ is 3-pyridyl which is unsubstituted or substituted with 1 or 2 chloro or fluoro.

In other embodiments, $R^4$ is an optionally substituted 3- to 7-membered heterocycle. In some embodiments, $R^4$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In another embodiment, $R^4$ may be a heterocyclic, bridged bicyclic group, which may be optionally substituted.

In some embodiments, $R^5$ and/or $R^{5'}$ are hydrogen.

In some embodiments, each $R^5$ and/or $R^{5'}$ are independently hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, each $R^5$ and/or $R^{5'}$ are independently hydrogen, methyl, ethyl, n-propyl, iso-propyl, n-butyl, sec-butyl, iso-butyl or tert-butyl.

In another embodiment, $R^5$ and/or $R^{5'}$ are independently hydrogen, $CF_3$, —$CH_2CF_3$, —$CHFCF_3$ or —$CF_2CF_3$.

In some embodiments, $R^5$ and/or $R^{5'}$ are independently hydrogen or halogen.

In another embodiment, $R^5$ and/or $R^{5'}$ are independently hydrogen, fluoro or chloro. In another embodiment, $R^5$ and/or $R^{5'}$ are independently hydrogen, $C_1$-$C_4$-alkoxy, $C_1$-$C_4$-haloalkoxy or $S(O)_p$($C_1$-$C_4$-alkyl or $C_1$-$C_4$-haloalkyl), where p is 0, 1 or 2.

In another embodiment, $R^5$ and/or $R^{5'}$ are independently hydrogen, methoxy, ethoxy, propoxy or butoxy.

In another embodiment, $R^5$ and/or $R^{5'}$ are independently hydrogen, methylthio, ethylthio, propylthio or butylthio.

In another embodiment, $R^5$ and/or $R^{5'}$ are independently hydrogen, —$OCF_3$ or —$SCF_3$. In some embodiments, $R^5$ and/or $R^{5'}$ are independently hydrogen, $C_1$-$C_4$-alkenyl or $C_1$-$C_4$-haloalkenyl.

In some embodiments, $R^5$ and/or $R^{5'}$ are independently hydrogen, $C_1$-$C_4$-alkylcarbonyl or $C_1$-$C_4$-alkoxycarbonyl.

In other embodiments, $R^5$ and/or $R^{5'}$ are independently hydrogen, $C_1$-$C_4$-alkylcarbonylamino.

In some embodiments, $R^5$ and/or $R^{5'}$ are independently hydrogen, optionally substituted cyclopentyl or optionally substituted cyclohexyl.

In some embodiments, $R^5$ and/or $R^{5'}$ are independently hydrogen, optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^5$ and/or $R^{5'}$ are independently hydrogen, optionally substituted phenyl.

In other embodiments, $R^5$ and/or $R^{5'}$ are independently hydrogen, phenyl substituted with 1, 2, or 3 substituents, which are independently halogen, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In other embodiments, $R^5$ and/or $R^{5'}$ are independently hydrogen, a 5- or 6-membered heteroaryl with 1 or 2 substituents, which are independently halogen, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^5$ and/or $R^{5'}$ are independently hydrogen, optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^5$ and $R^{5'}$ are independently hydrogen, aziridinyl, azetidinyl, oxetanyl, pyrrolidinyl, pyrrolyl, or morpholinyl, all of which are optionally substituted by one or more halogen.

In some embodiments, $R^6$ and $R^7$ are independently in each occurrence hydrogen, halogen, $C_1$-$C_4$-alkyl, $C_1$-$C_4$-haloalkyl. In another embodiment, $R^6$ and $R^7$ are independently hydrogen, halogen or $C_1$-$C_4$-alkyl. In another embodiment, $R^6$ and $R^7$ are each hydrogen. In one embodiment, $R^6$ and $R^7$ together with the carbon to which they are attached for a carbonyl group (C═O). In another embodiment, $R^6$ and $R^7$ together with the carbon to which they are attached for a thiocarbonyl group (C═S). In yet another embodiment, $R^6$ and $R^7$ together with the carbon to which they are attached for an imino group (C═NR').

In one embodiment, $R^9$ is H. In another embodiment, $R^9$ is $C_1$-$C_3$-alkyl or $C_1$-$C_3$-haloalkyl.

In some embodiments, Q is N.

In other embodiments, Q is C—$R^9$.

In some embodiments, X is O.

In some embodiments, X is S.

In some embodiments, X is NR'.

In some embodiments, W is $CH_2$.

In another embodiment, W is CH, C—$C_1$-$C_3$-alkyl or C—$C_1$-$C_3$-haloalkyl. In other embodiments, W is $CH_2$, $C(C_1$-$C_3$-alkyl$)_2$ or $C(C_1$-$C_3$-haloalkyl$)_2$.

In other embodiments, W is $CH_2$, $C(CH_3)_2$, $C(C_2H_5)_2$ or $C(CF_3)_2$.

In some embodiments, W is absent.

In some embodiments, $W^1$ is $CH_2$.

In another embodiment, $W^1$ is CH, C—$C_1$-$C_3$-alkyl or C—$C_1$-$C_3$-haloalkyl.

In other embodiments, $W^1$ is $CH_2$, $C(C_1$-$C_3$-alkyl$)_2$ or $C(C_1$-$C_3$-haloalkyl$)_2$.

In other embodiments, $W^1$ is $CH_2$, $C(CH_3)_2$, $C(C_2H_5)_2$ or $C(CF_3)_2$.

In some embodiments, Z is $CH_2$.

In another embodiment, Z is CH, C—$C_1$-$C_3$-alkyl or C—$C_1$-$C_3$-haloalkyl.

In other embodiments, Z is $C(C_1$-$C_3$-alkyl$)_2$ or $C(C_1$-$C_3$-haloalkyl$)_2$.

In some embodiments, Z is O.

In some embodiments, the compound of Formula (I), or a salt thereof, is the compound of Formula (I-1):

(I-1)

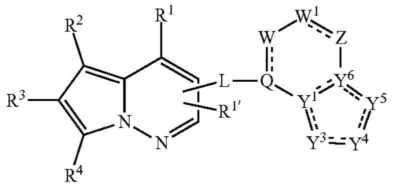

wherein variables L, $R^1$, $R^{1'}$, $R^2$, $R^3$, $R^4$, $Y^1$, $Y^3$, $Y^4$, $Y^5$, $Y^6$, Q, W, $W^1$ and Z are as defined for any of the embodiments of Formula (I) described above; and the dashed bonds (----) signify a single or double bond.

In another embodiment, a compound of Formula (I-1) is provided wherein variables L, $R^1$, $R^{1'}$, $R^2$, $R^3$, $R^4$, $Y^1$, $Y^3$, $Y^4$, $Y^5$, $Y^6$, Q, W, $W^1$ and Z are as defined for any of the embodiments of Formula (IA) described above; and the dashed bonds (----) signify a single or double bond. In one embodiment of Formula (I-1), Z is O. In one embodiment of Formula (I-1), W is $CH_2$ and Z is O. In one embodiment, W is absent. In another embodiment, W is absent and Z is $CH_2$. In one embodiment, Q is N. In another embodiment, Q is C—$R^9$. In another embodiment of Formula (I-1), Q is CH. In another embodiment of Formula (I-1), W is $CH_2$, $W^1$ is $CH_2$ and Z is $CH_2$. In another embodiment of Formula (I-1), W and $W^1$ are independently $CR^6R^7$ wherein $R^6$ and $R^7$ are H, $C_1$-$C_3$-alkyl or $C_1$-$C_3$-haloalkyl and Z is O. In another embodiment, W and $W^1$ are each $CH_2$ and Z is O.

In one embodiment of Formula (I-1), $Y^3$ is S. In another embodiment of Formula (I-1), $Y^5$ is S. In another embodiment, $Y^3$ is N. In another embodiment $Y^5$ is N. In another embodiment of Formula (I-1), $Y^5$ is N and $Y^3$ is S. In yet another embodiment of Formula (I-1), $Y^5$ is S and $Y^3$ is N. In another embodiment of Formula (I-1), $Y^6$ and $Y^3$ are each N. In another embodiment of Formula (I-1), $Y^6$ is N and $Y^4$ is N. In another embodiment, $Y^1$ is N and $Y^5$ is N. In another embodiment, $Y^3$ is N and $Y^5$ is N. In another embodiment, $Y^3$ is N and $Y^4$ is N. In another embodiment, $Y^3$ is NR' and $Y^4$ is N. In another embodiment, $Y^3$ is NR' where R' is hydrogen or $C_1$-$C_3$-alkyl and $Y^4$ is N.

In some embodiments, the compound of Formula (I), or a salt thereof, is the compound of formula (I-2):

(I-2)

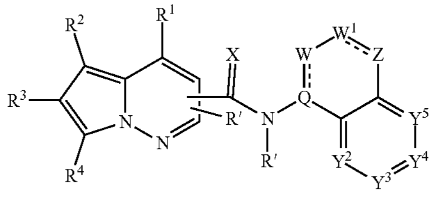

wherein variables $R^1$, $R^{1\prime}$, $R^2$, $R^3$, $R^4$, R', $Y^2$, $Y^3$, $Y^4$, $Y^5$, X, Q, W, $W^1$ and Z are as defined for any of the embodiments of Formula (I) described above; and the dashed bonds (----) signify a single or double bond.

In another embodiment, a compound of Formula (I-2) is provided wherein variables $R^1$, $R^{1\prime}$, $R^2$, $R^3$, $R^4$, R', $Y^2$, $Y^3$, $Y^4$, $Y^5$, X, Q, W, $W^1$ and Z are as defined for any of the embodiments of Formula (IA) described above.

In one embodiment of Formula (I-2), Q is C—$R^9$. In another embodiment of Formula (I-2), Q is CH. In another embodiment of Formula (I-2), Q is N.

In one embodiment of Formula (I-2), Z is O. In one embodiment of Formula (I-2), W is $CH_2$ and Z is O. In one embodiment, W is absent. In another embodiment, W is absent and Z is $CH_2$. In another embodiment, W is absent, Z is $CH_2$ and one of $Y^2$, $Y^3$, $Y^4$ and $Y^5$ is N. In another embodiment, W is absent, Z is $CH_2$ and two of $Y^2$, $Y^3$, $Y^4$ and $Y^5$ are N. In another embodiment, W is absent, Z is $CH_2$ and $Y^2$ is N. In another embodiment, W is absent, Z is $CH_2$ and $Y^4$ is N. In another embodiment, W is absent, Z is $CH_2$ and $Y^5$ is N. In another embodiment, W is absent and Z is O.

In another embodiment of Formula (I-2), W is $CH_2$, $W^1$ is $CH_2$ and Z is $CH_2$. In another embodiment of Formula (I-2), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl, and Z is O. In another embodiment, W and $W^1$ are each $CH_2$ and Z is O.

In one embodiment of Formula (I-2), each of $Y^2$, $Y^3$, $Y^4$ and $Y^5$ are independently $CR^5$. In one embodiment, each of $Y^2$, $Y^3$, $Y^4$ and $Y^5$ are independently CH.

In another embodiment, Z is O and W is $CR^6R^7$, wherein $R^6$ and $R^7$ together with the carbon atom to which they are attached form C═O.

In another embodiment of Formula (I-2), $W^1$ is $CR^6R^7$, wherein $R^6$ and $R^7$ together form a 2 to 5-membered chain, optionally containing one or two N, O, Si or S atoms, to form a carbocyclic or heterocyclic ring. In another embodiment, $W^1$ is $CR^6R^7$, wherein $R^6$ and $R^7$ together form a 3, 4 or 5-membered chain to form a cyclobutyl, cyclopentyl or cyclohexyl ring.

In other embodiments, the compound of Formula (I), or a salt thereof, is the compound of Formula (I-3) below:

(I-3)

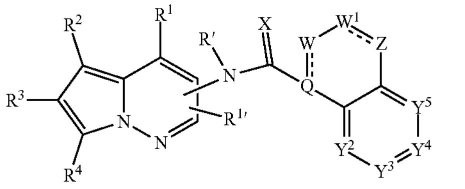

wherein variables $R^1$, $R^{1\prime}$, $R^2$, $R^3$, $R^4$, R', $Y^2$, $Y^3$, $Y^4$, $Y^5$, X, Q, W, $W^1$ and Z are as defined for any of the embodiments of Formula (I) described above; and the dashed bonds (----) signify a single or double bond.

In another embodiment, a compound of Formula (1-3) is provided wherein variables $R^1$, $R^1$, $R^2$, $R^3$, $R^4$, R', $Y^2$, $Y^3$, $Y^4$, $Y^5$, X, Q, W, $W^1$ and Z are as defined for any of the embodiments of Formula (IA) described above.

In one embodiment of Formula (I-3), Q is C—$R^9$. In another embodiment of Formula (I-3), Q is CH. In another embodiment of Formula (I-3), Q is N.

In one embodiment of Formula (I-3), Z is O. In one embodiment of Formula (I-3), W is $CH_2$ and Z is O. In one embodiment, W is absent. In another embodiment, W is absent and Z is $CH_2$. In another embodiment, W is absent, Z is $CH_2$ and one of $Y^2$, $Y^3$, $Y^4$ and $Y^5$ is N. In another embodiment, W is absent, Z is $CH_2$ and two of $Y^2$, $Y^3$, $Y^4$ and $Y^5$ are N. In another embodiment, W is absent, Z is $CH_2$ and $Y^2$ is N. In another embodiment, W is absent, Z is $CH_2$ and $Y^4$ is N. In another embodiment, W is absent, Z is $CH_2$ and $Y^5$ is N. In another embodiment, W is absent and Z is O.

In another embodiment of Formula (1-3), W is $CH_2$, $W^1$ is $CH_2$ and Z is $CH_2$. In another embodiment of Formula (I-3), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl and Z is O. In another embodiment, W and $W^1$ are each $CH_2$ and Z is O.

In one embodiment of Formula (I-3), each of $Y^2$, $Y^3$, $Y^4$ and $Y^5$ are independently $CR^5$. In one embodiment, each of $Y^2$, $Y^3$, $Y^4$ and $Y^5$ are independently CH.

In another embodiment, Z is O and W is $CR^6R^7$, wherein $R^6$ and $R^7$ together with the carbon atom to which they are attached form C═O.

In another embodiment of Formula (I-3), $W^1$ is $CR^6R^7$, wherein $R^6$ and $R^7$ together form a 2 to 5-membered chain, optionally containing one or two N, O, Si or S atoms, to form a carbocyclic or heterocyclic ring. In another embodiment, $W^1$ is $CR^6R^7$, wherein $R^6$ and $R^7$ together form a 3, 4 or 5-membered chain to form a cyclobutyl, cyclopentyl or cyclohexyl ring.

In some embodiments, the compound of formula (I), or a salt thereof, is the compound of Formula (Ia):

(Ia)

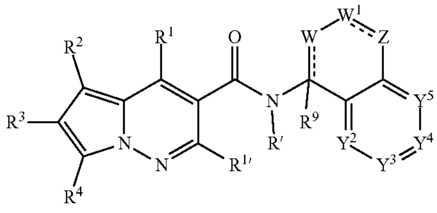

wherein variables $R^1$, $R^{1'}$, $R^2$, $R^3$, $R^4$, R', $R^9$, $W^1$, Z, $Y^2$, $Y^3$, $Y^4$ and $Y^5$ are as defined for any of the embodiments of Formula (I) described above; W is absent, or is —$CR^6R^7$—, —$NR^8$—, —O—or —$S(O)_p$—; and the dashed bonds (----) signify a single or double bond.

In another embodiment, a compound of Formula (Ia) is provided wherein variables $R^1$, $R^{1'}$, $R^2$, $R^3$, $R^4$, R', $R^9$, $W^1$, Z, $Y^2$, $Y^3$, $Y^4$ and $Y^5$ are as defined for any of the embodiments of Formula (IA) described above; W is absent, or is —$CR^6R^7$—; and the dashed bonds (----) signify a single or double bond.

In one embodiment of Formula (Ia), $R^9$ is CH. In another embodiment of Formula (Ia), R' is H. In another embodiment, W and $W^1$ are $CH_2$. In another embodiment, $R^{1'}$ is H. In one embodiment of Formula (Ia), Z is O. In one embodiment of Formula (Ia), W is $CH_2$ and Z is O. In one embodiment, W is absent. In another embodiment, W is absent and Z is $CH_2$. In another embodiment, W is absent, Z is $CH_2$ and one of $Y^2$, $Y^3$, $Y^4$ and $Y^5$ is N. In another embodiment, W is absent, Z is $CH_2$ and two of $Y^2$, $Y^3$, $Y^4$ and $Y^5$ are N. In another embodiment, W is absent, Z is $CH_2$ and $Y^2$ is N. In another embodiment, W is absent, Z is $CH_2$ and $Y^4$ is N. In another embodiment, W is absent, Z is $CH_2$ and $Y^5$ is N. In another embodiment, W is absent and Z is O.

In another embodiment of Formula (Ia), W is $CH_2$, $W^1$ is $CH_2$ and Z is $CH_2$. In another embodiment of Formula (Ia), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl and Z is O. In another embodiment, W and $W^1$ are each $CH_2$ and Z is O.

In one embodiment of Formula (Ia), each of $Y^2$, $Y^3$, $Y^4$ and $Y^5$ are independently $CR^5$. In one embodiment, each of $Y^2$, $Y^3$, $Y^4$ and $Y^5$ are independently CH.

In another embodiment, Z is O and W is $CR^6R^7$, wherein $R^6$ and $R^7$ together with the carbon atom to which they are attached form C═O.

In another embodiment of Formula (Ia), $W^1$ is $CR^6R^7$, wherein $R^6$ and $R^7$ together form a 2 to 5-membered chain, optionally containing one or two N, O, Si or S atoms, to form a carbocyclic or heterocyclic ring. In another embodiment, $W^1$ is $CR^6R^7$, wherein $R^6$ and $R^7$ together form a 3, 4 or 5-membered chain to form a cyclobutyl, cyclopentyl or cyclohexyl ring.

In some embodiments, the compound of formula (I), or a salt thereof, is the compound of Formula (Ib):

(Ib)

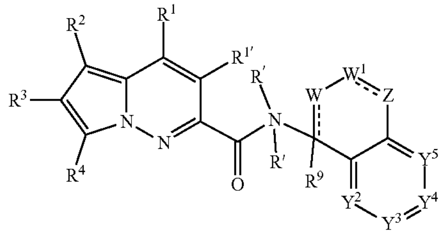

wherein variables $R^1$, $R^{1'}$, $R^2$, $R^3$, $R^4$, R', $R^9$, $Y^2$, $Y^3$, $Y^4$, $Y^5$, $W^1$ and Z are as defined for any of the embodiments of Formula (I) described above; W is absent, or is —$CR^6R^7$—, —$NR^8$—, —O—or —$S(O)_p$—; and the dashed bonds (----) signify a single or double bond.

In another embodiment, a compound of Formula (Ib) is provided wherein variables $R^1$, $R^{1'}$, $R^2$, $R^3$, $R^4$, R', $R^9$, $W^1$, Z, $Y^2$, $Y^3$, $Y^4$ and $Y^5$ are as defined for any of the embodiments of Formula (IA) described above; W is absent, or is —$CR^6R^7$—; and the dashed bonds (----) signify a single or double bond.

In one embodiment of Formula (Ib), $R^9$ is CH. In another embodiment of Formula (Ib), R' is H. In another embodiment W and $W^1$ are each $CH_2$. In another embodiment, $R^{1'}$ is H.

In one embodiment of Formula (Ib), Z is O. In one embodiment of Formula (Ib), W is $CH_2$ and Z is O. In one embodiment, W is absent. In another embodiment, W is absent and Z is $CH_2$. In another embodiment, W is absent, Z is $CH_2$ and one of $Y^2$, $Y^3$, $Y^4$ and $Y^5$ is N. In another embodiment, W is absent, Z is $CH_2$ and two of $Y^2$, $Y^3$, $Y^4$ and $Y^5$ are N. In another embodiment, W is absent, Z is $CH_2$ and $Y^2$ is N. In another embodiment, W is absent, Z is $CH_2$ and $Y^4$ is N. In another embodiment, W is absent, Z is $CH_2$ and $Y^5$ is N. In another embodiment, W is absent and Z is O.

In another embodiment of Formula (Ib), W is $CH_2$, $W^1$ is $CH_2$ and Z is $CH_2$. In another embodiment of Formula (Ib), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl and Z is O. In another embodiment, W and $W^1$ are each $CH_2$ and Z is O.

In one embodiment of Formula (Ib), each of $Y^2$, $Y^3$, $Y^4$ and $Y^5$ are independently $CR^5$. In one embodiment, each of $Y^2$, $Y^3$, $Y^4$ and $Y^5$ are independently CH.

In another embodiment, Z is O and W is $CR^6R^7$, wherein $R^6$ and $R^7$ together with the carbon atom to which they are attached form C═O.

In another embodiment of Formula (Ib), $W^1$ is $CR^6R^7$, wherein $R^6$ and $R^7$ together form a 2 to 5-membered chain, optionally containing one or two N, O, Si or S atoms, to form a carbocyclic or heterocyclic ring. In another embodiment, $W^1$ is $CR^6R^7$, wherein $R^6$ and $R^7$ together form a 3, 4 or 5-membered chain to form a cyclobutyl, cyclopentyl or cyclohexyl ring.

In some embodiments, the compound of formula (I), or a salt thereof, is the compound of Formula (Ic):

(Ic)

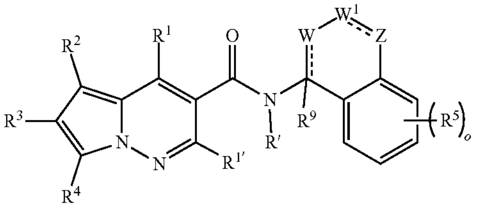

wherein variables $R^1$, $R^{1'}$, $R^2$, $R^3$, $R^4$, R', $R^9$, $R^5$, $W^1$ and Z are as defined for any of the embodiments of Formula (I) described above; W is absent, or is —$CR^6R^7$—, —$NR^8$, —O—or —$S(O)_p$—; 0 is 0, 1, 2, 3 or 4; and the dashed bonds ( ---- ) signify a single or double bond.

In another embodiment, a compound of Formula (Ic) is provided wherein variables $R^1$, $R^{1'}$, $R^2$, $R^3$, $R^4$, R', $R^9$, $R^5$, $W^1$ and Z are as defined for any of the embodiments of Formula (IA) described above; W is absent, or is —$CR^6R^7$—; o is 0, 1, 2, 3 or 4; and the dashed bonds ( ---- ) signify a single or double bond.

In one embodiment of Formula (Ic), $R^9$ is CH. In another embodiment of Formula (Ic), R' is H. In another embodiment, W and $W^1$ are each $CH_2$. In another embodiment, $R^{1'}$ is H.

In one embodiment of Formula (Ic), Z is O. In one embodiment of Formula (Ic), W is $CH_2$ and Z is O. In one embodiment, W is absent. In another embodiment, W is absent and Z is $CH_2$. In another embodiment, W is absent and Z is O.

In another embodiment of Formula (Ic), W is $CH_2$, $W^1$ is $CH_2$ and Z is $CH_2$. In another embodiment of Formula (Ic), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl and Z is O. In another embodiment, W and $W^1$ are each $CH_2$ and Z is O.

In one embodiment of Formula (Ic), o is 1. In another embodiment, o is 2. In still another embodiment, o is 3. In one embodiment, $R^5$ is halogen. In another embodiment, $R^5$ is chloro or fluoro. In another embodiment, o is 1 or 2 and $R^5$ is chloro or fluoro.

In other embodiments, the compound of Formula (I), or a salt thereof, is the compound of formula (Id):

(Id)

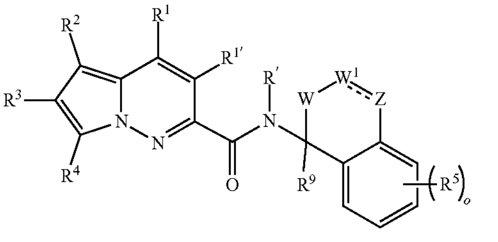

wherein variables $R^1$, $R^{1'}$, $R^2$, $R^3$, $R^4$, R', $R^9$, $R^5$, $W^1$ and Z are as defined for any of the embodiments of Formula (I) described above; W is absent, or is —$CR^6R^7$—, —$NR^8$—, —O—or —$S(O)_p$—; 0 is 0, 1, 2, 3 or 4; and the dashed bonds ( ---- ) signify a single or double bond.

In another embodiment, a compound of Formula (Id) is provided wherein variables $R^1$, $R^{1'}$, $R^2$, $R^3$, $R^4$, R', $R^9$, $R^5$, $W^1$ and Z are as defined for any of the embodiments of Formula (IA) described above; W is absent, or is —$CR^6R^7$—; o is 0, 1, 2, 3 or 4; and the dashed bonds ( ---- ) signify a single or double bond.

In one embodiment of Formula (Id), $R^9$ is CH. In another embodiment of Formula (Id), R' is H. In another embodiment, W and $W^1$ are each $CH_2$. In another embodiment, $R^{1'}$ is H.

In one embodiment of Formula (Id), Z is O. In one embodiment of Formula (Id), W is $CH_2$ and Z is O. In one embodiment, W is absent. In another embodiment, W is absent and Z is $CH_2$. In another embodiment, W is absent and Z is O.

In another embodiment of Formula (Id), W is $CH_2$, $W^1$ is $CH_2$ and Z is $CH_2$. In another embodiment of Formula (Id), W and $W^1$ are independently $CR^6R^7$ wherein $R^6$ and $R^7$ are H, $C_1$-$C_3$-alkyl or $C_1$-$C_3$-haloalkyl and Z is O. In an embodiment, W and $W^1$ are independently $CR^6R^7$ wherein $R^6$ and $R^7$ are H or methyl and Z is O. In another embodiment, W and $W^1$ are each $CH_2$ and Z is O.

In one embodiment of Formula (Id), o is 1. In another embodiment, o is 2. In still another embodiment, o is 3. In one embodiment, $R^5$ is halogen. In another embodiment, $R^5$ is chloro or fluoro. In another embodiment, o is 1 or 2 and $R^5$ is chloro or fluoro.

In another embodiment, the compound of formula (I), or a salt thereof, is the compound of formula (Ie):

(Ie)

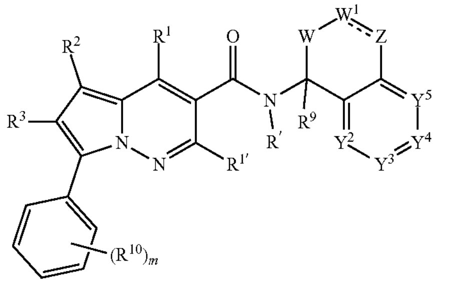

wherein variables $R^1$, $R^{1'}$, $R^2$, $R^3$, R', $R^9$, $Y^2$, $Y^3$, $Y^4$, $Y^5$, $W^1$ and Z are as defined for Formula (I); W is absent, or is —$CR^6R^7$—, —$NR^8$—, —O—or —$S(O)_p$—; m is 0, 1, 2, 3, 4 or 5; and each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$—$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), where p is 0, 1 or 2, $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted, wherein "optionally substituted" indicates that the group recited may be optionally substituted with the same groups defined for "optionally substituted" for the broadest embodiment of Formula (I) above.

In another embodiment, the present invention includes a compound of Formula (Ie) as described above, or a salt thereof, wherein variables $R^{1\prime}$, $R^2$, $R^3$, R', $R^9$, $Y^2$, $Y^3$, $Y^4$, $Y^5$, $W^1$ and Z are as defined for Formula (I); W is absent, or is —$CR^6R^7$—, —$NR^8$—, —O—or —$S(O)_p$—; m is 0, 1, 2, 3, 4 or 5; each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl) where p is 0, 1 or 2; —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4- or 5-membered-heterocyclyl group, which may include one to three additional heteroatoms selected from the group consisting of N, O, Si and S and may be optionally substituted;

wherein "optionally substituted" indicates that the group recited may be optionally substituted with the same groups defined for "optionally substituted" for the broadest embodiment of Formula (I) above.

In another embodiment, the present invention includes a compound of Formula (Ie) as described above, or a salt thereof, wherein variables $R^{1\prime}$, $R^2$, $R^3$, R', $R^9$, $Y^2$, $Y^3$, $Y^4$, $Y^5$, $W^1$ and Z are as defined for Formula (I); W is absent, or is —$CR^6R^7$—, —$NR^8$—, —O—or —$S(O)_p$—; m is 0, 1, 2, 3, 4 or 5; each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7- or 8-membered heterocyclyl group, which may include one to three additional heteroatoms selected from the group consisting of N, O, Si and S and may be optionally substituted; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl) where p is 0, 1 or 2; —$SF_5$, or —$NR^aR^b$, wherein $R^a$ and $R^b$ are independently H or optionally substituted alkyl; or $R^a$ and $R^b$ may form, with the nitrogen to which they are attached, a 6-, 7- or 8-membered-heterocyclyl group, which may include one to three additional heteroatoms selected from the group consisting of N, O, Si and S and may be optionally substituted;

wherein "optionally substituted" indicates that the group recited may be optionally substituted with the same groups defined for "optionally substituted" for the broadest embodiment of Formula (I) described above.

In another embodiment, a compound of Formula (Ie) is provided wherein variables $R^1$, $R^{1\prime}$, $R^2$, $R^3$, R', $R^9$, $W^1$, Z, $Y^2$, $Y^3$, $Y^4$ and $Y^5$ are as defined for Formula (IA); W is absent, or is —$CR^6R^7$; m is 0, 1, 2, 3, 4 or 5; and each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl), where p is 0, 1 or 2, $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted, wherein "optionally substituted" indicates that the group recited may be optionally substituted with the same groups defined for "optionally substituted" for the broadest embodiment of Formula (IA) above.

In another embodiment, the present invention includes a compound of Formula (Ie) as described above, or a salt thereof, wherein variables $R^{1'}$, $R^2$, $R^3$, R', $R^9$, $Y^2$, $Y^3$, $Y^4$, $Y^5$, $W^1$ and Z are as defined for Formula (IA); W is absent, or is —$CR^6R^7$—; m is 0, 1, 2, 3, 4 or 5; each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted; and

- $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl) where p is 0, 1 or 2; —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4- or 5-membered-heterocyclyl group, which may include one to three additional heteroatoms selected from the group consisting of N, O, Si and S and may be optionally substituted;
- wherein "optionally substituted" indicates that the group recited may be optionally substituted with the same groups defined for "optionally substituted" for the broadest embodiment of Formula (IA) described above.

In another embodiment, the present invention includes a compound of Formula (Ie) as described above, or a salt thereof, wherein variables $R^{1'}$, $R^2$, $R^3$, R', $R^9$, $Y^2$, $Y^3$, $Y^4$, $Y^5$, $W^1$ and Z are as defined for Formula (IA); W is absent, or is —$CR^6R^7$—; m is 0, 1, 2, 3, 4 or 5; each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted; and

- $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl) where p is 0, 1 or 2; —$SF_5$, or —$NR^aR^b$, wherein $R^a$ and $R^b$ are independently H or optionally substituted alkyl; or $R^a$ and $R^b$ may form, with the nitrogen to which they are attached, a 6-, 7- or 8-membered-heterocyclyl group, which may include one to three additional heteroatoms selected from the group consisting of N, O, Si and S and may be optionally substituted;
- wherein "optionally substituted" indicates that the group recited may be optionally substituted with the same groups defined for "optionally substituted" for the broadest embodiment of Formula (IA) above.

In another embodiment, the invention provides a compound of Formula (Ie) described above wherein:

- R' is hydrogen, optionally substituted $C_1$-$C_6$-alkyl, $C_1$-$C_6$-haloalkyl, or optionally substituted benzyl;

$R^1$ is optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, optionally substituted $C_3$-$C_8$-cycloalkyl, optionally substituted $C_3$-$C_8$-cycloalkenyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5-membered-heterocyclyl group, which may include one to three additional heteroatoms selected from the group consisting of N, O, Si and S and may be optionally substituted;

$R^{1'}$ hydrogen, halogen, optionally substituted $C_1$-$C_6$-alkyl or $C_1$-$C_6$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

each $R^5$ is independently in each occurrence, hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy;

$R^6$ and $R^7$ are independently hydrogen, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^9$ is hydrogen, halogen, $C_1$-$C_6$-alkyl or $C_1$-$C_6$-haloalkyl;

each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$—$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted;

m is 0, 1, 2, 3, 4 or 5; and $Y^2$, $Y^3$, $Y^4$, $Y^5$, $W^1$, Z, X and the dashed bonds (- - - -) are as defined above for the compound of Formula (IA); and W is absent, or is —$CR^6R^7$—;

wherein the term "optionally substituted" indicates that the group recited is optionally substituted by one or more halogen (chloro, fluoro, bromo, iodo), hydroxyl, $C_1$-$C_6$-alkyl, $C_1$-$C_6$-haloalkyl, 3- to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, $SF_5$, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl or $C_1$-$C_6$-haloalkylsulfonyl.

In another embodiment, the invention provides a compound of Formula (Ie) described above wherein:

R' is hydrogen, optionally substituted $C_1$-$C_6$-alkyl, $C_1$-$C_6$-haloalkyl, or optionally substituted benzyl;

$R^1$ is optionally substituted $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkylamino-$C_1$-$C_6$-alkyl, $C_1$-$C_6$-haloalkylamino-$C_1$-$C_6$-alkyl, di-$C_1$-$C_6$-alkylamino-$C_1$-$C_6$-alkyl, di-$C_1$-$C_6$-haloalkylamino-$C_1$-$C_6$-alkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, optionally substituted $C_3$-$C_8$-cycloalkyl, optionally substituted $C_3$-$C_8$-cycloalkenyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 6-, 7-, 8-membered-heterocyclyl group, which may include one to three additional heteroatoms selected from the group consisting of N, O, Si and S and may be optionally substituted;

$R^{1'}$ hydrogen, halogen, optionally substituted $C_1$-$C_6$-alkyl or $C_1$-$C_6$-haloalkyl;

$R^2$ is hydrogen, cyano, halogen, hydroxyl, optionally substituted $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

$R^3$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl or $C_1$-$C_6$-haloalkoxy-$C_1$-$C_6$-alkyl;

each $R^5$ is independently in each occurrence, hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy;

$R^6$ and $R^7$ are independently hydrogen, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, or $R^6$ together with $R^7$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

$R^9$ is hydrogen, halogen, $C_1$-$C_6$-alkyl or $C_1$-$C_6$-haloalkyl;

each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$—$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted;

m is 0, 1, 2, 3, 4 or 5;

$Y^2$, $Y^3$, $Y^4$, $Y^5$, $W^1$, Z, X and the dashed bonds (----) are as defined above for the compound of Formula (IA); and W is absent, or is —$CR^6R^7$—;

wherein the term “optionally substituted” indicates that the group recited is optionally substituted by one or more halogen (chloro, fluoro, bromo, iodo), hydroxyl, $C_1$-$C_6$-alkyl, $C_1$-$C_6$-haloalkyl, 3- to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, $SF_5$, acetyl, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl or $C_1$-$C_6$-haloalkylsulfonyl.

In another embodiment, the present invention includes a compound of Formula (Ie) as described above, or a salt thereof, wherein variables $R^{1'}$, $R^2$, $R^3$, R', $R^9$, $Y^2$, $Y^3$, $Y^4$, $Y^5$, $W^1$ and Z are as defined for Formula (IA); W is absent, or is —$CR^6R^7$—; m is 0, 1, 2, 3, 4 or 5; each $R^{10}$ is cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2; $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted; and $R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, optionally substituted trialkylsilyl, optionally substituted trialkylsilyloxy, —$SO_p$(optionally substituted alkyl or haloalkyl) where p is 0, 1 or 2; —$SF_5$, or —$NR^aR^b$, wherein $R^a$ and $R^b$ are independently H or optionally substituted alkyl; or $R^a$ and $R^b$ may form, with the nitrogen to which they are attached, a 6-, 7- or 8-membered-heterocyclyl group, which may include one to three additional heteroatoms selected from the group consisting of N, O, Si and S and may be optionally substituted;

wherein “optionally substituted” indicates that the group recited may be optionally substituted with the same groups defined for “optionally substituted” for the broadest embodiment of Formula (IA) above; and with the proviso that the compound below is excluded:

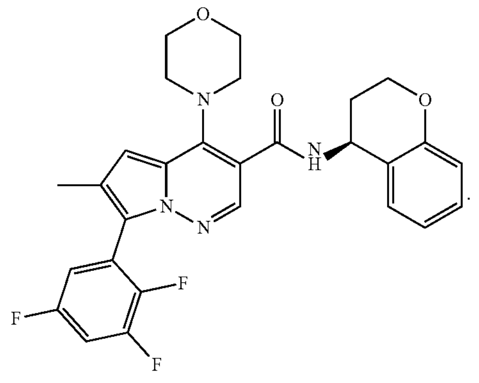 [SMILES: Cc1cc2c(N3CCOCC3)c(C(=O)N[C@H]3CCOc4ccccc43)cnn2c1-c1cc(F)cc(F)c1F]

In one embodiment of formula (Ie), $R^{10}$ is halogen. In another embodiment, $R^{10}$ is chloro. In yet another embodiment, $R^{10}$ is fluoro. In another embodiment, $R^{10}$ is chloro or fluoro and m is 1, 2 or 3. In yet another embodiment, $R^{10}$ is fluoro and m is 2. In another embodiment, $R^{10}$ is chloro and m is 2. In another embodiment, $R^{10}$ is fluoro or chloro, m is 2 and the fluoro or chloro are substituted are the 3- and 5-positions of the phenyl ring. In another embodiment, $R^{10}$ is fluoro or chloro, m is 2 and the fluoro or chloro are substituted at the 2- and 6-positions.

In another embodiment of formula (Ie), $R^{10}$ is fluoro or chloro and m is 3. In another embodiment, $R^{10}$ is fluoro or chloro, m is 3 and the fluoro or chloro are substituted at the 2-, 3- and 5-positions of the phenyl ring. In another embodiment of formula (Ie), $R^{10}$ is fluoro or chloro, m is 3, wherein chloro is substituted at the 2- and 3-positions and fluoro is substituted at the 5-position of the phenyl ring. In another embodiment, $R^{10}$ is fluoro, m is 3 and the fluoro is substituted at the 2-, 3- and 5-positions of the phenyl ring. In yet another embodiment, $R^{10}$ is chloro, m is 3 and the fluoro is substituted at the 2-, 3- and 5-positions of the phenyl ring.

In one embodiment of Formula (Ie), $R^9$ is H. In another embodiment of Formula (Ie), R' is H. In another embodiment, $R^{1'}$ is H. In another embodiment, W and $W^1$ are each $CH_2$.

In another embodiment of Formula (Ie), W is $CH_2$, $W^1$ is $CH_2$ and Z is $CH_2$. In another embodiment of Formula (Ie), W and $W^1$ are independently $CR^6R^7$ wherein $R^6$ and $R^7$ are H, $C_1$-$C_3$-alkyl or $C_1$-$C_3$-haloalkyl and Z is O. In another embodiment, W and $W^1$ are each $CH_2$ and Z is O.

In one embodiment of Formula (Ie), $R^1$ is optionally substituted $C_1$-$C_6$-alkyl, optionally substituted $C_3$-$C_6$-cycloalkyl, —$NR^aR^b$, wherein $R^a$ and $R^b$ are independently H or optionally substituted $C_1$-$C_3$-alkyl, or wherein $R^a$ and $R^b$ together with the nitrogen form an optionally-substituted 3-, 4-, 5- or 6-membered heterocycle, which may include one additional heteroatom selected from O or N; $R^2$ is hydrogen or optionally substituted $C_1$-$C_3$-alkyl; $R^3$ is hydrogen, optionally substituted $C_1$-$C_3$-alkyl or halogen; $R^{1'}$ is hydrogen; R' is hydrogen or $C_1$-$C_3$-alkyl; $R^9$ is hydrogen; $R^{10}$ is halogen and m is 2 or 3; W is $CH_2$ or is absent; $W^1$ is $CH_2$; Z is $CH_2$ or O and $Y^2$, $Y^3$, $Y^4$ and $Y^5$ are each independently N, CH or C-halogen; wherein the optional substituents are one or more halogen, hydroxy, cyano, $C_1$-$C_3$-alkyl, $C_1$-$C_3$-haloalkyl, 3- to 8-membered cycloalkyl, amino, $C_1$-$C_3$-alkylamino, $C_1$-$C_3$-dialkylamino, $C_1$-$C_3$-alkoxy and $C_1$-$C_3$-haloalkoxy.

In another embodiment of Formula (Ie), $R^1$ is $C_1$-$C_4$-alkyl, —$NR^aR^b$, wherein $R^a$ and $R^b$ are independently H or optionally substituted $C_1$-$C_3$-alkyl, or wherein $R^a$ and $R^b$ together with the nitrogen form an optionally substituted 3- or 4-membered heterocycle; $R^2$ is hydrogen; $R^3$ is hydrogen, optionally substituted $C_1$-$C_3$-alkyl, chloro or fluoro; $R^{1'}$ is hydrogen; R' is hydrogen; $R^9$ is hydrogen; $R^{10}$ is chloro or fluoro and m is 2 or 3; W and $W^1$ are each $CH_2$; Z is O and $Y^2$, $Y^3$, $Y^4$ and $Y^5$ are each independently CH or C-halogen; wherein the optional substituents are one or more halogen, hydroxy, $C_1$-$C_3$-alkyl, $C_1$-$C_3$-haloalkyl, $C_1$-$C_3$-alkoxy or $C_1$-$C_3$-haloalkoxy.

In another embodiment of Formula (Ie), $R^1$ is methyl, ethyl, n-propyl, iso-propyl, n-butyl, iso-butyl, sec-butyl, tert-butyl, —$NR^aR^b$, wherein $R^a$ and $R^b$ are independently H or optionally substituted $C_1$-$C_3$-alkyl, or wherein $R^a$ and $R^b$ together with the nitrogen form an aziridine, azetidine or pyrrolidinyl ring, each of which is optionally substituted by one or more fluoro or methyl; $R^2$ is hydrogen; $R^3$ is hydrogen, optionally substituted $C_1$-$C_3$-alkyl, chloro or fluoro; $R^{1'}$ is hydrogen; R' is hydrogen or $C_1$-$C_3$-alkyl; $R^9$ is hydrogen; $R^{10}$ is chloro or fluoro and m is 2 or 3; W and $W^1$ are each $CH_2$; Z is O and $Y^2$, $Y^3$, $Y^4$ and $Y^5$ are each independently CH or C-halogen; wherein the optional substituents are one or more chloro, fluoro, hydroxy, $C_1$-$C_3$ alkyl or $C_1$-$C_3$-haloalkyl.

In another embodiment of Formula (Ie), $R^1$ is iso-propyl, tert-butyl, —$N(CH_3)_2$, azetidinyl optionally substituted by one or more fluoro or methyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro or fluoro and m is 2 or 3; W and $W^1$ are each $CH_2$; Z is O and $Y^2$, $Y^3$, $Y^4$ and $Y^5$ are each CH.

In another embodiment of Formula (Ie), $R^1$ is iso-propyl, tert-butyl, —$N(CH_3)_2$, azetidinyl optionally substituted by one or more fluoro or methyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro or fluoro and m is 3, wherein the chloro or fluoro substituents are located at the 2, 3 and 5 positions of the phenyl ring; W and $W^1$ are each $CH_2$; Z is O and $Y^2$, $Y^3$, $Y^4$ and $Y^5$ are each CH.

In another embodiment of Formula (Ie), $R^1$ is iso-propyl, tert-butyl, —$N(CH_3)_2$, azetidinyl optionally substituted by one or more fluoro or methyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro and m is 3, wherein the chloro substituents are substituted at the 2, 3 and positions of the phenyl ring; W and $W^1$ are each $CH_2$; Z is O and $Y^2$, $Y^3$, $Y^4$ and $Y^5$ are each CH.

In another embodiment of Formula (Ie), $R^1$ is iso-propyl, tert-butyl, —$N(CH_3)_2$, azetidinyl optionally substituted by one or more fluoro or methyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is fluoro and m is 3, wherein the fluoro substituents are substituted at the 2, 3 and 5 positions of the phenyl ring; W and $W^1$ are each $CH_2$; Z is O and $Y^2$, $Y^3$, $Y^4$ and $Y^5$ are each CH.

In another embodiment of Formula (Ie), $R^1$ is morpholinyl, piperidinyl or piperazinyl optionally substituted by one or more fluoro or methyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro or fluoro and m is 2 or 3; W and $W^1$ are each $CH_2$; Z is O and $Y^2$, $Y^3$, $Y^4$ and $Y^5$ are each CH.

In another embodiment of Formula (Ie), $R^1$ is morpholinyl, piperidinyl or piperazinyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro or fluoro and m is 3, wherein the chloro or fluoro substituents are located at the 2, 3 and 5 positions of the phenyl ring; W and $W^1$ are each $CH_2$; Z is O and $Y^2$, $Y^3$, $Y^4$ and $Y^5$ are each CH.

In another embodiment of Formula (Ie), $R^1$ is morpholinyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is chloro and m is 3, wherein the chloro substituents are substituted at the 2, 3 and positions of the phenyl ring; W and $W^1$ are each $CH_2$; Z is O and $Y^2$, $Y^3$, $Y^4$ and $Y^5$ are each CH.

In another embodiment of Formula (Ie), $R^1$ is morpholinyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; $R^{10}$ is fluoro and m is 3, wherein the fluoro substituents are substituted at the 2, 3 and positions of the phenyl ring; W and $W^1$ are each $CH_2$; Zis O and $Y^2$, $Y^3$, $Y^4$ and $Y^5$ are each CH.

In other embodiments, the compound of Formula (I) is the compound of Formula (If):

(If)

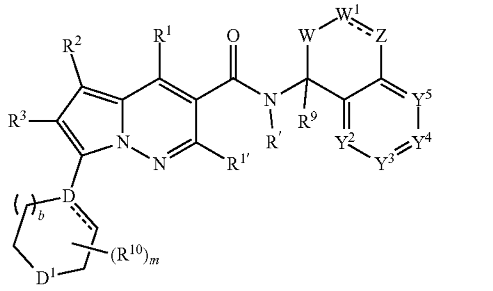

wherein variables $R^1$, $R^{1'}$, $R^2$, $R^3$, R', R°, $Y^2$, $Y^3$, $Y^4$, $Y^5$, $W^1$ and Z are as defined for any of the embodiments of Formula (I); W is absent, or is —$CR^6R^7$—, —$NR^8$—, —O—or —$S(O)_p$—; $R^{10}$ and m are as defined for formula (Ie) above; b is 0 or 1; the dashed bond (- - - -) signifies a single or double bond; D is N, $SiR^{11}$ where $R^{11}$ is $C_1$-$C_6$ alkyl or $C_1$-$C_6$haloalkyl, C or C—$R^5$; $D^1$ is N—R', O, $SiR^{11}R^{12}$, where $R^{11}$ and $R^{12}$ are independently $C_1$-$C_6$ alkyl or $C_1$-$C_6$ haloalkyl, —$CR^5R^{5'}$, $S(O)_p$, where p is 0, 1 or 2, or $D^1$ is $CR^5R^{5'}$, wherein $R^5$ and $R^{5'}$ together form a 2- to 5-membered chain optionally substituted with one heteroatom in the chain to form a spirocyclic group. In another embodiment, a compound of Formula (If) is provided wherein variables $R^1$, $R^{1'}$, $R^2$, $R^3$, R', $R^9$, $W^1$, Z, $Y^2$, $Y^3$, $Y^4$ and $Y^5$ are as defined for any of the embodiments of Formula (IA) described above; W is absent, or is —$CR^6R^7$—; $R^{10}$ and m are as defined for formula (Ie); b is 0 or 1; the dashed bond (- - - -) signifies a single or double bond; D is N, $SiR^{11}$ where $R^{11}$ is $C_1$-$C_6$alkyl or $C_1$-$C_6$haloalkyl, C or C—$R^5$; $D^1$ is N—R', O, $SiR^{11}R^{12}$ where $R^{11}$ and $R^{12}$ are independently $C_1$-$C_6$ alkyl or $C_1$-$C_6$haloalkyl, —$CR^5R^{5'}$, $S(O)_p$, where p is 0, 1 or 2, or $D^1$ is $CR^5R^{5'}$, wherein $R^5$ and $R^{5'}$ together form a 2- to 5-membered chain optionally substituted with one heteroatom in the chain to form a spirocyclic group.

In one embodiment of Formula (If), $R^9$ is CH. In another embodiment of Formula (If), R' is CH. In another embodiment, $R^{1'}$ is H. In another embodiment, W and $W^1$ are each $CH_2$.

In one embodiment of Formula (If), $R^1$ is optionally substituted $C_1$-$C_6$-alkyl, optionally substituted $C_3$-$C_6$-cycloalkyl, —$NR^aR^b$, wherein $R^a$ and $R^b$ are independently H or optionally substituted $C_1$-$C_3$-alkyl, or wherein $R^a$ and $R^b$ together with the nitrogen form an optionally-substituted 3-, 4-, 5- or 6-membered heterocycle, which may include one additional heteroatom selected from O or N; $R^2$ is hydrogen or optionally substituted $C_1$-$C_3$-alkyl; $R^3$ is hydrogen, optionally substituted $C_1$-$C_3$-alkyl or halogen; $R^{1'}$ is hydrogen; R' is hydrogen or $C_1$-$C_3$-alkyl; $R^9$ is hydrogen; D is N or CH; $D^1$ is $CH_2$, $CF_2$, N or O; $R^{10}$ is halogen or $C_1$-$C_3$-alkyl and m is 1 or 2; W is $CH_2$ or is absent; $W^1$ is $CH_2$; Z is $CH_2$ or O and $Y^2$, $Y^3$, $Y^4$ and $Y^5$ are each independently N, CH or C-halogen; wherein the optional substituents are one or more halogen, hydroxy, cyano, $C_1$-$C_3$-alkyl, $C_1$-$C_3$-haloalkyl, 3- to 8-membered cycloalkyl, amino, $C_1$-$C_3$-alkylamino, $C_1$-$C_3$-dialkylamino, $C_1$-$C_3$-alkoxy and $C_1$-$C_3$-haloalkoxy.

In another embodiment of Formula (If), $R^1$ is $C_1$-$C_4$-alkyl, —$NR^aR^b$, wherein $R^a$ and $R^b$ are independently H or optionally substituted $C_1$-$C_3$-alkyl, or wherein $R^a$ and $R^b$ together with the nitrogen form an optionally substituted 3- or 4-membered heterocycle; $R^2$ is hydrogen; $R^3$ is hydrogen, optionally substituted $C_1$-$C_3$-alkyl, chloro or fluoro; $R^{1'}$ is hydrogen; R' is hydrogen; $R^9$ is hydrogen; D is N; $D^1$ is $CH_2$, $CF_2$ or O; $R^{10}$ is fluoro or methyl and m is 1 or 2; W and $W^1$ are each $CH_2$; Z is O and $Y^2$, $Y^3$, $Y^4$ and $Y^5$ are each independently CH or C-halogen; wherein the optional substituents are one or more halogen, hydroxy, $C_1$-$C_3$-alkyl, $C_1$-$C_3$-haloalkyl, $C_1$-$C_3$-alkoxy or $C_1$-$C_3$-haloalkoxy.

In another embodiment of Formula (If), $R^1$ is iso-propyl, tert-butyl, —$N(CH_3)_2$, azetidinyl optionally substituted by one or more fluoro or methyl, or morpholinyl; $R^2$ is hydrogen; $R^3$ is hydrogen, methyl, —$CF_3$, —$CH_2F$, —$CHF_2$, chloro or fluoro; $R^{1'}$ is hydrogen; R' is hydrogen or $C_1$-$C_3$-alkyl; $R^9$ is hydrogen; D is N; $D^1$ is $CH_2$, $CF_2$ or O; $R^{10}$ is fluoro or methyl and m is 1 or 2; W and $W^1$ are each $CH_2$; Z is O and $Y^2$, $Y^3$, $Y^4$ and $Y^5$ are each CH. In another embodiment of Formula (If), W is $CH_2$, $W^1$ is $CH_2$ and Z is $CH_2$. In another embodiment of Formula (If), W and $W^1$ are independently $CR^6R^7$ wherein $R^6$ and $R^7$ are H, $C_1$-$C_3$-alkyl or $C_1$-$C_3$-haloalkyl and Zis O. In another embodiment, W and $W^1$ are each $CH_2$ and Z is O.

In some embodiments, the present invention provides compounds of formula (If), wherein the dashed bond is a single bond.

In some embodiments, the present invention provides compounds of formula (If), wherein the dashed bond is a double bond.

It will be appreciated by persons of skill in the art that in Formulae (Ic) and (Id) above, where variable $R^5$ is indicated to be present as substituents on the aromatic rings (e.g. $(R^5)$, groups, where o is 0, 1, 2, 3 or 4), they will represent non-hydrogen substituents since in embodiments where o is 0, $R^5$ will not be present. The same principle applies to variable $R^{11}$ in the compounds of formula (Ie) and (If).

In other embodiments, the invention provides compounds of Formula (Ia), wherein variables $R^1$, $R^{1'}$, $R^2$, $R^3$, $R^4$, R', $R^5$, $R^9$, $W^1$ and Z are as defined for Formula (I) above, W is absent, or is —$CR^6R^7$—, —$NR^8$—, —O—or —$S(O)_p$—, and $Y^2$, $Y^3$, $Y^4$ and $Y^5$ are as shown in Table 1:

In other embodiments, the invention provides compounds of Formula (Ia), wherein variables $R^1$, $R^{1'}$, $R^2$, $R^3$, $R^4$, R', $R^5$, $R^9$, $W^1$ and Z are as defined for any of the embodiments of Formula (IA) described above, W is absent, or is —$CR^6R^7$—, and $Y^2$, $Y^3$, $Y^4$ and $Y^5$ are as shown in Table 1:

(Ia)

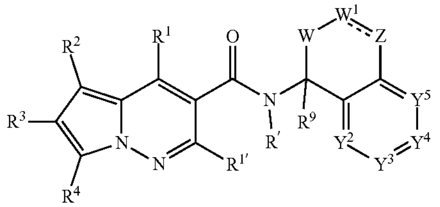

TABLE 1

| Formula | $Y^2$ | $Y^3$ | $Y^4$ | $Y^5$ |
|---|---|---|---|---|
| Ia-1 | $CR^5$ | $CR^5$ | $CR^5$ | $CR^5$ |
| Ia-2 | N | $CR^5$ | $CR^5$ | $CR^5$ |
| Ia-3 | $CR^5$ | N | $CR^5$ | $CR^5$ |
| Ia-4 | $CR^5$ | $CR^5$ | N | $CR^5$ |
| Ia-5 | $CR^5$ | $CR^5$ | $CR^5$ | N |

TABLE 1-continued

| Formula | $Y^2$ | $Y^3$ | $Y^4$ | $Y^5$ |
|---|---|---|---|---|
| Ia-6 | N | N | $CR^5$ | $CR^5$ |
| Ia-7 | $CR^5$ | N | N | $CR^5$ |
| Ia-8 | $CR^5$ | $CR^5$ | N | N |
| Ia-9 | N | $CR^5$ | N | $CR^5$ |
| Ia-10 | $CR^5$ | N | $CR^5$ | N |
| Ia-11 | N | $CR^5$ | $CR^5$ | N |

In other embodiments, the invention provides compounds of Formula (Ib), wherein variables $R^1$, $R^{1'}$, $R^2$, $R^3$, $R^4$, $R^5$, R', $R^9$, $W^1$ and Z are as defined for any of the embodiments of Formula (IA) described above, W is absent, or is $—CR^6R^7—$, and $Y^2$, $Y^3$, $Y^4$ and $Y^5$ are as shown in Table 2:

(Ib)

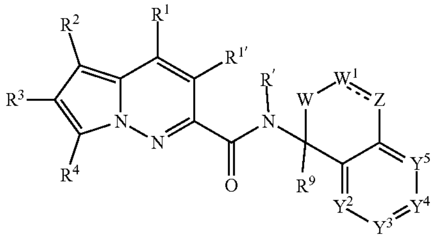

TABLE 2

| Formula | $Y^2$ | $Y^3$ | $Y^4$ | $Y^5$ |
|---|---|---|---|---|
| Ib-1 | $CR^5$ | $CR^5$ | $CR^5$ | $CR^5$ |
| Ib-2 | N | $CR^5$ | $CR^5$ | $CR^5$ |
| Ib-3 | $CR^5$ | N | $CR^5$ | $CR^5$ |
| Ib-4 | $CR^5$ | $CR^5$ | N | $CR^5$ |
| Ib-5 | $CR^5$ | $CR^5$ | $CR^5$ | N |
| Ib-6 | N | N | $CR^5$ | $CR^5$ |
| Ib-7 | $CR^5$ | N | N | $CR^5$ |
| Ib-8 | $CR^5$ | $CR^5$ | N | N |
| Ib-9 | N | $CR^5$ | N | $CR^5$ |
| Ib-10 | $CR^5$ | N | $CR^5$ | N |
| Ib-11 | N | $CR^5$ | $CR^5$ | N |

In other embodiments, the present invention provides compounds of formulae (IA-1) shown in Table 3 below, wherein L, $R^1$, $R^{1'}$, $R^2$, $R^3$ and $R^4$ are defined in the table; L1, L2 and L3 are as defined for Formula (I); X is O unless otherwise noted in the table, R' is hydrogen unless otherwise noted in the table, and wherein the group

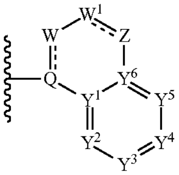

is one of the following Ring Systems:

Ring System A

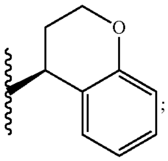

;

Ring System B

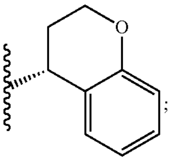

;

Ring System C

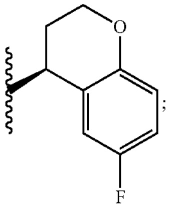

;

Ring System D

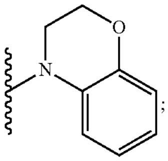

;

Ring System E

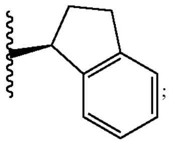

;

Ring System F

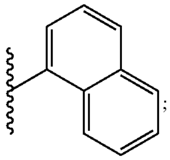

;

Ring System G

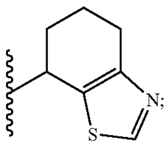

;

Ring System H

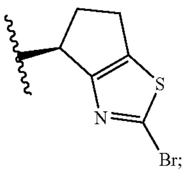

;

Ring System I

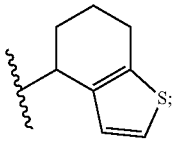

;

-continued
Ring System J
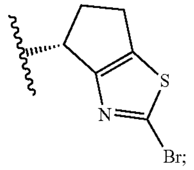
Ring System K
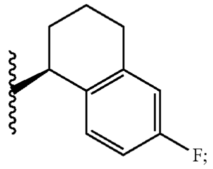
Ring System L
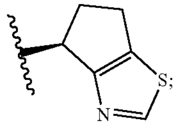
Ring System M
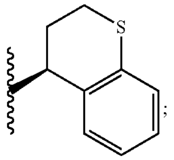
Ring System N
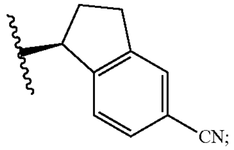
Ring System O
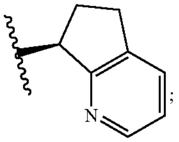
Ring System P
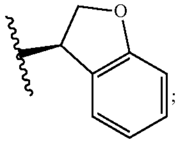
Ring System Q
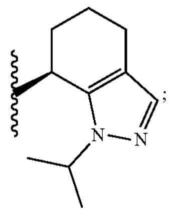
Ring System R
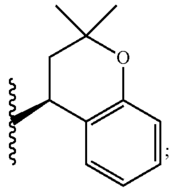
-continued
Ring System S
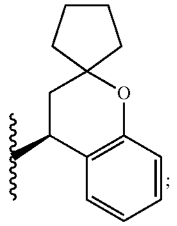
Ring System T
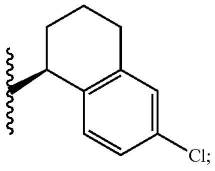
Ring System U
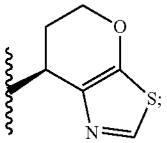
Ring System V
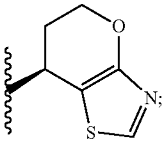
Ring System W
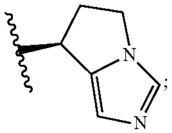
Ring System X
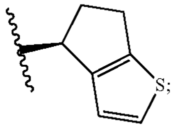
Ring System Y
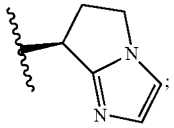
Ring System Z
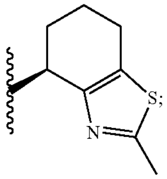
Ring System AA
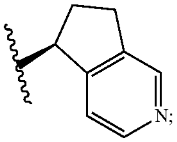

-continued

Ring System AB

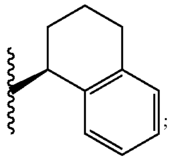

Ring System AC

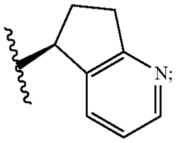

Ring System AD

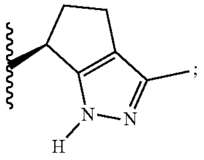

-continued

Ring System AE

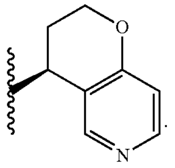

In Table 3, "Me" represents methyl, "i-Pr" means isopropyl, "t-Bu" means tert-butyl; the expression "3,5-di-$C_1$-Ph" represents the 3,5-dichlorophenyl group; "2,6-di-$C_{1-4}$—F-Ph" means 2,6-dichloro-4-fluorophenyl; "2,4,6-tri-F-Ph" means 2,4,6-trifluorophenyl; "2,3,5-tri-F-Ph" represents 2,3,5-trifluorophenyl; "2,3,5-tri-$C_1$-Ph means 2,3,5-trichlorophenyl; and "2,3-di-$C_{1-5}$—F-Ph" means 2,3-dichloro-5-fluorophenyl, and so on.

Formula (IA-1)

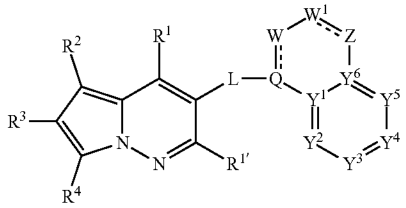

TABLE 3

| Cmpd. # | L | $R^1$ | $R^{1*}$ | $R^2$ | $R^3$ | $R^4$ | Ring Sys. | ESI-MS |
|---|---|---|---|---|---|---|---|---|
| A461 | L.2 | i-Pr | H | H | Me | 3,5-Di-Cl—Ph | B | 494 $[M + H]^+$ |
| A462 | L2 | i-Pr | H | H | Me | 3,5-di-Cl—Ph | A | 494 $[M + H]^+$ |
| A463 | L1 | i-Pr | H | H | Cl | 3,5-di-Cl—Ph | A | 514 $[M + H]^+$ |
| A464 | L1 | t-Bu | H | H | Me | 3,5-di-Cl—Ph | A | 508 $[M + H]^+$ |
| A465 | L1 | i-Pr | H | H | Me | 3,5-di-Cl—Ph | A | 495 $[M + H]^+$ |
| A466 | L1 | i-Pr | H | H | F | 3,5-di-Cl—Ph | A | 498 $[M + H]^+$ |
| A467 | L1 | i-Pr | H | Cl | H | 3,5-di-Cl—Ph | A | 514 $[M + H]^+$ |
| A468 | L1 | i-Pr | H | $CF_3$ | H | 3,5-di-Cl—Ph | A | 548 $[M + H]^+$ |
| A469 | L1 | i-Pr | H | Me | H | 3,5-di-Cl—Ph | A | 494 $[M + H]^+$ |
| A470 | L1 | i-Pr | H | H | H | 3,5-di-Cl—Ph | A | 480 $[M + H]^+$ |
| A483 | L1 | t-Bu | H | H | $CF_3$ | 3,5-di-Cl—Ph | A | 562 $[M + H]^+$ |
| A482 | L1 | t-Bu | H | H | Me | 3,5-di-Cl—Ph | D | 509 $[M + H]^+$ |
| A484 | L1 | t-Bu | H | H | Cl | 2,4,6-tri-F—Ph | A | 514 $[M + H]^+$ |
| A485 | L1 | t-Bu | H | H | Cl | 2,6-di-Cl—4-F—Ph | A | 547 $[M + H]^+$ |
| A486 | L1 | t-Bu | H | H | Cl | 2,3,5-tri-F—Ph | A | 514 $[M + H]^+$ |
| A472 | L1 | t-Bu | H | H | Me | 2,3,5-tri-Cl—Ph | A | 544 $[M + H]^+$ |
| A471 | L1 | t-Bu | H | H | Me | 2,3,5-tri-F—Ph | A | 494 $[M + H]^+$ |
| A476 | L1 | t-Bu | H | H | Me | 2,4,6-tri-F—Ph | A | 494 $[M + H]^+$ |

TABLE 3-continued

| Cmpd. # | L | $R^1$ | $R^{1*}$ | $R^2$ | $R^3$ | $R^4$ | Ring Sys. | ESI-MS |
|---|---|---|---|---|---|---|---|---|
| A487 | L1 | t-Bu | H | H | Me | 2,6-di-Cl-4-F—Ph | A | 526 $[M + H]^+$ |
| A499 | L1 | 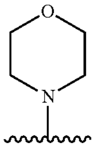 | H | H | Me | 3,5-di-Cl—Ph | A | 537 $[M + H]^+$ |
| A475 | L1 | —$N(CH_3)_2$ | H | H | Cl | 3,5-di-Cl—Ph | A | 516 $[M + H]^+$ |
| A473 | L1 | —$N(CH_3)_2$ | H | H | Cl | 2,3,5-tri-Cl—Ph | A | 550 $[M + H]^+$ |
| A474 | L1 | —$N(CH_3)_2$ | H | H | Cl | 2,3,5-tri-F—Ph | A | 551 $[M + H]^+$ |
| A477 | L1 | t-Bu | H | H | Cl | 3,5-di-Cl—Ph | A | 529 $[M + H]^+$ |
| A478 | L1 | —$N(CH_3)_2$ | H | H | Cl | 2,3-di-Cl-5-F—Ph | A | 534 $[M + H]^+$ |
| A490 | L1 | 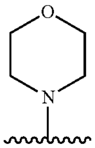 | H | H | Me | 2,3-di-Cl-5-F—Ph | A | 555 $[M + H]^+$ |
| A491 | L1 | 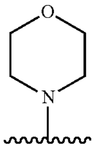 | H | H | Me | 2,3,5-tri-F—Ph | A | 523 $[M + H]^+$ |
| A488 | L1 | t-Bu | H | H | Me | 2,3-di-Cl-5-F—Ph | C | 544 $[M + H]^+$ |
| A479 | L1 | i-Pr | H | H | Cl | 3,5-di-Cl—Ph | D | 516 $[M + H]^+$ |
| A489 | L1 | i-Pr | H | H | Me | 2,3-di-Cl-5-F—Ph | A | 512 $[M + H]^+$ |
| A480 | L1 | t-Bu | H | H | Me | 3,5-di-Cl—Ph | E | 492 $[M + H]^+$ |
| A481 | L1 | t-Bu | H | H | Me | 2,3-di-Cl-5-F—Ph | A | 526 $[M + H]^+$ |
| A502 | L1 | t-Bu | H | H | Cl | 2,3-di-Cl-5-F—Ph | A | 547 $[M + H]^+$ |
| A492 | L1 | t-Bu | H | H | Cl | 3,5-di-Cl—Ph | E | 513 $[M + H]^+$ |
| A493 | L1 | —$N(CH_3)_2$ | H | H | Me | 2,3-di-Cl-5-F—Ph | A | 513 $[M + H]^+$ |
| A516 | L1 | t-Bu | H | H | Cl | 3,5-di-Cl—Ph | D | 530 $[M + H]^+$ |
| A494 | L1 | t-Bu | H | H | Cl | 2,3-di-Cl-5-F—Ph | D | 548 $[M + H]^+$ |
| A482 | L1 | t-Bu | H | H | Me | 3,5-di-Cl—Ph | D | 509 $[M + H]^+$ |
| A495 | L1 | t-Bu | H | H | Me | 2,3-di-Cl-5-F—Ph | D | 527 $[M + H]^+$ |
| A496 | L1 | i-Pr | H | H | Cl | 2,3-di-Cl-5-F—Ph | D | 534 $[M + H]^+$ |
| A497 | L1 | i-Pr | H | H | Me | 3,5-di-Cl—Ph | D | 495 $[M + H]^+$ |
| A498 | L1 | i-Pr | H | H | Me | 2,3-di-Cl-5-F—Ph | D | 513 $[M + H]^+$ |
| A501 | L1 | 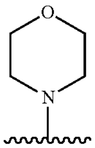 | H | H | Me | 2,3,5-tri-Cl—Ph | A | 572 $[M + H]^+$ |

TABLE 3-continued
| Cmpd. # | L | R[1] | R[1*] | R[2] | R[3] | R[4] | Ring Sys. | ESI-MS |
|---|---|---|---|---|---|---|---|---|
| A505 | L1 | 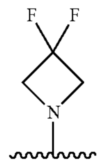 | H | H | Me | 2,3,5-tri-Cl—Ph | A | 578 $[M + H]^+$ |
| A504 | L1 | 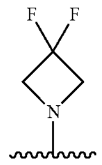 | H | H | Me | 2,3-di-Cl-5-F—Ph | A | 561 $[M + H]^+$ |
| A511 | L1 | 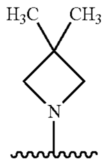 | H | H | Me | 2,3,5-tri-Cl—Ph | A | 570 $[M + H]^+$ |
| A512 | L1 | 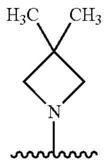 | H | H | M | 2,3,5-di-Cl-5-F—Ph | A | 553 $[M + H]^+$ |
| A508 | L1 | 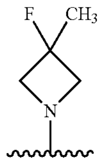 | H | H | Me | 2,3,5-tri-Cl—Ph | A | 574 $[M + H]^+$ |
| A510 | L1 | 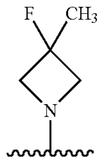 [SMILES: *N1CC(C)(F)C1] | H | H | Me | 2,3-di-Cl-5-F—Ph | A | 557 $[M + H]^+$ |
| A506 | L1 | 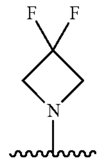 | H | H | Cl | 2,3,5-tri-Cl—Ph | A | 598 $[M + H]^+$ |
| A507 | L1 | 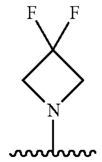 | H | H | Cl | 2,3-di-Cl-5-F—Ph | A | 582 $[M + H]^+$ |

TABLE 3-continued

| Cmpd. # | L | R¹ | R^1* | R² | R³ | R⁴ | Ring Sys. | ESI-MS |
|---|---|---|---|---|---|---|---|---|
| A515 | L1 | 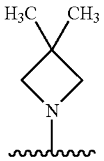 | H | H | Cl | 2,3,5-tri-Cl—Ph | A | 590 [M + H]+ |
| A520 | L1 | 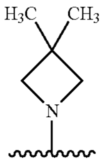 | H | H | Cl | 2,3-di-Cl-5-F—Ph | A | 574 [M + H]+ |
| A503 | L1 | 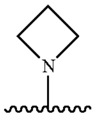 | H | H | Cl | 2,3-di-Cl-5-F—Ph | A | 546 [M + H]+ |
| A509 | L1 | 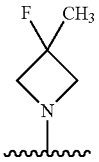 | H | H | Cl | 2,3,5-tri-Cl—Ph | A | 594 [M + H] |
| A514 | L1 | 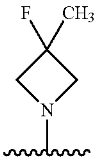 | H | H | Cl | 2,3-di-Cl-5-F—Ph | A | 578 [M + H]+ |
| A521 | L1 | i-Pr | H | H | Me | 3,5-di-Cl—Ph | F | 488 [M + H]+ |
| A513 | L1 | i-Pr | H | H | Me | 2,3,5-tri-F—Ph | A | 479 [M + H]+ |
| A517 | L1 | i-Pr | H | H | Me | 2,3,5-tri-Cl—Ph | A | 529 [M + H]+ |
| A518 | L1 | t-Bu | H | Br | Me | 2,3-di-Cl—Ph | A | 587 [M + H]+ |
| A519 | L1 | t-Bu | H | H | Me | 2,3-di-Cl—Ph | A | 508 [M + H]+ |
| A522 | L1 | t-Bu | H | H | Cl | 2,3,5-tri-Cl—Ph | A | 563 [M + H]+ |
| A523 | L1 | i-Pr | H | H | Cl | 2,3-di-Cl-5-F—Ph | A | 532 [M + H]+ |
| A500 | L1 | H | i-Pr | H | H | 3,5-di-Cl—Ph | A | 572 [M + H]+ |
| A525 | L1 | 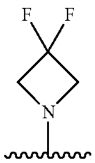 | H | H | Me | 2,3,5-tri-Cl—Ph | A | 578 [M + H]+ |
| A526 | L1 | 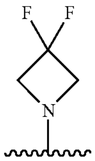 | H | H | Me | 2,3-di-Cl-5-F—Ph | A | 562 [M + H]+ |

TABLE 3-continued

| Cmpd. # | L | $R^1$ | $R^{1*}$ | $R^2$ | $R^3$ | $R^4$ | Ring Sys. | ESI-MS |
|---|---|---|---|---|---|---|---|---|
| A527 | L1 | t-Bu | H | H | Me | 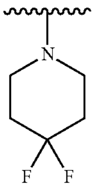 | A | 483 $[M + H]^+$ |
| A528 | L1 | t-Bu | H | H | Me | 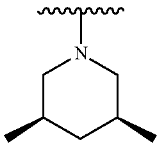 | A | 475 $[M + H]^+$ |
| A524 | L1 | t-Bu | H | H | Me | 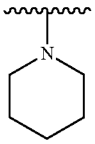 [SMILES: *N1CCCCC1] | A | 447 $[M + H]^+$ |
| A529 | L1 | t-Bu | H | H | Me | 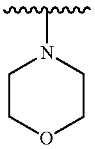 [SMILES: *N1CCOCC1] | A | 449 $[M + H]^+$ |
| A530 | L1 | t-Bu | H | H | Me | 2,3,5-tri-Cl—Ph | A | 543 $[M + H]^+$ |
| A531 | L1 | t-Bu | H | H | Me | 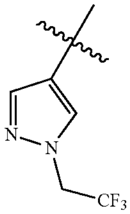 [SMILES: *c1cnn(CC(F)(F)F)c1] | A | 512 $[M + H]^+$ |
| A532 | L1 | t-Bu | H | H | Me | 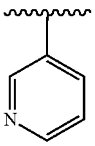 [SMILES: *c1cccnc1] | A | 440 $[M + H]^+$ |
| A533 | L1 | t-Bu | H | H | Me | 2,3-di-Cl-5-F—Ph | G | 532 $[M + H]^+$ |
| A534 | L1 | t-Bu | H | H | Cl | 2,3-di-Cl-5-F—Ph | A | 547 $[M + H]^+$ |
| A535 | L3 | t-Bu | H | H | Me | 2,3-di-Cl-5-F—Ph | G | 547 $[M + H]^+$ |
| A536A | L1 | t-Bu | H | H | Me | 2,3-di-Cl-5-F—Ph | H | 597 $[M + H]^+$ |
| A537 | L1 | t-Bu | H | H | Me | 2,3-di-Cl-5-F—Ph | 1 | 531 $[M + H]^+$ |
| A536b | L1 | t-Bu | H | H | Me | 2,3-di-Cl-5-F—Ph | J | 597 $[M + H]^+$ |
| A538 | L1 | t-Bu | H | H | Me | 2,3-di-Cl-5-F—Ph | K | 543 $[M + H]^+$ |
| A539 | L1; X = S | i-Pr | H | H | Cl | 2,3-di-Cl-5-F—Ph | A | 548 $[M + H]^+$ |
| A540 | L1 | t-Bu | H | H | Me | 2,3-di-Cl-5-F—Ph | L | 518 $[M + H]^+$ |

TABLE 3-continued

| Cmpd. # | L | $R^1$ | $R^{1*}$ | $R^2$ | $R^3$ | $R^4$ | Ring Sys. | ESI-MS |
|---|---|---|---|---|---|---|---|---|
| A541 | L1 | t-Bu | H | H | Me | 2,3-di-Cl-5-F—Ph | M | 543 $[M + H]^+$ |
| A542 | L1 | t-Bu | H | H | Me | 2,3-di-Cl-5-F—Ph | N | 536 $[M + H]^+$ |
| A543 | L1; R' = Me | t-Bu | H | H | Me | 2,3-di-Cl-5-F—Ph | A | 541 $[M + H]^+$ |
| A544 | L1 | t-Bu | H | H | Me | 2,3-di-Cl-5-F—Ph | O | 512 $[M + H]^+$ |
| A545 | L1 | t-Bu | H | H | Me | 2,3-di-Cl-5-F—Ph | P | 513 $[M + H]^+$ |
| A546 | L1 | t-Bu | H | H | Me | 2,3-di-Cl-5-F—Ph | Q | 557 $[M + H]^+$ |
| A547 | L1 | t-Bu | H | H | Me | 2,3-di-Cl-5-F—Ph | R | 555 [M + H] |
| A548 | L1 | t-Bu | H | H | Me | 2,3-di-Cl-5-F—Ph | S | 582 $[M + H]^+$ |
| A549 | L1 | t-Bu | H | H | Me | 2,3-di-Cl-5-F—Ph | T | 559 $[M + H]^+$ |
| A550 | L1 | t-Bu | H | H | Me | 2,3-di-Cl-5-F—Ph | U | 534 $[M + H]^+$ |
| A551 | L1 | t-Bu | H | H | Me | 2,3-di-Cl-5-F—Ph | V | 534 $[M + H]^+$ |
| A552 | L1 | t-Bu | H | H | Me | 2,3-di-Cl-5-F—Ph | W | 501 $[M + H]^+$ |
| A553 | L1 | t-Bu | H | H | Me | 2,3-di-Cl-5-F—Ph | X | 517 $[M + H]^+$ |
| A554 | L1 | t-Bu | H | H | Me | 2,3-di-Cl-5-F—Ph | Y | 501 $[M + H]^+$ |
| A555 | L1 | t-Bu | H | H | Me | 2,3-di-Cl-5-F—Ph | Z | 546 $[M + H]^+$ |
| A556 | L1 | t-Bu | H | H | Me | 2,3-di-Cl-5-F—Ph | AA | 512 $[M + H]^+$ |
| A557 | L1 | t-Bu | H | H | Me | 2,3-di-Cl-5-F—Ph | AB | 525 $[M + H]^+$ |
| A558 | L1 | t-Bu | H | H | Me | 2,3-di-Cl-5-F—Ph | E | 511 $[M + H]^+$ |
| A559 | L1 | t-Bu | H | H | Me | 2,3-di-Cl-5-F—Ph | AC | 512 $[M + H]^+$ |
| A560 | L1 | t-Bu | H | H | Me | 2,3-di-Cl-5-F—Ph | AD | 515 $[M + H]^+$ |
| A561 | L1 | 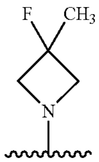 [SMILES: *N1CC(C)(F)C1] | H | H | Me | 2,3,5-tri-Cl—Ph | A | 575 $[M + H]^+$ |
| A562 | L1 | 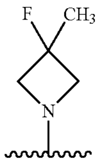 [SMILES: *N1CC(C)(F)C1] | H | H | Me | 2,3-di-Cl-5-F—Ph | A | 558 $[M + H]^+$ |
| A563 | L1 | 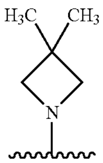 | H | H | Me | 2,3,5-tri-Cl—Ph | A | 571 $[M + H]^+$ |
| A564 | L1 | 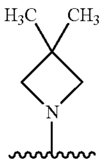 | H | H | Me | 2,3-di-Cl-5-F—Ph | A | 554 $[M + H]^+$ |

TABLE 3-continued

| Cmpd. # | L | $R^1$ | $R^{1*}$ | $R^2$ | $R^3$ | $R^4$ | Ring Sys. | ESI-MS |
|---|---|---|---|---|---|---|---|---|
| A565 | L1 | t-Bu | H | H | Cl | 3,5-di-Cl—Ph | D | 531 $[M + H]^+$ |
| A566 | L1 | t-Bu | H | H | Me | 2,3,5-tri-F—Ph | A | 495 $[M + H]^+$ |
| A567 | L1 | 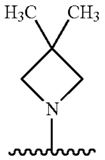 | H | H | Cl | 2,3-di-Cl-5-F—Ph | A | 575 $[M + H]^+$ |
| A568 | L1 | —$N(CH_3)_2$ | H | H | Me | 2,3,5-tri-Cl—Ph | A | 531 $[M + H]^+$ |
| A569 | L1 | t-Bu | H | H | Me | 2,3-di-Cl-5-F—Ph | AE | 528 $[M + H]^+$ |

For avoidance of doubt, each of the compounds presented in Table 3 has been prepared and characterized.

Veterinary Compositions

The compositions of the invention which comprise effective amounts of compounds of the invention or salts thereof, including those of formulae (I), (IA), (I-1), (I-2), (I-3), (Ia), (Ib), (Ic), (Id), (Ie), (If) and (IA-1), in combination with an acceptable carrier or diluent.

In another embodiment, the invention comprises an effective amount of a compound of the invention, or a pharmaceutically acceptable salt thereof, in combination with one or more additional active agents and an acceptable carrier or diluent.

The compositions may be in a variety of solid and liquid forms which are suitable for various methods of application or administration to an animal. For example, the veterinary compositions comprising the compound may be in compositions suitable for oral administration, injectable administration, including subcutaneous and parenteral administration, and topical administration (e.g. spot-on or pour-on), dermal or subdermal administration. The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compound to protect companion animals such as dogs and cats from endoparasites is particularly useful.

In some embodiments, the compositions of the invention may be in a form suitable for oral use. Suitable dosage forms for oral administration include dietary supplements, troches, lozenges, chewables, tablets, hard or soft capsules, bolus, emulsions, aqueous or oily suspensions, aqueous or oily solutions, oral drench compositions, dispersible powders or granules, premixes, syrups or elixirs, enteric compositions or pastes. Compositions intended for oral use may be prepared according to any method known in the art for the manufacture of pharmaceutical compositions.

Suitable tablets may be obtained, for example, by mixing one or more compounds of formula (I) with known excipients, for example inert diluents, carriers, disintegrants, adjuvants, surfactants, binders and/or lubricants.

In one embodiment of the invention, a soft chewable veterinary composition is provided comprising an effective amount of at least one compound of formula (I), optionally in combination with an effective amount of at least one second active agent in a pharmaceutically acceptable carrier.

In another embodiment, the compositions for oral administration include a tablet or capsule. In yet another embodiment, the compositions for oral administration include a chewable tablet.

Methods of Treatment

As discussed above, the compounds of the invention are effective against endoparasites and may be used to treat, control and/or prevent parasitic infections in animals. In one embodiment, the present invention provides a method of treating, controlling and/or preventing an endoparasite infection in an animal (e.g. a mammal or bird) comprising administering an effective amount of a compound of the invention, including the compounds of formulae (I), (IA), (I-1), (1-2), (I-3), (Ia), (Ib), (Ic), (Id), (Ie), (If) or (IA-1), or pharmaceutically acceptable salts thereof, or a composition comprising the compound, to the animal. In some embodiments, the animals which can be treated are mammals that include, but are not limited to, humans, cats, dogs, cattle, chickens, cows, bison, deer, goats, horses, llamas, camels, pigs, sheep and yaks. In one embodiment of the invention, the mammals treated are humans, cats or dogs. In another embodiment, the invention provides a method of treating or preventing endoparasite infections in horses. In another embodiment, the mammals treated are livestock animals such as cattle or sheep. In another embodiment, the compound of the invention may be used to treat fish.

The present invention also provides a use of the compound of formulae (I), (IA), (I-1), (I-2), (1-3), (Ia), (Ib), (Ic), (Id), (Ie), (If) or (IA-1) in the preparation of a medicament for the treatment, control and/or prevention of parasitic infections in animals. The present invention also provides the compounds of the invention for use in the treatment, control and/or prevention of a parasitic infection in animals.

In another embodiment, the compound of formulae (I), (IA), (I-1), (I-2), (I-3), (Ia), (Ib), (Ic), (Id), (Ie), (If) or (IA-1) may be combined with at least a second active agent that is active against ectoparasites (e.g. fleas and ticks) for use in the treatment, control and/or prevention of an endoparasitic infection and an ectoparasitic infestation in and on an animal. In another embodiment, the invention provides methods for the treatment, control and/or prevention of an endoparasitic infection and an ectoparasitic infestation in and on an animal comprising administering to the animal an effective amount of the compound of formulae (I), (IA), (I-1), (I-2), (I-3), (Ia), (Ib), (Ic), (Id), (Ie), (If) or (IA-1) in combination with at least one additional active agent that is active against ectoparasites. In addition, the present invention provides the use of a compound of the invention in combination with at least a second active agent for the preparation of a medicament for the treatment, control and/or prevention of an endoparasitic infection and an ectoparasitic infestation is provided.

In still another embodiment of the invention, a method is provided for the treatment, control and/or prevention of a parasitic infestation at a locus, which comprises administering or applying an effective amount of a compound of Formula (I), Formula (IA), (I-1), (1-2), (1-3), (Ia), (Ib), (Ic), (Id), (Ie), (If) or (IA-1), or pharmaceutically acceptable salts thereof, to the locus. With respect to animal health applications, "locus" is intended to mean a habitat, breeding ground, area, material or environment in which a parasite is growing or may grow, excluding in or on an animal.

In one embodiment of the invention, the compounds of Formula (I), Formula (IA), (I-1), (I-2), (I-3), (Ia), (Ib), (Ic), (Id), (Ie), (If) or (IA-1) have been found to have superior efficacy against endoparasites, and in particular against endoparasites that are resistant to active agents of the macrocyclic lactone class. In one embodiment, the invention provides method for the treatment and/or prevention of parasitic infections of endoparasites that are resistant to treatment with macrocyclic lactones.

In another embodiment, the invention provides a method for the treatment, control and/or prevention of a parasitic infestation and/or infection in an animal, comprising administering an effective amount of an anthelmintic compound of the invention in combination with an effective amount of another antiparasitic active agent to the animal in need thereof.

In one embodiment, the compounds and compositions of the invention may be used for treating, controlling and/or preventing an endoparasitic infection of the following parasite genuses: *Anaplocephala* (*Anoplocephala*), *Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In a particularly preferred embodiment of the invention, the compounds and compositions of the invention are used to treat, control and/or prevent an infection by *Dirofilaria immitis*. The compounds have been found to be highly effective against *D. immitis* microfilaria and L4 larvae, including isolates of *D. immitis* that are resistant to macrocyclic lactone therapy. Thus, the compounds may be used to protect animals from developing heartworm disease by killing the immature stages of *D. immitis* before they can develop into adult worms, including those that are resistant to macrocyclic lactones and other active agents. In one embodiment, the compound and compositions comprising the compounds may be used to prevent the development of heartworm disease by killing immature stages of *D. immitis* that are resistant to macrocyclic lactones. In another embodiment the compounds and compositions of the invention are used to treat, control and/or prevent an infection by *Dirofilaria repens* or *Dirofilaria hongkongensis*.

In another embodiment, the compound of Formula (I), Formula (IA), (I-1), (I-2), (I-3), (Ia), (Ib), (Ic), (Id), (Ie), (If) or (IA-1) may be used to treat, control and/or prevent a parasitic infection by a parasite selected from *Haemonchus contortus, Ostertagia circumcincta, Trichostrongylus axei, Trichostrongylus colubriformis, Cooperia curticei, Nematodirus battus* and combinations thereof.

In another embodiment for treatment against both endoparasites and ectoparasites when combined with ectoparasiticidal agents, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes*, and/or *Felicola*. In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. And the like), ticks (*Rhipicephalus* spp., *Ixodes* spp., *Dermacentor* spp., *Amblyomma* spp. And the like), and mites (*Demodex* spp., *Sarcoptes* spp., *Otodectes* spp. And the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include, but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In each aspect of the invention, the compounds and compositions of the invention can be applied against a single pest or combinations thereof.

Mixtures with Other Active Agents

In another embodiment, the compositions comprising the compounds of the invention, including those of formulae (I), (IA), (I-1), (I-2), (I-3), (Ia), (Ib), (Ic), (Id), (Ie), (If) and (IA-1), may also include other veterinary pharmaceutical agents. Veterinary pharmaceutical agents that may be included in the compositions of the invention are well-known in the art (see e.g. *Plumb' Veterinary Drug Handbook,* 5th Edition, ed. Donald C. Plumb, Blackwell Publishing, (2005) or The Merck Veterinary Manual, 9th Edition, (January 2005)).

In one embodiment of the invention, arylpyrazole compounds such as phenylpyrazoles, known in the art may be combined with the compounds of Formula (I) or Formula (IA) in the compositions of the invention.

In another embodiment of the invention, one or more macrocyclic lactones, which act as an acaricide, anthelmintic agent and/or insecticide, can be added to the compositions of the invention. Macrocyclic lactones include both avermectins and milbemycin active agents.

In another embodiment of the invention, a composition comprising a compound of the invention in combination with a class of acaricides or insecticides known as insect growth regulators (IGRs) is provided. Compounds belonging to this group are well known to the practitioner and represent a wide range of different chemical classes. These compounds all act by interfering with the development or growth of the insect pests.

In one embodiment the IGR is a compound that mimics juvenile hormone.

In another embodiment, the IGR compound is a chitin synthesis inhibitor.

In yet another embodiment of the invention, adulticide insecticides and acaricides can also be added to the composition of the invention. In some embodiments, the compositions of the invention may include one or more antinematodal agents.

In other embodiments, the compositions of the invention may include antitrematodal agents.

Anticestodal compounds may also be advantageously used in the compositions of the invention.

In yet other embodiments, the compositions of the invention may include other active agents that are effective against arthropod parasites.

An antiparasitic agent that can be combined with the compound of the invention to form a composition can be a biologically active peptide or protein including, but not limited to, cyclic depsipeptides, which act at the neuromuscular junction by stimulating presynaptic receptors belonging to the secretin receptor family resulting in the paralysis and death of parasites.

In another embodiment, the compositions of the invention may comprise an active agent from the neonicotinoid class of pesticides. The neonicotinoids bind and inhibit insect specific nicotinic acetylcholine receptors.

In another embodiment, the compositions of the invention may advantageously include one or more isoxazoline active agents known in the art. Isoxazoline active agents are highly effective against ectoparasites such as fleas and ticks, among others.

In another embodiment of the invention, nodulisporic acid and its derivatives (a class of known acaricidal, anthelmintic, anti-parasitic and insecticidal agents) may be added to the compositions of the invention.

In another embodiment, anthelmintic compounds of the amino acetonitrile class (AAD) of compounds may be added to the compositions of the invention. In another embodiment, aryloazol-2-yl cyanoethylamino compounds may be included in compositions.

The compositions of the invention may also be combined with paraherquamide compounds and derivatives of these compounds. The paraherquamide family of compounds is a known class of compounds that include a spirodioxepino indole core with activity against certain parasites. In addition, the structurally related marcfortine family of compounds are also known and may be combined with the formulations of the invention.

In another embodiment of the invention, the compositions may include a spinosyn active agent produced by the soil actinomycete *Saccharopolyspora spinosa* or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention.

The invention will now be further described by way of the following non-limiting examples.

Methods of Synthesis

The compounds of the invention, including the compounds of Formula (I), Formula (IA), (I-1), (I-2), (1-3), (Ia), (Ib), (Ic), (Id), (Ie), (If) and (IA-1), or salts thereof, described herein may be prepared according to the process described in schemes 1 and 2 shown below. A person of skill in the art will be able to prepare a variety of compounds of the invention by adapting processes described below with alternate starting materials and/or reagents known in the art.

Scheme 1

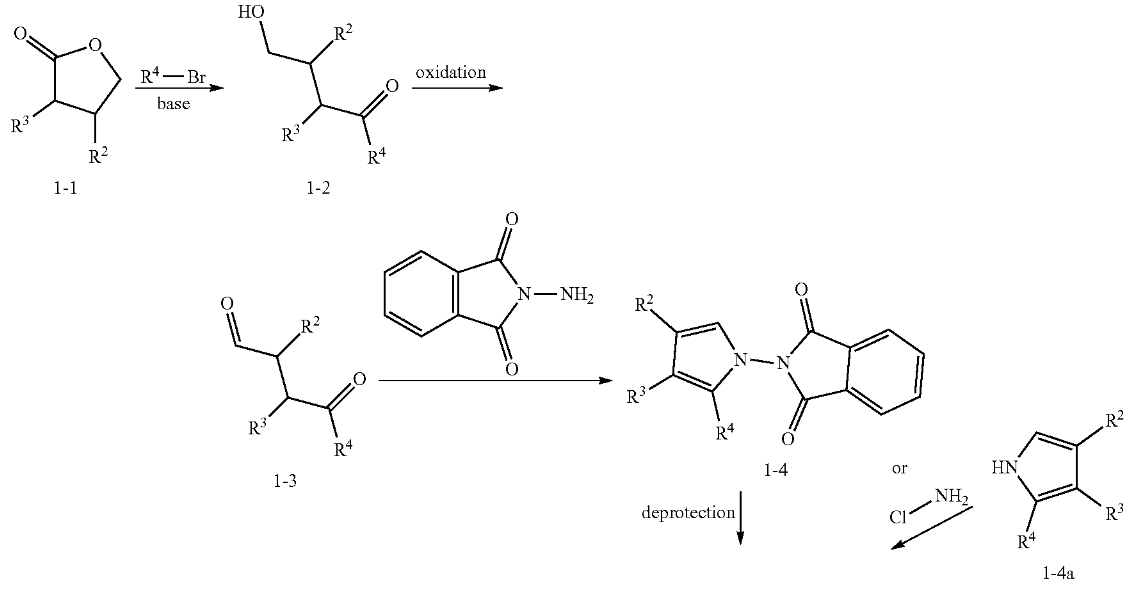

1-1 1-2 1-3 1-4 or 1-4a

-continued
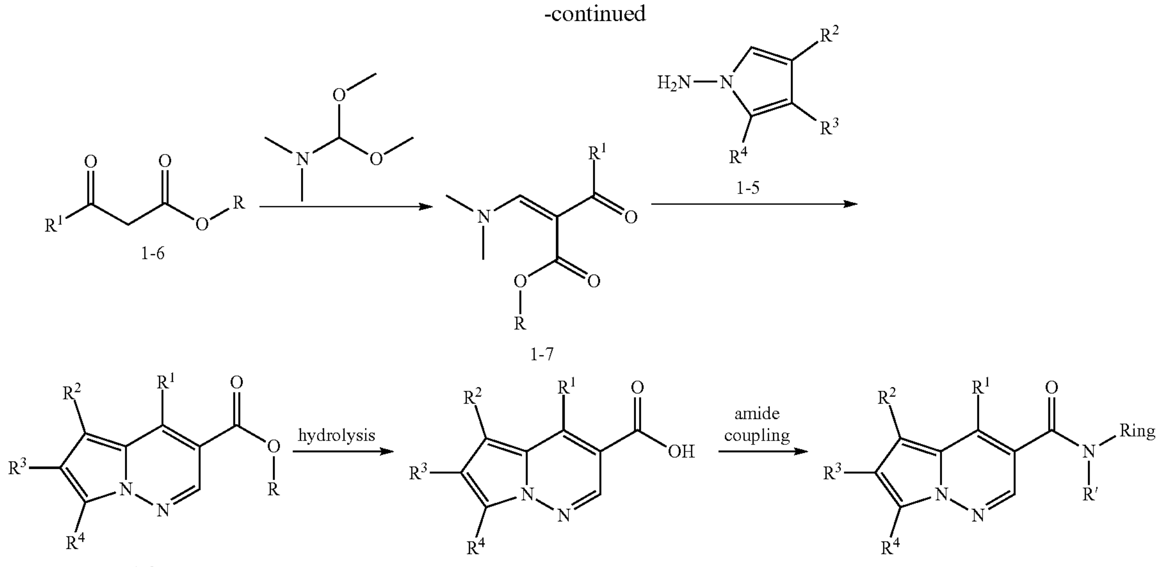
1-6 1-7 1-5 1-8 1-9 1-10
Scheme 2
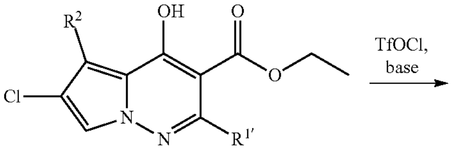
2-1
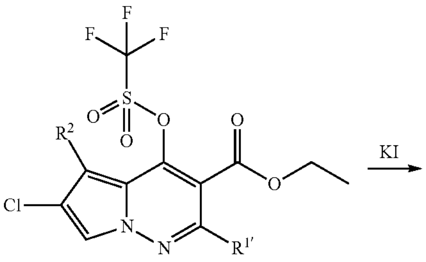
2-2
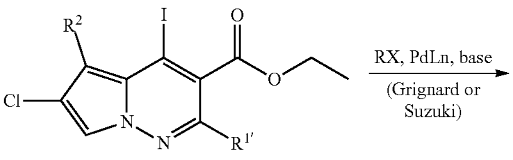
2-3
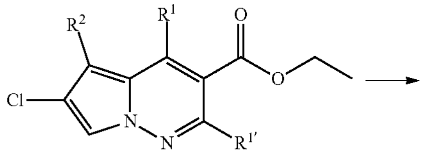
2-4
-continued
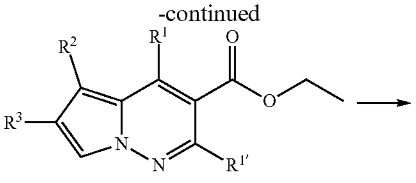
2-5
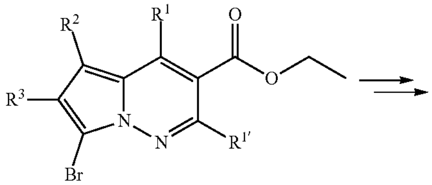
2-6
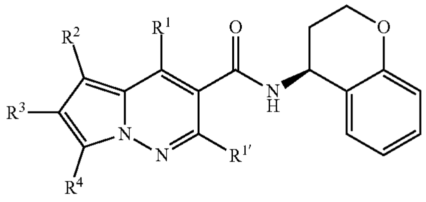
2-7
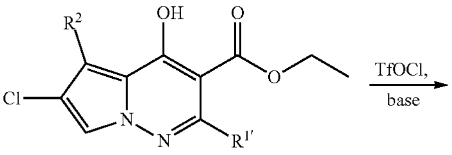
2-1

-continued

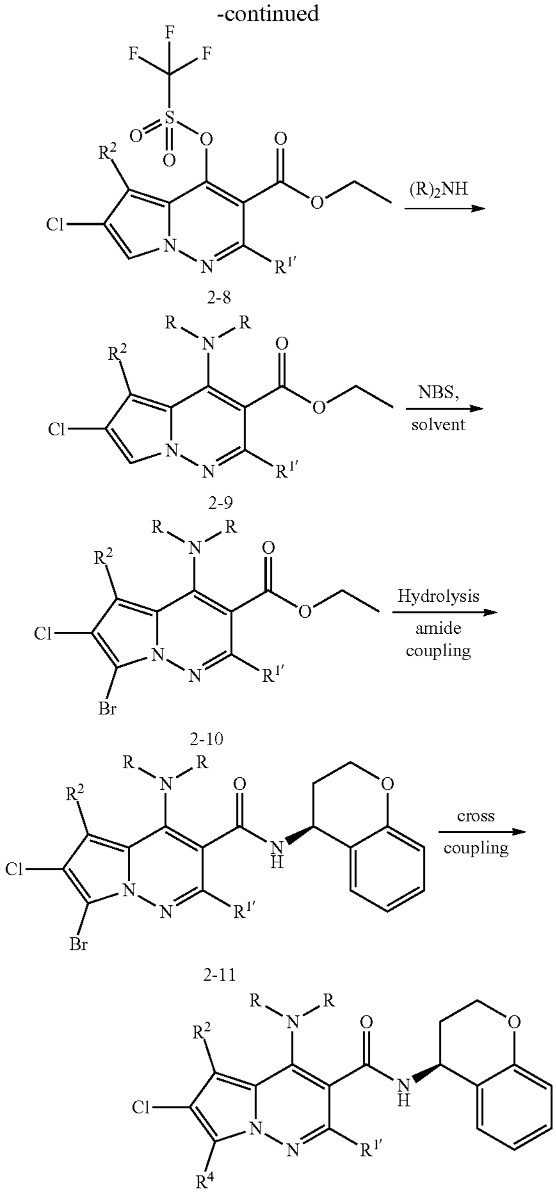

2-8

2-9

2-10

2-11

2-12

Examples

Preparation Examples

The Examples that follow are intended to only illustrate the present invention without restricting it. The compounds of the invention, including those of formulae (I), (IA), (I-1), (I-2), (I-3), (Ia), (Ib), (Ic), (Id), (Ie), (If) and (IA-1), or salts thereof, may be prepared by adopting one of the following reaction schemes. The starting materials for their preparation may be commercially available or can be prepared by methods known by persons of skill in the art and as described in the literature or may be an intermediate in any other of the schemes described herein. It will be appreciated that the following procedures may be modified by persons of skill in the art to prepare additional compounds according to the invention. For example, a person of skill in the art will understand that replacement of certain starting materials or the use of different intermediates will enable the preparation of different compounds of Formula (I), Formula (IA), (I-1), (I-2), (I-3), (Ia), (Ib), (Ic), (Id), (Ie), (If) and (IA-1).

The terms "ambient temperature" and "room temperature" are used interchangeably and designate a temperature of about 20° C. Although the following subject matter is described in some detail by way of illustration and example for purposes of clarity of understanding, it will be understood by those skilled in the art that certain changes and modifications can be practiced within the scope of the Examples.

Abbreviations:

| | |
|---|---|
| ACN | acetonitrile |
| Alox | aluminium oxide |
| Aq. | aqueous |
| Atm | atmosphere |
| ° C. | degree celsius |
| CyH/CH | cyclohexane |
| conc. | concentrated |
| DCC | N,N'-dicyclohexylmethanediimine |
| DCM | dichloromethane |
| 1,2-DCE | 1,2-dichloroethane |
| DEE/$Et_2O$ | diethyl ether |
| DIPE | diisopropyl ether |
| DIPEA | N,N-diisopropylethylamine |
| 1,2-DME | 1,2-dimethyl ether |
| DMF | N,N-dimethyformamide |
| DMSO | dimethyl sulfoxide |
| ESI-MS | electrospray ionisation mass spectrometry |
| EtOAc/EE/EA | ethyl acetate |
| ex | example |
| eq | equivalent |
| h | hour |
| HAc/HOAc | acetic acid |
| HATU | N,N,N',N'-tetramethyl-O-(7-azabenzotriazol-1-yl)uranium hexafluorophosphate |
| HCl | hydrochlorid acid |
| $HNO_3$ | nitric acid |
| HPLC | high performance liquid chromatography |
| iPrMgCl | isopropylmagnesium chloride |
| $K_3PO_4$ | tripotassium phosphate |
| LiHMDS | lithium-bis(trimethylsilyl)amide |
| LAH | lithium aluminum hydride |
| LiOH | lithium hydroxide |
| MeI | methyl iodide |
| MeOH | methanol |
| NaH | sodium hydride |
| $NaHCO_3$ | sodium bicarbonate |
| $Na_2SO_4$ | sodium sulfate |
| NBS | N-bromosuccinimide |
| NClS/NCS | N-chlorosuccinimide |
| $NH_3$ | ammonia |
| $NH_4Cl$ | ammonium chloride |
| NBS | N-bromosuccinimide |
| NIS | N-iodosuccinimide |
| NMP | N-methyl-2-pyrrolidone |
| min | minute |
| mL | milliliter |
| mmol | millimole |
| Pd/C | palladium on activated carbon |
| Pd(dppf)$Cl_2$ | [1,1'-bis(diphenylphosphino)ferrocene]dichloropalladium(II) |
| PE | petroleum ether |
| psi | pound per square inch |
| $PtO_2$ | platinum dioxide |
| RT | room temperature (about 20° C.) |
| $R_t$ | retention time |
| sat. | saturated |
| TBAF | tetra-n-butylammonium fluoride |
| tBuOH | tert-butyl alcohol |
| tBuOK | potassium tert-butoxide |
| TEA | triethylamine |
| TFA | trifluoroacetic acid |
| THF | tetrahydrofuran |
| TLC | thin-layer chromatography on $SiO_2$ |
| TMSOK | potassium trimethylsilanolate |

Some examples of Formula (I), Formula (IA), (I-1), (I-2), (I-3), (Ia), (Ib), (Ic), (Id), (Ie), (If) and (IA-1), or salts thereof, are derived after separation of racemic mixtures and obtained as enantiomerically pure products. The stereochemistry is in some cases arbitrarily assigned and the respective compound characterized by analytical methods.

Preparation Example 1: Compound A465. Compound A465 was prepared according to general Scheme 1 shown above as described below. In addition, the following compounds of the invention can be prepared by adapting general Scheme 1 and the reactions described below for the synthesis of example A465 as well as by employing and modifying reactions known in the literature (see for example WO2021030379, WO2012125886 and WO2012125893): A461, A462, A463, A464, A469, A466, A467, A468, A470, A471, A473, A474, A475, A476, A483, A484, A486, A487, A488, A489, A492, A494, A495, A496, A497, A498, A500.

1. Synthesis of 1-(3,5-dichlorophenyl)-4-hydroxy-2-methylbutan-1-one

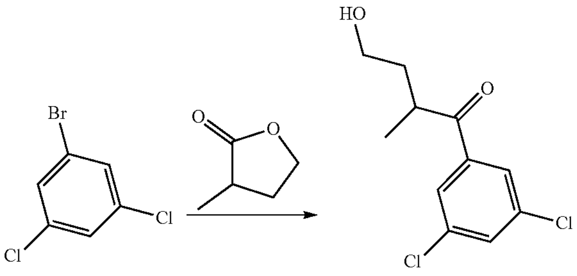

A mixture of 3.0 g (13.3 mmol) 1-bromo-3,5-dichlorobenzene in 50 mL THF anhydrous was cooled to −95° C. with a MeOH/nitrogen bath, 10.8 mL (17.3 mmol) tert-butyllithium was added dropwise, followed by 1.99 g (19.9 mmol) alpha-methyl-gamma-butyrolactone in 10 mL THF anhydrous. The reaction mixture was stirred at −85° C. for 1 h. The reaction mixture was quenched with sat. $NH_4Cl$ solution at −90° C. and the solution warmed to RT and extracted twice with EE. The organic layers are collected, dried, filtered and the filtrate is evaporated to obtain 3.6 g (27%) of the crude product as yellow oil.

2. Synthesis of 4-(3,5-dichlorophenyl)-3-methyl-4-oxobutanal

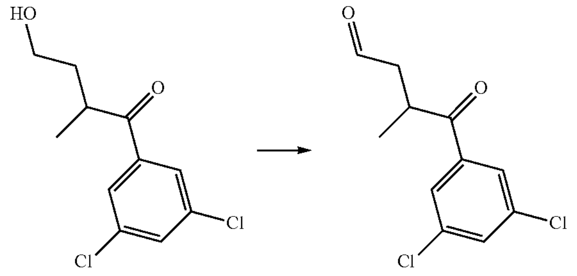

A mixture of 2.59 mL (26.42 mL) DMSO in 25 mL DCM was cooled to −78° C. 1.6 mL (18.9 mmol) oxalyl chloride was added dropwise and the solution was stirred for 15 min. 3.6 g (3.6 mmol) 1-(3,5-dichlorophenyl)-4-hydroxy-2-methylbutan-1-one in 8 mL DCM was added and the reaction mixture was stirred at −78° C. for 1 h. 11.67 mL (83.76 mmol) TEA was added and the solution warmed to RT and stirred at RT for 1.5 h. The reaction mixture was quenched with water and extracted with DCM. The organic layers were collected, dried, filtered and the filtrate was evaporated. The residue was purified by column chromatography (silica gel; PE/EtOAc) and the solvents were removed in vacuo to obtain 1.10 g (92.0%) of the product as yellow oil.

3. Synthesis of 2-[2-(3,5-dichlorophenyl)-3-methyl-1H-pyrrol-1-yl]-2,3-dihydro-1H-isoindole-1,3-dione

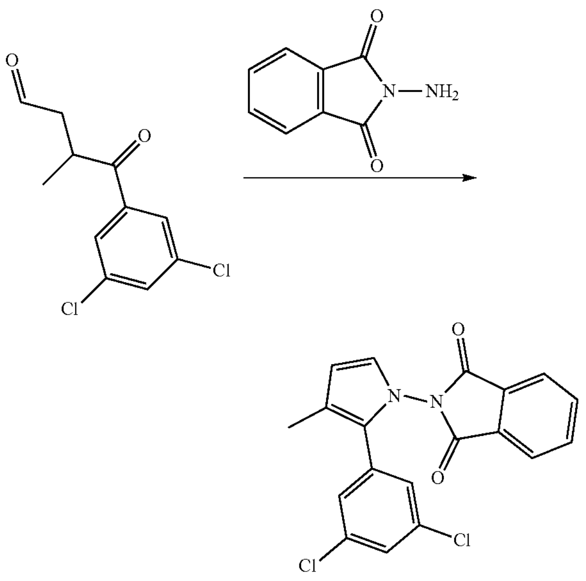

A mixture of 1.10 g (3.36 mmol) 4-(3,5-dichlorophenyl)-3-methyl-4-oxobutanal, 600 mg (3.7 mmol) N-amino phthalimide and 9.26 mL (37.0 mmol) was stirred at 100° C. for 1 h. The reaction mixture was evaporated and the crude residue was crystallized with PE/EE to obtain 720 mg (57.0%) of 2-[2-(3,5-dichlorophenyl)-3-methyl-1H-pyrrol-1-yl]-2,3-dihydro-1H-isoindole-1,3-dione as a white solid.

4. Synthesis of 2-(3,5-dichlorophenyl)-3-methyl-1H-pyrrol-1-amine

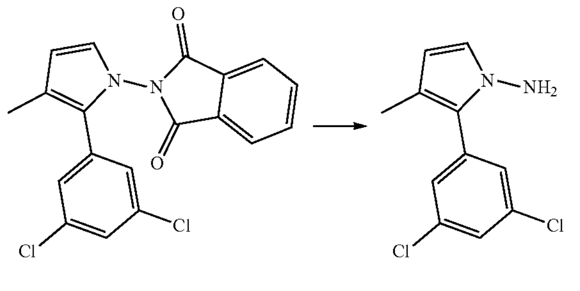 [SMILES: Cc1ccn(N2C(=O)c3ccccc3C2=O)c1-c1cc(Cl)cc(Cl)c1 ; Cc1ccn(N)c1-c1cc(Cl)cc(Cl)c1]

A mixture of 1.1 g (3.0 mmol)$_2$-[2-(3,5-dichlorophenyl)-3-methyl-1H-pyrrol-1-yl]-2,3-dihydro-1H-isoindole-1,3-dione and 0.2 mL (7.4 mmol) hydrazine monohydrate in 12 mL EtOH was stirred at reflux for 2 h. The reaction mixture was filtered and the filtrate was evaporated. The crude residue was purified by column chromatography (silica gel; PE/EtOAc) and the solvents were removed in vacuo to obtain 650 mg (91%) of the product as white solid 5. Synthesis of methyl 7-(3,5-dichlorophenyl)-6-methyl-4-(propan-2-yl)pyrrolo[1,2-b]pyridazine-3-carboxylate

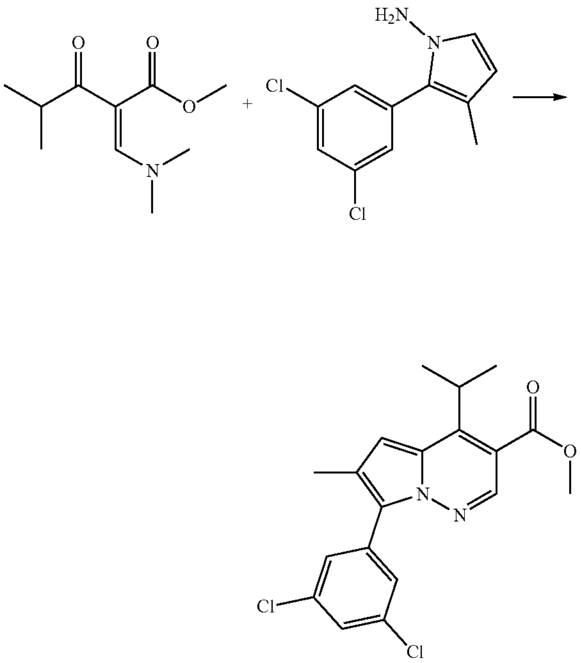

To a mixture of 1.1 g (4.6 mmol) of 2-(3,5-dichlorophenyl)-3-methyl-1H-pyrrol-1-amine in 40 mL of methanol were added 820.0 mg (4.1 mmol) of methyl (2Z)-2-(dimethylamino)-methylidene]-4-methyl-3-oxopentanoate and 1.2 mL of 4M HCl in dioxane and the mixture was stirred at 80° C. for 3 h. After evaporation of the solvents, the crude residue was purified by column chromatography (silica gel; cyclohexane/EtOAc) and the solvents were removed in vacuo to obtain 380 mg (24%) of the product as a solid.

6. Synthesis of 7-(3,5-dichlorophenyl)-6-methyl-4-(propan-2-yl)pyrrolo[1,2-b]pyridazine-3-carboxylic acid

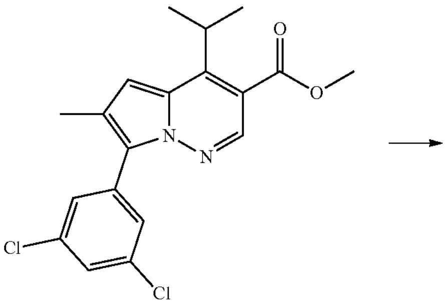

-continued

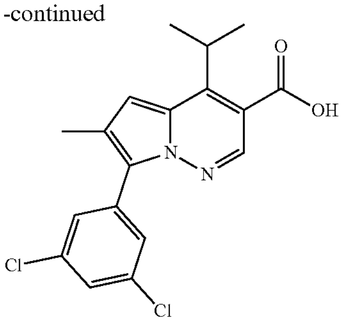

To a mixture of 94.5 mg (0.2 mmol) of methyl 7-(3,5-dichlorophenyl)-6-methyl-4-(propan-2-yl)pyrrolo[1,2-b]pyridazine-3-carboxylate and 1.5 mL solution of LiOH (1M) was added 1.5 mL of THF. After stirring for 2 h at 40° C. the reaction mixture was heated to 60° C. over night. Then, the solution was acidified with 4 M HCl at RT and the resulting residue was filtered off and washed with 2 mL of $H_2O$. After drying of the residue, 84 mg (93.0%) of 7-(3,5-dichlorophenyl)-6-methyl-4-(propan-2-yl)pyrrolo[1,2-b]pyridazine-3-carboxylic acid were obtained as a yellow solid.

7. Synthesis of 7-(3,5-dichlorophenyl)-N-[(4S)-3,4-dihydro-2H-1-benzopyran-4-yl]-6-methyl-4-(propan-2-yl)pyrrolo[1,2-b]pyridazine-3-carboxamide (A465)

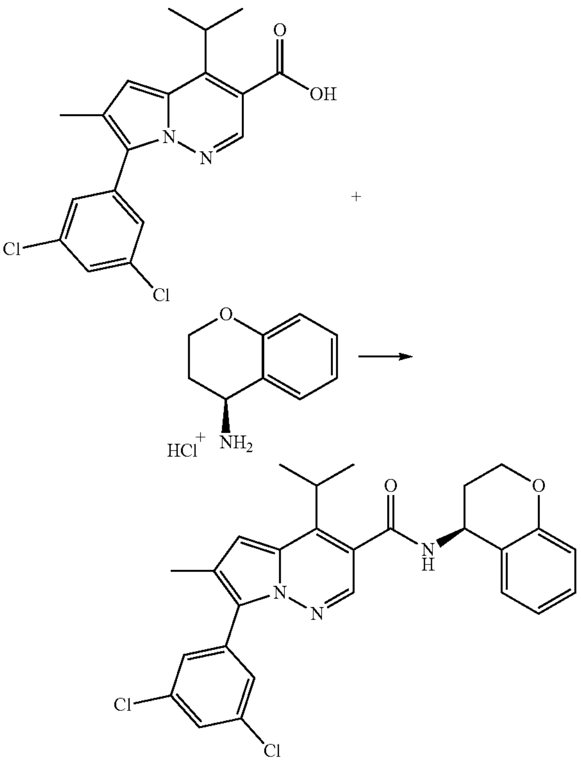

A465

A solution of 350 mg (0.9 mmol) of 7-(3,5-dichlorophenyl)-6-methyl-4-(propan-2-yl)pyrrolo[1,2-b]pyridazine-3-carboxylic acid in 8 mL of DMF was treated with 650 μl of DIPEA and 410 mg (1.7 mmol) of HATU and stirred for 10 min. After addition of 200 mg (1.1 mmol) of(S)-chroman-4-amine hydrochloride the mixture was stirred for 16 h at room temperature. The solvents were removed in vacuo and the residue was purified by column chromatography (silica gel; PE/EtOAc). After removal of the solvents in vacuo 310 mg (65.0%) of 7-(3,5-dichlorophenyl)-N-[(4S)-3,4-dihydro-2H-1-benzopyran-4-yl]-6-methyl-4-(propan-2-yl)pyrrolo[1,2-b]pyridazine-3-carboxamide (A465) were obtained as white solid. (ESI, m/z): 495 $[M+H]^+$ Preparation Example 2: Synthesis of 3,4-dihydro-2H-1,4-benzoxazin-4-amine 3,4-dihydro-2H-1,4-benzoxazin-4-amine, which is used in the synthesis of compounds of the invention containing Ring System D (see Table 3 above) such as compounds A479, A482, A494, A495, A496, A497, A498, A516 and A565, is prepared according to the process described below.

1. Synthesis of 4-nitroso-3,4-dihydro-2H-1,4-benzoxazine

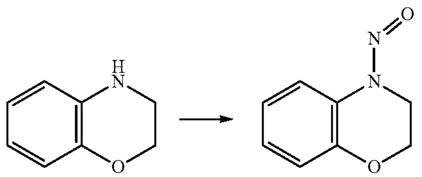 [SMILES: c1ccc2c(c1)NCCO2 ; O=NN1CCOc2ccccc21]

Into a 500 mL round-bottom flask. were added 3,4-dihydro-2H-1,4-benzoxazine (3.0 g, 22.2 mmol) and HCl (300 ml, 3M) and $NaNO_2$ (1.8 g, 26.1 mmol) was added in portions at 2 h at 0° C. under nitrogen atmosphere. The resulting mixture was concentrated under reduced pressure. The residue was purified by silica gel column chromatography, eluted with PE/EA (10:1) to afford 4-nitroso-3,4-dihydro-2H-1,4-benzoxazine (2.7 g, 75%) as a yellow oil.

2. Synthesis of 3,4-dihydro-2H-1,4-benzoxazin-4-amine

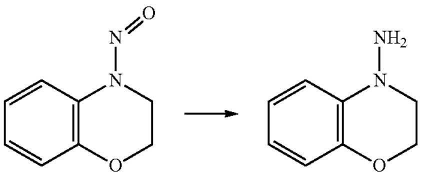 [SMILES: O=NN1CCOc2ccccc21 ; NN1CCOc2ccccc21]

Into a 500 mL round-bottom flask. were added 4-nitroso-3,4-dihydro-2H-1,4-benzoxazine (2.7 g, 19.2 mmol) and THF (300 ml) and LAH (1.35 g, 1.9 mmol) was added in portions at 2 h at 0° C. under nitrogen atmosphere. The resulting mixture was concentrated under reduced pressure. The residue was purified by silica gel column chromatography, eluted with PE/EA (10:1) to afford 3,4-dihydro-2H-1,4-benzoxazin-4-amine (2.2 g, 45%) as a yellow oil.

Preparation Example 3: Scheme 3 below describes the synthesis of intermediate compounds INT-1, INT-2 and INT-3, which correspond respectively to compounds 2-1 wherein $R^{1'}$ and $R^2$ are hydrogen; compound 2-4 wherein $R^1$ is tert-butyl, $R^2$ and $R^{1'}$ are hydrogen and compound and $R^3$ is chloro; and compound 2-5 wherein $R^1$ is tert-butyl, $R^2$ and $R^{1'}$ are hydrogen and compound and $R^3$ is methyl. These intermediates are used to prepare various compounds of the invention as depicted in Scheme 2 and described in detail below.

Scheme 3

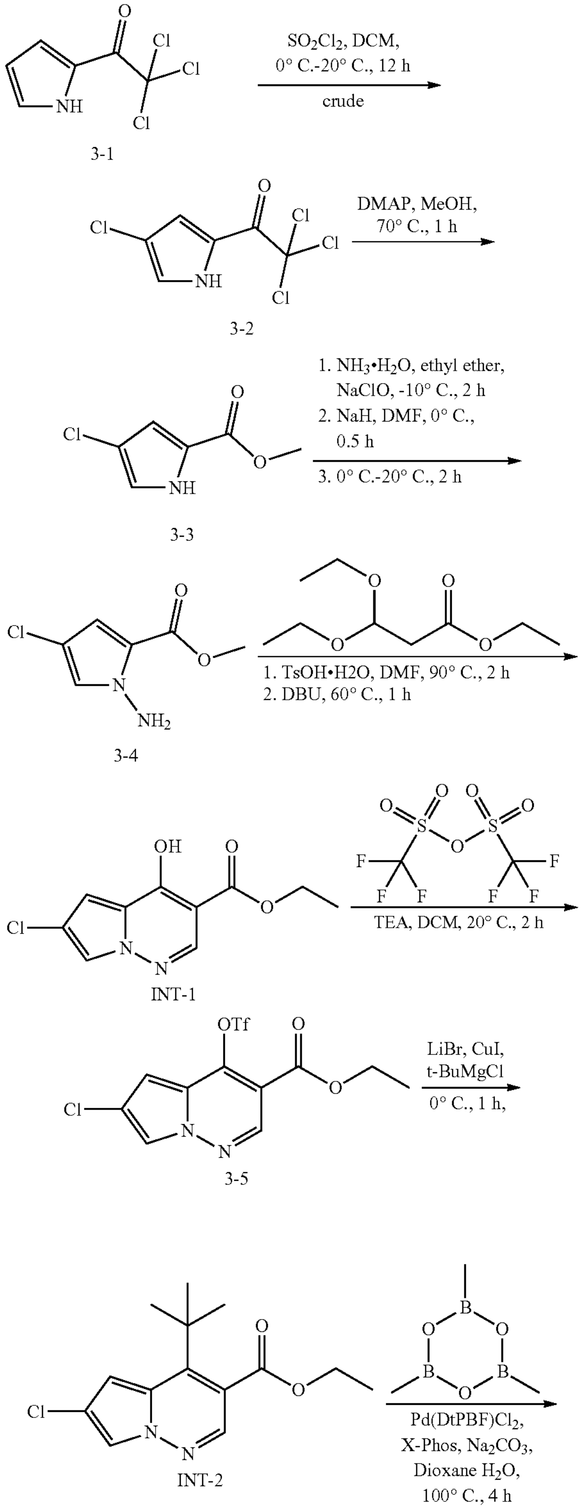

-continued

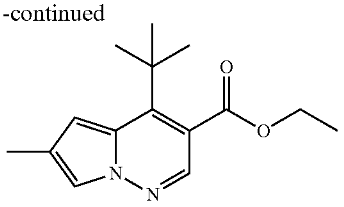

INT-3

1. Synthesis of 2,2,2-trichloro-1-(4-chloro-1H-pyrrol-2-yl) ethanone (3-2)

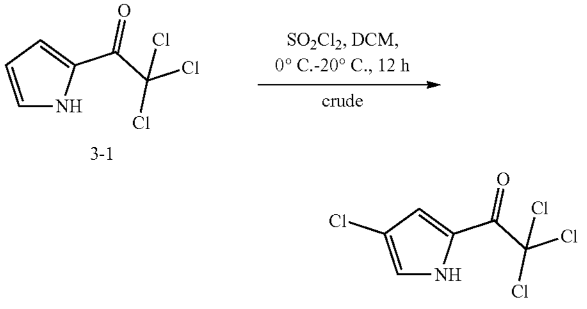

3-1

3-2

Into a 5.0 L 3-necked round-bottom flask, was placed 2,2,2-trichloro-1-(1H-pyrrol-2-yl) ethanone (3-1, 600 g, 2824.2 mmol) in DCM (4.0 L). To this was added $SO_2Cl_2$ (419.30 g, 3106.6 mmol) dropwise at 0° C. The reaction mixture was stirred for 12 h at 20° C. The resulting mixture was adjusted to pH 8 with aqueous $Na_2CO_3$ (2 M). The resulting mixture was extracted with DCM (2.0 L x 3). The combined organic layers were dried over anhydrous $Na_2SO_4$ and concentrated under reduced pressure to afford 2,2,2-trichloro-1-(4-chloro-1H-pyrrol-2-yl) ethanone (3-2, 730 g, crude) as a black solid which was used directly in the next step.

2. Synthesis of methyl 4-chloro-1H-pyrrole-2-carboxylate (3-3)

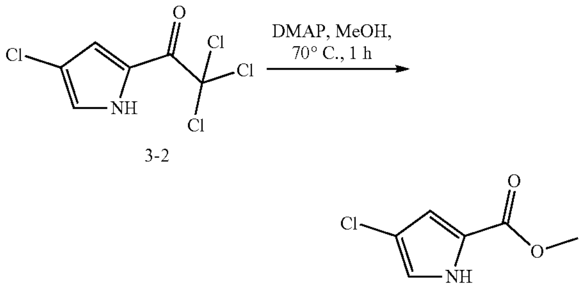

3-2

3-3

Into a 3.0 L 3-necked round-bottom flask, was placed 2,2,2-trichloro-1-(4-chloro-1H-pyrrol-2-yl) ethanone (3-2, 730 g, crude), MeOH (2.5 L) and DMAP (72.34 g, 592.1 mmol). The reaction mixture was stirred at 70° C. for 1 h. The mixture was allowed to cool down to room temperature and concentrated under reduced pressure. The residue was purified by silica gel column chromatography, eluted with PE/EA (10/1) to afford methyl 4-chloro-1H-pyrrole-2-carboxylate (3-3, 330 g, 73% 2 steps) as a white solid.

3. Synthesis of methyl 1-amino-4-chloropyrrole-2-carboxylate (3-4)

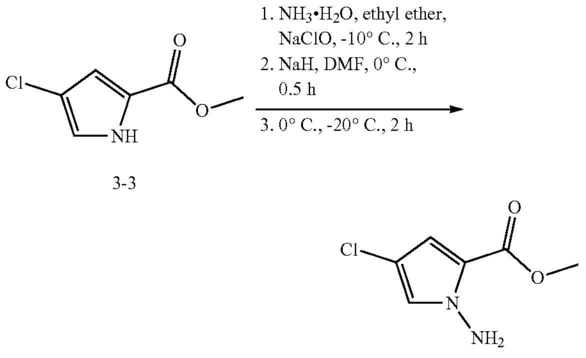

3-3

3-4

Into a 5 L 3-necked round-bottom flask, was placed $NH_4Cl$ (80 g, 1495.6 mmol), ethyl ether (1.5 L) and $NH_3.H_2O$(120 mL). To this was added NaClO(1.7 L) dropwise at −10° C. The reaction mixture was stirred at −10° C. for 2 h. Then the aqueous phase was removed by separation funnel. The organic layer was washed with 1.0 L of cooled brine. The organic layer (1.5 L) was dried over anhydrous $Na_2SO_4$ and stored at −40° C. for 1 h. Into another 2.0 L 3-necked round-bottom flask was placed methyl 4-chloro-1H-pyrrole-2-carboxylate (3-3, 80 g, 501.3 mmol) in DMF (800 mL). This was followed by addition of NaH (30.08 g, 752.0 mmol, 60%) in portion at 0° C. The reaction mixture was stirred at 0° C. for 30 min. Then the above organic layers (1.5 L) were added. The combined reaction mixture was stirred at 20° C. for 2 h. The reaction was then quenched by the addition of 600 mL of $Na_2S_2O_4$ Saturated aqueous solution and the reaction mixture was stirred for 15 min. The resulting mixture was extracted with EA (3×1.0 L). The combined organic layers were dried over anhydrous $Na_2SO_4$ and concentrated under reduced pressure. The reaction was repeated one more time and the combined residue was purified by silica gel column chromatography, eluted with PE/EA (20/1) to afford methyl 1-amino-4-chloropyrrole-2-carboxylate (3-4, 188 g, 71%) as a white solid.

4. Synthesis of ethyl 6-chloro-4-hydroxypyrrolo[1,2-b]pyridazine-3-carboxylate (INT-1)

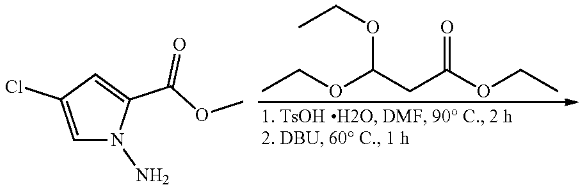

3-4

-continued

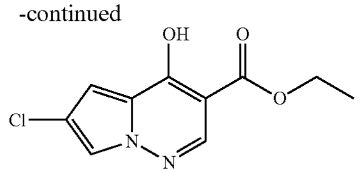

INT-1

Into a 3.0 L round-bottom flask, was placed methyl 1-amino-4-chloropyrrole-2-carboxylate (3-4, 150 g, 859.2 mmol) in DMF (1.5 L) and ethyl 3,3-diethoxypropanoate (196.15 g, 1031.0 mmol) and PTSA (22.19 g, 128.9 mmol) were added. The reaction mixture was stirred at 90° C. for 2 h. The mixture was allowed to cool down to 60° C. Then the DBU (261.61 g, 1718.4 mmol) was added at 60° C. The reaction mixture was stirred at 60° C. for 1 h. The mixture was allowed to cool down to room temperature. The resulting mixture was diluted with EA (4.0 L) and washed with 3×1.0 L of water. The resulting solution was dried $Na_2SO_4$ and concentrated under reduced pressure. The crude product was stirred as a slurry with EtOH/water (3/1) to afford ethyl 6-chloro-4-hydroxypyrrolo[1,2-b]pyridazine-3-carboxylate (INT-1, 127 g, 61%) as a white solid after filtration. (ES, m/z): 239 $[M-H]^-$; $^1H$ NMR (300 MHz, $CDCl_3$, ppm): δ 12.28 (s, 1H), 8.30 (s, 1H), 7.69 (d, J=2.0 Hz, 1H), 6.89 (d, J=1.6 Hz, 1H), 4.44 (q, J=7.2 Hz, 2H), 1.43 (t, J=7.2 Hz, 3H).

5. Synthesis of ethyl 6-chloro-4-(trifluoromethanesulfonyloxy)pyrrolo[1,2-b]pyridazine-3-carboxylate (3-5)

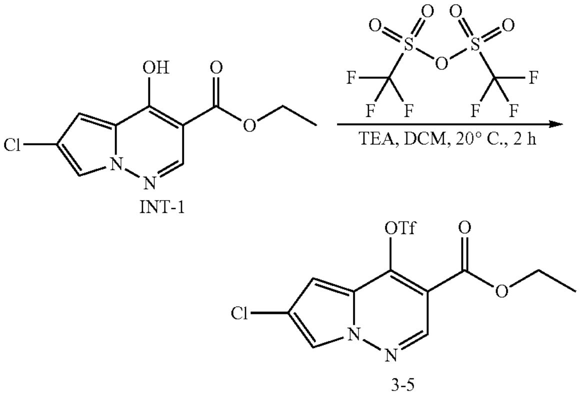

INT-1

3-5

Into a 2.0 L round-bottom flask, was placed ethyl 6-chloro-4-hydroxypyrrolo[1,2-b]pyridazine-3-carboxylate (INT-1, 82 g, 340.8 mmol), DCM (800 mL), TEA (103.44 g, 1022.3 mmol). To this was added triflic anhydride (153.82 g, 545.2 mmol) dropwise at 0° C. The reaction mixture was stirred at 20° C. for 2 h. The resulting mixture was diluted with DCM (1.0 L) and washed with 3×500 mL of water. The organic phase was collected and dried over $Na_2SO_4$ and concentrated under reduced pressure. The residue was purified by silica gel column chromatography, eluted with PE/EA (50/1) to afford ethyl 6-chloro-4-(trifluoromethanesulfonyloxy)pyrrolo[1,2-b]pyridazine-3-carboxylate (3-5, 90.5 g, 71%) as a yellow solid.

6. Synthesis of ethyl 4-tert-butyl-6-chloropyrrolo[1,2-b]pyridazine-3-carboxylate (INT-2)

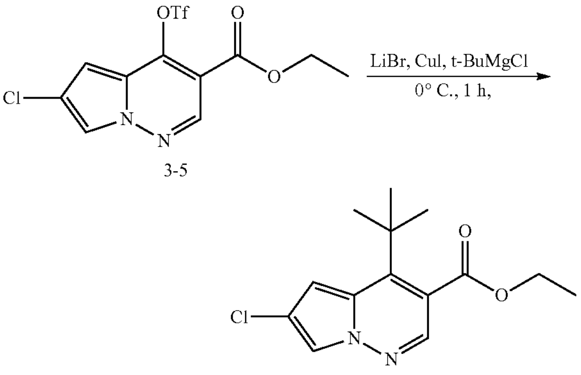

3-5

INT-2

Into a 2.0 L three necks round-bottom flask, was placed ethyl 6-chloro-4-(trifluoromethanesulfonyloxy)pyrrolo[1,2-b]pyridazine-3-carboxylate (3-5, 62 g, 166.3 mmol), THF (1.2 L). To this was added LiBr (108.35 g, 1247.6 mmol) and CuI (237.62 g, 1247.6 mmol) at 0° C. The reaction mixture was stirred at 0° C. for 30 min. This was followed addition of tert-butylmagnesium chloride (38.88 g, 332.7 mmol) at 0° C. The reaction mixture was stirred at 0° C. for 30 min. The reaction was quenched by the addition of $NH_4Cl$ (4 M in $H_2O$, 1.0 L) at 0° C. The mixture was extracted with EA (3×500 mL). The organic phase was collected and dried over $Na_2SO_4$ and concentrated under reduced pressure. The residue was purified by silica gel column chromatography, eluted with PE/EA (25/1) to afford ethyl 4-tert-butyl-6-chloropyrrolo[1,2-b]pyridazine-3-carboxylate (INT-2, 42.5 g, 91%) as a yellow oil.

7. Synthesis of ethyl 4-tert-butyl-6-methylpyrrolo[1,2-b]pyridazine-3-carboxylate (INT-3)

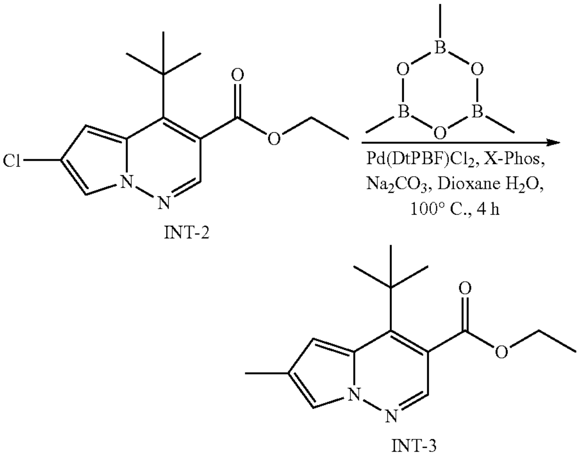

INT-2

INT-3

Into a 1.0 L round bottom flask, was placed ethyl 4-tert-butyl-6-chloropyrrolo[1,2-b]pyridazine-3-carboxylate (INT-2, 42 g, 149.6 mmol), dioxane (500 mL), $H_2O$(25 mL, 1387.7 mmol), $Na_2CO_3$ (39.64 g, 374.0 mmol), trimethylboroxine (65.73 g, 524.0 mmol), X-Phos (7.13 g, 14.7 mmol) and Pd(DtBPF)$Cl_2$ (9.75 g, 14.9 mmol) under nitrogen atmosphere. The reaction mixture was stirred at 100° C. for 4 h. The mixture was allowed to cool down to room temperature. The resulting mixture was diluted with EA (1.5 L) and washed with 3×500 mL of water. The organic phase was collected and dried over $Na_2SO_4$ and concentrated under reduced pressure. The residue was purified by silica gel column chromatography, eluted with PE/EA (20/1) to afford ethyl 4-tert-butyl-6-methylpyrrolo[1,2-b]pyridazine-3-carboxylate (INT-3, 31 g, 79%) as a yellow oil. (ES, m/z): 261 $[M+H]^+$; $^1H$ NMR (300 MHz, $CDCl_3$, ppm): δ 7.75 (s, 1H), 7.54 (s, 1H), 6.68 (s, 1H), 4.36 (q, J=7.2 Hz, 2H), 2.37 (s, 3H), 1.58 (s, 9H), 1.40 (t, J=7.2 Hz, 3H).

Utilizing intermediates INT-1, INT-2 and INT-3 described above, the following compounds of the invention can be obtained by adapting the process shown in Scheme 2: A477, A478, A479, A480, A481, A482, A490, A491, A493, A499, A501, A502, A503, A504, A505, A506, A507, A508, A509, A510, A511, A512, A513, A514, A515, A516, A517, A518, A519, A520, A521, A522, A523, A524; A525, A526, A527, A528, A529, A530, A531, A532, A533, A534, A535, A536a, A536b, A538, A540, A541, A542, A544, A545, A546, A547, A548, A549, A550, A551, A552, A553, A554, A556, A557, A558, A559, A560, A561, A562, A563, A564, A565, A566, A567, A568.

It is understood by persons of ordinary skill in the art that the order of reactions depicted in the chemical schemes described herein may be changed according to the reactivity of substituents. Furthermore, it will be understood that reactants known in the literature can be prepared according to published procedures. In addition, it is understood that in case racemic mixtures are obtained by the chemical reactions described herein, desired enantiomers may be isolated in pure form by known purification methods known in the art, including but not limited to chiral HPLC methods.

Preparation Example 4:7-(2,3-dichloro-5-fluorophenyl)-N-[(4S)-3,4-dihydro-2H-1-benzopyran-4-yl]-4-(dimethylamino)-6-methylpyrrolo[1,2-b]pyridazine-3-carboxamide (A493)

Compound A493 was prepared according to the general process described in Scheme 2. The specific synthesis details are provided below.

1. Synthesis of ethyl 6-chloro-4-(trifluoromethanesulfonyloxy)pyrrolo[1,2-b]pyridazine-3-carboxylate (3-5)

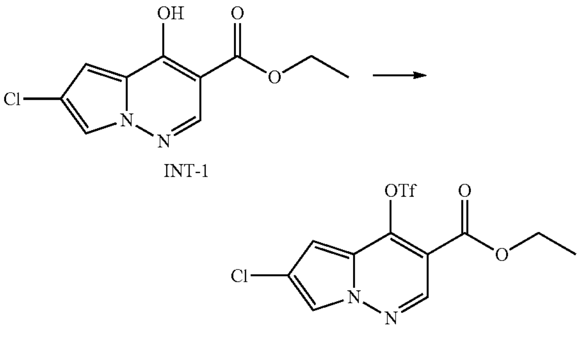

INT-1

3-5

To a solution of 613.0 mg (2.5 mmol) of ethyl 6-chloro-4-hydroxypyrrolo[1,2-b]pyridazine-3-carboxylate (INT-1) and 776 μL (5.6 mmol) triethylamine in 5 mL of dichloromethane was added 471 μL (2.8 mmol) trifluoromethane anhydride at 0° C. The solution was stirred over night at RT. Afterwards, water was added and the layers separated by phase transfer cartridge. The organic layer was dried over $Na_2SO_4$ and the solvent was evaporated under reduced pressure to yield 1.2 g of crude product as a brown oil. (3-5, ESI, m/z): 373 $[M+H]^+$.

2. Synthesis of ethyl 6-chloro-4-(dimethylamino)pyrrolo[1,2-b]pyridazine-3-carboxylate (4-1)

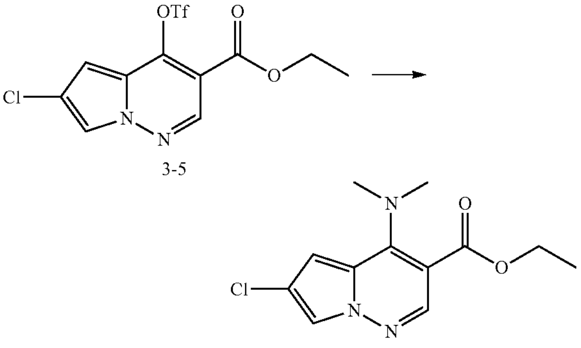

3-5

4-1

A solution of 31.0 g (83.1 mmol) of ethyl 6-chloro-4-(trifluoromethanesulfonyloxy)pyrrolo[1,2-b]pyridazine-3-carboxylate (3-5) in 300 mL of ethanol was added 40 mL (0.22 mol) of dimethylamine in ethanol (5.6 mol/L) and the solution heated to reflux for 15 min. After cooling to RT, the solution was diluted with ethyl acetate, washed with 1N HCl, 10% $Na_2CO_3$ solution and brine. After filtering through Celite, the solvent was evaporated under reduced pressure. Silica gel chromatography (CH/EA 9:1-2:8) yielded 22.3 g (70%) of 4-1 as yellow solid. (ESI, m/z): 268 $[M+H]^+$.

3. Synthesis of ethyl 4-(dimethylamino)-6-methylpyrrolo[1,2-b]pyridazine-3-carboxylate (4-2)

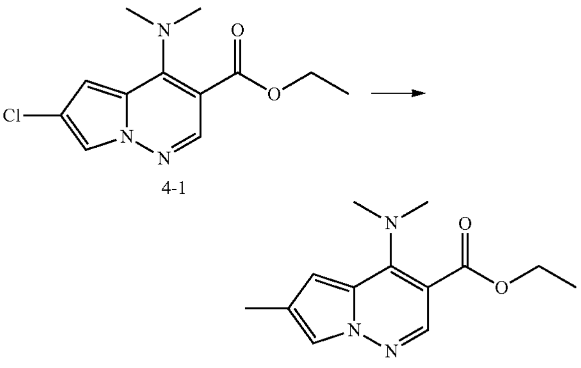

4-1

4-2

To a solution of 7.4 g (27.6 mmol) ethyl 6-chloro-4-(dimethylamino)pyrrolo[1,2-b]pyridazine-3-carboxylate (4-1) in 150 mL of dioxane in a three-necked flask was added 10 mL trimethylboroxine and 80 mL of 1M $Na_2CO_3$ solution. The mixture was purged with Argon for 5 min then heated to 50° C. and treated with 3.0 g (3.5 mmol) XPHOS Pd G3 under Argon and stirred for 1 h at 90° C. After cooling to RT, the solution was diluted with ethyl acetate, washed with 10% $Na_2CO_3$ solution and brine. After filtering through Celite, the solvent was evaporated under reduced pressure. Silica gel chromatography (CH/EA 95:5-1:9) yielded 5.6 g (81%) of the title compound (4-2) as yellow oil that solidifies upon standing. (ESI, m/z): 248 $[M+H]^+$.

4. Synthesis of ethyl 7-bromo-4-(dimethylamino)-6-methylpyrrolo[1,2-b]pyridazine-3-carboxylate (4-3)

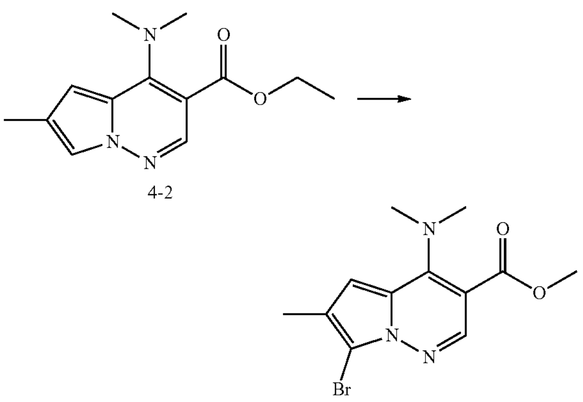

4-2

4-3

To a solution of 5.6 g (22.6 mmol) ethyl 4-(dimethylamino)-6-methylpyrrolo[1,2-b]pyridazine-3-carboxylate (4-2) in 120 mL DMF was added 3.9 g (21.9 mmol) NBS at 0° C. and the mixture stirred for 1 h at RT. The solution was diluted with ethyl acetate, washed with 10% $Na_2CO_3$ solution and brine. After filtering through Celite, the solvent was evaporated under reduced pressure. Silica gel chromatography (CH/EA 95:5-2:8) yielded 6.4 g (86%) of the title compound (4-3) as yellow solid. (ESI, m/z): 327 $[M+H]^+$.

5. Synthesis of potassium 7-bromo-4-(dimethylamino)-6-methylpyrrolo[1,2-b]pyridazine-3-carboxylate (4-4)

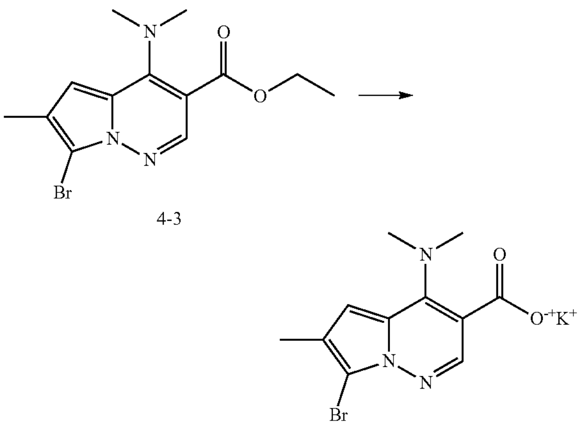

4-3

4-4

To a solution of 14.6 g (44.7 mmol) of ethyl 7-bromo-4-(dimethylamino)-6-methylpyrrolo[1,2-b]pyridazine-3-carboxylate (4-3) in 400 mL THF was added 12.7 g (89.0 mmol) TMSOK and the mixture stirred at 70° C. for 7 h. After evaporation of volatiles 15 g of crude product (4-4) was obtained and directly used in the next step. (ESI, m/z): 337 $[M+H]^+$.

6. Synthesis of 7-bromo-N-[(4S)-3,4-dihydro-2H-1-benzopyran-4-yl]-4-(dimethylamino)-6-methylpyrrolo[1,2-b]pyridazine-3-carboxamide (4-5)

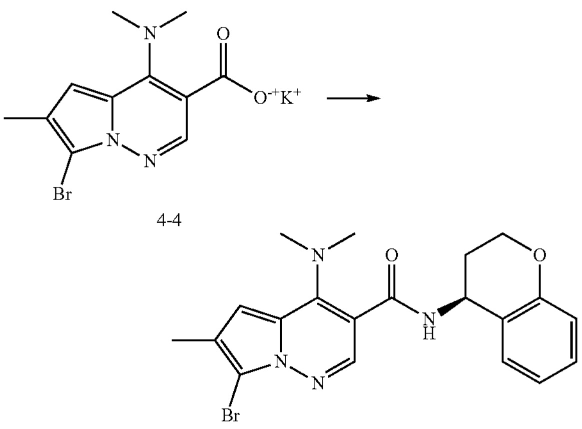

4-4

4-5

To a solution of 15 g (35.6 mmol) potassium 7-bromo-4-(dimethylamino)-6-methylpyrrolo[1,2-b]pyridazine-3-carboxylate (4-4) in 400 mL of DMF was added 28 mL (159.9 mmol) DIPEA and 24.0 g (63.1 mmol) HATU at RT. After stirring for 5 min at RT 13 g (70.0 mmol) (S)-chroman-4-amine hydrochloride were added and the mixture stirred for 30 min at 50° C. After cooling to RT, the solution was diluted with ethyl acetate, washed with 1N HCl, 10% $Na_2CO_3$ solution and brine. After filtering through Celite, the solvent was evaporated under reduced pressure to about 200 mL and the product crystallized. The filtered solids were washed with little EA and dried to yield 10.6 g of product which was combined with the remaining mother liquor purified via silica gel chromatography (CH/EA 85:15-3:7) to yield a total of 11.9 g (77%) of the title compound (4-5) as beige solid. (ESI, m/z): 430 $[M+H]^+$.

7. Synthesis of 7-(2,3-dichloro-5-fluorophenyl)-N-[(4S)-3,4-dihydro-2H-1-benzopyran-4-yl]-4-(dimethylamino)-6-methylpyrrolo[1,2-b]pyridazine-3-carboxamide (A493)

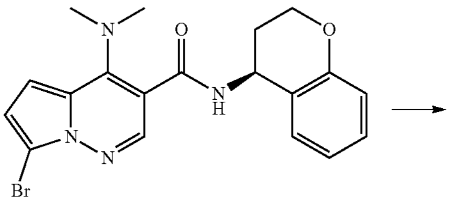

4-5

-continued

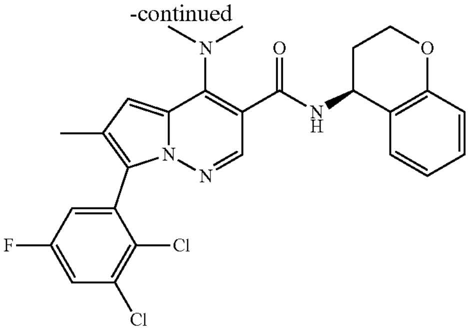

A493

To a solution of 720 mg (1.5 mmol) of 7-bromo-N-[(4S)-3,4-dihydro-2H-1-benzopyran-4-yl]-4-(dimethylamino)-6-methylpyrrolo[1,2-b]pyridazine-3-carboxamide (4-5) in 25 mL of dioxane was added 430 mg (2.0 mmol)$_{2,3}$-dichloro-5-fluorophenyl) boronic acid under Argon followed by 200 mg (0.3 mmol) of 1,1'-Bis-(di-tert-butylphosphino-) ferrocen-palladiumdichloride and 3 mL $Na_2CO_3$ solution (2 mol/L). The mixture was stirred for 2 h at 80° C. in a sealed vessel. After cooling to RT, the solution was diluted with water and extracted with EA. After combining the organic layers, the solvent was evaporated under reduced pressure. Silica gel chromatography (CH to CH/EA 8:2) yielded 680 mg (51%) of the title compound (A493) as brown solid. (ESI, m/z): 514 $[M+H]^+$.

Preparation Example 5: Synthesis of 4-tert-butyl-6-chloro-7-(2,3-dichloro-5-fluorophenyl)-N-[(4S)-3,4-dihydro-2H-1-benzopyran-4-yl]pyrrolo[1,2-b]pyridazine-3-carboxamide (A502)

Compound A502 was prepared according to the general process described in Scheme 2. The specific synthesis details are provided below.

1. Synthesis of ethyl 7-bromo-4-tert-butyl-6-chloro-pyrrolo[1,2-b]pyridazine-3-carboxylate (5-1)

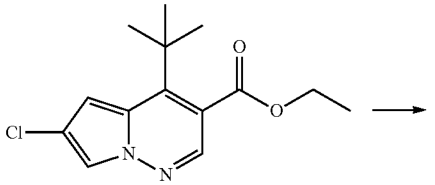

INT-2

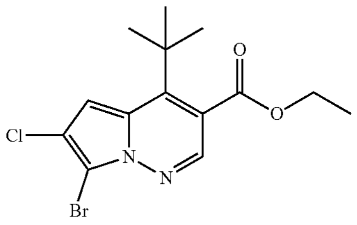

5-1

To a solution of 325 mg (1.0 mmol) ethyl 4-tert-butyl-6-chloropyrrolo[1,2-b]pyridazine-3-carboxylate (INT-2) in 5 mL DMF was added 166 mg (0.9 mmol) NBS at RT and the mixture stirred for 1 h at RT. The solution was diluted with water and extracted with ethyl acetate. The combined organic layers were dried over $Na_2SO_4$ and the solvent was evaporated under reduced pressure. Preparative HPLC ($ACN/H_2O/TFA$) yielded 323 mg (86%) of the title compound (5-1) as yellow solid. (5-1, ESI, m/z): 360 $[M+H]^+$.

2. Synthesis of ethyl 4-tert-butyl-6-chloro-7-(2,3-dichloro-5-fluorophenyl)pyrrolo[1,2-b]pyridazine-3-carboxylate (5-2)

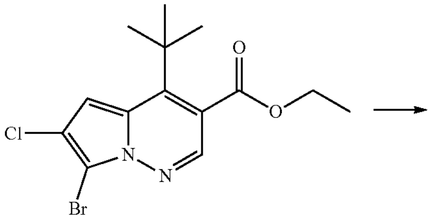

5-1

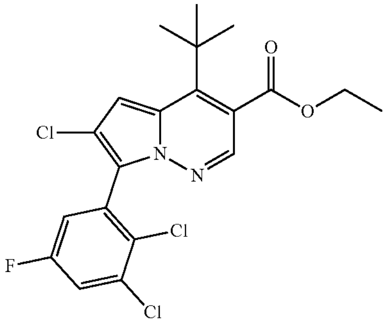

5-2

To a solution of 100 mg (0.27 mmol) of ethyl 7-bromo-4-tert-butyl-6-chloropyrrolo[1,2-b]pyridazine-3-carboxylate (5-1) in 3 mL of dioxane was added 63 mg (0.3 mmol)$_{2,3}$-dichloro-5-fluorophenyl) boronic acid under Argon followed by 0.5 mL $Na_2CO_3$ solution (2 mol/L) and 45 mg (0.05 mmol) of 1,1'-Bis-(di-tert-butylphosphino-) ferrocen-palladiumdichloride. The mixture was stirred for 2 h at 80° C. in a sealed vessel. After cooling to RT, the solution was diluted with water and extracted with EA. After combining the organic layers were dried over $Na_2SO_4$ and the solvent was evaporated under reduced pressure. Preparative HPLC ($ACN/H_2O/TFA$) yielded 45 mg (37%) of the title compound (5-2) as brown solid. (ESI, m/z): 444 $[M+H]^+$.

3. Synthesis of 4-tert-butyl-6-chloro-7-(2,3-dichloro-5-fluorophenyl)pyrrolo[1,2-b]pyridazine-3-carboxylic acid (5-3)

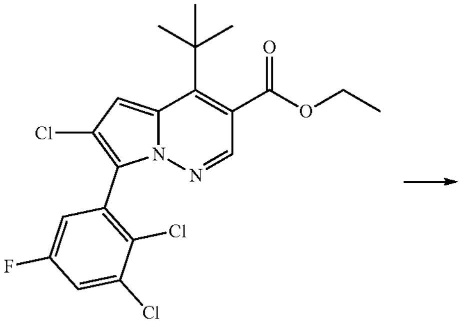

5-2

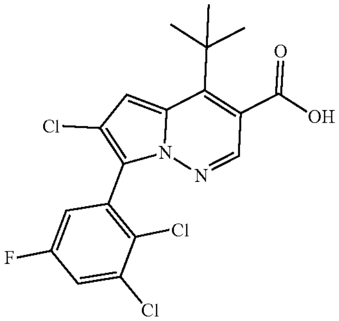

5-3

To a solution of 45 mg (0.1 mmol) ethyl 4-tert-butyl-6-chloro-7-(2,3-dichloro-5-fluorophenyl)pyrrolo[1,2-b]pyridazine-3-carboxylate (5-2) in 1 mL dioxane/ethanol was added 0.5 mL NaOH-solution (4 mol/L) at RT and the mixture stirred for 12 h at 90° C. After cooling to RT, the solution was treated with HCl (4 mol/L) until acidic pH at 0° C. and diluted with DCM. After filtration through a phase separation cartridge, the organic phase was evaporated under reduced pressure and the crude title product (5-3) directly used in the subsequent step. (ESI, m/z): 416 $[M+H]^+$.

4. Synthesis of 4-tert-butyl-6-chloro-7-(2,3-dichloro-5-fluorophenyl)-N-[(4S)-3,4-dihydro-2H-1-benzopyran-4-yl]pyrrolo[1,2-b]pyridazine-3-carboxamide (A502)

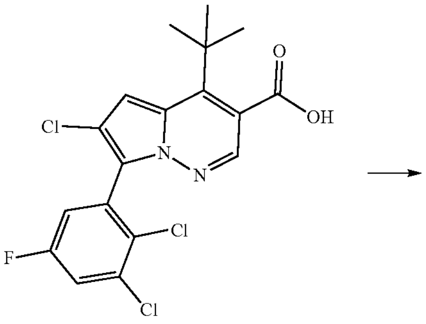

5-3

-continued

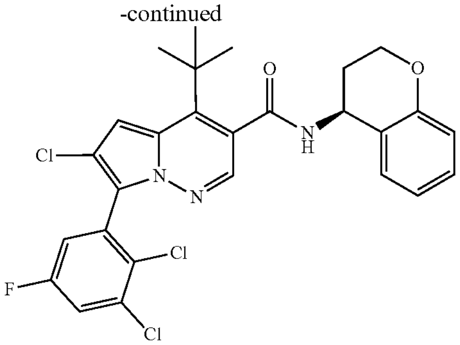

A502

To a solution of 42 mg (0.1 mmol) 4-tert-butyl-6-chloro-7-(2,3-dichloro-5-fluorophenyl)pyrrolo[1,2-b]pyridazine-3-carboxylic acid (5-3) in 1.5 mL DMF was added 51 μL (0.3 mmol) DIPEA and 38 mg (0.1 mmol) HATU at RT. After stirring for 5 min at RT 28 mg (0.15 mmol) (S)-chroman-4-amine hydrochloride were added and the mixture stirred for 2 h at RT. After acidifying with TFA, the mixture was directly purified via preparative HPLC ($ACN/H_2O/TFA$) to yield 10 mg (18%) of the title compound (A502) as yellow solid. (ESI, m/z): 547 $[M+H]^+$.

Preparation Example 6: Synthesis of N-[(4S)-3,4-dihydro-2H-1-benzopyran-4-yl]-6-methyl-4-(propan-2-yl)-7-(2,3,5-trifluorophenyl)pyrrolo[1,2-b]pyridazine-3-carboxamide (A513)

1. Synthesis of ethyl 6-chloro-4-(prop-1-en-2-yl)pyrrolo[1,2-b]pyridazine-3-carboxylate (6-1)

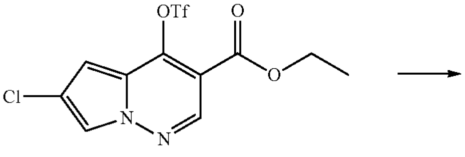

3-5

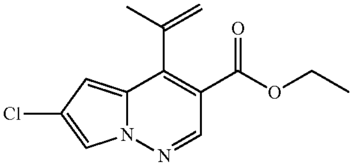

6-1

A solution of 1.55 g (8.1 mmol) of ethyl 6-chloro-4-(trifluoromethanesulfonyloxy)pyrrolo[1,2-b]pyridazine-3-carboxylate (3-5) in 25 mL 1.2-Dimethoxyethane was treated with 9.24 g (28.3 mmol) $Cs_2CO_3$ dissolved in 5 mL of water under Argon, followed by addition of 2.59 mL (13.7 mmol) of Isopropenylboronic acid pinacol ester. After degassing for 5 min, 794 mg (1.0 mmol) of 1,1'-Bis-(di-tert-butylphosphino-) ferrocen-palladiumdichloride were added under Argon and the sealed vessel stirred for 3 h at 80° C. After cooling to RT, the solution was diluted with ethyl acetate and washed with 10% $Na_2CO_3$ solution and brine. The solvent was dried over $Na_2SO_4$ and the evaporated under reduced pressure. Preparative HPLC ($ACN/H_2O/$ TFA) yielded 578 mg (27%) of the title compound (6-1) as solid. (ESI, m/z): 265 $[M+H]^+$.

2. Synthesis of ethyl 6-chloro-4-(propan-2-yl)pyrrolo[1,2-b]pyridazine-3-carboxylate (6-2)

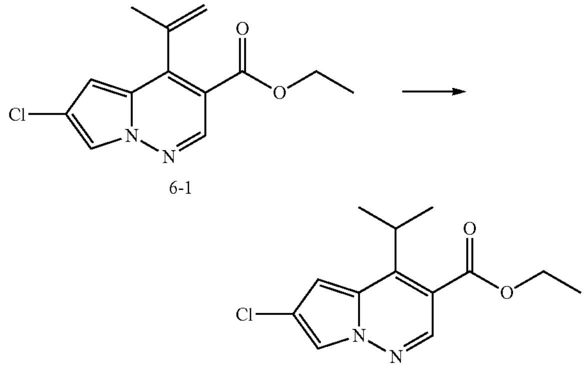

6-1

6-2

A solution of 578 mg (2.1 mmol) ethyl 6-chloro-4-(prop-1-en-2-yl)pyrrolo[1,2-b]pyridazine-3-carboxylate (6-1) in 25 mL of acetic acid was treated with 50 mg of $PtO_2$ and stirred for 30 min at RT under 50 psi of hydrogen. The crude mixture was filtrated, and the filtrate evaporated. Preparative HPLC ($ACN/H_2O/TFA$) yielded 337 mg (57%) of the title compound (6-2) as solid. (ESI, m/z): 267 $[M+H]^+$.

3. Synthesis of ethyl 6-methyl-4-(propan-2-yl)pyrrolo[1,2-b]pyridazine-3-carboxylate (6-3)

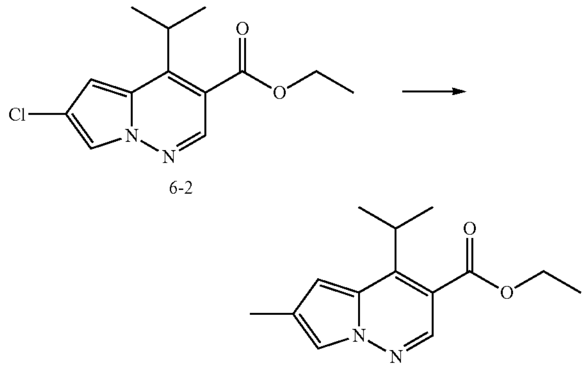

6-2

6-3

To a solution of 2.0 g (7.5 mmol) ethyl 6-chloro-4-(propan-2-yl)pyrrolo[1,2-b]pyridazine-3-carboxylate (6-2) in 22 mL of dioxane in a vial was added 505 mg (0.75 mmol) XPHOS Pd G3 under Argon, followed by 3.5 mL (24.7 mmol) trimethylboroxine and 11.2 mL of 2M $Na_2CO_3$ solution. The mixture was purged with Argon for 5 min then heated for 6 h at 80° C. After cooling to RT, the solution was diluted with water and extracted with ethyl acetate. The combined organic layers were dried over $Na_2SO_4$ and the solvent was evaporated under reduced pressure. Silica gel chromatography (CH/EA 9:1) yielded 1.43 g (69%) of the title compound (6-3) as solid. (ESI, m/z): 247 $[M+H]^+$.

4. Synthesis of ethyl 7-bromo-6-methyl-4-(propan-2-yl)pyrrolo[1,2-b]pyridazine-3-carboxylate (6-4)

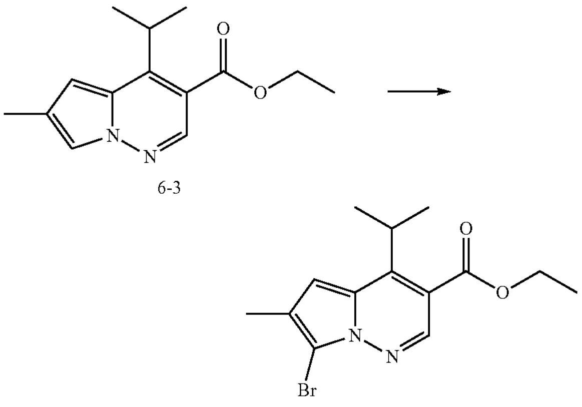

6-3

6-4

To a solution of 1.43 g (5.2 mmol) of ethyl 6-methyl-4-(propan-2-yl)pyrrolo[1,2-b]pyridazine-3-carboxylate (6-3) in 14 mL DMF was added 837 mg (4.7 mmol) NBS at RT and the mixture stirred for 30 min at RT. After acidifying with TFA, the mixture was directly purified via preparative HPLC ($ACN/H_2O/TFA$) to yield a total of 1.14 g (67%) of the title compound (6-4) as yellow oil. (ESI, m/z): 326 $[M+H]^+$.

5. Synthesis of ethyl 6-methyl-4-(propan-2-yl)-7-(2,3,5-trifluorophenyl)pyrrolo[1,2-b]pyridazine-3-carboxylate (6-5)

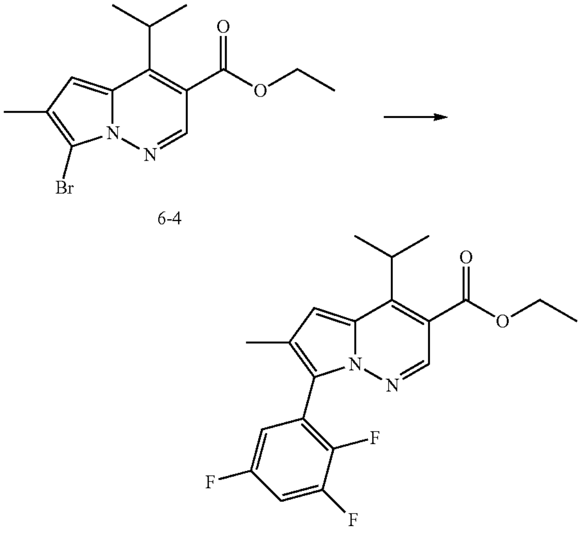

6-4

6-5

To a solution of 25 mg (0.1 mmol) of ethyl 7-bromo-6-methyl-4-(propan-2-yl)pyrrolo[1,2-b]pyridazine-3-carboxylate (6-4) in 1 mL of dioxane was added 20 mg (0.1 $mmol)_{2,3}$-dichloro-5-fluorophenyl) boronic acid under Argon followed by 153 μL $Na_2CO_3$ solution (2 mol/L) and 10 mg (0.015 mmol) of 1,1'-Bis-(di-tert-butylphosphino-)

ferrocen-palladiumdichloride. The mixture was stirred for 1 h at 80° C. in a sealed vessel. After cooling to RT, the solution was diluted with DCM and brine. After filtration through a phase separation cartridge, the organic phase was evaporated under reduced pressure and the mixture purified via preparative HPLC (ACN/$H_2O$/TFA) to yield 10 mg (34%) of the title compound (6-5) as brown solid. (ESI, m/z): 377 $[M+H]^+$.

6. Synthesis of 6-methyl-4-(propan-2-yl)-7-(2,3,5-trifluorophenyl)pyrrolo[1,2-b]pyridazine-3-carboxylic acid (6-6)

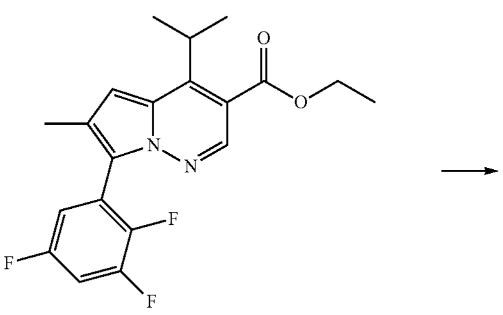

6-5

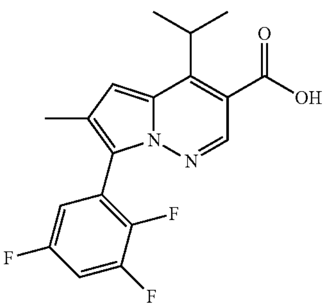

6-6

To a solution of 10 mg (0.02 mmol) ethyl 6-methyl-4-(propan-2-yl)-7-(2,3,5-trifluorophenyl)pyrrolo[1,2-b]pyridazine-3-carboxylate (6-5) in 2 mL ethanol was added 0.13 mL NaOH-solution (4 mol/L) at RT and the mixture stirred for 2 h at 90° C. After cooling to RT, the solution was treated with HCl (4 mol/L) until acidic pH at 0° C. and diluted with DCM. After filtration through a phase separation cartridge, the organic phase was evaporated under reduced pressure and the crude title product (6-6) directly used in the subsequent step. (ESI, m/z): 349 $[M+H]^+$.

7. Synthesis of N-[(4S)-3,4-dihydro-2H-1-benzopyran-4-yl]-6-methyl-4-(propan-2-yl)-7-(2,3,5-trifluorophenyl)pyrrolo[1,2-b]pyridazine-3-carboxamide (A513)

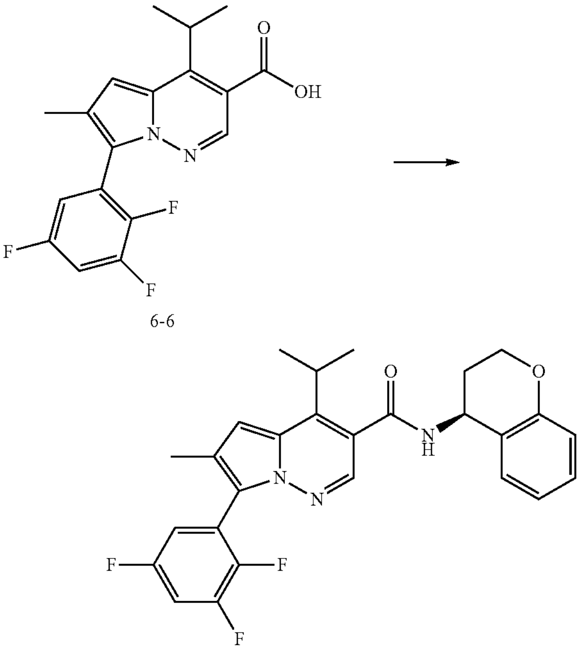

6-6

A513

To a solution of 9 mg (0.02 mmol) 6-methyl-4-(propan-2-yl)-7-(2,3,5-trifluorophenyl)pyrrolo[1,2-b]pyridazine-3-carboxylic acid (6-6) in 1 mL DMF was added 13 μL (0.078 mmol) DIPEA and 9.8 mg (0.026 mmol) HATU at RT. After stirring for 10 min at RT 5.7 mg (0.03 mmol) (S)-chroman-4-amine hydrochloride were added and the mixture stirred at RT overnight. After diluting with ACN and acidifying with TFA, the mixture was directly purified via preparative HPLC (ACN/$H_2O$/TFA) to yield 9 mg (72%) of the title compound (A513) as solid. (ESI, m/z): 480 $[M+H]^+$.

Preparation Example 7: Synthesis of 4-tert-butyl-N-[(4S)-3,4-dihydro-2H-1-benzopyran-4-yl]-6-methyl-7-(piperidin-1-yl)pyrrolo[1,2-b]pyridazine-3-carboxamide (A524)

1. Synthesis of ethyl 7-bromo-4-tert-butyl-6-methylpyrrolo[1,2-b]pyridazine-3-carboxylate (7-1)

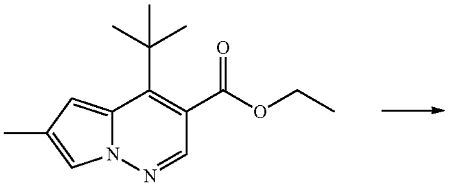

INT-3

-continued

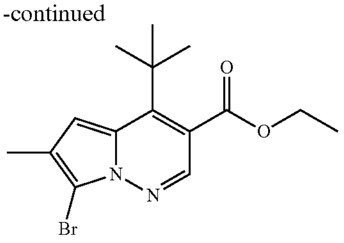

7-1

To a solution of 680 mg (2.6 mmol) of ethyl 4-tert-butyl-6-methylpyrrolo[1,2-b]pyridazine-3-carboxylate (INT-3) in 10 mL DMF was added 360 mg (2.0 mmol) NBS at RT and the mixture stirred for 30 min at RT. The solution was diluted with ethyl acetate and washed with 10% $Na_2CO_3$ solution and brine. The combined organic layers were filtered over Celite and the solvent was evaporated under reduced pressure. Silica gel chromatography (CH/EA gradient) yielded 730 mg (74%) of the title compound (7-1) as yellow oil. (ESI, m/z): 340 $[M+H]^+$.

2. Synthesis of potassium 7-bromo-4-tert-butyl-6-methylpyrrolo[1,2-b]pyridazine-3-carboxylate (7-2)

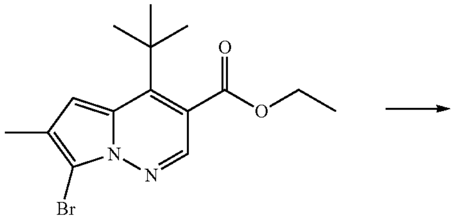

7-1

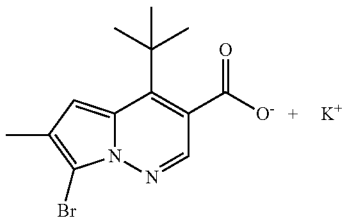

7-2

To a solution of 3 g (7.0 mmol) of ethyl 7-bromo-4-tert-butyl-6-methylpyrrolo[1,2-b]pyridazine-3-carboxylate (7-1) in 100 mL THF was added 3.0 g (21.2 mmol) TMSOK and the mixture stirred at 70° C. for 7 h. After evaporation of volatiles 2.2 g of crude product (7-2) was obtained and directly used in the next step. (ESI, m/z): 350 $[M+H]^+$.

3. Synthesis of 7-bromo-4-tert-butyl-N-[(4S)-3,4-dihydro-2H-1-benzopyran-4-yl]-6-methylpyrrolo[1,2-b]pyridazine-3-carboxamide (7-3)

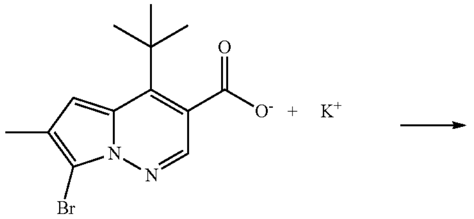

7-2

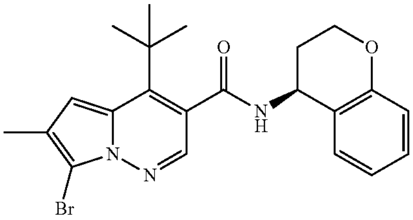

7-3

To a solution of 2.2 g (6.8 mmol) potassium 7-bromo-4-tert-butyl-N-[(4S)-3,4-dihydro-2H-1-benzopyran-4-yl]-6-methylpyrrolo[1,2-b]pyridazine-3-carboxylate (7-2) in 85 mL DMF was added 4.2 mL (24.7 mmol) DIPEA and 3.78 g (9.9 mmol) HATU at RT. After stirring for 5 min at RT 2.0 g (11.0 mmol) (S)-chroman-4-amine hydrochloride were added and the mixture stirred for 1 h at 50° C. The mixture was diluted with ethyl acetate, washed with 1N HCl, 10% $Na_2CO_3$ solution and brine. The organic layer was dried over $Na_2SO_4$ and the solvent was evaporated under reduced pressure. Silica gel chromatography (CH/EA gradient) yielded 2.0 g (68%) of the title compound (7-3) as solid. (ESI, m/z): 443 $[M+H]^+$.

4. Synthesis of 4-tert-butyl-N-[(4S)-3,4-dihydro-2H-1-benzopyran-4-yl]-6-methyl-7-(piperidin-1-yl)pyrrolo[1,2-b]pyridazine-3-carboxamide (A524)

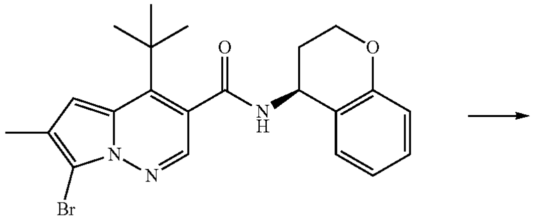

7-3

-continued

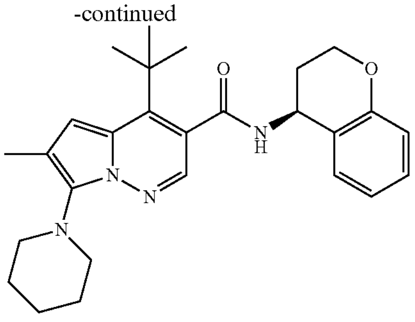

A524

A 5 mL vial was charged with 50 mg (0.1 mmol) 7-bromo-4-tert-butyl-N-[(4S)-3,4-dihydro-2H-1-benzopyran-4-yl]-6-methylpyrrolo[1,2-b]pyridazine-3-carboxamide (7-3), dioxane 1 mL, 11 μL (0.1 mmol) piperidine and degassed with Argon. After addition of 43 mg (0.45 mmol) of t-BuONa and additional degassing with Argon, 1.45 mg (0.002 mmol) of Pd-PEPPSI-IPent Cl were added and the sealed vial heated to 80° C. over night. After cooling to RT the mixture was diluted with MeOH and directly purified via preparative HPLC (ACN/$H_2O$/TFA) to yield 3 mg (6%) of the title compound (A524) as solid. (ESI, m/z): 447 $[M+H]^+$.

Preparation Example 8: Synthesis of 6-chloro-7-(2,3-dichloro-5-fluorophenyl)-N-[(4S)-3,4-dihydro-2H-1-benzopyran-4-yl]-4-(propan-2-yl)pyrrolo[1,2-b]pyridazine-3-carbothioamide (A539)

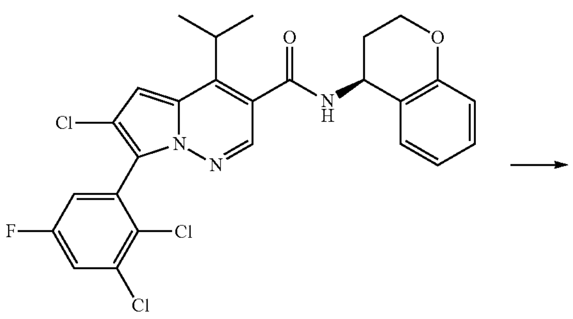

A523

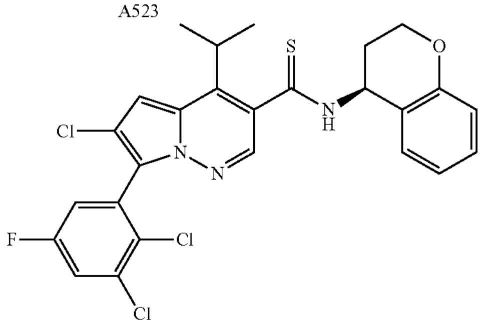

A539

To as solution of 48 mg (0.1 mmol) of 6-chloro-7-(2,3-dichloro-5-fluorophenyl)-N-[(4S)-3,4-dihydro-2H-1-benzopyran-4-yl]-4-(propan-2-yl)pyrrolo[1,2-b]pyridazine-3-carboxamide (A523) in 3 mL of THF was added 54 mg (0.14 mmol) Lawesson's reagent. The mixture was stirred for 3 h at RT, then heated to 50° C. over night. After cooling to RT, the mixture was acidified with TFA and directly purified via preparative HPLC (ACN/$H_2O$/TFA) to yield 16.5 mg (33%) of the title compound (A539) as yellow solid. (ESI, m/z): 549 $[M+H]^+$.

Preparation Example 9: Synthesis of 4-tert-butyl-7-(2,3-dichloro-5-fluorophenyl)-N-[(4S)-3,4-dihydro-2H-1-benzopyran-4-yl]-N,6-dimethylpyrrolo[1,2-b]pyridazine-3-carboxamide (A543)

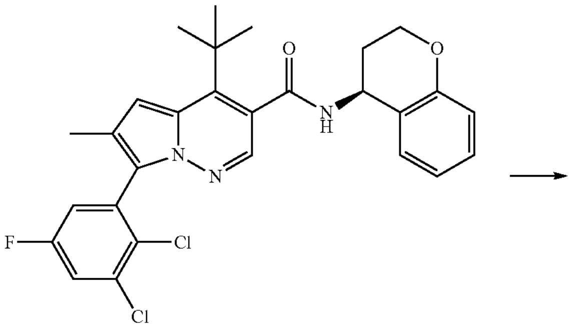

A481

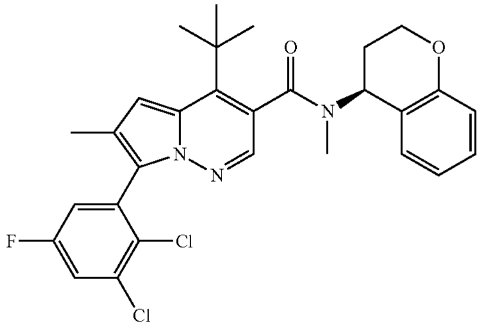

A543

To a solution of 20 mg (0.03 mmol) 4-tert-butyl-7-(2,3-dichloro-5-fluorophenyl)-N-[(4S)-3,4-dihydro-2H-1-benzopyran-4-yl]-6-methylpyrrolo[1,2-b]pyridazine-3-carboxamide (A481) in 3 mL of DMF was added 3.3 mg (0.077 mmol) of NaH. After addition of 2.6 μL (0.042 mmol) MeI the mixture was stirred for 1 h at RT and then directly purified via preparative HPLC (ACN/$H_2O$/TFA) to yield 9.5 mg (41%) of the title compound (A543) as yellow solid. (ESI, m/z): 541 $[M+H]^+$.

Preparation Example 10: Synthesis of 5H,6H,7H-pyrano[3,2-d][1,3]thiazol-7-amine (11-9) The amine group (11-9) used in the preparation of Ring System U in Compound A550 is synthesized from commercially available starting materials via the following reaction process:

1. Synthesis of 3-[(tert-butyldimethylsilyl)oxy]-1-(2,5-dibromo-1,3-thiazol-4-yl)propan-1-ol (10-2)

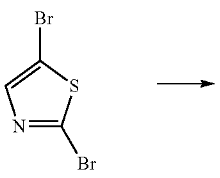

10-1

-continued

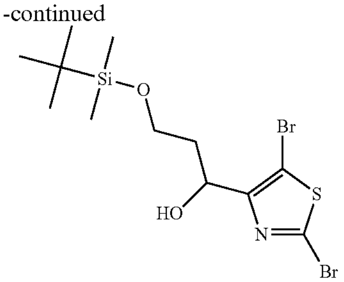

10-2

Into a 250-mL 3-necked round-bottom flask, was placed LDA (2 M) (15.50 mL, 30.9 mmol) in THF (20.00 mL). The resulting solution was cooled to −78° C. Then a solution of 2,5-dibromo-1,3-thiazole (10-1, 5.00 g, 20.6 mmol) in 15 mL THF was added. The resulting solution was stirred for 30 min at −78° C. A solution of 3-[(tert-butyldimethylsilyl)oxy] propanal (3.88 g, 20.6 mmol) in 15 mL THF was added. The resulting solution was stirred for 1 h at −78° C. The resulting solution was allowed to react, with stirring, for an additional 15 hours at room temperature. The pH value of the solution was adjusted to 6-7 with HCl (1 mol/L). The resulting solution was extracted with 2×100 mL of ethyl acetate and the organic layers combined. The organic layer was washed with 100 ml of brine. The organic layer was dried over anhydrous sodium sulfate and concentrated. The residue was applied onto a silica gel column with ethyl acetate/petroleum ether (1:15). This resulted in 4.00 g (45%) of 3-[(tert-butyldimethylsilyl)oxy]-1-(2,5-dibromo-1,3-thiazol-4-yl) propan-1-ol (10-2) as yellow oil.

2. Synthesis of 2,5-dibromo-4-[3-[(tert-butyl dimethylsilyl)oxy]-1-(oxan-2-yloxy)propyl]-1,3-thiazole (10-3)

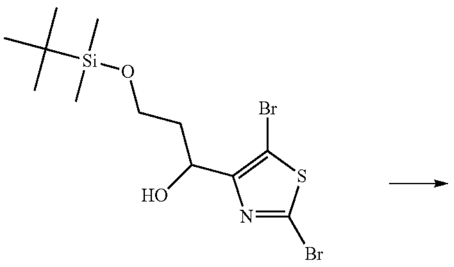

10-2

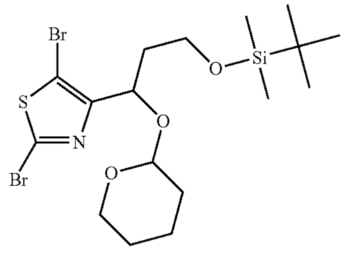

10-3

Into a 250-mL round-bottom flask, was placed 3-[(tert-butyldimethylsilyl)oxy]-1-(2,5-dibromo-1,3-thiazol-4-yl) propan-1-ol (10-2, 4.0 g, 9.3 mmol), DCM (40.00 mL), DHP (3.90 g, 46.4 mmol), PPTS(0.23 g, 0.9 mmol). The resulting solution was stirred for 3 h at 40° C. The resulting mixture was washed with 30 ml of $H_2O$ and 30 mL of brine. The organic layer was dried over anhydrous sodium sulfate and concentrated. The residue was applied onto a silica gel column with ethyl acetate/petroleum ether (1:10). This resulted in 3.62 g (75%) of 2,5-dibromo-4-[3-[(tert-butyl dimethylsilyl)oxy]-1-(oxan-2-yloxy)propyl]-1,3-thiazole (10-3) as yellow oil.

3. Synthesis of 5-bromo-4-[3-[(tert-butyldimethylsilyl)oxy]-1-(oxan-2-yloxy)propyl]-1,3-thiazole (10-4)

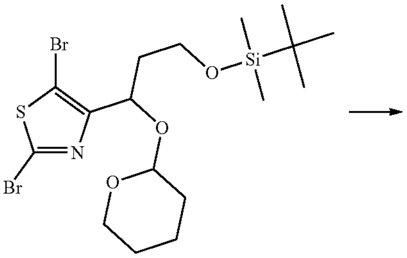

10-3

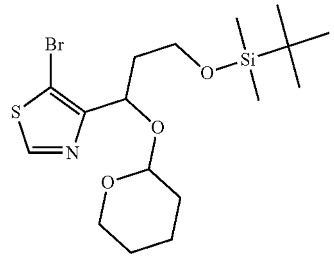

10-4

Into a 100-mL 3-necked round-bottom flask, was placed 2,5-dibromo-4-[3-[(tert-butyldimethylsilyl)oxy]-1-(oxan-2-yloxy)propyl]-1,3-thiazole (10-3, 3.60 g, 7.0 mmol) in 40 mL THF. The resulting solution was cooled to −10° C. And i-PrMgCl (2 M) (3.70 mL, 7.3 mmol) was added. The resulting solution was stirred for 1 h at −10° C. The reaction was then quenched by the addition of 100 mL of saturated aqueous $NH_4Cl$. The resulting solution was extracted with 2×50 mL of ethyl acetate and the organic layers combined. The organic layer was washed with 50 ml of brine. The organic layer was dried over anhydrous sodium sulfate and concentrated. This resulted in 2.60 g (85%) of 5-bromo-4-[3-[(tert-butyldimethylsilyl)oxy]-1-(oxan-2-yloxy)propyl]-1,3-thiazole (10-4) as yellow oil.

4. Synthesis of 3-(5-bromo-1,3-thiazol-4-yl)-3-(oxan-2-yloxy)propan-1-ol (10-5)

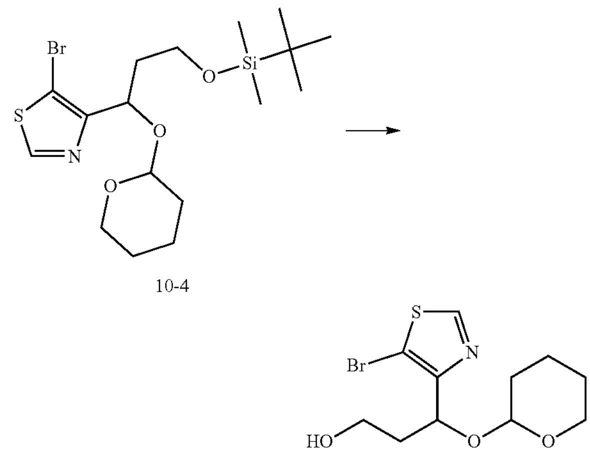

10-4

10-5

Into a 250-mL round-bottom flask, was placed 5-bromo-4-[3-[(tert-butyldimethylsilyl)oxy]-1-(oxan-2-yloxy)propyl]-1,3-thiazole (10-4, 2.60 g, 6.0 mmol), THF (30.00 mL) and TBAF (1 M) (7.20 mL, 7.2 mmol). The resulting solution was stirred for 2 h at room temperature. The resulting mixture was washed with 30 ml of $H_2O$ and 30 mL of brine. The organic layer was dried over anhydrous sodium sulfate and concentrated. The residue was applied onto a silica gel column with ethyl acetate/petroleum ether (1:1). This resulted in 1.55 g (81%) of 3-(5-bromo-1,3-thiazol-4-yl)-3-(oxan-2-yloxy)propan-1-ol (10-5) as yellow oil.

5. Synthesis of 7-(oxan-2-yloxy)-5H,6H,7H-pyrano[3,2-d][1,3]thiazole (10-6)

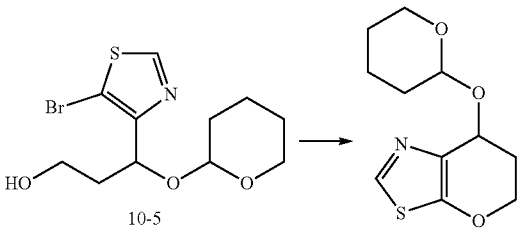

10-5

10-6

Into a 40-mL vial, was placed 3-(5-bromo-1,3-thiazol-4-yl)-3-(oxan-2-yloxy)propan-1-ol (10-5, 1.55 g, 4.8 mmol), toluene (16.00 mL), $Cs_2CO_3$ (2.35 g, 7.2 mmol), t-BuBrettPhos Pd G3 (0.33 g, 0.4 mmol). The resulting solution was stirred for 15 h at 120° C. The solids were filtered out and washed with 20 mL of EA. The filtrate was concentrated. The residue was applied onto a silica gel column with ethyl acetate/petroleum ether (1:4). This resulted in 0.60 g (52%) of 7-(oxan-2-yloxy)-5H,6H,7H-pyrano[3,2-d][1,3]thiazole (10-6) as yellow oil.

6. Synthesis of 5H,6H,7H-pyrano[3,2-d][1,3]thiazol-7-ol (10-7)

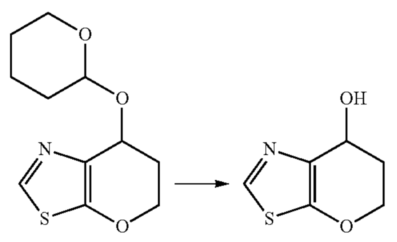

10-6 10-7

Into a 20-mL vial, was placed 7-(oxan-2-yloxy)-5H,6H,7H-pyrano[3,2-d][1,3]thiazole (10-6, 0.60 g, 2.5 mmol), THF (3.00 mL), $H_2O$(3.00 mL), PTSA (85.63 mg, 0.35 mmol). The resulting solution was stirred for 2 h at room temperature. The resulting solution was diluted with 10 mL of $H_2O$. The resulting solution was extracted with 3×15 mL of ethyl acetate and the organic layers combined. The organic layer was washed with 30 ml of brine. The organic layer was dried over anhydrous sodium sulfate and concentrated. The residue was applied onto a silica gel column with ethyl acetate/petroleum ether (1:1). This resulted in 0.20 g (51%) of 5H,6H,7H-pyrano[3,2-d][1,3]thiazol-7-ol (10-7) as yellow oil.

7. Synthesis of 7-azido-5H,6H,7H-pyrano[3,2-d][1,3]thiazole (10-8)

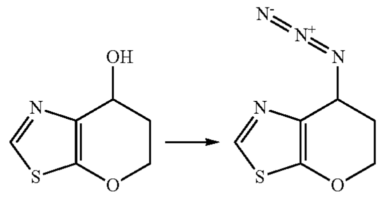

10-7 10-8

Into a 20-mL vial, was placed 5H,6H,7H-pyrano[3,2-d][1,3]thiazol-7-ol (10-7, 200 mg, 1.3 mmol), THF (4.00 mL), DPPA (420 mg, 1.5 mmol). The resulting solution was cooled to 0° C. and DBU (232 mg, 1.5 mmol) was added. The resulting solution was stirred for 15 h at room temperature. The resulting solution was added 10 mL of 10% HCl. The resulting solution was extracted with 2×10 mL of ethyl acetate and the organic layers combined. The organic layer was washed with 20 ml of brine. The organic layer was dried over anhydrous sodium sulfate and concentrated. The residue was applied onto a silica gel column with ethyl acetate/petroleum ether (1:4). This resulted in 110 mg (47%) of 7-azido-5H,6H,7H-pyrano[3,2-d][1,3]thiazole (10-8) as yellow oil.

8. Synthesis of 5H,6H,7H-pyrano[3,2-d][1,3]thiazol-7-amine (10-9)

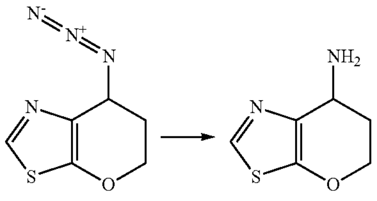

10-8 10-9

Into a 50-mL pressure tank reactor, was placed 7-azido-5H,6H,7H-pyrano[3,2-d][1,3]thiazole (10-8, 0.30 g, 1.65 mmol), EtOH (9.00 mL), Pd/C (30 mg, 10 w %). The resulting solution was stirred for 6 h at 40° C. under 10 atm hydrogen pressure. The solids were filtered out and washed with 10 mL of EtOH. The filtrate was concentrated. The crude product was purified by Flash-Prep-HPLC with the following conditions (IntelFlash-1): Column, C18 silica gel; mobile phase, $H_2O$:ACN=100:0 increasing to $H_2O$:ACN=70:30 within 15 min; Detector, 254 nm. This resulted in 206.2 mg (80%) of 5H,6H,7H-pyrano[3,2-d][1,3]thiazol-7-amine (10-9) as yellow solid. MS (ES, m/z): 157 $[M+H]^+$; $^1H$ NMR (300 MHz, $CDCl_3$, ppm) δ:8.53 (s, 1H), 4.44-4.28 (m, 2H), 4.21 (t, J=5.4 Hz, 1H), 2.23 (m, 1H), 1.86 (m, 1H).

Preparation Example 11: Synthesis of 5H,6H,7H-pyrano[2,3-d][1,3]thiazol-7-amine

The amine group used in the preparation of Ring System V in Compound A551 is synthesized from commercially available starting materials via the following reaction process:

1. Synthesis of 3-[(tert-butyldimethylsilyl)oxy]-1-(2,4-dibromo-1,3-thiazol-5-yl)propan-1-ol (11-2)

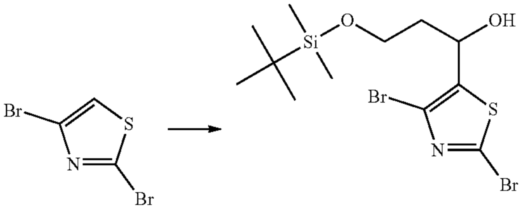

11-1 11-2

Into a 250-mL 3-necked round-bottom flask, was placed LDA (2 M,15.50 mL, 30.9 mmol), THF (20 mL). The resulting solution was cooled to −78° C. Then the solution of 2,4-dibromo-1,3-thiazole (11-1, 5.00 g, 20.6 mmol) in THF (15 mL) was added. The resulting solution was stirred for 30 min at −78° C. To the above solution, 3-[(tert-butyl dimethylsilyl)oxy]propanal (3.88 g, 20.6 mmol) in THF (15.00 mL) was added. The resulting solution was stirred for 1 h at −78° C. The resulting solution was allowed to react, with stirring, for an additional 15 h at room temperature. The pH value of the solution was adjusted to 6-7 with HCl (1 mol/L). The resulting solution was extracted with 2×100 mL of ethyl acetate and the organic layers combined. The organic layer was washed with 100 ml of brine. The organic layer was dried over anhydrous sodium sulfate and concentrated. The residue was applied onto a silica gel column with ethyl acetate/petroleum ether (1:12). This resulted in 5.00 g (56%) of 3-[(tert-butyldimethylsilyl)oxy]-1-(2,4-dibromo-1,3-thiazol-5-yl)propan-1-ol (11-2) as yellow oil 2. Synthesis of 2,4-dibromo-5-[3-[(tert-butyldimethyl silyl)oxy]-1-(oxan-2-yloxy)propyl]-1,3-thiazole (11-3)

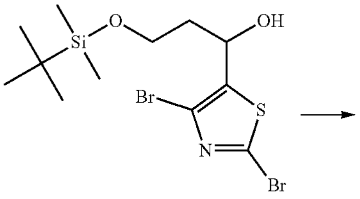

11-2

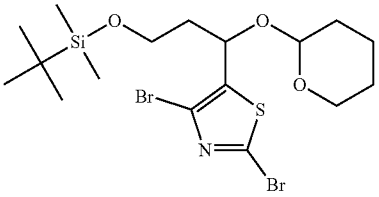

11-3

Into a 250-mL round-bottom flask, was placed 3-[(tert-butyldimethylsilyl)oxy]-1-(2,4-dibromo-1,3-thiazol-5-yl) propan-1-ol (11-2, 4.00 g, 9.3 mmol), DCM (60 mL), DHP (3.90 g, 46.4 mmol), PPTS(0.23 g, 0.9 mmol). The resulting solution was stirred for 2 h at 40° C. The resulting mixture was washed with 1×50 mL of $H_2O$ and 1×50 mL of brine. The organic layer was dried over anhydrous sodium sulfate and concentrated. The residue was applied onto a silica gel column with ethyl acetate/petroleum ether (1:15). This resulted in 4.30 g (90%) of 2,4-dibromo-5-[3-[(tert-butyldimethyl silyl)oxy]-1-(oxan-2-yloxy)propyl]-1,3-thiazole (11-3) as a yellow oil.

3. Synthesis of 4-bromo-5-[3-[(tert-butyldimethylsilyl)oxy]-1-(oxan-2-yloxy)propyl]-1,3-thiazole (11-4)

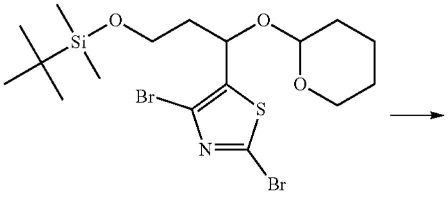

11-3

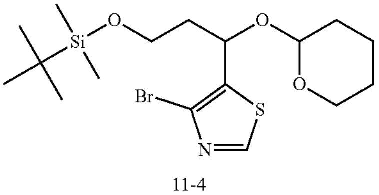

11-4

Into a 100-mL 3-necked round-bottom flask, was placed 2,4-dibromo-4-[3-[(tert-butyldimethylsilyl)oxy]-1-(oxan-2-yloxy)propyl]-1,3-thiazole (11-3, 5.46 g, 10.6 mmol), THF (50.0 mL). The resulting solution was cooled to −10° C., and i-PrMgCl (2 M) (5.60 mL, 11.1 mmol) was added. The resulting solution was stirred for 1 h at −10° C. The reaction was then quenched by the addition of 100 mL of saturated aqueous $NH_4Cl$. The resulting solution was extracted with 2×50 mL of ethyl acetate and the organic layers combined. The organic layer was washed with 50 ml of brine. The organic layer was dried over anhydrous sodium sulfate and concentrated. This resulted in 4.00 g (86%) of 4-bromo-5-[3-[(tert-butyldimethylsilyl)oxy]-1-(oxan-2-yloxy)propyl]-1,3-thiazole (11-4) as yellow oil.

4. Synthesis of 3-(4-bromo-1,3-thiazol-5-yl)-3-(oxan-2-yloxy)propan-1-ol (11-5)

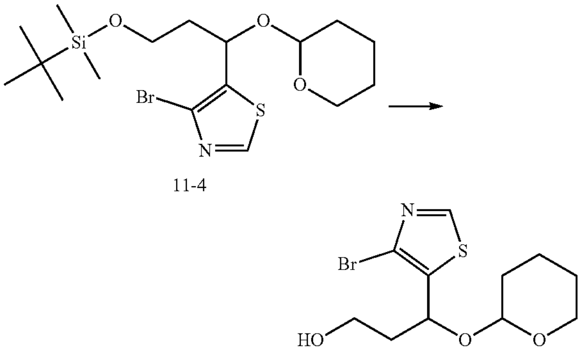

11-4

11-5

Into a 250-mL round-bottom flask, was placed 4-bromo-5-[3-[(tert-butyldimethylsilyl)oxy]-1-(oxan-2-yloxy)propyl]-1,3-thiazole (11-4, 4.00 g, 9.2 mmol), THF (40 mL), TBAF (1 M) (11 mL, 11.1 mmol). The resulting solution was stirred for 2 hrs at room temperature. The resulting mixture was washed with 30 ml of $H_2O$ and 30 mL of brine. The organic layer was dried over anhydrous sodium sulfate and concentrated. The residue was applied onto a silica gel column with ethyl acetate/petroleum ether (1:1). This resulted in 2.75 g (93%) of 3-(4-bromo-1,3-thiazol-5-yl)-3-(oxan-2-yloxy)propan-1-ol (11-5) as yellow oil.

5. Synthesis of 7-(oxan-2-yloxy)-5H,6H,7H-pyrano[2,3-d][1,3]thiazole (11-6)

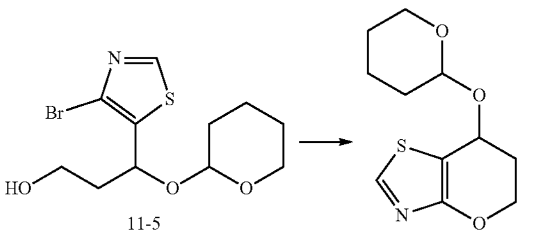

11-5

11-6

Into a 40-mL vial, was placed 3-(4-bromo-1,3-thiazol-5-yl)-3-(oxan-2-yloxy)propan-1-ol (11-5, 2.75 g, 8.5 mmol), toluene (25.00 mL), $Cs_2CO_3$ (4.17 g, 12.8 mmol), t-BuBrettPhos Pd G3 (0.58 g, 0.7 mmol). The resulting solution was stirred for 15 h at 100° C. The solids were filtered out and washed with 20 mL of EA. The filtrate was concentrated. The residue was applied onto a silica gel column with ethyl acetate/petroleum ether (1:4). This resulted in 1.20 g (58%) of 7-(oxan-2-yloxy)-5H,6H,7H-pyrano[2,3-d][1,3]thiazole (11-6) as yellow oil.

6. Synthesis of 5H,6H,7H-pyrano[2,3-d][1,3]thiazol-7-ol (11-7)

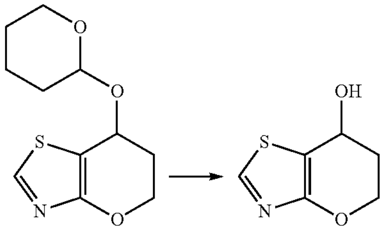

11-6 11-7

Into a 20-mL vial, was placed 7-(oxan-2-yloxy)-5H,6H,7H-pyrano[2,3-d][1,3]thiazole (11-6, 1.20 g, 5.0 mmol), THF (4 mL), $H_2O$(4 mL), PTSA (0.17 g, 1.0 mmol). The resulting solution was stirred for 15 h at room temperature. The resulting solution was diluted with 10 mL of $H_2O$. The resulting solution was extracted with 3×15 mL of ethyl acetate and the organic layers combined. The organic layer was washed with 30 ml of brine. The organic layer was dried over anhydrous sodium sulfate and concentrated. The residue was applied onto a silica gel column with ethyl acetate/petroleum ether (9:1). This resulted in 0.40 g (51%) of 5H,6H,7H-pyrano[2,3-d][1,3]thiazol-7-ol (11-7) as yellow oil.

7. 7-azido-5H,6H,7H-pyrano[2,3-d][1,3]thiazole (11-8)

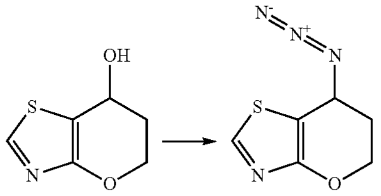

11-7 11-8

Into a 40-mL vial, was placed 5H,6H,7H-pyrano[2,3-d][1,3]thiazol-7-ol (11-7, 400 mg, 2.5 mmol), THF (8 mL), DBU (465 mg, 3.0 mmol). The resulting solution was cooled to 0° C. Then DPPA (840 mg, 3.0 mmol) was added. The resulting solution was stirred for 2 h at room temperature. The resulting solution was added 20 mL of 10% HCl. The resulting solution was extracted with 2×20 mL of ethyl acetate and the organic layers combined. The organic layer was washed with 20 ml of brine. The organic layer was dried over anhydrous sodium sulfate and concentrated. The residue was applied onto a silica gel column with ethyl acetate/ petroleum ether (1:3). This resulted in 0.22 g (47%) of 7-azido-5H,6H,7H-pyrano[2,3-d][1,3]thiazole (11-8) as a yellow oil.

8. Synthesis of 5H,6H,7H-pyrano[2,3-d][1,3]thiazol-7-amine (11-9)

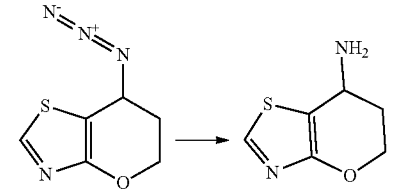

11-8 11-9

Into a 30-mL pressure tank reactor, was placed 7-azido-5H,6H,7H-pyrano[2,3-d][1,3]thiazole (11-8, 300 mg, 1.65 mmol), EtOH (6 mL), Pd/C (30 mg, 0.3 mmol). The resulting solution was stirred for 15 h at room temperature under 5 atm of hydrogen pressure. The solids were filtered out and washed with 20 mL of EtOH. The filtrate was concentrated. The crude product was purified by Flash-Prep-HPLC with the following conditions (IntelFlash-1): Column, C18 silica gel; mobile phase, $H_2O$:ACN=80:20 increasing to $H_2O$:ACN=40:60 within 15 min; Detector, 254 nm. This resulted in 210.6 mg (82%) of 5H,6H,7H-pyrano[2,3-d][1,3]thiazol-7-amine (11-9) as a light-yellow solid. MS(ES, m/z): 157 $[M+H]^+$; $^1H$ NMR (300 MHZ, $CDCl_3$, ppm) 8:8.47 (s, 1H), 4.41-4.29 (m, 2H), 4.21 (t, J=5.4 Hz, 1H), 2.23 (m, 1H), 1.83 (m, 1H).

Preparation Example 12: Synthesis of 2H,3H,4H-pyrano[3,2-c]pyridin-4-amine (12-2)

The bicyclic amine used in the preparation of Ring System AF present in compound A569 (see Table 3) is prepared from commercially available materials according to the process shown below.

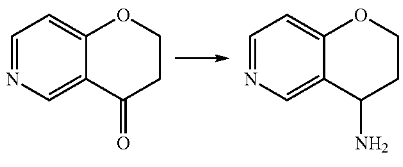

12-1 12-2

To a solution of 400 mg (2.6 mmol)2H-Pyrano[3,2-c]pyridin-4 (3H)-one (12-1) and 1.35 g (21.4 mmol) ammonium formate in 13.4 mL methanol were added 887 mg (13.4 mmol) sodium cyanoborohydride at RT and the mixture was then stirred at 60° C. over night. After addition of further same amount of ammonium formate and sodium cyanoborohydride and stirring for 3 h at 60° C., the reaction mixture was cooled to RT, diluted with ethyl acetate and quenched with water. After phase separation the organic phase was dried over anhydrous $Na_2SO_4$ and the solvent was evaporated to yield 120 mg (23%) of the title compound (12-2) as crude oil. The crude material was used without further purification. (ESI, m/z): 151 $[M+H]^+$.

Table 4 below includes $^1H$ NMR data for certain compounds shown in Table 3 and prepared according to the processes outlined in schemes 1, 2 and 3 and the preparation examples shown above:

TABLE 4

$^1H$ NMR data for Compounds of the Invention

| Compound | $^1H$ NMR Spectra |
|---|---|
| A461 | (400 MHz, DMSO-d6, ppm) δ 9.93 (s, 1H), 7.99 (s, 1H), 7.68 (d, J = 2.03 Hz, 2H), 7.57 (t, J = 1.90 Hz, 1H), 6.75-7.26 (m, 5H), 4.30-4.43 (m, 1H), 4.17 (s, 1H), 3.99 (s, 1H), 3.34-3.47 (m, 1H), 2.52-2.55 (m, 3H), 2.11-2.32 (m, 2H), 1.36-1.46 (m, 6H) |
| A462 | (400 MHz, DMSO-d6, ppm) δ 9.93 (s, 1H), 7.99 (s, 1H), 7.68 (d, J = 2.03 Hz, 2H), 7.57 (t, J = 1.90 Hz, 1H), 6.75-7.26 (m, 5H), 4.30-4.43 (m, 1H), 4.17 (s, 1H), 3.99 (s, 1H), 3.34-3.47 (m, 1H), 2.52-2.55 (m, 3H), 2.11-2.32 (m, 2H), 1.36-1.46 (m, 6H) |
| A463 | (400 MHz, DMSO-d6) δ ppm 9.02 (d, J = 8.11 Hz, 1 H) 8.27 (s, 1 H) 7.77 (d, J = 1.90 Hz, 2 H) 7.68 (t, J = 1.90 Hz, 1 H) 7.31 (d, J = 7.37 Hz, 1 H) 7.20 (s, 1 H) 7.17 (dt, J = 7.80, 1.63 Hz, 1 H) 6.91 (t, J = 7.08 Hz, 1 H) 6.79 (dd, J = 8.17, 1.08 Hz, 1 H) 5.15-5.27 (m, 1 H) 4.25 (br d, J = 3.42 Hz, 2 H) 3.42-3.58 (m, 1 H) 2.12-2.24 (m, 1 H) 1.96-2.08 (m, 1 H) 1.44 (dd, J = 10.52, 7.10 Hz, 6 H) |
| A464 | (400 MHz, DMSO-d6) δ ppm 9.03 (d, J = 8.11 Hz, 1 H) 7.98 (s, 1 H) 7.65 (d, J = 1.90 Hz, 2 H) 7.58-7.62 (m, 1 H) 7.33 (d, J = 7.10 Hz, 1 H) 7.16 (t, J = 7.42 Hz, 1 H) 6.89-6.94 (m, 2 H) 6.79 (dd, J = 8.17, 0.95 Hz, 1 H) 5.13-5.19 (m, 1 H) 4.17-4.29 (m, 2 H) 2.33-2.44 (m, 3 H) 2.09-2.22 (m, 1 H) 1.95-2.09 (m, 1 H) 1.57(s, 9 H) |
| A465 | (400 MHz, DMSO-d6) δ ppm 8.95 (d, J = 8.24 Hz, 1 H) 8.12 (s, 1 H) 7.68 (d, J = 1.90 Hz, 2 H) 7.60 (t, J = 1.90 Hz, 1 H) 7.30 (d, J = 7.22 Hz, 1 H) 7.16 (t, J = 7.69 Hz, 1 H) 6.88-6.94 (m, 2 H) 6.79 (d, J = 7.96 Hz, 1 H) 5.18-5.24 (m, 1 H) 4.20-4.30 (m, 2 H) 3.49-3.64 (m, 1 H) 2.39 (s, 3 H) 2.09-2.22 (m, 1 H) 1.98-2.09 (m, 1 H) 1.45 (dd, J = 10.27, 7.10 Hz, 6 H) |
| A466 | (400 MHz, DMSO-d6) δ ppm 9.04 (br d, J = 7.86 Hz, 1 H) 8.39 (s, 1 H) 8.01 (s, 2 H) 7.58-7.63 (m, 1 H) 7.32 (br d, J = 7.60 Hz, 1 H) 7.12-7.21 (m, 1 H) 7.09 (s, 1 H) 6.92 (t, J = 7.41 Hz, 1 H) 6.79 (d, J = 8.24 Hz, 1 H) 5.17-5.26 (m, 1 H) 4.17-4.32 (m, 2 H) 3.44-3.60 (m, 1 H) 2.11-2.22 (m, 1 H) 1.94-2.11 (m, 1 H) 1.44-1.53 (m, 6 H) |
| A467 | (400 MHz, DMSO-d6) δ ppm 9.10 (d, J = 8.11 Hz, 1 H) 8.32 (s, 1 H) 8.18 (d, J = 1.90 Hz, 2 H) 7.70 (s, 1 H) 7.57 (t, J = 1.90 Hz, 1 H) 7.36 (d, J = 7.48 Hz, 1 H) 7.16-7.22 (m, 1 H) 6.86-6.96 (m, 1 H) 6.80 (dd, J = 8.17, 0.82 Hz, 1 H) 5.15-5.23 (m, 1 H) 4.05-4.33 (m, 3 H) 2.11-2.24 (m, 1 H) 1.97-2.11 (m, 1 H) 1.42-1.52 (m, 6 H) |
| A468 | (400 MHz, DMSO-d6) δ ppm 9.14 (d, J = 7.98 Hz, 1 H) 8.54 (s. 1 H) 8.22 (d, J = 1.77 Hz, 2 H) 8.02 (s, 1 H) 7.62 (s, 1 H) 7.38 (d, J = 7.60 Hz, 1 H) 7.18 (t, J = 7.73 Hz, 1 H) 6.93 (t, J = 7.48 Hz, 1 H) 6.80 (d, J = 8.11 Hz, 1 H) 5.18-5.24 (m, 1 H) 4.18-4.32 (m, 2 H) 3.54 (dt, J = 13.97, 7.02 Hz, 1 H) 2.14-2.25 (m, 1 H) 2.02-2.14 (m, 1 H) 1.48 (t, J = 7.03 Hz, 6 H) |

TABLE 4-continued $^1$H NMR data for Compounds of the Invention

| Compound | $^1$H NMR Spectra |
| --- | --- |
| A469 | (400 MHz, DMSO-d6) δ ppm 9.02 (d, J = 7.98 Hz, 1 H) 8.16-8.24 (m, 3 H) 7.49 (t, J = 1.84 Hz, 1 H) 7.44 (s, 1 H) 7.36 (d, J = 7.48 Hz, 1 H) 7.15-7.27 (m, 1 H) 6.93 (t, J = 7.41 Hz, 1 H) 6.80 (d, J = 7.98 Hz, 1 H) 5.15-5.23 (m, 1 H) 4.18-4.33 (m, 2 H) 3.79 (dt, J = 14.04, 6.99 Hz, 1 H) 2.58 (s, 3 H) 2.11-2.25 (m, 1 H) 1.99-2.11 (m, 1 H) 1.23-1.52 (m, 6 H) |
| A470 | (400 MHz, DMSO-d6) δ ppm 9.00 (d, J = 8.11 Hz, 1 H) 8.34 (s, 1 H) 8.25 (d, J = 1.77 Hz, 2 H)7.60 (d, J = 4.82Hz, 1 H) 7.51 (t, J = 1.84 Hz, 1 H) 7.33 (d, J = 7.48 Hz, 1 H)7.12-7.19 (m, 1 H) 7.07 (d, J = 4.82 Hz, 1 H) 6.90-7.00 (m, 1 H) 6.79 (d, J = 7.99 Hz, 1 H) 5.20-5.26 (m, 1 H) 4.21-4.31 (m, 2 H) 3.59 (spt, J = 7.03 Hz, 1 H) 2.12-2.24 (m, 1 H) 1.99-2.12 (m, 1 H) 1.41-1.52 (m, 6 H) |
| A472 | (400 MHz, DMSO-d6, ppm) δ 9.03-9.08 (m, 1H), 7.96 (d, 1H), 7.89-7.90 (d, 1H), 7.56-7.61 (dd, 1H), 7.29-7.33 (t, 1H), 7.13-7.17 (t, 1H), 6.89-6.92 (m, 2H), 6.77-6.79 (d, 1H), 5.13-5.17 (m, 1H), 4.17-4.27 (m, 2H), 2.21 (s, 3H), 1.99-2.14 (m, 2H), 1.58 (s, 9H) |
| A471 | (400 MHz, DMSO-d6) δ ppm 9.05 (d, J = 7.98 Hz, 1 H) 7.94 (s, 1 H) 7.56-7.69 (m, 1 H) 7.25-7.37 (m, 2 H) 7.16 (t, J = 7.67 Hz, 1 H) 6.86-6.96 (m, 2 H) 6.78 (d, J = 8.11 Hz, 1 H) 5.12-5.19 (m, 1 H) 4.15-4.30 (m, 2 H) 2.29 (s, 3 H) 2.09-2.25 (m, 1 H) 1.94-2.09 (m, 1 H) 1.58 (s, 9 H) |
| A475 | (400 MHz, DMSO-d6, ppm) δ 8.80-8.82 (d, 1H), 8.00 (s, 1H), 7.74-7.75 (d, 2H), 7.65-7.66 (t, 1H), 7.29-7.30 (d, 1H), 7.16-7.18 (t, 1H), 7.11 (s, 1H), 6.88-6.92 (t, 1H), 6.78-6.80 (d, 1H), 5.15-5.19 (m, 1H), 4.18-4.28 (m, 2H), 3.18 (s, 6H), 1.99-2.16 (m, 2H) |
| A473 | (400 MHz, DMSO-d6, ppm) δ 8.79-8.81 (dd, 1H), 8.01-8.02 (d, 1H), 7.90 (s, 1H), 7.60-7.62 (dd, 1H), 7.26-7.28 (m, 1H), 7.13-7.17 (t, 1H), 7.11 (s, 1H), 8.86-8.90 (t, 1H), 6.77-6.79 (d, 1H), 5.15-5.17 (m, 1H), 4.19-4.27 (m, 2H), 3.19 (d, 6H), 1.91-2.17 (m, 2H) |
| A474 | (400 MHz, DMSO-d6, ppm) δ 8.80-8.82 (d, 1H), 7.94 (s, 1H), 7.66-7.73 (m, 1H), 7.27-7.32 (m, 2H), 7.14-7.18 (m, 2H), 6.87-6.91 (t, 1H), 6.77-6.79 (d, 1H), 5.14-5.19 (m, 1H), 4.20-4.24 (m, 2H), 3.19 (s, 6H), 1.98-2.16 (m, 2H) |
| A522 | (400 MHz, DMSO-d6) δ ppm 9.12 (t, J = 9.08 Hz, 1 H) 8.07 (d, J = 7.10 Hz, 1 H) 8.04 (d, J = 2.53 Hz, 1 H) 7.69 (dd, J = 12.04, 2.41 Hz, 1 H) 7.32 (t, J = 8.17 Hz, 1 H) 7.20 (s, 1 H) 7.16 (t, J = 7.60 Hz, 1 H) 6.87-6.92 (m, 1 H) 6.78 (d, J = 7.35 Hz, 1 H) 5.11-5.18 (m, 1 H) 4.15-4.28 (m, 2 H) 2.52-2.65 (m, 3 H) 2.14 (br d, J = 3.42 Hz, 1 H) 1.98-2.07 (m, 1 H) 1.57 (s, 9 H) |
| A525 | (400 MHz, DMSO-d6) δ ppm 8.83 (dd, J = 8.11, 3.17 Hz, 1 H) 7.95 (d, J = 2.41 Hz, 1 H) 7.83 (d, J = 1.14 Hz, 1 H) 7.54 (dd, J = 8.17, 2.47 Hz, 1 H) 7.29 (d, J = 7.73 Hz, 1 H) 7.15 (t, J = 7.30 Hz, 1 H) 6.89 (td, J = 7.45, 1.08 Hz, 1 H) 6.78 (dd, J = 8.17, 0.82 Hz, 1 H) 6.75 (s, 1 H) 5.13 (br d, J = 5.70 Hz, 1 H) 4.75-4.93 (m, 4 H) 4.23 (br t, J = 4.50 Hz, 2 H) 2.05-2.23 (m, 4 H) 1.94-2.04 (m, 1 H) 1.40 (s, 1 H) |
| A526 | (400 MHz, DMSO-d6) δ ppm 8.84 (dd, J = 8.05, 4.12 Hz, 1 H) 7.79-7.85 (m, 2 H) 7.40 (td, J = 8.46, 2.98 Hz, 1 H) 7.29 (d, J = 7.73 Hz, 1 H) 7.15 (t, J = 7.73 Hz, 1 H) 6.89 (t, J = 7.45 Hz, 1 H) 6.78 (d, J = 7.98 Hz, 1 H) 6.75 (s, 1 H) 5.13 (br d, J = 5.45 Hz, 1 H) 4.72-4.94 (m, 4 H) 4.23 (br t, J = 4.44 Hz, 2 H) 2.07-2.23 (m, 4H ) 1.92-2.05 (m, 1 H) |
| A527 | (400 MHz, DMSO-d6) δ ppm 8.93 (d, J = 8.11 Hz, 1 H) 7.86 (s, 1 H) 7.32 (d, J = 7.48 Hz, 1 H) 7.16 (t, J = 7.74 Hz, 1 H) 6.91 (t, J = 7.18 Hz, 1 H) 6.78 (d, J = 7.98 Hz, 1 H) 6.62 (s, 1 H) 5.11-5.18 (m, 1 H) 4.16-4.28 (m, 2 H) 3.27-3.34 (m, 5 H) 2.25 (s, 3 H) 1.95-2.20 (m, 6 H) 1.53 (s, 9 H) 0.97-1.12 (m, 1 H) 0.66-0.76 (m, 1 H) |
| A528 | (400 MHz, DMSO-d6) δ ppm 8.89 (br s, 1 H) 7.81 (br s, 1 H) 7.32 (br d, J = 7.35 Hz, 1 H) 7.16 (t, J = 7.37 Hz, 1 H) 6.92 (t, J = 7.04 Hz, 1 H) 6.78 (d, J = 8.11 Hz, 1 H) 6.59 (br s, 1 H) 5.15 (br d, J = 6.59 Hz, 1 H) 4.11-4.34 (m, 2 H) 2.72-3.06 (m, 4 H) 2.12-2.27 (m, 3 H) 1.66-1.83 (m, 3 H) 1.41-1.63 (m, 9 H) 0.84 (br s, 5 H) |
| A524 | (400 MHz, DMSO-d6) δ ppm 8.91 (d, J = 8.11 Hz, 1 H) 7.81 (s, 1 H) 7.32 (d, J = 7.48 Hz, 1 H) 7.16 (t, J = 7.36 Hz, 1 H) 6.81-6.95 (m, 1 H) 6.78 (d, J = 8.11 Hz, 1H)6.59(s, 1 H) 5.11-5.18 (m, 1 H) 4.11-4.35 (m, 2 H) 3.15 (br d, J = 5.20 Hz, 5 H) 2.20-2.35 (m, 4 H) 2.11-2.18 (m, 1 H) 1.95-2.03 (m, 1 H) 1.62 (br d, J = 4.56 Hz, 4 H) 1.45-1.58 (m, 11 H) 0.68-0.82 (m, 1 H) |
| A529 | (400 MHz, DMSO-d6) δ ppm 8.93 (d, J = 8.11 Hz, 1 H) 7.84 (s, 1 H) 7.32 (d, J = 7.35 Hz, 1 H) 7.16 (t, J = 7.72 Hz, 1 H) 6.91 (t, J = 7.17 Hz, 1 H) 6.78 (d, J = 7.48 Hz, 1 H) 6.61 (s, 1 H) 5.12-5.18 (m, 1 H) 4.12-4.28 (m, 2 H) 3.64-3.77 (m, 4 H) 3.10-3.29 (m, 5 H) 2.27 (s, 3 H) 2.09-2.19 (m, 1 H) 1.94-2.03 (m, 1H) 1.53 (s, 9 H) |
| A530 | 1H NMR (400 MHz, DMSO-d6) δ ppm 9.05 (dd, J = 10.46, 8.17 Hz, 1 H) 7.96 (d, J = 2.53 Hz, 1 H) 7.89 (d, J = 5.20 Hz, 1 H) 7.60 (d, J = 2.53 Hz, 1 H) 7.31 (t, J = 6.65 Hz, 1 H) 7.15 (t, J = 7.73 Hz, 1 H) 6.87-6.93 (m, 2 H) 6.78 (d, J = 7.95 Hz, 1 H) 5.12-5.18 (m, 1 H) 4.17-4.28 (m, 2 H) 2.67 (dt, J = 3.61, 1.74 Hz, 1 H) 2.31-2.34 (m, 1 H) 2.21 (s, 3 H) 1.58 (s, 9 H) |
| A531 | (400 MHz, DMSO-d6) δ ppm 9.01 (d, J = 8.11 Hz, 1 H) 8.50 (s, 1 H) 8.16 (s, 1 H) 7.98 (s, 1 H) 7.34 (d, J = 7.48 Hz, 1 H) 7.17 (t, J = 7.69 Hz, 1 H) 6.93 (t, J = 7.23 Hz, 1 H) 6.88 (s, 1 H) 6.79 (d, J = 8.29 Hz, 1 H) 5.15-5.29 (m, 3 H) 4.18-4.30 (m, 2 H) 2.47 (s, 3 H) 2.10-2.22 (m, 1 H) 1.96-2.08 (m, 1 H) 1.58 (s, 9 H) |
| A532 | (400 MHz, DMSO-d6) δ ppm 9.03 (d, J = 8.11 Hz, 1 H) 8.79 (d, J = 1.65 Hz, 1 H) 8.55 (dd, J = 4.82, 1.65 Hz, 1 H) 8.02 (dt, J = 7.98, 1.96 Hz, 1 H) 7.90 (s, 1 H) 7.52 (dd, J = 7.98, 4.82 Hz, 1 H) 7.32 (d, J = 7.48 Hz, 1 H) 7.16 (t, J = 7.75 Hz, 1 H) 6.88-6.94 (m, 2 H) 6.78 (d, J = 8.30 Hz, 1 H) 5.12-5.19 (m, 1 H) 4.16-4.31 (m, 2 H) 2.38 (s, 3 H) 2.29 (s, 1 H) 1.52-1.62 (m, 10 H) |
| A533 | (400 MHz, DMSO-d6) δ ppm 9.10 (t, J = 7.10 Hz, 1 H) 8.95 (d, J = 2.15 Hz, 1 H) 7.82 (dd, J = 8.30, 2.98 Hz, 1 H) 7.73 (d, J = 6.21 Hz, 1 H) 7.44 (ddd, J = 8.74, 5.96, 3.04 Hz, 1 H) 6.91 (s, 1 H) 5.24 (br d, J = 4.56 Hz, 1 H) 2.69-2.81 (m, 2 H) 2.21 (s, 3 H) 1.77-1.90 (m, 2 H) 1.57 (s, 9 H) |
| A534 | (400 MHz, DMSO-d6) δ ppm 9.12 (dd, J = 9.70, 8.30 Hz, 1 H) 8.06 (d, J = 6.59 Hz, 1 H) 7.90 (dd, J = 8.30, 2.98 Hz, 1 H) 7.55 (ddd, J = 11.94, 8.71, 3.04 Hz, 1 H) 7.32 (t, J = 7.86 Hz, 1 H) 7.20 (s, 1 H) 7.16 (t, J = 7.73 Hz, 1 H) 6.90 (tdd, 1 |

TABLE 4-continued

| $^1$H NMR data for Compounds of the Invention | |
|---|---|
| Compound | $^1$H NMR Spectra |
| | H) 6.78 (dd, J = 8.24, 0.89 Hz, 1 H) 5.11-5.18 (m, 1 H) 4.15-4.28 (m, 2 H) 2.52-2.55 (m, 1 H) 2.15 (ddd, J = 11.03, 5.45, 2.53 Hz, 1 H) 1.95-2.04 (m, 1 H) 1.57 (s, 9 H) |
| A535 | (400 MHz, DMSO-d6) δ ppm 8.90 (s, 1 H) 7.80 (dd, J = 8.30, 2.98 Hz, 1 H) 7.71 (d, J = 0.76 Hz, 1 H) 7.50 (d, J = 2.28 Hz, 1 H) 7.41 (ddd, J = 8.68, 2.98, 1.65 Hz, 1 H) 6.90 (dd, J = 8.49, 3.42 Hz, 1 H) 6.80 (s, 1 H) 4.97 (q, J = 6.93 Hz, 1 H) 3.99-4.06 (m, 1 H) 2.68-2.79 (m, 2 H) 2.52-2.65 (m, 1 H) 2.18 (s, 3 H) 1.87-2.08 (m, 3 H) 1.69-1.87 (m, 2 H) 1.56 (s, 9 H) 1.51-1.61 (m, 1 H) |
| A536a | (400 MHz, DMSO-d6) δ ppm 8.95 (d, J = 7.98 Hz, 1 H) 7.81 (dd, J = 8.30, 2.98 Hz, 1 H) 7.73 (d, J = 2.66 Hz, 1 H) 7.44 (dt, J = 8.62, 3.30 Hz, 1 H) 6.90 (s, 1 H) 5.27-5.35 (m, 1 H) 2.92-3.01 (m, 1 H) 2.79-2.90 (m, 2 H) 2.23-2.31 (m, 1 H) 2.21 (s, 3 H) 1.57 (s, 9 H) |
| A537 | (400 MHz, DMSO-d6) δ ppm 8.86 (dd, J = 11.85, 8.43 Hz, 1 H) 7.79-7.85 (m, 2 H) 7.44 (ddd, J = 16.51, 8.71, 3.04 Hz, 1 H) 7.27 (dd, J = 5.13, 2.72 Hz, 1 H) 6.98 (dd, J = 7.29, 5.26 Hz, 1 H) 6.88 (s, 1 H) 5.05 (br s, 1 H) 2.66-2.79 (m, 2 H) 2.65-2.79 (m, 1 H) 2.21 (s, 3 H) 1.89-2.04 (m, 2 H) 1.71-1.84 (m, 2 H) 1.56-1.63 (m, 9 H) 1.52 (br s, 1 H) |
| A536b | (400 MHz, DMSO-d6) δ ppm 8.95 (d, J = 7.98 Hz, 1 H) 7.81 (dd, J = 8.30, 2.98 Hz, 1 H) 7.73 (d, J = 2.66 Hz, 1 H) 7.44 (dt, J = 8.62, 3.30 Hz, 1 H) 6.90 (s, 1 H) 5.27-5.35 (m, 1 H) 2.92-3.01 (m, 1 H) 2.79-2.90 (m, 2 H) 2.23-2.31 (m, 1 H) 2.21 (s, 3 H) 1.57 (s, 9 H) |
| A538 | (400 MHz, DMSO-d6) δ ppm 8.92 (dd, J = 18.31.8.43 Hz, 1 H) 7.87 (d, J = 4.31 Hz, 1 H) 7.81 (dd, J = 8.36, 2.91 Hz, 1 H) 7.44-7.51 (m, 1 H) 7.35-7.43 (m, 1 H) 6.90-7.07 (m, 2 H) 6.89 (s, 1 H) 5.06-5.13 (m, 1 H) 2.64-2.83 (m, 2 H) 2.21 (s, 3 H) 1.58 (s, 9 H) |
| A539 | (400 MHz, DMSO-d6) δ ppm 11.06 (br s, 2 H) 8.11 (s, 1 H) 8.07 (s, 1 H) 7.88-7.92 (m, 2 H) 7.51-7.59 (m, 2 H) 7.30 (t, J = 7.73 Hz, 2 H) 7.20 (t, J = 7.71 Hz, 2 H) 7.12 (d, J = 1.01 Hz, 2 H) 6.93 (t, J = 7.44 Hz, 2 H) 6.83 (d, J = 8.11 Hz, 2 H) 5.83 (br d, J = 4.44 Hz, 2 H) 4.26-4.33 (m, 2 H) 4.16-4.24 (m, 2 H) 3.33-3.48 (m, 2 H) 2.24-2.30 (m, 2 H) 2.05-2.19 (m, 2 H) 1.45 (dd, J = 6.97, 5.58 Hz, 6 H) 1.41 (dd, J = 7.03, 4.88 Hz, 6 H) |
| A540 | (400 MHz, DMSO-d6) δ ppm 8.97 (d, J = 3.04 Hz, 1 H) 8.92 (dd, J = 8.24, 2.28 Hz, 1 H) 7.81 (dd, J = 8.30, 2.98 Hz, 1 H) 7.73 (d, J = 3.42 Hz, 1 H) 7.44 (d, J = 8.80 Hz, 1 H) 6.89 (s, 1 H) 5.31-5.39 (m, 1 H) 2.77-3.08 (m, 3 H) 2.30-2.38 (m, 1 H) 2.20 (s, 3 H) 1.58 (s, 9 H) |
| A541 | (400 MHz, DMSO-d6) δ ppm 9.08 (dd, J = 13.69, 8.24 Hz, 1 H) 7.86 (d, J = 2.15 Hz, 1 H) 7.82 (dd, J = 8.30, 2.98 Hz, 1 H) 7.44 (ddd, J = 13.94, 8.68, 2.98 Hz, 1 H) 7.34 (t, J = 6.72 Hz, 1 H) 7.04-7.17 (m, 3 H) 6.90 (s, 1 H) 5.19 (dq, J = 8.36, 4.35 Hz, 1 H) 3.08-3.20 (m, 1 H) 2.98-3.07 (m, 1 H) 2.18-2.29 (m, 4 H) 1.57 (s, 9 H) |
| A542 | (400 MHz, DMSO-d6) δ ppm 9.02 (dd, J = 11.60, 8.05 Hz, 1 H) 7.93 (d, J = 7.73 Hz, 1 H) 7.82 (dd, J = 8.36, 2.91 Hz, 1 H) 7.73 (s, 1 H) 7.66 (d, J = 7.86 Hz, 1 H) 7.56 (t, J = 7.35 Hz, 1 H) 7.44 (ddd, J = 16.51, 8.65, 2.98 Hz, 1 H) 6.91 (s, 1 H) 5.48 (quin, J = 7.45 Hz, 1 H) 2.96-3.05 (m, 1 H) 2.84-2.95 (m, 1 H) 2.52-2.53 (m, 1 H) 2.22 (s, 3 H) 1.88-1.99 (m, 1 H) 1.57 (s, 9 H) |
| A543 | (400 MHz, DMSO-d6) δ ppm 8.03 (s, 1 H) 7.77-7.85 (m, 1 H) 7.47-7.54 (m, 1 H) 7.22-7.27 (m, 1 H) 7.12-7.21 (m, 1 H) 6.89-6.97 (m, 2 H) 6.78-6.86 (m, 1 H) 5.95-6.01 (m, 1 H) 4.15-4.36 (m, 2 H) 2.68-2.71 (m, 1 H) 2.62-2.66 (m, 1 H) 2.52-2.56 (m, 2 H) 2.20-2.28 (m, 4 H) 1.50-1.61 (m, 8 H) |
| A544 | (400 MHz, DMSO-d6) δ ppm 8.89 (dd, J = 8.24, 5.83 Hz, 1 H) 8.38-8.42 (m, 1 H) 7.79-7.83 (m, 2 H) 7.66 (d, J = 7.60 Hz, 1 H) 7.44 (ddd, J = 11.60, 8.68, 3.04 Hz, 1 H) 7.21 (ddd, J = 7.38, 5.04, 2.03 Hz, 1 H) 6.90 (s, 1 H) 5.36 (quin, J = 8.02 Hz, 1 H) 2.93-3.01 (m, 1 H) 2.81-2.90 (m, 1 H) 2.52-2.56 (m, 1 H) 2.19-2.23 (m, 3 H) 1.88-2.05 (m, 1 H) 1.60 (s, 9 H) |
| A545 | (400 MHz, DMSO-d6) δ ppm 9.19 (d, J = 6.94 Hz, 1 H) 7.85 (s, 1 H) 7.81 (dd, J = 8.05, 2.85 Hz, 1 H) 7.44 (d, J = 8.75 Hz, 1 H) 7.39 (t, J = 7.03 Hz, 1 H) 7.22 (t, J = 7.73 Hz, 1 H) 6.88-6.94 (m, 2 H) 6.85 (d, J = 8.11 Hz, 1 H) 5.62-5.70 (m, 1 H) 4.73 (dd, J = 9.57, 8.81 Hz, 1 H) 4.36 (ddd, J = 9.73, 8.02, 4.82 Hz, 1 H) 2.21 (s, 3 H) 1.56 (s, 9 H) |
| A546 | (400 MHz, DMSO-d6) δ ppm 9.06 (dd, J = 10.46, 8.30 Hz, 1 H) 7.81 (dt, J = 8.30, 2.69 Hz, 1 H) 7.70 (d, J = 2.28 Hz, 1 H) 7.45 (ddd, J = 18.53, 8.65, 2.98 Hz, 1 H) 7.23 (s, 1 H) 6.90 (s, 1 H) 5.20 (br t, J = 8.74 Hz, 1 H) 4.40 (dt, J = 12.90, 6.54 Hz, 1 H) 2.52-2.68 (m, 1 H) 2.19-2.38 (m, 4 H) 2.01 (br s, 1 H) 1.58 (s, 9 H) 1.31-1.43 (m, 6 H) |
| A547 | (400 MHz, DMSO-d6) δ ppm 8.95 (dd, J = 21.42, 8.36 Hz, 1 H) 7.96 (d, J = 6.97 Hz, 1 H) 7.83 (dd, J = 8.30, 2.98 Hz, 1 H) 7.46 (ddd, J = 20.56, 8.65, 2.98 Hz, 1 H) 7.35 (t, J = 6.17 Hz, 1 H) 7.14 (t, J = 7.67 Hz, 1 H) 6.92 (s, 1 H) 6.86-6.91 (m, 1 H) 6.73 (dd, J = 8.11, 0.89 Hz, 1 H) 5.18-5.28 (m, 1 H) 3.57 (s, 2 H) 2.11-2.18 (m, 1 H) 1.75-1.83 (m, 1 H) 1.60 (s, 9 H) 1.40 (s, 3 H) 1.29 (s, 3 H) |
| A548 | (400 MHz, DMSO-d6) δ ppm 8.96 (dd, J = 17.55, 8.30 Hz, 1 H) 7.95 (d, J = 7.22 Hz, 1 H) 7.82 (dd, J = 8.30, 2.98 Hz, 1 H) 7.46 (ddd, J = 18.69, 8.68, 2.91 Hz, 1 H) 7.34 (t, J = 6.18 Hz, 1 H) 7.13 (t, J = 7.67 Hz, 1 H) 6.86-6.93 (m, 1 H) 6.72 (d, J = 7.92 Hz, 1 H) 5.17-5.27 (m, 1 H) 3.57 (s, 1 H) 2.22 (s, 1 H) 2.10-2.18 (m, 1 H) 1.53-1.96 (m, 9 H) |
| A549 | (400 MHz, DMSO-d6) δ ppm 8.94 (dd, J = 18.76, 8.36 Hz, 1 H) 7.87 (d, J = 4.31 Hz, 1 H) 7.82 (dd, J = 8.36, 3.04 Hz, 1 H) 7.47 (dd, J = 8.62, 2.92 Hz, 1 H) 7.34-7.43 (m, 2 H) 7.17-7.23 (m, 2 H) 6.90 (s, 1 H) 5.06-5.12 (m, 1 H) 2.68-2.79 (m, 2 H) 2.52-2.52 (m, 1 H) 2.21 (s, 3 H) 1.58 (s, 9 H) |
| A550 | (400 MHz, DMSO-d6) δ ppm 9.13 (d, J = 7.22 Hz, 1 H) 8.81 (d, J = 2.79 Hz, 1 H) 7.82 (dd, J = 8.36, 2.91 Hz, 1 H) 7.78 (d, J = 8.24 Hz, 1 H) 7.44 (ddd, J = 8.71, 5.80, 2.98 Hz, 1 H) 7.07 (br s, 1 H) 6.92 (d, J = 1.14 Hz, 1 H) 5.11-5.18 (m, 1 H) 4.35-4.41 (m, 1 H) 4.23-4.32 (m, 1 H) 2.16-2.26 (m, 4 H) 1.98-2.08 (m, 1 H) 1.55 (s, 9 H) |
| A551 | (400 MHz, DMSO-d6) δ ppm 9.13 (d, J = 7.22 Hz, 1 H) 8.81 (d, J = 2.92 Hz, 1 H) 7.82 (dd, J = 8.36, 2.91 Hz, 1 H) 7.78 (d, J = 8.36 Hz, 1 H) 7.44 (ddd, J = 8.68, 5.83, 2.98 Hz, 1 H) 6.92 (s, 1 H) 5.11-5.19 (m, 1 H) 4.35-4.43 (m, 1 H) 4.22- |

TABLE 4-continued $^1$H NMR data for Compounds of the Invention

| Compound | $^1$H NMR Spectra |
|---|---|
| | 4.32 (m, 1 H) 2.21 (s, 3 H) 1.96-2.07 (m, 1 H) 1.55 (s, 9 H) |
| A552 | 1H NMR (400 MHz, DMSO-d6) δ ppm 9.14 (br d, J = 7.10 Hz, 1 H) 8.21 (br s, 1 H) 7.80-7.85 (m, 2 H) 7.45 (ddd, J = 8.65, 2.88, 1.27 Hz, 1 H) 7.10 (br s, 1 H) 6.92 (s, 1 H) 5.30-5.40 (m, 1 H) 4.20-4.28 (m, 1 H) 4.09-4.17 (m, 1 H) 2.87-3.06 (m, 1 H) 2.52-2.52 (m, 1 H) 2.21 (s, 3 H) 2.11-2.13 (m, 1 H) 1.54 (s, 9 H) |
| A553 | (400 MHz, DMSO-d6) δ ppm 8.87 (dd, J = 7.79, 1.84 Hz, 1 H) 7.77-7.84 (m, 2 H) 7.41-7.47 (m, 1 H) 7.38 (dd, J = 4.88, 3.11 Hz, 1 H) 6.92 (dd, J = 8.87, 4.94 Hz, 1 H) 6.89 (s, 1 H) 5.25-5.33 (m, 1 H) 2.93-3.01 (m, 1 H) 2.75-2.89 (m, 2 H) 2.21 (s, 3 H) 1.56 (s, 9 H) |
| A554 | (400 MHz, DMSO-d6) δ ppm 9.09 (br d, J = 7.98 Hz, 1 H) 7.76-7.84 (m, 2 H) 7.39-7.51 (m, 1 H) 7.17 (s, 1 H) 7.03 (br s, 1 H) 6.91 (s, 1 H) 5.23-5.35 (m, 1 H) 4.04-4.14 (m, 1 H) 3.97 (ddd, J = 10.39, 8.24, 5.70 Hz, 1 H) 2.91-3.03 (m, 1 H) 2.21 (s, 3 H) 1.57 (s, 9 H) |
| A555 | 1H NMR (400 MHz, DMSO-d6) δ ppm 8.84 (dd, J = 11.09, 8.30 Hz, 1 H) 7.81 (dd, J = 8.36, 2.91 Hz, 1 H) 7.71 (d, J = 2.28 Hz, 1 H) 7.44 (ddd, J = 14.13, 8.68, 2.91 Hz, 1 H) 6.88 (s, 1 H) 5.07 (br dd, J = 7.86, 4.18 Hz, 1 H) 3.57 (s, 2 H) 2.57 (d, J = 3.68 Hz, 3 H) 2.20 (s, 3 H) 1.58 (s, 9 H) |
| A556 | (400 MHz, DMSO-d6) δ ppm 9.11 (dd, J = 11.85, 7.92 Hz, 1 H) 8.64 (br s, 1 H) 8.55 (br s, 1 H) 7.97 (d, J = 9.00 Hz, 1 H) 7.83 (dd, J = 8.36, 3.04 Hz, 1 H) 7.66 (dd, J = 12.67, 5.20 Hz, 1 H) 7.45 (ddd, J = 17.87, 8.62, 3.04 Hz, 1 H) 6.93 (s, 1 H) 5.52 (quin, J = 8.52 Hz, 1 H) 3.03-3.15 (m, 1 H) 2.91-3.01 (m, 1 H) 2.52-2.57 (m, 1 H) 2.22 (s, 3 H) 1.58 (s, 9 H) |
| A557 | (400 MHz, DMSO-d6) δ ppm 8.93 (dd, J = 16.98, 8.49 Hz, 1 H) 7.86 (d, J = 3.68 Hz, 1 H) 7.81 (dd, J = 8.30, 2.98 Hz, 1 H) 7.44 (ddd, J = 22.21, 8.65, 2.98 Hz, 1 H) 7.31-7.37 (m, 1 H) 7.12-7.20 (m, 2 H) 7.07-7.12 (m, 1 H) 6.89 (s, 1 H) 5.12 (br d, J = 5.83 Hz, 1 H) 2.65-2.82 (m, 2 H) 2.21 (s, 3 H) 1.87-2.03 (m, 2 H) 1.70-1.85 (m, 2 H) 1.59 (s, 9 H) |
| A558 | (400 MHz, DMSO-d6) δ ppm 8.91 (t, J = 8.43 Hz, 1 H) 7.88 (d, J = 4.82 Hz, 1 H) 7.82 (dd, J = 8.36, 2.91 Hz, 1 H) 7.44 (ddd, J = 13.56, 8.68, 2.98 Hz, 1 H) 7.36 (t, J = 5.87 Hz, 1 H) 7.17-7.27 (m, 3 H) 6.90 (s, 1 H) 5.40-5.48 (m, 1 H) 2.91-3.07 (m, 1 H) 2.78-2.87 (m, 1 H) 2.37-2.48 (m, 1 H) 2.21 (s, 3 H) 1.84-1.95 (m, 1 H) 1.58 (s, 9 H) |
| A559 | (400 MHz, DMSO-d6) δ ppm 9.10 (dd, J = 10.84, 7.79 Hz, 1 H) 8.56 (br s, 1 H) 8.09 (dd, J = 10.90, 7.86 Hz, 1 H) 7.94 (d, J = 7.10 Hz, 1 H) 7.82 (dd, J = 8.30, 2.98 Hz, 1 H) 7.35-7.58 (m, 2 H) 6.92 (s, 1 H) 5.50 (quin, J = 7.76 Hz, 1 H) 3.01-3.19 (m, 2 H) 2.52-2.62 (m, 1 H) 2.22 (s, 3 H) 1.99-2.10 (m, 1 H) 1.57 (s, 9 H) |
| A560 | (400 MHz, DMSO-d6) δ ppm 8.92 (d, J = 7.60 Hz, 1 H) 7.81 (dd, J = 8.36, 2.91 Hz, 1 H) 7.75 (d, J = 3.42 Hz, 1 H) 7.44 (ddd, J = 8.59, 4.59, 3.04 Hz, 1 H) 6.89 (s, 1 H) 5.19-5.28 (m, 1 H) 2.68-2.81 (m, 1 H) 2.52-2.65 (m, 1 H) 2.43-2.48 (m, 1 H) 2.21-2.31 (m, 1 H) 1.56 (s, 9 H) |
| A561 | (400 MHz, DMSO-d6) δ ppm 8.73(dd, J = 8.11, 3.80 Hz, 1H) 7.94 (d, J = 2.41 Hz, 1 H) 7.77 (d, J = 1.14 Hz, 1 H) 7.52 (dd, J = 8.17, 2.47 Hz, 1 H) 7.27 (d, J = 7.22 Hz, 1 H) 7.15 (t, J = 7.32 Hz, 1 H) 6.71-6.91 (m, 3 H) 5.13 (br d, J = 5.70 Hz, 1 H) 4.37-4.62 (m, 4 H) 4.20-4.26 (m, 2 H) 2.09-2.16 (m, 4 H) 1.95-2.03 (m, 1 H) 1.60-1.65 (m, 3 H) |
| A562 | (400 MHz, DMSO-d6) δ ppm 8.74 (dd, J = 8.17, 4.88 Hz, 1 H) 7.80 (dd, J = 8.36, 2.92 Hz, 1 H) 7.77 (d, J = 0.63 Hz, 1 H) 7.38 (td, J = 8.52, 2.98 Hz, 1 H) 7.27 (d, J = 7.48 Hz, 1 H) 7.15 (t, J = 7.74 Hz, 1 H) 6.89 (td, J = 7.48, 1.14 Hz, 1 H) 6.78 (d, J = 7.82 Hz, 1 H) 6.71 (s, 1 H) 5.10-5.17 (m, 1 H) 4.37-4.61 (m, 4 H) 4.17-4.28 (m, 2 H) 2.52-2.52 (m, 1 H) 2.07-2.19 (m, 4 H) 1.94-2.04 (m, 1 H) 1.60-1.65 (m, 3 H) |
| A563 | (400 MHz, DMSO-d6) δ ppm 8.66 (br d, J = 7.10 Hz, 1 H) 7.93 (d, J = 2.41 Hz, 1 H) 7.70 (s, 1 H) 7.50 (dd, J = 6.97, 2.53 Hz, 1 H) 7.25 (d, J = 7.35 Hz, 1 H) 7.14 (t, J = 7.37 Hz, 1 H) 6.88 (t, J = 7.13 Hz, 1 H) 6.77 (d, J = 8.11 Hz, 1 H) 6.67 (s, 1 H) 5.09-5.16 (m, 1 H) 4.19-4.30 (m, 2 H) 4.08-4.17 (m, 4 H) 2.52-2.58 (m, 1 H) 2.08-2.15 (m, 4 H) 1.89-2.03 (m, 1 H) 1.30 (s, 6 H) |
| A564 | (400 MHz, DMSO-d6) δ ppm 8.66 (dd, J = 8.24, 2.15 Hz, 1 H) 7.78 (dd, J = 8.36, 2.91 Hz, 1 H) 7.70 (s, 1 H) 7.30-7.44 (m, 1 H) 7.25 (d, J = 7.60 Hz, 1 H) 7.14 (t, J = 7.76 Hz, 1 H) 6.88 (t, J = 7.09 Hz, 1 H) 6.77 (d, J = 8.24 Hz, 1 H) 6.67 (s, 1 H) 5.09-5.16 (m, 1 H) 4.23 (br t, J = 5.01 Hz, 2 H) 4.05-4.18 (m, 4 H) 2.52-2.58 (m, 1 H) 2.12 (s, 3 H) 1.93-2.02 (m, 1 H) 1.30 (s, 6 H) |
| A565 | (400 MHz, DMSO-d6) δ ppm 10.55 (s, 1 H) 8.25 (s, 1 H) 7.79 (d, J = 1.90 Hz, 2 H) 7.71 (t, J = 1.90 Hz, 1 H) 7.29 (s, 1 H) 7.00 (dd, J = 8.05, 1.20 Hz, 1 H) 6.85 (t, J = 7.16 Hz, 1 H) 6.69-6.79 (m, 2 H) 4.30-4.40 (m, 2 H) 3.61 (br s, 2 H) 1.60 (s, 9 H) |
| A566 | (400 MHz, DMSO-d6) δ ppm 9.05 (d, J = 7.98 Hz, 1 H) 7.94 (s, 1 H) 7.53-7.71 (m, 1 H) 7.24-7.39 (m, 2 H) 7.16 (t, J = 7.67 Hz, 1 H) 6.87-6.96 (m, 2 H) 6.78 (d, J = 8.11 Hz, 1 H) 5.12-5.19 (m, 1 H) 4.15-4.30 (m, 2 H) 2.29 (s, 3 H) 2.09-2.20 (m, 1 H) 1.94-2.05 (m, 1 H) 1.58 (s, 9 H) |
| A567 | (400 MHz, DMSO-d6) δ ppm 8.74 (dd, J = 8.17, 2.60 Hz, 1 H) 7.87 (dd, J = 8.30, 2.98 Hz, 1 H) 7.81 (s, 1 H) 7.45 (ddd, J = 8.68, 5.96, 2.98 Hz, 1 H) 7.25 (d, J = 7.48 Hz, 1 H) 7.15 (t, J = 7.66 Hz, 1 H) 6.92 (s, 1 H) 6.86-6.90 (m, 1 H) 6.78 (dd, J = 8.24, 1.01 Hz, 1 H) 5.09-5.16 (m, 1 H) 4.09-4.28 (m, 6 H) 2.89 (s, 1 H) 2.68-2.78 (m, 1 H) 2.05-2.16 (m, 1 H) 1.92-2.02 (m, 1 H) 1.31 (s, 6 H) |
| A568 | 1H NMR (400 MHz, DMSO-d6) δ ppm 8.73 (dd, J = 8.24, 3.04 Hz, 1 H) 7.94 (d, J = 2.41 Hz, 1 H) 7.80 (s, 1 H) 7.52 (dd, J = 8.36, 2.41 Hz, 1 H) 7.27 (dd, J = 6.97, 4.69 Hz, 1 H) 7.14 (t, J = 7.72 Hz, 1 H) 6.88 (t, J = 7.48 Hz, 1 H) 6.84 (s, 1 H) 6.78 (d, J = 7.98 Hz, 1 H) 5.13-5.20 (m, 1 H) 4.43 (q, J = 7.10 Hz, 1 H) 3.18 (d, J = 2.15 Hz, 6 H) 2.06-2.21 (m, 4 H) 1.93-2.04 (m, 1 H) |
| A569 | (400 MHz, DMSO-d6) δ ppm 9.20 (dd, J = 17.81, 7.41 Hz, 1 H) 8.80 (s, 1 H) 8.56 (d, J = 6.72 Hz, 1 H) 8.05 (d, J = 9.13 Hz, 1 H) 7.83 (dd, J = 8.36, 3.04 Hz, 1 H) 7.36-7.49 (m, 2 H) 6.95 (s, 1 H) 5.29 (quin, J = 6.18 Hz, 1 H) 4.61-4.73 (m, 1 H) 4.50-4.60 (m, 1 H) 2.21-2.31 (m, 4 H) 2.07-2.18 (m, 1 H) 1.57 (s, 9 H) |

Biological Examples

The disclosure is further illustrated by the following biological examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Biological Example 1: Screening method to test activity of compounds against microfilaria of *Dirofilaria immitis.*

Four hundred to six hundred microfilariae of *Dirofilaria immitis* were added to wells of a microtiter plate containing RPMI media and the test compound formulated in 100% DMSO. Plates were held for three days at 37° C. and 5% $CO_2$. The efficacy of a compound was determined based on the motility of the microfilaria as compared to average motility of control wells containing DMSO only. A dose response assay was conducted to determine an $EC_{50}$ value. Compounds A468, A470, A480, A482, A508, A510, A514, A529, A536b, A538, A543, A547, A548, A552, A556, A561, A562, A563, A564 and A567 exhibited $EC_{50}$ values between 1000 nM and 10000 nM. Compounds A465, A467, A475, A509, A527, A524, A549, A554 and A560 exhibited $EC_{50}$ values of between 100 and 1000 nM. Compounds A518, A497, A494, A481, A479, A478, A473, A487, A476, A483, A469, A466, A462, A492, A528, A532, A533, A539, A544, A550, A551, A555, A559 exhibited $EC_{50}$ values between 10 nM and 100 nM. Compounds A463, A464, A484, A485, A486, A499, A471, A472, A474, A477, A488, A489, A490, A491, A492, A493, A495, A496, A498, A501, A502, A503, A504, A505, A506, A507, A513, A516, A517, A519, A522, A523, A525, A526, A530, A534, A536a, A537, A540, A541, A553, A557, A558, A565, A566, A568 and A569 exhibited $EC_{50}$ values of less than 10 nM.

Biological Example 2: Screening method to test activity of compounds against *Haemonchus contortus.*

Twenty L1 *Haemonchus contortus* larvae were added to wells of a microtiter plate containing a nutrient medium and the test compound in DMSO. An analysis was conducted at 4 days to determine the extent of development of the larvae from L1 to L3. Larvae exposed to DMSO alone served as controls. A dose response assay was conducted to determine an $EC_{50}$ value. Compounds A512, A515, A535, A549, A554, A563, A564 and A567 exhibited $EC_{50}$ values of between 1000 nM and 10000 nM. Compounds A462, A466, A479, A492, A482, A527, A528, A524, A532, A533, A544, A560, were found to be active with $EC_{50}$ values of between 100 nM and 1000 nM. Compounds A463, A465, A483, A476, A487, A475, A474, A477, A478, A488, A481, A494, A496, A497, A498, A499, A501, A503, A504, A505, A506, A513, A516, A517, A518, A525, A526, A536a, A540, A541, A550, A551, A555, A559 and A565 exhibited $EC_{50}$ values of between nM and 100 nM. Compounds A484, A485, A486, A472, A471, A473, A493, A495, A502, A507, A523, A522, A530, A534, A553, A557, A558, A566 and A568 exhibited $EC_{50}$ values of less than 10 nM.

Biological Example 3: Screening method to test activity of compounds against L4 stage larvae of *Dirofilaria immitis.*

Four to six L4 stage *Dirofilaria immitis* worms are added to wells of a microtiter plate containing maintenance nutrient media and the test compound formulated in 100% DMSO. Plates are held at 37° C. and 5% $CO_2$ for three days and then assessed to determine the motility of the larvae. Efficacy of a compound is determined by comparison of the treated L4 motility of the relative to the average motility of worms in control wells containing DMSO only. A dose response assay is conducted to determine an $EC_{50}$ value. Compounds 536b, 538, A543, A545, A546, A547, A548, A552, A556, A561, A562, A563 and A564 exhibited $EC_{50}$ values of between 1000 nM and 10000 nM Compounds A467, A478, A479, A480, A521, A524, A529, A532, A533, A539, A544, A549, A554 and A567 exhibited $EC_{50}$ values of between 100 nM and 1000 nM; compounds A462, A463, A465, A466, A469, A482, A488, A496, A527, A528, A536a, A537, A540, A550, A551, A555 and A559 were found to have $EC_{50}$ values of between 10 nM and 100 nM. Compounds A464, A483, A484, A485, A486, A471, A473, A474, A476, A477, A487, A489, A482, A499, A491, A481, A490, A493, A494, A495, A498, A501, A502, A503, A504, A505, A506, A507, A513, A516, and A519, A522, A523, A525, A526, A530, A534, A541, A553, A557, A558, A565 and A566 exhibited $EC_{50}$ values of less than 10 nM.

Biological Example 4; In vivo efficacy against the resistant JYD-34 isolate of *Dirofilaria immitis* in immune-deficient (NOD-scid-gama, NSG) mice.

The efficacy of the compounds of the invention against a resistant isolate of *Dirofilaria immitis* (JYD-34 isolate) was evaluated in immune-deficient mice (NOD-scid-gama, NSG) as an intermediate host of the parasite (see WO 2018/148392 A1). Mice were infected with approximately 50 third stage *Dirofilaria immitis* (JYD-34 isolate) by subcutaneous injection on Day 0. Mice were treated orally with the placebo and test articles at a dosage of 25 mg/kg body weight on Day 1, Day 15, and Day 30. The dose of 25 mg/kg in the rodent model is believed to be equivalent to a dose of 5 mg/kg in dogs. Fifteen days after the last dose, at Day 45 after treatment, mice were euthanized, and live *Dirofilaria immitis* larvae were recovered from tissues and counted.

In this model, compound A491 exhibited efficacy of <50%; compounds A465, A484 and A495 exhibited efficacy between 50% and 70%; compounds A464, A486, A471, A481, A489, A501, A502 and A566 exhibited an efficacy of between 70% and 90%; and compounds A472, A473, A493, A504, A507, A522 and A530 exhibited efficacy of >90%. Mice treated with the macrocyclic lactone ivermectin dosed orally at a dosage of 0.2 mg/kg exhibited efficacy of <50%. For comparison, the recommended minimum dose level of ivermectin for dogs in the commercial product HEARTGARD® Plus (ivermectin/pyrantel) is 6 μg/kg.

Biological Example 5: Comparison of In vivo efficacy against the resistant JYD-34 isolate of *Dirofilaria immitis* in immune-deficient (NOD-scid-gama, NSG) mice with closest prior art compound.

It has been found that the compounds of the invention having the bicyclic pyrrolopyridazine core structure are highly efficacious against immature stages of *Dirofilaria immitis* such as microfilaria and the L4 stage worm, including *Dirofilaria immitis* isolates that have been shown to be resistant to macrocyclic lactone treatment. Such resistant isolates of *Dirofilaria immitis* include the JYD34 isolate and others. Importantly, the compounds of the invention having the 5-6 fused bicyclic pyrrolopyridazine core structure demonstrate surprising and unexpected superior efficacy against immature stages of *Dirofilaria immitis* compared with compounds having a different 5-6 fused nitrogen-containing bicyclic core but having the same substituents around the bicyclic core.

Using the in vivo protocol described in Biological Example 4 above, the efficacies of Compound A465 of the present invention and prior art compound 156 described in WO 2020/014068 (see page 124) were evaluated. The compounds described in WO 2020/014068 include a different 5-6 fused bicyclic ring core (pyrazolo[1,5-a]pyridine) compared with the pyrrolopyridazine core ring system of the compounds of the invention. With the exception of the different core ring systems, compound A465 and prior art compound 156 contain the same substituents around the bicyclic ring. The structures of compound A465 of the invention and prior art compound 156 are shown below for illustration:

A465

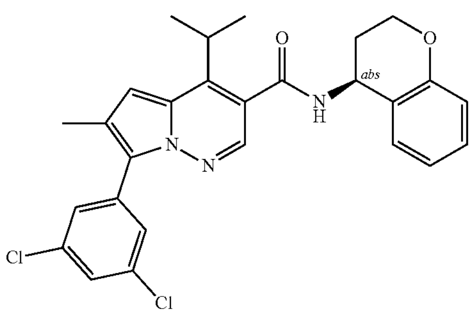

156

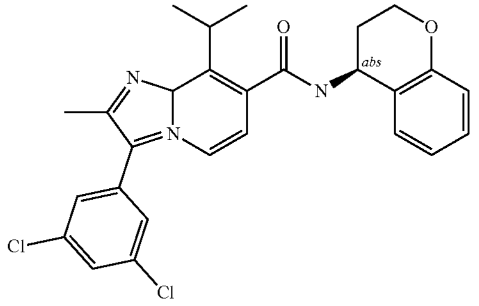

In this in vivo model system, compound A465 exhibited an efficacy of 68% while compound 156 exhibited an efficacy of 29% at a dosage of 25 mg/kg. The difference in efficacy is significant in this model. This example clearly shows the importance of the pyrrolopyridazine bicyclic ring on the in vivo efficacy of the compounds against a resistant isolate of *Dirofilaria immitis*. As illustrated by the two structures above, with the exception of the bicyclic ring systems, the substitution pattern of the compounds is exactly the same.

Biological Example 6: In vivo efficacy against the resistant JYD-34 isolate of *Dirofilaria immitis* in dogs.

Beagle dogs were tested for microfilaria and heartworm antigen and received a full physical examination prior to inclusion in the study. Each dog was inoculated with 50 infective third-stage *D. immitis* larvae on Day-30 using the JYD-34 isolate which has been demonstrated to be resistant to macrocyclic lactones. Antigen testing performed on blood collected on Day 90 confirmed that animals had not been exposed to *D. immitis* prior to the induced infection.

Dogs were ranked by decreasing body weight within sex to form blocks of eight dogs each with approximately equal numbers of each sex and randomly assigned to each treatment group. Each study group contained five dogs. Dogs in the negative control group (Group 1) were untreated. Dogs in Group 2 were treated orally four times at monthly intervals with the commercial product Interceptor™ (milbemycin oxime) according to the product label. Dogs in Groups 3 and 4 were treated orally four times at monthly intervals (Days 0, 27, 55 and 84) with capsules containing an oral solution of Compound A471 and A464, respectively, at a dosage of 5 mg/kg body weight. On study day 120 dogs were euthanized and necropsied for evaluation of the presence adult heartworms. The results of the study are shown in Table 5 below.

TABLE 5

Efficacy against *D. immitis* in beagles.

| Trt. Group | Investigational Material | Dose | Geometric Mean Live Heartworm Count | % Efficacy |
|---|---|---|---|---|
| 1 | (−) control | n/a | 27.1 | n/a |
| 2 | Interceptor ™ (milbemycin oxime) | 0.5 mg/kg | 21.2 | 21.8 |
| 3 | A471 | 5 mg/kg | 16.5 | 39.0 |
| 4 | A464 | 5 mg/kg | 16.7 | 38.2 |

As shown in Table 5, compounds A471 and A464 of the invention were found to be more effective than the commercial product Interceptor™ administered according to the label dose against the resistant JYD-34 isolate of *Dirofilaria immitis*.

Biological Example 7: In vivo efficacy at two dosages against the resistant JYD-34 isolate of *Dirofilaria immitis* in dogs.

In a further in vivo study conducted according to the procedure described in Biological Example 6 above, the efficacy of compounds A481 and A493 was tested against a resistant heartworm isolate (JYD-34) in beagles at two different dosage rates compared with a negative control group (Group 1) and a positive control group (Group 2) treated with Interceptor™ (milbemycin oxime). The objective of dosing the test compounds, in the higher dosage rate, on consecutive days was to evaluate the impact of increased exposure to the compounds on the efficacy against heartworm. Given the length of the heartworm lifecycle for the target L4 stage worm (see, for example, page 1, line 25 to page 2, line 10) and the study duration, it is considered that splitting the total dose into two administrations on consecutive days would not adversely impact the study outcome. In the study, Group 3 was treated with Compound A481 at a dosage of 5 mg/kg body weight on days 0, 27, 55 and 84. Dogs in Group 4 were treated with Compound A481 at a dosage of 5 mg/kg body weight on days-1, 0, 26, 27, 54, 55, 83 and 84. Similarly, dogs in Group 5 were treated with Compound A493 at a dosage of 5 mg/kg body weight on days 0, 27, 55 and 84, and dogs in Group 6 were treated with Compound A493 at a dosage of 5 mg/kg body weight on days-1, 0, 26, 27, 54, 55, 83 and 84. The results of the study are shown in Table 6 below.

TABLE 6

Efficacy against *D. immitis* in beagles at two dosages.

| Trt. Group | Investigational Material | Dose | Geometric Mean Live Heartworm Count | % Efficacy |
|---|---|---|---|---|
| 1 | (−) control | n/a | 31.5 | n/a |
| 2 | Interceptor ™ (milbemycin oxime) | 0.5 mg/kg | 5.6 | 82.1 |

TABLE 6-continued

Efficacy against *D. immitis* in beagles at two dosages.

| Trt. Group | Investigational Material | Dose | Geometric Mean Live Heartworm Count | % Efficacy |
|---|---|---|---|---|
| 3 | A481 | 5 mg/kg | 11.3 | 64.2 |
| 4 | A481 | 10 mg/kg (over 2 consecutive days) | 0.6 | 98.0 |
| 5 | A493 | 5 mg/kg | 0.3 | 99.0 |
| 6 | A493 | 10 mg/kg (over 2 consecutive days) | 0 | 100.0 |

As shown in Table 6, compounds A481 and A493 are highly efficacious against the resistant JD-34 isolate of *Dirofilaria immitis* compared with the positive control. It is important to note that the Interceptor™ group (Group 2) was dosed monthly according to the product label while the optimum dosage of the test compounds has not yet been determined. It is also noted that the efficacy of the Interceptor™ group (Group 2) in the present study was significantly higher than the efficacy observed in the studies described in Biological Example 6 and Biological Example 9 (below). Compounds A481 and A493 exhibited efficacy of about 98% and 100% against the resistant JYD-34 isolate of *Dirofilaria immitis* at a dosage of 5 mg/kg administered monthly for four months on two consecutive days, while Compound A493 exhibited efficacy of 99% when one single dosage at 5 mg/kg was administered monthly for four months. These results against a resistant isolate of *Dirofilaria immitis* are significant and surprising.

Biological Example 8: In vivo efficacy against resistant JYD-34 isolate of *Dirofilaria immitis* in dogs.

In a further in vivo study using the procedure described in Biological Example 6, the efficacy of compound A472 was tested for efficacy against a resistant heartworm isolate (JYD-34) in beagles compared with a negative control group (Group 1) and a positive control group (Group 2) treated with Interceptor™ (milbemycin oxime). In this study, Compound A472 was found to be 100% efficacious at preventing infections with adult heartworm when administered in a dosage of 5 mg/kg body weight monthly for four months. In comparison, the milbemycin oxime control group was only found to be 16.6% efficacious. Table 7 below summarizes the results of the study.

TABLE 7

Efficacy against *D. immitis* (JYD-34 isolate) in beagles.

| Trt. Group | Investigational Material | Dose | Live Heartworm Count (geo. mean) | % Efficacy |
|---|---|---|---|---|
| 1 | (−) control | n/a | 33.9 | n/a |
| 2 | Interceptor ™ (milbemycin oxime) | 0.5 mg/kg | 28.3 | 16.6 |
| 3 | A472 | 5 mg/kg | 0 | 100.0 |

As shown above in comparison with the commercial product Interceptor™ (milbemycin oxime), the excellent in vivo efficacy of the compounds of the invention against a resistant isolate of *Dirofilaria immitis* is noteworthy and demonstrates the inventiveness of the compounds described herein.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the prevention, control, and/or treatment of a parasitic infection in an animal in need thereof, wherein the method comprises administering to the animal an effective amount of a compound of Formula (I):

(I)

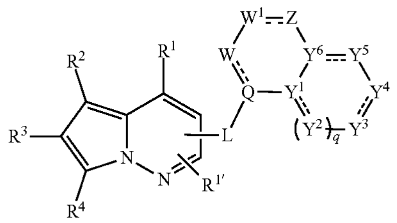

or a pharmaceutically acceptable salt or stereoisomer thereof, wherein:

each ---- is independently a single bond or double bond;

$R^1$ is H, halogen, CN, alkyl, alkyl-$NH_2$, alkyl-NH(alkyl), alkyl-N(alkyl)$_2$, alkyl-O(alkyl), alkenyl, alkynyl, C(O)alkyl, C(O)$NH_2$, C(O)NH(alkyl), C(O)N(alkyl)$_2$, C(O)O(alkyl), Si(alkyl)$_3$, $NR^aR^b$, OH, O(alkyl), O(alkenyl), O(alkynyl), OSi(alkyl)$_3$, O(aryl), $SF_5$, $S(O)_p$alkyl, $S(O)_p$haloalkyl, cycloalkyl, cycloalkenyl, cycloalkoxy, heterocyclyl, aryl, or heteroaryl, wherein the alkyl, alkyl-$NH_2$, alkyl-NH(alkyl), alkyl-N(alkyl)$_2$, alkyl-O(alkyl), alkenyl, alkynyl, C(O)alkyl, C(O)$NH_2$, C(O)NH(alkyl), C(O)N(alkyl)$_2$, C(O)O(alkyl), Si(alkyl)$_3$, O(alkyl), O(alkenyl), O(alkynyl), O(aryl), OSi(alkyl)$_3$, $S(O)_p$alkyl, $S(O)_p$haloalkyl, cycloalkyl, cycloalkenyl, cycloalkoxy, heterocyclyl, aryl, or heteroaryl is optionally substituted with one or more independently selected substituents;

$R^{1'}$ is H, halogen, alkyl, or haloalkyl;

$R^2$ is H, halogen, CN, alkyl, alkyl-$NH_2$, alkyl-NH(alkyl), alkyl-N(alkyl)$_2$, alkyl-O(alkyl), alkenyl, alkynyl, C(O)alkyl, C(O)$NH_2$, C(O)NH(alkyl), C(O)N(alkyl)$_2$, C(O)O(alkyl), $NR^aR^b$, OH, O(alkyl), O(aryl), $SF_5$, $S(O)_p$alkyl, $S(O)_p$haloalkyl, cycloalkyl, cycloalkenyl, cycloalkoxy, heterocyclyl, aryl, or heteroaryl, wherein the alkyl, alkyl-$NH_2$, alkyl-NH(alkyl), alkyl-N(alkyl)$_2$, alkyl-O(alkyl), alkenyl, alkynyl, C(O)alkyl, C(O)$NH_2$, C(O)NH(alkyl), C(O)N(alkyl)$_2$, C(O)O(alkyl), O(alkyl), O(aryl), $S(O)_p$alkyl, $S(O)_p$haloalkyl, cycloalkyl, cycloalkenyl, cycloalkoxy, heterocyclyl, aryl, or heteroaryl is optionally substituted with one or more independently selected substituents;

$R^3$ is H, halogen, CN, alkyl, alkyl-$NH_2$, alkyl-NH(alkyl), alkyl-N(alkyl)$_2$, alkyl-O(alkyl), alkenyl, alkynyl, C(O)alkyl, C(O)$NH_2$, C(O)NH(alkyl), C(O)N(alkyl)$_2$, C(O)O(alkyl), $NR^aR^b$, OH, O(alkyl), O(aryl), $SF_5$, $S(O)_p$alkyl, $S(O)_p$haloalkyl, cycloalkyl, cycloalkenyl, cycloalkoxy, heterocyclyl, aryl, or heteroaryl, wherein the alkyl, alkyl-$NH_2$, alkyl-NH (alkyl), alkyl-N(alkyl)$_2$, alkyl-O(alkyl), alkenyl, alkynyl, C(O)alkyl, C(O)NH$_2$, C(O)NH(alkyl), C(O)N(alkyl)$_2$, C(O)O(alkyl), O(alkyl), O(aryl), S(O)$_p$alkyl, S(O)$_p$haloalkyl, cycloalkyl, cycloalkenyl, cycloalkoxy, heterocyclyl, aryl, or heteroaryl is optionally substituted with one or more independently selected substituents;

$R^4$ is H, alkyl, alkenyl, alkynyl, C(O)alkyl, C(O)NH$_2$, C(O)NH(alkyl), C(O)N(alkyl)$_2$, C(O)O(alkyl), NR$^a$R$^b$, SF$_5$, S(O)$_p$alkyl, S(O)$_p$haloalkyl, cycloalkyl, cycloalkenyl, carbocyclyl-(spirocyclic carbocyclyl), carbocyclyl-(spirocyclic heterocyclyl), heterocyclyl, heterocyclyl-(spirocyclic carbocyclyl), heterocyclyl-(spirocyclic heterocyclyl), aryl, or 5- to 10-membered heteroaryl, wherein the alkyl, alkenyl, alkynyl, C(O)alkyl, C(O)NH$_2$, C(O)NH(alkyl), C(O)N(alkyl)$_2$, C(O)O(alkyl), S(O)$_p$alkyl, S(O)$_p$haloalkyl, cycloalkyl, cycloalkenyl, heterocyclyl, aryl, or 5- to 10-membered heteroaryl is optionally substituted with one or more independently selected substituents;

each $R^a$ is independently H or alkyl, wherein each alkyl is optionally and independently substituted with one or more independently selected substituents;

each $R^b$ is independently H or alkyl, wherein each alkyl is optionally and independently substituted with one or more independently selected substituents; or any $R^a$ and $R^b$, taken together with the nitrogen atom to which they are attached, independently forms a 3- to 8-membered heterocyclyl;

wherein each 3- to 8-membered heterocyclyl independently contains 0, 1, 2, or 3 additional heteroatoms independently selected from the group consisting of N, O, Si, and S; and wherein each 3- to 8-membered heterocyclyl is optionally and independently substituted with one or more independently selected substituents;

L is (L1), (L2), (L3), (L4), (L5), (L6), (L7), (L8), (L9), (L10), (L11), (L12), (L13), (L14), (L15), (L16), or (L17):

—C(X)NR'-(L1), —NR'C(X)-(L2), —NR'C(X)NR'-(L3), —S(NR') (O)CH$_2$-(L4), —CH$_2$S(NR') (O)-(L5), —S(O)$_2$NR'-(L6), —NR'S(O)$_2$-(L7), —S(O)$_2$CH$_2$-(L8), —CH$_2$S(O)$_2$-(L9), —CH(CF$_3$)NR'-(L10), —NR'CH(CF$_3$)-(L11), —CH(CHF$_2$)NR'-(L12), —NR'CH(CHF$_2$)-(L13), (L14)

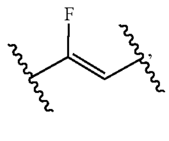

(L15)

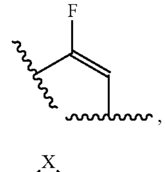

(L16)

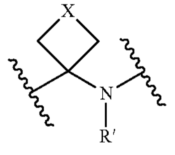

, or

-continued (L17)

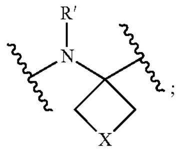

each X is independently NR', O, or S;

R' is H, alkyl, haloalkyl, cycloalkyl, aralkyl, or aryl, wherein the alkyl, haloalkyl, cycloalkyl, aralkyl, or aryl is optionally substituted with one or more independently selected substituents; or two R', together with the atoms to which they are attached, form a 2- to 4-membered carbon chain resulting in a 5- to 7-membered heterocyclyl;

$Y^1$ is C, CR$^5$, or N;

$Y^2$ is CR$^5$, —CR$^5$R$^{5'}$—, N, —NR'—, —O—, or —S—;

$Y^3$ is CR$^5$, —CR$^5$R$^{5'}$—, N, —NR'—, —O—, or —S—;

$Y^4$ is CR$^5$, —CR$^5$R$^{5'}$—, N, —NR'—, —O—, or —S—;

$Y^5$ is CR$^5$, —CR$^5$R$^{5'}$—, N, —NR'—, —O—, or —S—;

$Y^6$ is C, CR$^5$, or N;

W is absent, CR$^6$, —CR$^6$R$^7$—, N, —NR$^8$—, —O—, or —S(O)$_p$—;

$W^1$ is CR$^6$, —CR$^6$R$^7$, N, —NR$^8$—, —O—, or —S(O)$_p$—;

Z is CR$^7$, —CR$^6$R$^7$—, N, —NR$^8$—, —O—, or —S(O)$_p$—;

Q is CR$^9$ or N;

each $R^5$ is independently H, halogen, CN, NO$_2$, alkyl, alkyl-NH$_2$, alkyl-NH(alkyl), alkyl-N(alkyl)$_2$, alkyl-O(alkyl), alkenyl, alkynyl, C(O)alkyl, C(O)NH$_2$, C(O)NH(alkyl), C(O)N(alkyl)$_2$, C(O)O(alkyl), NR$^c$R$^d$, NHC(O)alkyl, OH, O(alkyl), OC(O)alkyl, SF$_5$, S(O)$_p$alkyl, S(O)$_p$haloalkyl, cycloalkyl, cycloalkoxy, aryl, or heteroaryl, wherein each alkyl, alkyl-NH$_2$, alkyl-NH(alkyl), alkyl-N(alkyl)$_2$, alkyl-O(alkyl), alkenyl, alkynyl, C(O)alkyl, C(O)NH$_2$, C(O)NH(alkyl), C(O)N(alkyl)$_2$, C(O)O(alkyl), NHC(O)alkyl, O(alkyl), OC(O)alkyl S(O)$_p$alkyl, S(O)$_p$haloalkyl, cycloalkyl, cycloalkoxy, aryl, and heteroaryl is optionally and independently substituted with one or more independently selected substituents;

each $R^{5'}$ is independently H, halogen, CN, NO$_2$, alkyl, alkyl-NH$_2$, alkyl-NH(alkyl), alkyl-N(alkyl)$_2$, alkyl-O(alkyl), alkenyl, alkynyl, C(O)alkyl, C(O)NH$_2$, C(O)NH(alkyl), C(O)N(alkyl)$_2$, C(O)O(alkyl), NR$^c$R$^d$, NHC(O)alkyl, OH, O(alkyl), OC(O)alkyl, SF$_5$, S(O)$_p$alkyl, S(O)$_p$haloalkyl, cycloalkyl, cycloalkoxy, aryl, or heteroaryl, wherein each alkyl, alkyl-NH$_2$, alkyl-NH(alkyl), alkyl-N(alkyl)$_2$, alkyl-O(alkyl), alkenyl, alkynyl, C(O)alkyl, C(O)NH$_2$, C(O)NH(alkyl), C(O)N(alkyl)$_2$, C(O)O(alkyl), NHC(O)alkyl, O(alkyl), OC(O)alkyl, S(O)$_p$alkyl, S(O)$_p$haloalkyl, cycloalkyl, cycloalkoxy, aryl, and heteroaryl is optionally and independently substituted with one or more independently selected substituents; or any $R^5$ and $R^{5'}$, taken together with the carbon atom to which they are attached, independently forms a 2- to 6-membered chain resulting in a 3- to 7-membered carbocyclyl or heterocyclyl;

wherein each 3- to 7-membered carbocyclyl or heterocyclyl optionally and independently contains 1 or 2 heteroatoms independently selected from the group consisting of N, O, Si, and S; and wherein each 3- to 7-membered carbocyclyl or heterocyclyl is optionally and independently substituted with one or more independently selected substituents;

each $R^c$ is independently H or alkyl, wherein each alkyl is optionally and independently substituted with one or more independently selected substituents;

each $R^d$ is independently H or alkyl, wherein each alkyl is optionally and independently substituted with one or more independently selected substituents; or any $R^c$ and $R^d$, taken together with the nitrogen atom to which they are attached, independently forms a 3- to 8-membered heterocyclyl;

wherein each 3- to 8-membered heterocyclyl independently contains 0, 1, 2, or 3 additional heteroatoms independently selected from the group consisting of N, O, Si, and S; and wherein each 3- to 8-membered heterocyclyl is optionally and independently substituted with one or more independently selected substituents;

each $R^6$ is independently H, halogen, alkyl, alkenyl, alkynyl, O(alkyl), cycloalkyl, or cycloalkoxy, wherein each alkyl, alkenyl, alkynyl, O(alkyl), cycloalkyl, and cycloalkoxy is optionally and independently substituted with one or more independently selected substituents;

each $R^7$ is independently H, halogen, alkyl, alkenyl, alkynyl, O(alkyl), cycloalkyl, or cycloalkoxy, wherein each alkyl, alkenyl, alkynyl, O(alkyl), cycloalkyl, and cycloalkoxy is optionally and independently substituted with one or more independently selected substituents; or any $R^6$ and $R^7$, taken together with the carbon atom to which they are attached, independently forms a 2- to 6-membered chain resulting in a 3- to 7-membered carbocyclyl or heterocyclyl;

wherein each 3- to 7-membered carbocyclyl or heterocyclyl optionally and independently contains 1 or 2 heteroatoms independently selected from the group consisting of N, O, Si, and S; and wherein each 3- to 7-membered carbocyclyl or heterocyclyl is optionally and independently substituted with one or more independently selected substituents;

$R^8$ is H or $C_1$-$C_4$ alkyl;

$R^9$ is H, halogen, alkyl, haloalkyl, alkenyl, alkynyl, or cycloalkyl;

each p is independently 0, 1, or 2; and q is 0 or 1;

wherein each optional substituent is independently selected from the group consisting of halogen, CN, $NO_2$, alkyl, haloalkyl, CH(NH), CH(NOH), C(NH)$NH_2$, C(O)alkyl, C(O)haloalkyl, C(O)$NH_2$, C(O)NH (alkyl), C(O)NH (haloalkyl), C(O)N(alkyl)$_2$, C(O)N (haloalkyl)$_2$, C(O)OH, C(O)O(alkyl), C(O)O(haloalkyl), C(O)SR, C(S)$NH_2$, Si(R)$_3$, $NH_2$, NH(alkyl), NHC(NH)$NH_2$, $NHNH_2$, NH(aryl), N(alkyl)$_2$, N (aryl)$_2$, OH, O(alkyl), O(haloalkyl), OSi(R)$_3$, O(aryl), =O, SH, $SF_5$, S(alkyl), S(haloalkyl), S(O) alkyl, S(O)haloalkyl, S(O)$_2$alkyl, S(O)$_2$haloalkyl, cycloalkyl, cycloalkenyl, heterocyclyl, aryl, and heteroaryl; and each R is independently alkyl, haloalkyl, or aryl;

with the proviso that no more than three of $Y^1$, $Y^2$, $Y^3$, $Y^4$, $Y^5$, and $Y^6$ are heteroatoms.

2. The method of claim 1, wherein:

(a) the method is for preventing a parasitic infection in an animal in need thereof; and (b) the parasitic infection is caused by *Dirofilaria immitis*.

3. The method of claim 1, wherein the compound is of Formula (IA):

(IA)

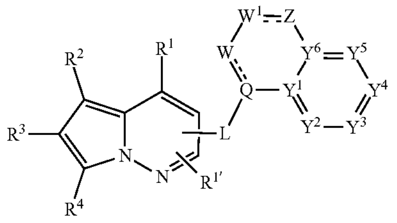

or a pharmaceutically acceptable salt or stereoisomer thereof, wherein:

each ---- is independently a single bond or double bond;

$R^1$ is H, halogen, CN, alkyl, alkyl-$NH_2$, alkyl-NH (alkyl), alkyl-N(alkyl)$_2$, alkyl-O(alkyl), alkenyl, alkynyl, $NR^aR^b$, O(alkyl), O(alkenyl), O(alkynyl), cycloalkyl, cycloalkenyl, or heterocyclyl, wherein the alkyl, alkyl-$NH_2$, alkyl-NH(alkyl), alkyl-N(alkyl)$_2$, alkyl-O(alkyl), alkenyl, alkynyl, O(alkyl), O(alkenyl), O(alkynyl), cycloalkyl, cycloalkenyl, or heterocyclyl is optionally substituted with one or more independently selected substituents;

$R^{1'}$ is H, halogen, alkyl, or haloalkyl;

$R^2$ is H, halogen, CN, alkyl, alkyl-$NH_2$, alkyl-NH (alkyl), alkyl-N(alkyl)$_2$, alkyl-O(alkyl), alkenyl, alkynyl, OH, or O(alkyl), wherein the alkyl, alkyl-$NH_2$, alkyl-NH(alkyl), alkyl-N(alkyl)$_2$, alkyl-O(alkyl), alkenyl, alkynyl, or O(alkyl) is optionally substituted with one or more independently selected substituents;

$R^3$ is H, halogen, CN, alkyl, alkyl-$NH_2$, alkyl-NH (alkyl), alkyl-N(alkyl)$_2$, alkyl-O(alkyl), alkenyl, alkynyl, OH, or O(alkyl), wherein the alkyl, alkyl-$NH_2$, alkyl-NH(alkyl), alkyl-N(alkyl)$_2$, alkyl-O(alkyl), alkenyl, alkynyl, or O(alkyl) is optionally substituted with one or more independently selected substituents;

$R^4$ is cycloalkyl, cycloalkenyl, heterocyclyl, phenyl, or 5- or 6-membered heteroaryl, wherein the cycloalkyl, cycloalkenyl, heterocyclyl, phenyl, or 5- or 6-membered heteroaryl is optionally substituted with one or more independently selected substituents;

each $R^a$ is independently H or alkyl, wherein each alkyl is optionally and independently substituted with one or more independently selected substituents;

each $R^b$ is independently H or alkyl, wherein each alkyl is optionally and independently substituted with one or more independently selected substituents; or any $R^a$ and $R^b$, taken together with the nitrogen atom to which they are attached, independently forms a 3- to 8-membered heterocyclyl;

wherein each 3- to 8-membered heterocyclyl independently contains 0, 1, 2, or 3 additional heteroatoms independently selected from the group consisting of N, O, Si, and S; and wherein each 3- to 8-membered heterocyclyl is optionally and independently substituted with one or more independently selected substituents;

L is (L1), (L2), (L6), (L7), (L16), or (L17):

C(X)NR'-(L1), —NR'C(X)-(L2), —$S(O)_2NR'$-(L6), —$NR'S(O)_2$-(L7), (L16)

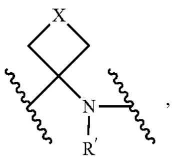

, or (L17)

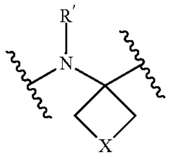

;

each X is independently NR', O, or S;

R' is H, alkyl, haloalkyl, or aralkyl, wherein the alkyl, haloalkyl, or aralkyl is optionally substituted with one or more independently selected substituents;

$Y^1$ is C or N;

$Y^2$ is $CR^5$ or N;

$Y^3$ is $CR^5$ or N;

$Y^4$ is $CR^5$ or N;

$Y^5$ is $CR^5$ or N;

$Y^6$ is C or N;

W is absent, $CR^6$, or —$CR^6R^7$—;

$W^1$ is $CR^6$ or —$CR^6R^7$—;

Z is $CR^7$, —$CR^6R^7$—, or —O—;

Q is $CR^9$ or N;

each $R^5$ is independently H, halogen, CN, alkyl, alkenyl, alkynyl, or O(alkyl), wherein each alkyl, alkenyl, alkynyl, and O(alkyl) is optionally and independently substituted with one or more independently selected substituents;

each $R^{5'}$ is independently H, halogen, CN, alkyl, alkenyl, alkynyl, or O(alkyl), wherein each alkyl, alkenyl, alkynyl, and O(alkyl) is optionally and independently substituted with one or more independently selected substituents;

each $R^6$ is independently H, halogen, alkyl, alkenyl, alkynyl, or O(alkyl), wherein each alkyl, alkenyl, alkynyl, and O(alkyl) is optionally and independently substituted with one or more independently selected substituents;

each $R^7$ is independently H, halogen, alkyl, alkenyl, alkynyl, or O(alkyl), wherein each alkyl, alkenyl, alkynyl, and O(alkyl) is optionally and independently substituted with one or more independently selected substituents; or any $R^6$ and $R^7$, taken together with the carbon atom to which they are attached, independently forms a 2- to 6-membered chain resulting in a 3- to 7-membered carbocyclyl or heterocyclyl;

wherein each 3- to 7-membered carbocyclyl or heterocyclyl optionally and independently contains 1 or 2 heteroatoms independently selected from the group consisting of N, O, Si, and S; and wherein each 3- to 7-membered carbocyclyl or heterocyclyl is optionally and independently substituted with one or more independently selected substituents;

$R^9$ is H, halogen, alkyl, or haloalkyl;

wherein each optional substituent is independently selected from the group consisting of halogen, CN, alkyl, haloalkyl, C(O)alkyl, C(O)haloalkyl, $C(O)NH_2$, C(O)NH(alkyl), C(O)NH (haloalkyl), $C(O)N(alkyl)_2$, $C(O)N(haloalkyl)_2$, C(O)OH, C(O)O(alkyl), C(O)O(haloalkyl), $C(S)NH_2$, $Si(R)_3$, $NH_2$, NH(alkyl), $N(alkyl)_2$, OH, O(alkyl), O(haloalkyl), $OSi(R)_3$, SH, $SF_5$, S(alkyl), S(haloalkyl), S(O)alkyl, $S(O)_2$alkyl, $S(O)_2$haloalkyl, and cycloalkyl; and each R is independently alkyl, haloalkyl, or aryl;

with the proviso that no more than three of $Y^1$, $Y^2$, $Y^3$, $Y^4$, $Y^5$, and $Y^6$ are N.

4. The method of claim 1, wherein L is (L1) or (L2):

—C(X)NR'-(L1) or —NR'C(X)-(L2).

5. The method of claim 1, wherein each X is independently O or S.

6. The method of claim 1, wherein:

W is —$CR^6R^7$—;

$W^1$ is —$CR^6R^7$—; and

Z is —O—.

7. The method of claim 1, wherein Q is $CR^9$.

8. The method of claim 1, wherein Q is N.

9. The method of claim 1, wherein the compound, or stereoisomer thereof, is of Formula (IA-1):

(IA-1)

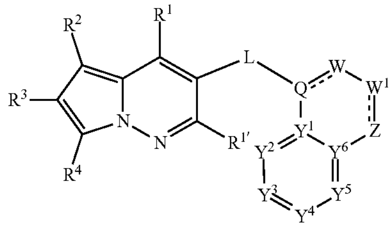

or a pharmaceutically acceptable salt thereof, wherein:

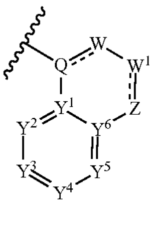

is Ring System A, Ring System B, Ring System C, Ring System D, Ring System E, Ring System F, Ring System G, Ring System H, Ring System I, Ring System J, Ring System K, Ring System L, Ring System M, Ring System N, Ring System O, Ring System P, Ring System Q, Ring System R, Ring System S, Ring System T, Ring System U, Ring System V, Ring System W, Ring System X, Ring System Y, Ring System Z, Ring System AA, Ring System AB, Ring System AC, Ring System AD, or Ring System AE:

Ring System A
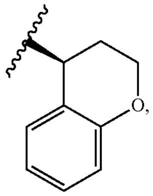
Ring System B
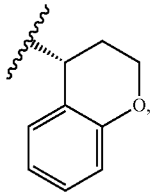
Ring System C
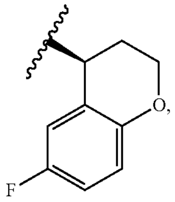
Ring System D
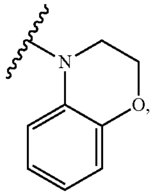
Ring System E
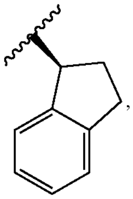
Ring System F
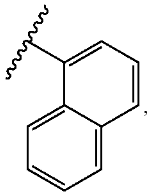
Ring System G
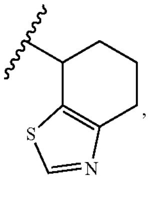
-continued
Ring System H
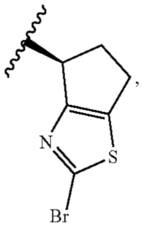
Ring System I
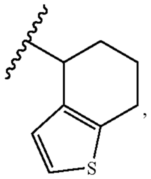
Ring System J
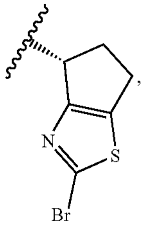
Ring System K
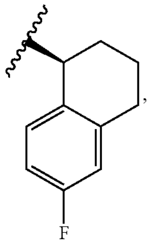
Ring System L
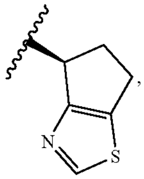
Ring System M
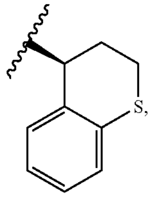
Ring System N
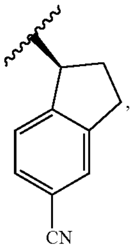

-continued
Ring System O
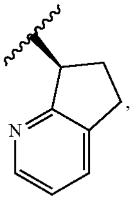
Ring System P
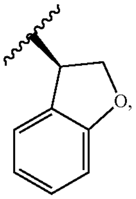
Ring System Q
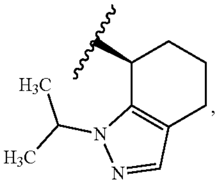
Ring System R
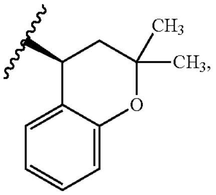
Ring System S
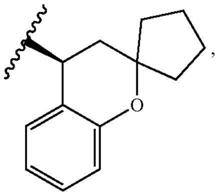
Ring System T
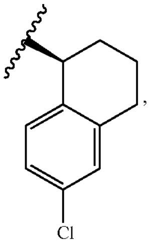
Ring System U
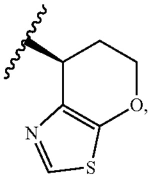
-continued
Ring System V
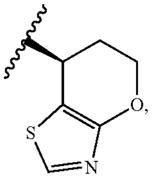
Ring System W
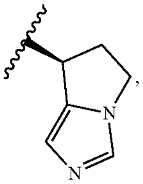
Ring System X
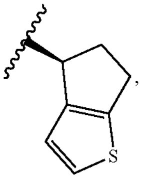
Ring System Y
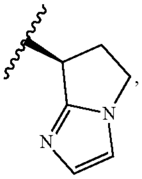
Ring System Z
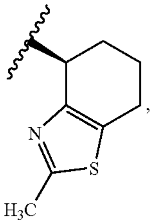
Ring System AA
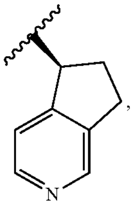
Ring System AB
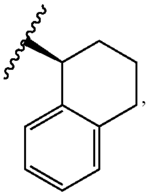
Ring System AC
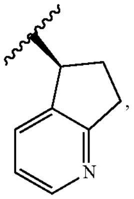

-continued

Ring System AD

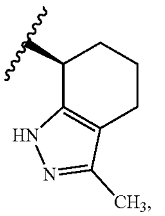

or

Ring System AE

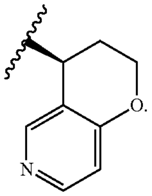

10. The method of claim 1, wherein the compound is of Formula (Ie):

(Ie)

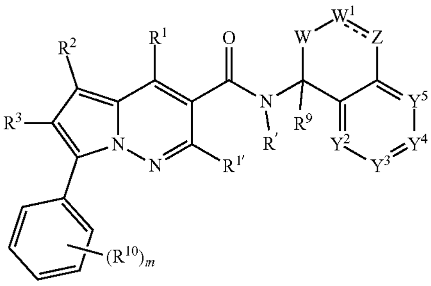

or a pharmaceutically acceptable salt or stereoisomer thereof, wherein:

- - - - is a single bond or double bond;

W is absent or —$CR^6R^7$—;

each $R^{10}$ is independently halogen, CN, $C_1$-$C_4$ alkyl, $C_1$-$C_4$ haloalkyl, C(O)$C_1$-$C_6$ alkyl, C(O)$C_1$-$C_6$ haloalkyl, C(O)$NH_2$, C(O)NH($C_1$-$C_6$ alkyl), C(O)NH($C_1$-$C_6$ haloalkyl), C(O)N($C_1$-$C_6$ alkyl)$_2$, C(O)N($C_1$-$C_6$ haloalkyl)$_2$, C(O)O($C_1$-$C_6$ alkyl), C(O)O($C_1$-$C_6$ haloalkyl), $NH_2$, NH($C_1$-$C_6$ alkyl), N($C_1$-$C_6$ alkyl)$_2$, OH, O($C_1$-$C_4$ alkyl), O($C_1$-$C_4$ haloalkyl), O(phenyl), $SF_5$, S($C_1$-$C_6$ alkyl), S($C_1$-$C_6$ haloalkyl), S(O)$C_1$-$C_6$ alkyl, S(O)$C_1$-$C_6$ haloalkyl, S(O)$_2C_1$-$C_6$ alkyl, S(O)$_2C_1$-$C_6$ haloalkyl, $C_3$-$C_8$ cycloalkyl, 3- to 7-membered heterocyclyl, phenyl, or 5- or 6-membered heteroaryl, wherein each 3- to 7-membered heterocyclyl independently contains 1, 2, or 3 heteroatoms independently selected from the group consisting of N, O, Si, and S; and m is 0, 1, 2, 3, 4, or 5.

11. The method of claim 10, wherein:

each $R^{10}$ is independently halogen; and m is 2 or 3.

12. The method of claim 10, wherein:

$R^1$ is $C_1$-$C_4$ alkyl or $NR^aR^b$;

$R^{1'}$ is H;

$R^2$ is H, halogen, $C_1$-$C_3$ alkyl, or $C_1$-$C_3$ haloalkyl;

$R^3$ is H, halogen, $C_1$-$C_3$ alkyl, or $C_1$-$C_3$ haloalkyl;

W is —$CH_2$—;

$W^1$ is —$CH_2$—;

Z is —O—;

each $R^{10}$ is independently F or $C_1$; and m is 2 or 3.

13. The method of claim 12, wherein:

$R^1$ is $C_1$-$C_4$ alkyl or $NR^aR^b$;

$R^2$ is H;

$R^3$ is halogen or $C_1$-$C_3$ alkyl; and

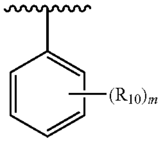

is:

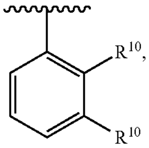

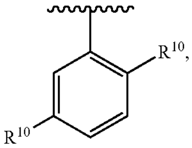

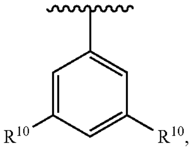

or

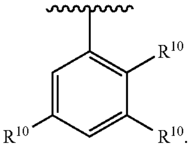

14. The method of claim 13, wherein $R^1$ is $CH(CH_3)_2$, $C(CH_3)_3$, $N(CH_3)_2$, or azetidin-1-yl, wherein the azetidin-1-yl is optionally substituted with one or more substituents independently selected from the group consisting of F and $CH_3$.

15. The method of claim 13, wherein:

$Y^2$ is $CR^5$;

$Y^3$ is $CR^5$;

$Y^4$ is $CR^5$; and $Y^5$ is $CR^5$.

16. A method for the prevention, control, and/or treatment of a parasitic infection in an animal in need thereof, wherein the method comprises administering to the animal an effective amount of a compound selected from the group consisting of A461-A524, A527-A529, A531-A533, A535, A536*a*, A536*b*, A537-A560, A568, and A569:

A461

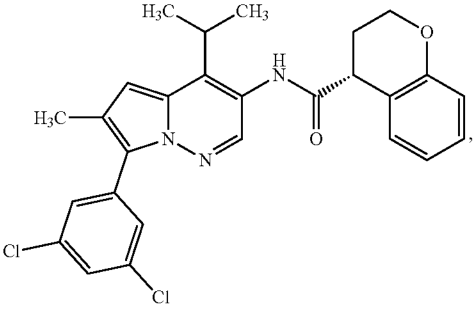

-continued
A462
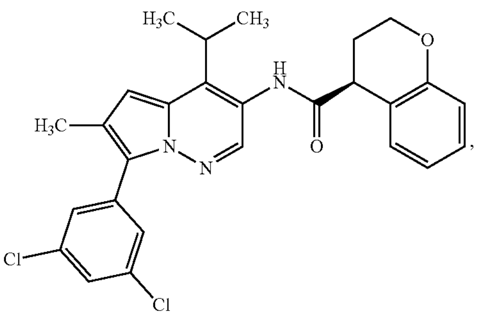,
A463
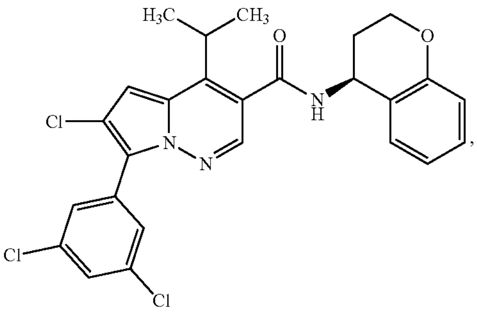,
A464
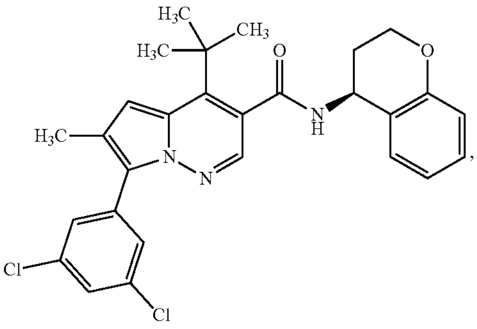,
A465
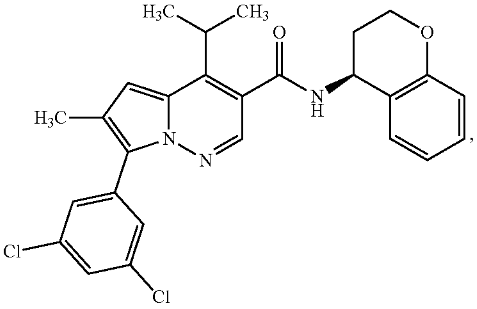,
-continued
A466
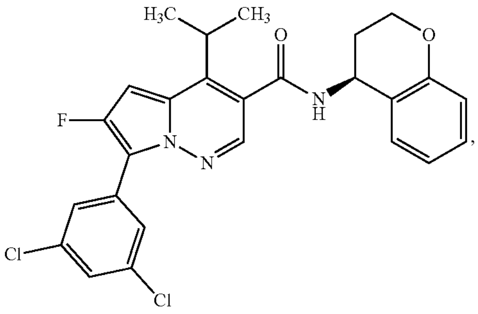,
A467
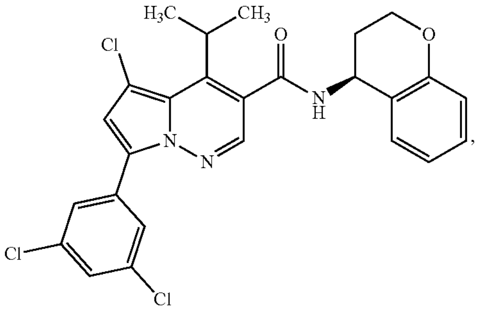,
A468
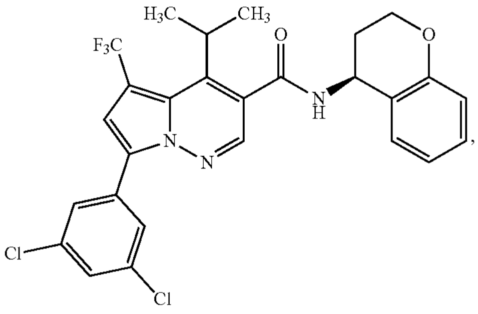,
A469
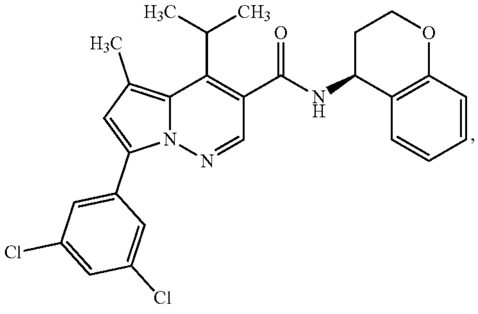,
A470
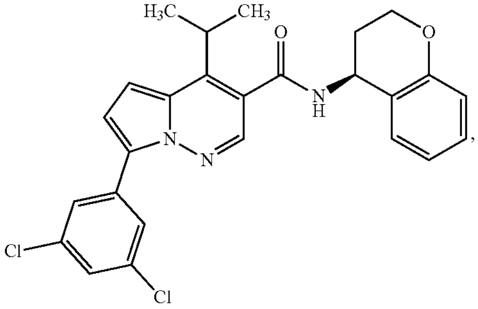, -continued
A471
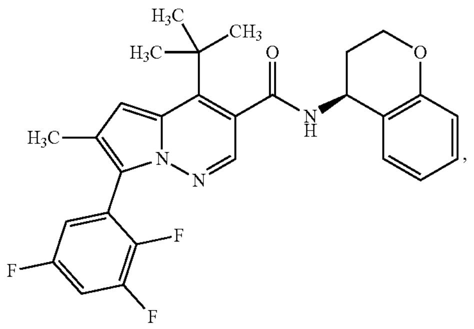
A472
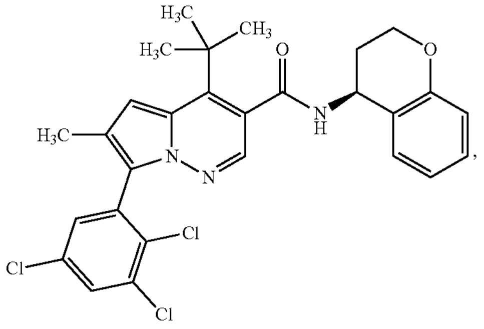
A473
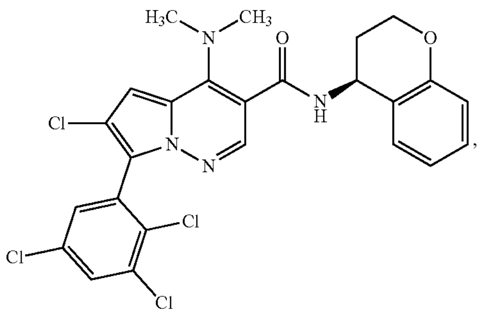
A474
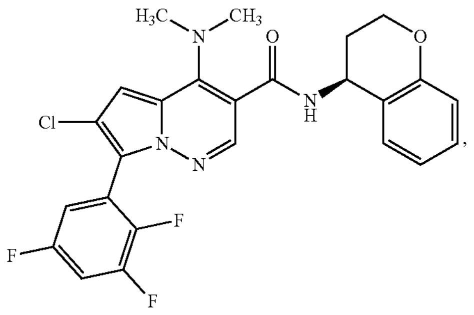
-continued
A475
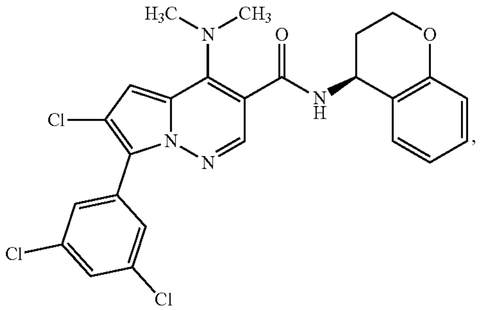
A476
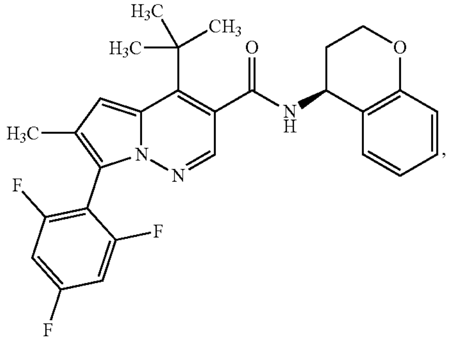
A477
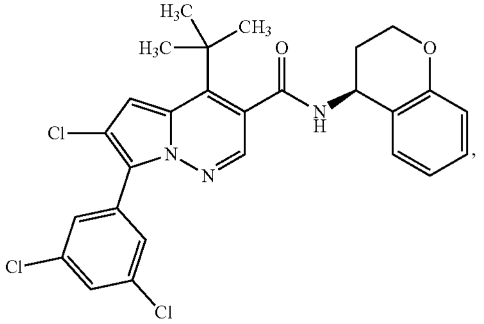
A478
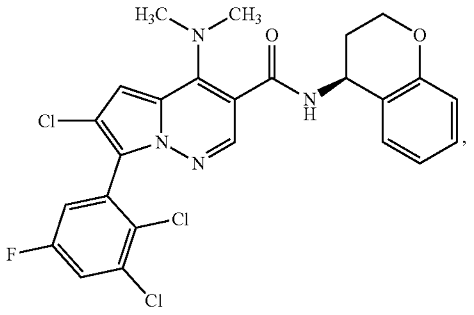

-continued
A479
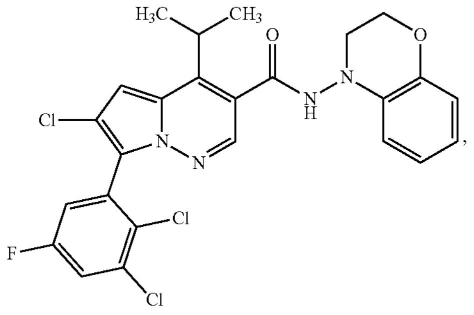
A480
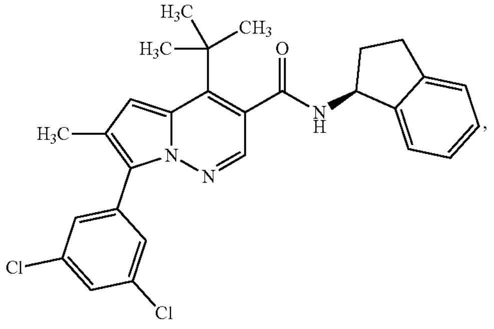
A481
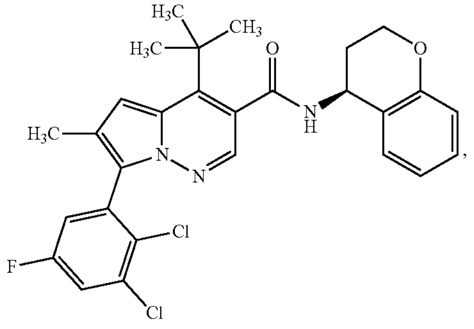
A482
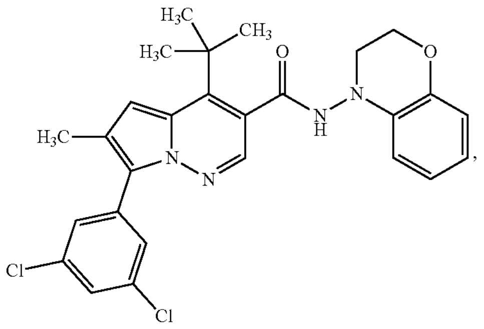
-continued
A483
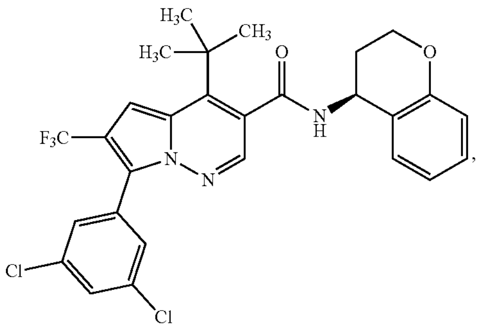
A484
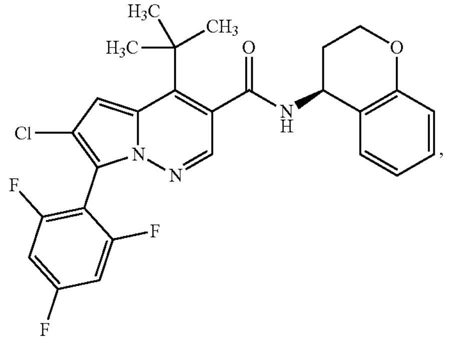
A485
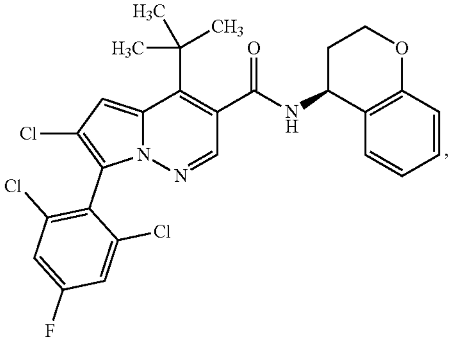
A486
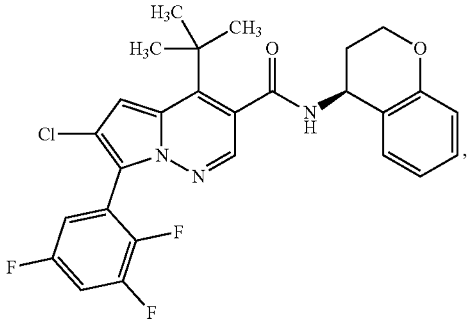

-continued
A487
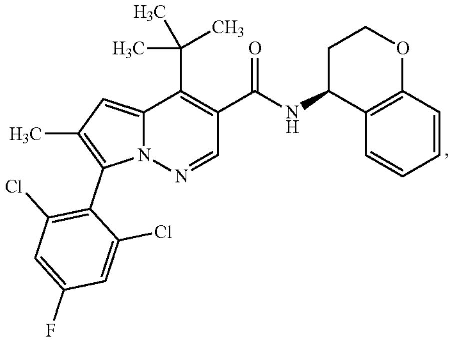
A488
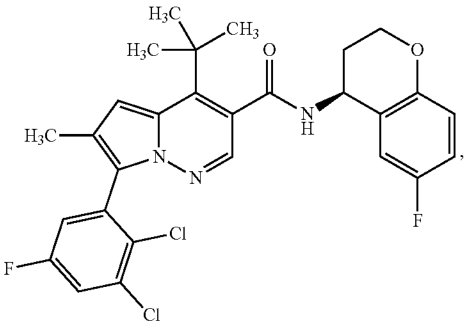
A489
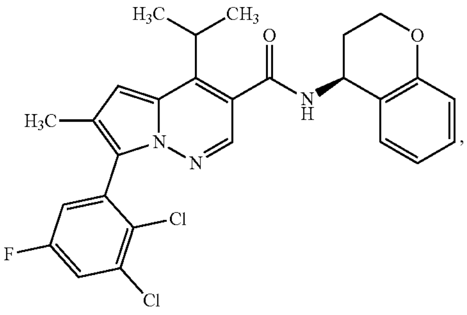
A490
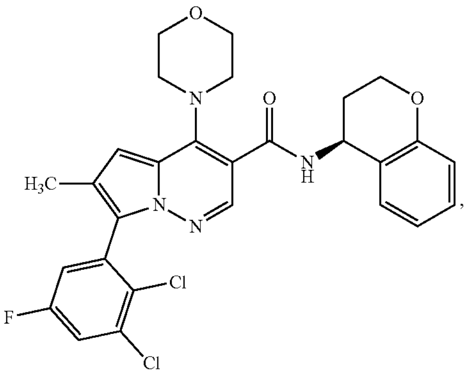
-continued
A491
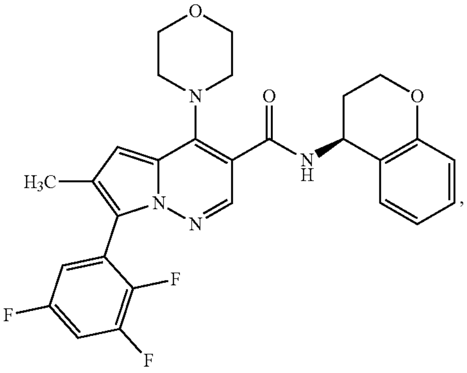
A492
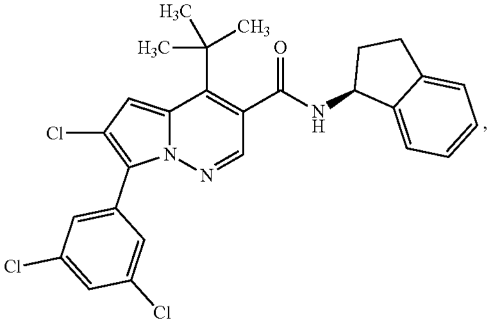
A493
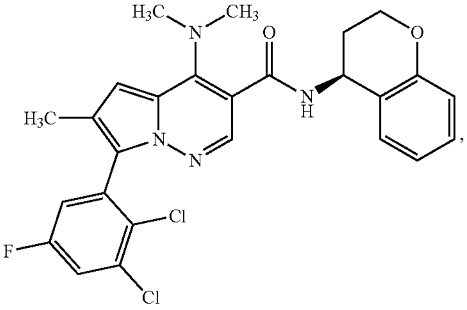
A494
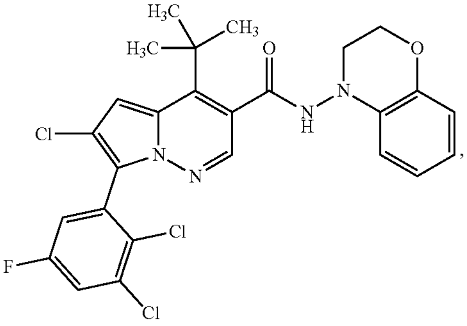

-continued
A495
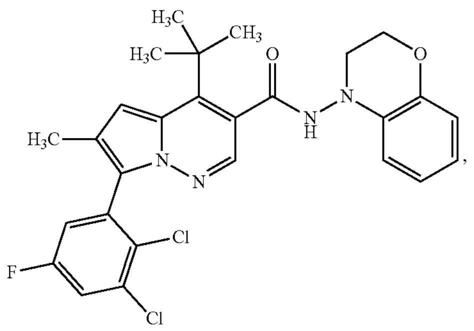
A496
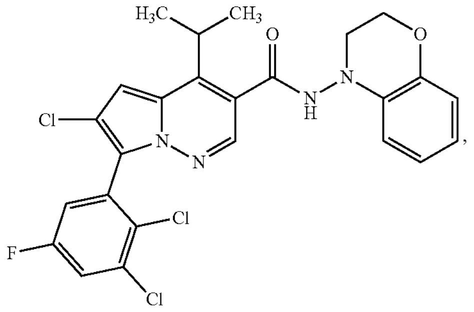
A497
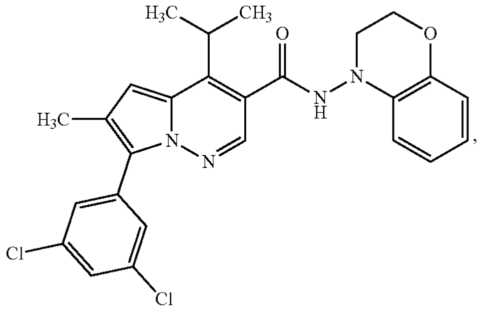
A498
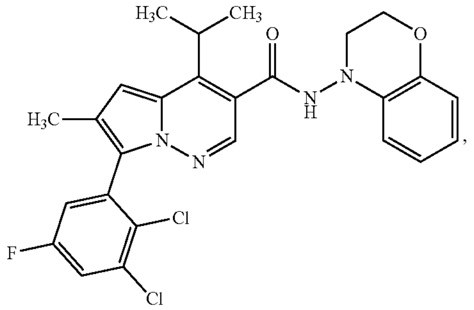
-continued
A499
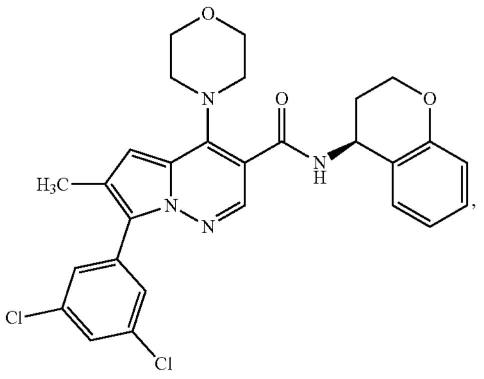
A500
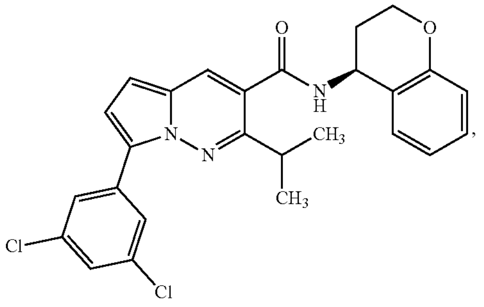
A501
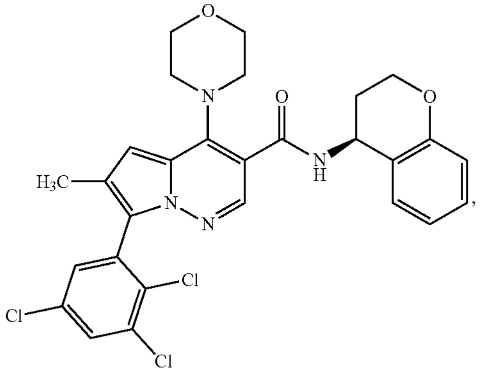
A502
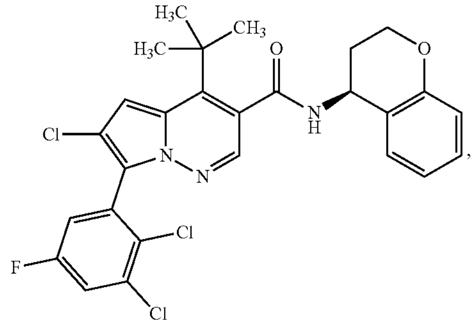

-continued
A503
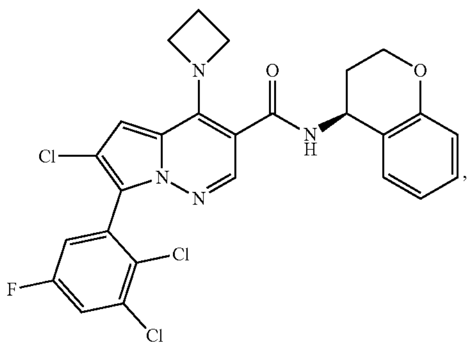
A504
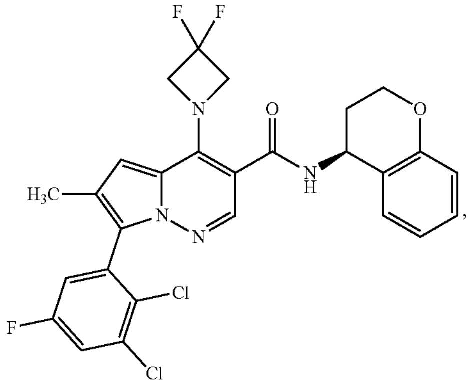
A505
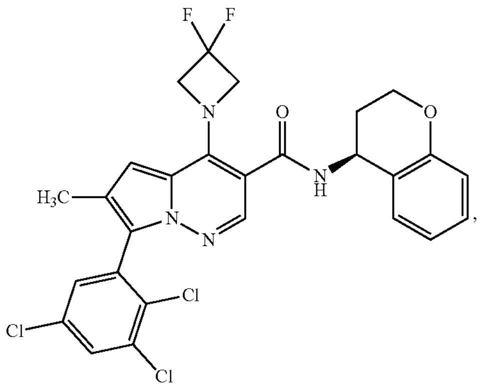
A506
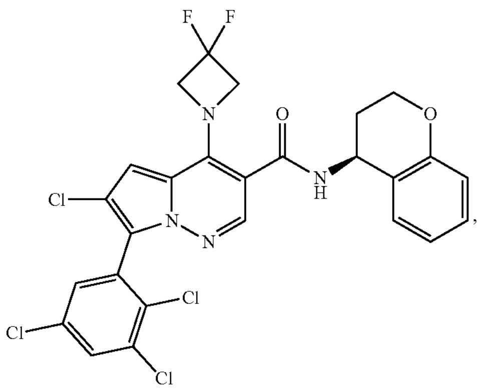
-continued
A507
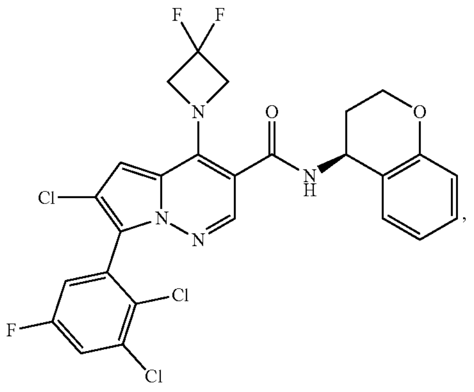
A508
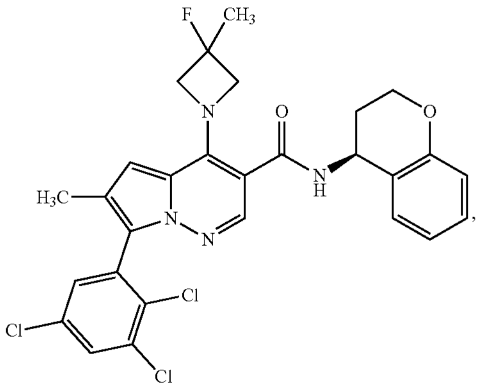
A509
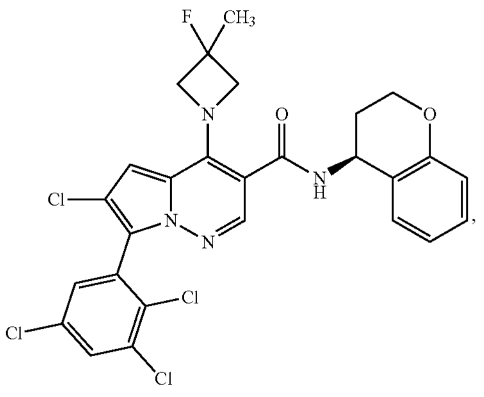
A510
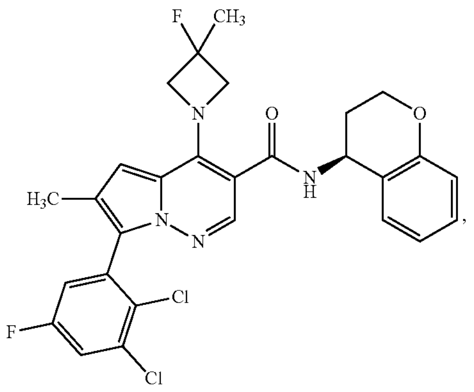

-continued
A511
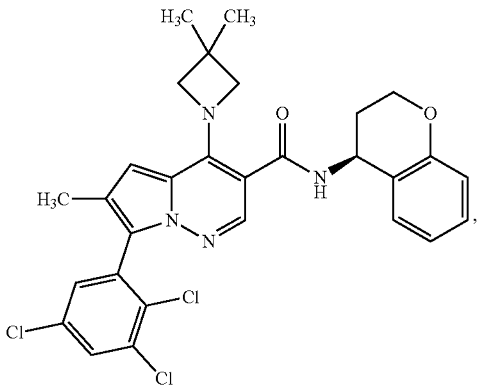
A512
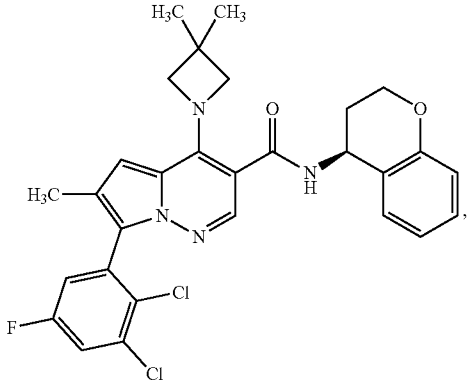
A513
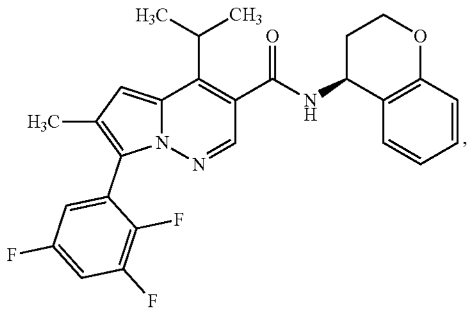
A514
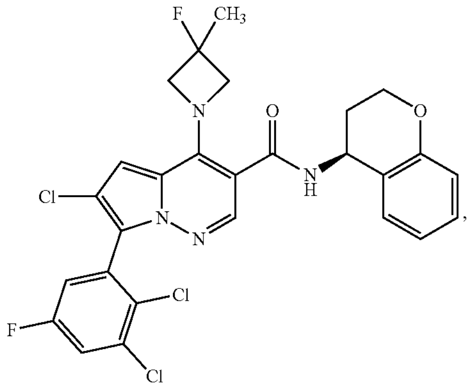
-continued
A515
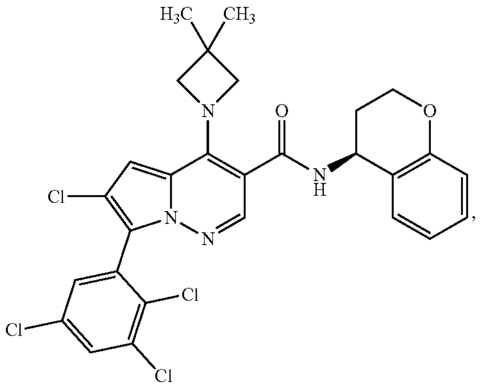
A516
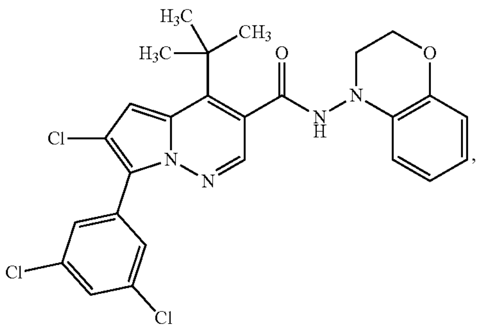
A517
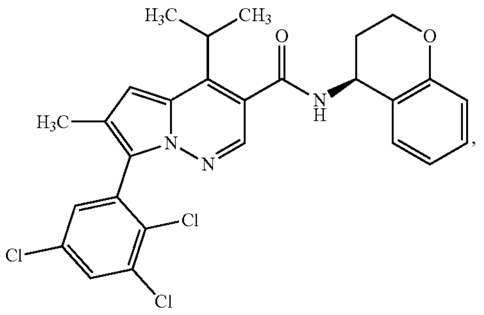
A518
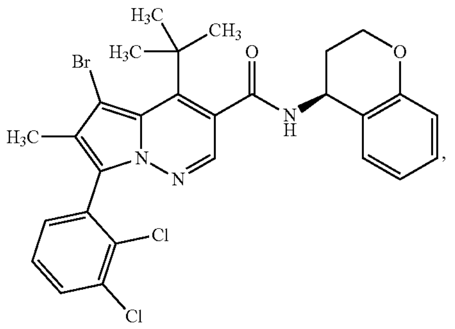

A519
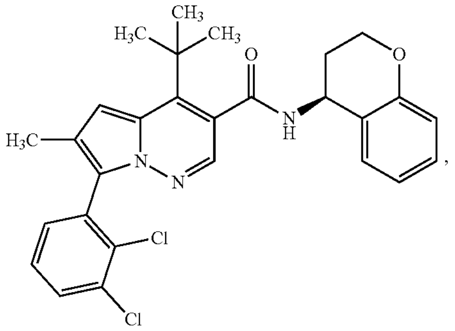
A520
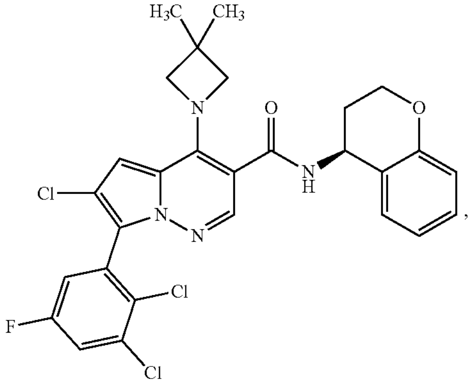
A521
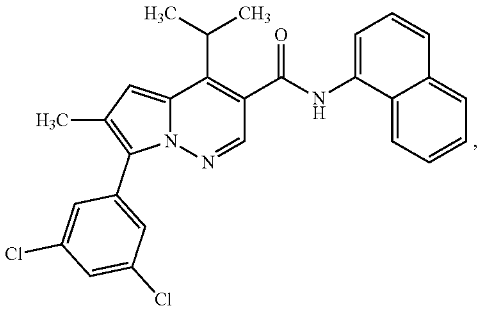
A522
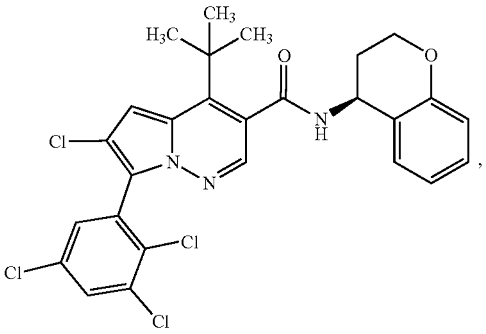
-continued
A523
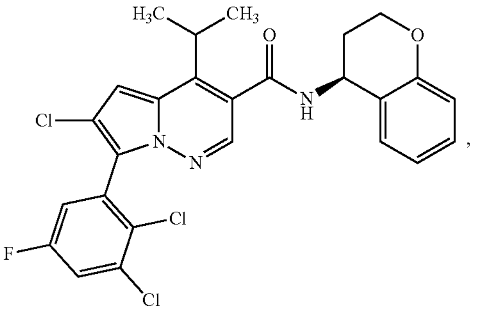
A524
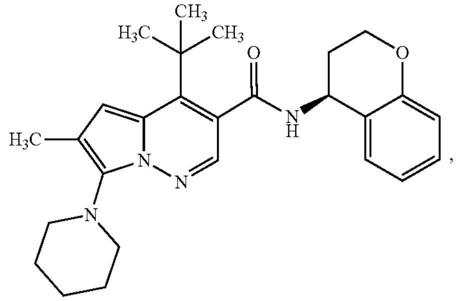
A527
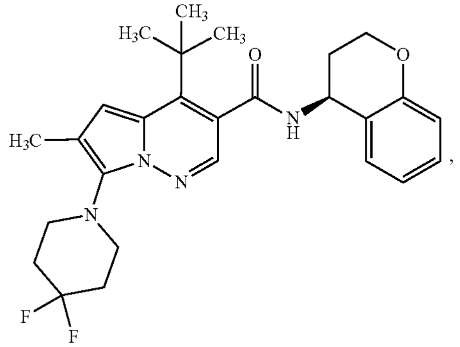
A528
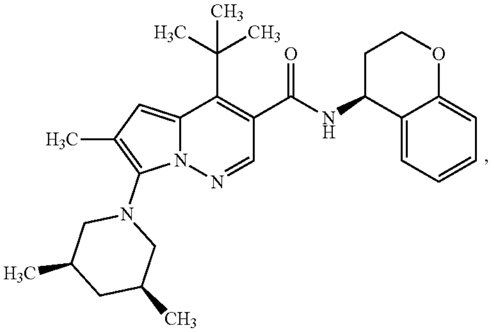
A529
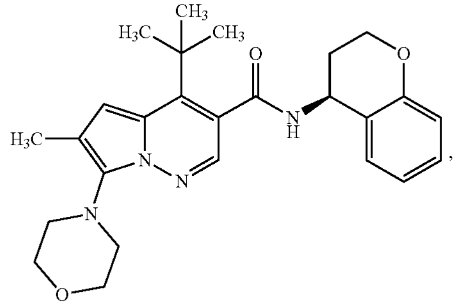

-continued
A531
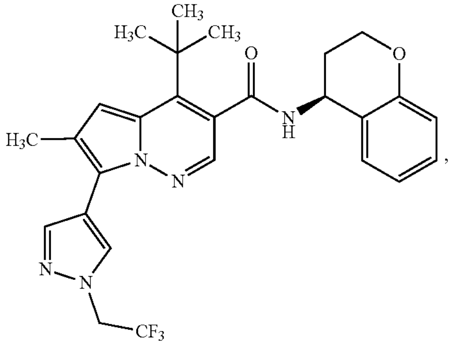
A532
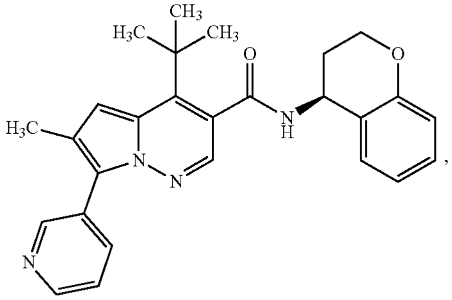
A533
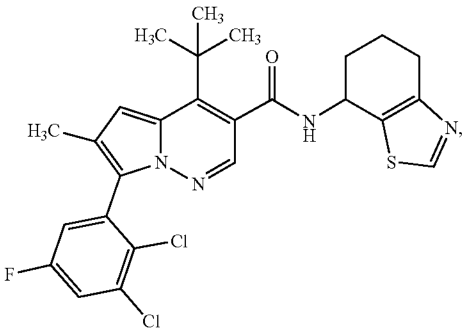
A535
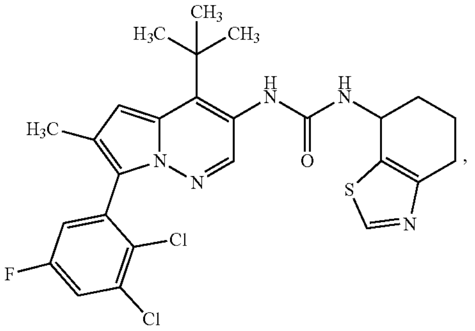
-continued
A536a
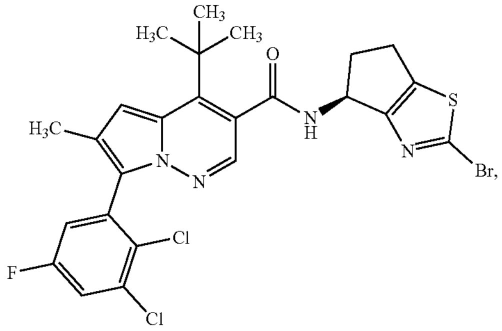
A536b
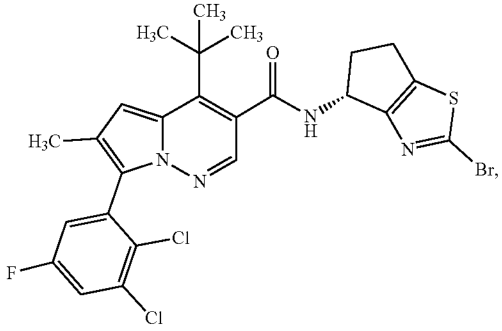
A537
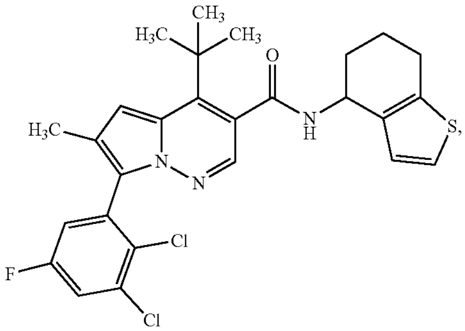
A538
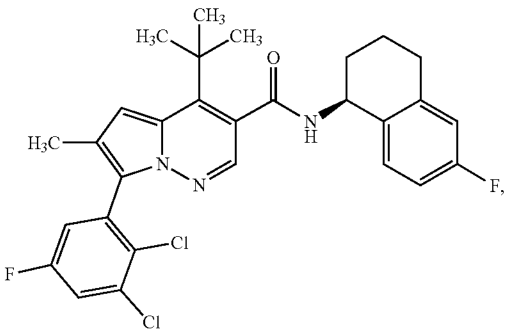

-continued
A539
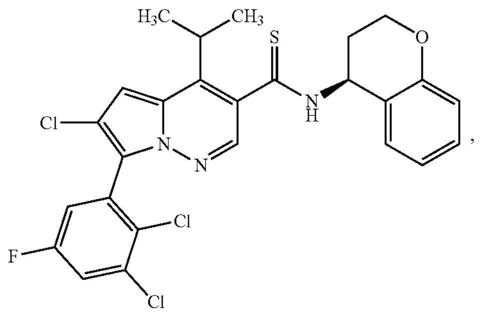
A540
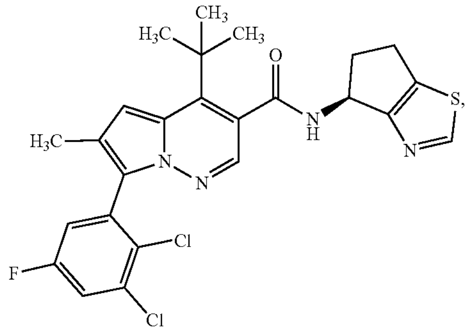
A541
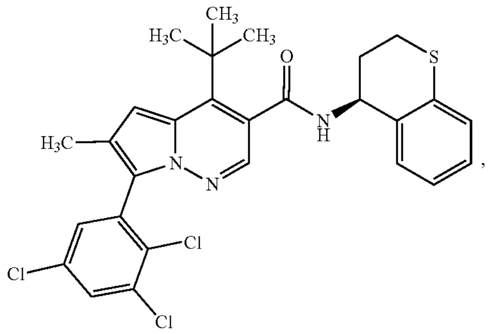
A542
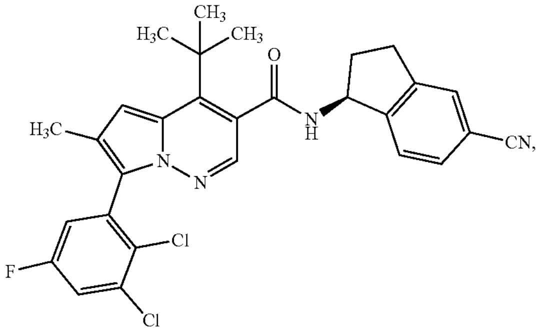
A543
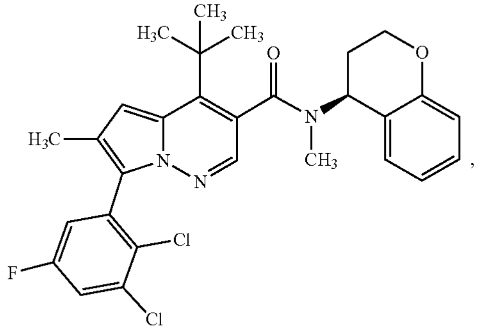
A544
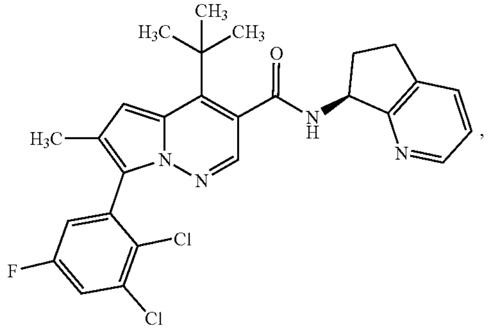
A545
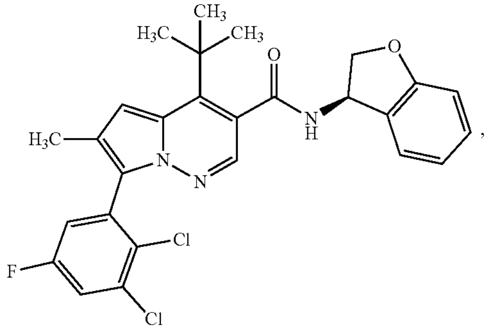
A546
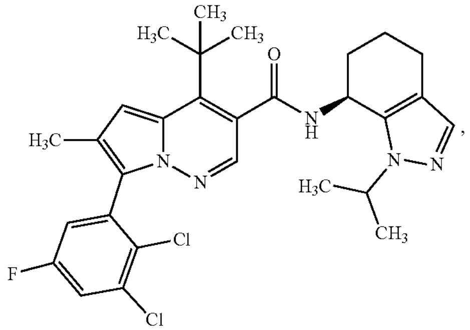

-continued
A547
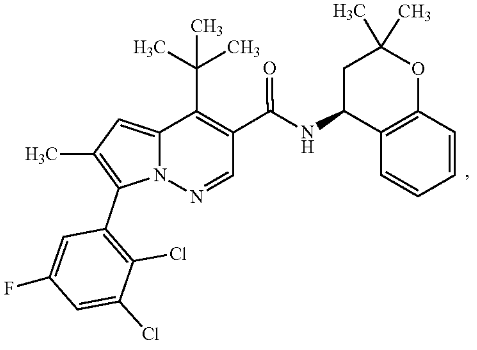
A548
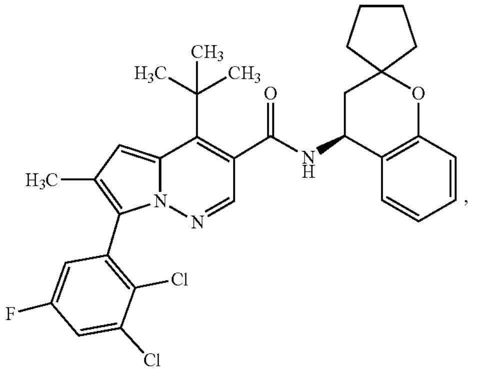
A549
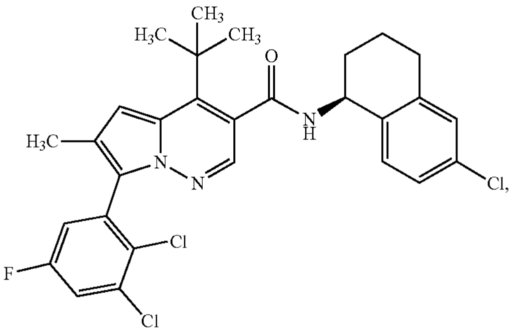
A550
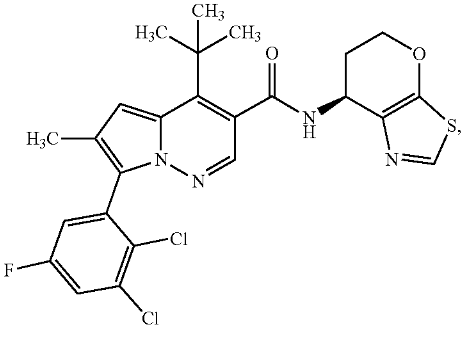
-continued
A551
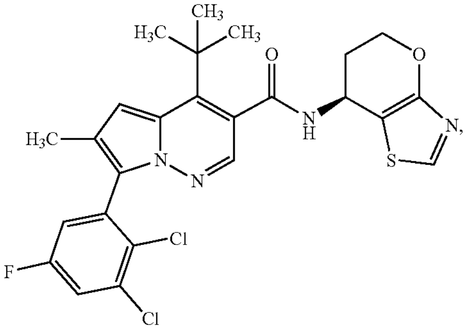
A552
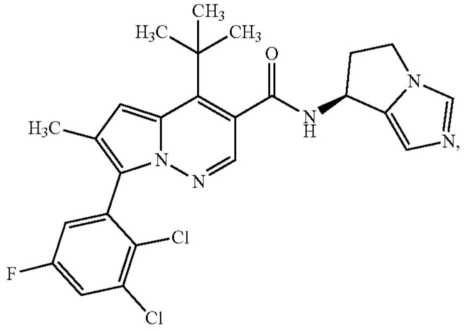
A553
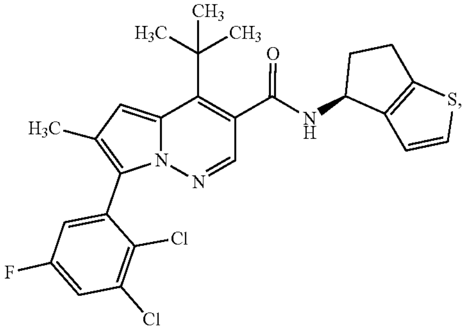
A554
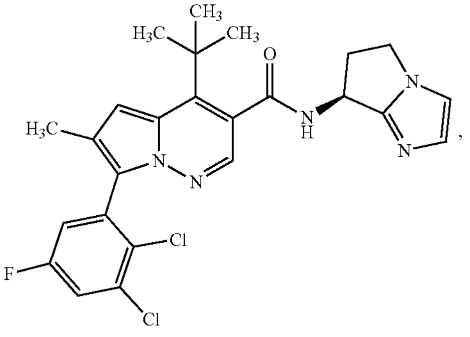

-continued
A555
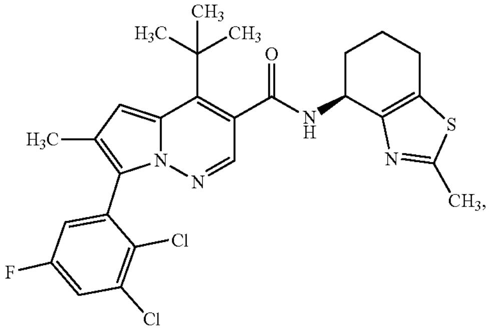
A556
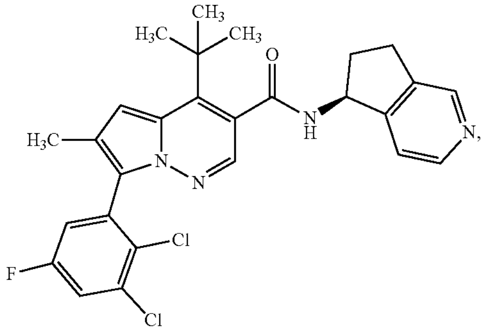
A557
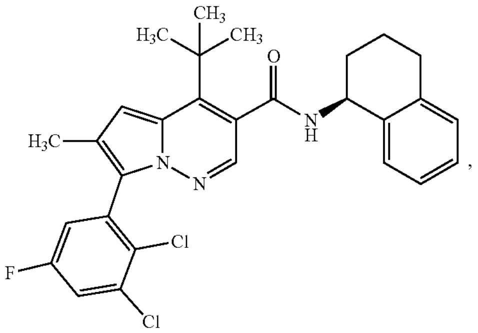
A558
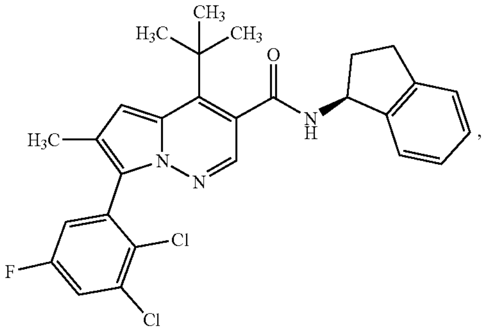
-continued
A559
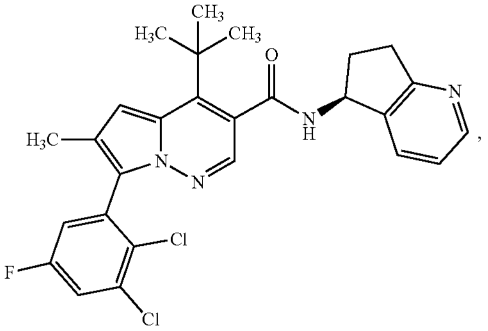
A560
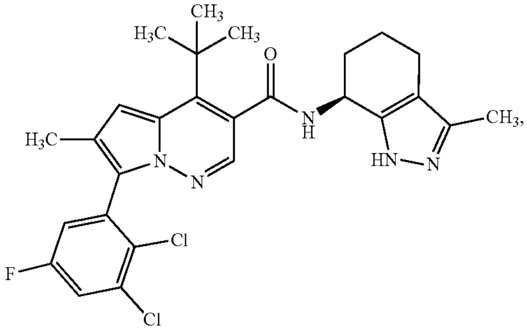
A568
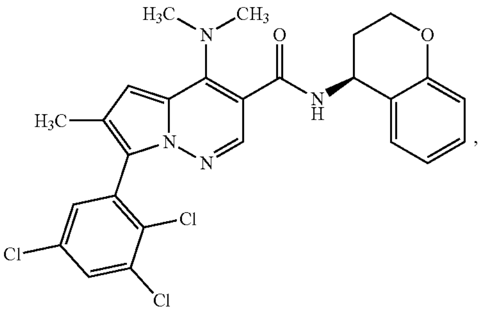
and
A569
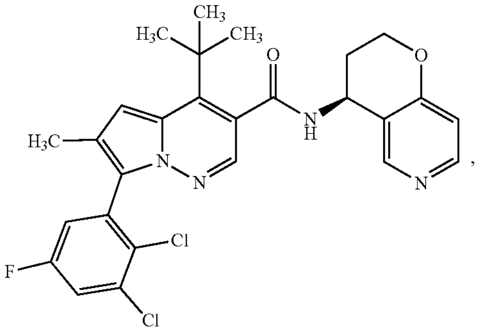
or a pharmaceutically acceptable salt thereof.
17. The method of claim 16, wherein:
(a) the method is for preventing a parasitic infection in an animal in need thereof; and
(b) the parasitic infection is caused by *Dirofilaria immitis*.

18. The method of claim 16, wherein the compound is:

A464

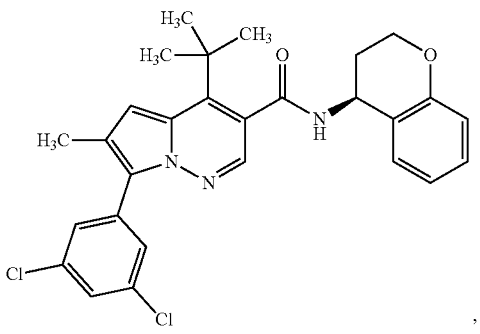

, or a pharmaceutically acceptable salt thereof.

19. The method of claim 16, wherein the compound is:

A465

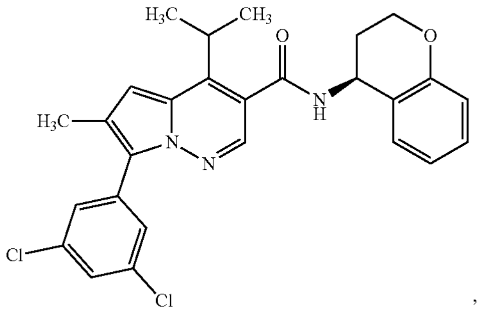

, or a pharmaceutically acceptable salt thereof.

20. The method of claim 16, wherein the compound is:

A471

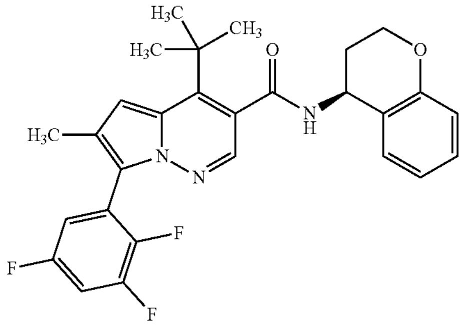

, or a pharmaceutically acceptable salt thereof.

21. The method of claim 16, wherein the compound is:

A472

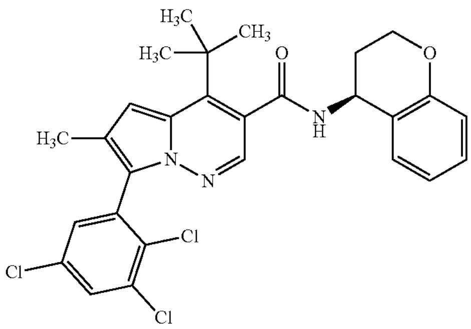

, or a pharmaceutically acceptable salt thereof.

22. The method of claim 16, wherein the compound is:

A473

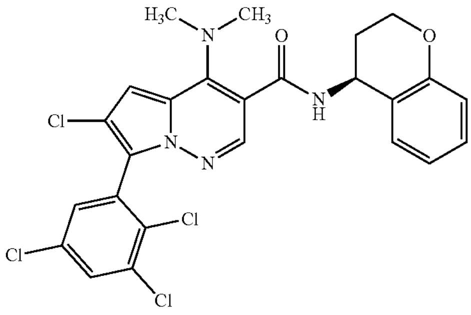

, or a pharmaceutically acceptable salt thereof.

23. The method of claim 16, wherein the compound is:

A481

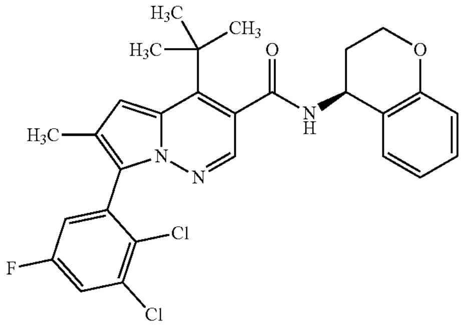

, or a pharmaceutically acceptable salt thereof.

24. The method of claim 16, wherein the compound is:

A493

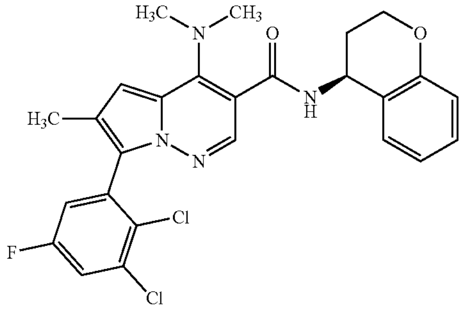

, or a pharmaceutically acceptable salt thereof.

25. The method of claim 16, wherein the compound is:

A504

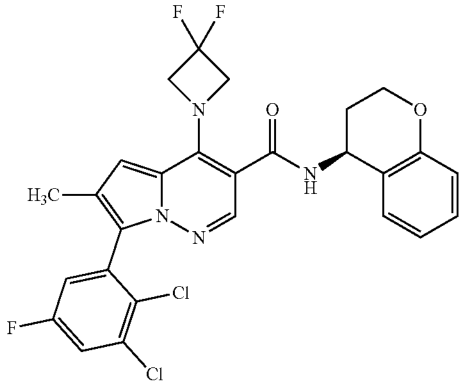

, or a pharmaceutically acceptable salt thereof.

26. The method of claim 16, wherein the compound is:

A522

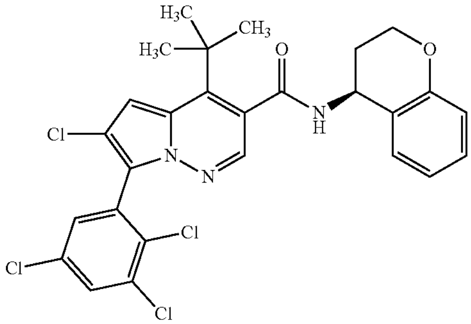

, or a pharmaceutically acceptable salt thereof.

27. The method of claim 16, wherein the compound is:

A568

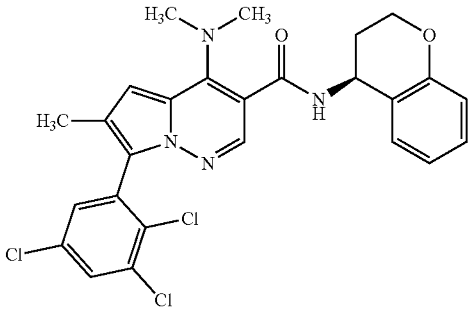

, or a pharmaceutically acceptable salt thereof.

* * * * *